(12) United States Patent
Lewis et al.

(10) Patent No.: US 7,199,106 B2
(45) Date of Patent: *Apr. 3, 2007

(54) LINCOMYCIN DERIVATIVES POSSESSING ANTIMICROBIAL ACTIVITY

(75) Inventors: Jason G. Lewis, Hayward, CA (US); Sampath-Kumar Anandan, Fremont, CA (US); Hardwin O'Dowd, Hayward, CA (US); Mikhail F. Gordeev, Castro Valley, CA (US)

(73) Assignee: Vicuron Pharmaceuticals, Inc., King of Prussia, PA (US)

(*) Notice: Subject to any disclaimer, the term of this patent is extended or adjusted under 35 U.S.C. 154(b) by 328 days.

This patent is subject to a terminal disclaimer.

(21) Appl. No.: 10/871,618

(22) Filed: Jun. 17, 2004

(65) Prior Publication Data

US 2005/0043248 A1  Feb. 24, 2005

Related U.S. Application Data

(63) Continuation-in-part of application No. 10/777,455, filed on Feb. 11, 2004, which is a continuation-in-part of application No. 10/642,807, filed on Aug. 15, 2003.

(60) Provisional application No. 60/479,296, filed on Jun. 17, 2003, provisional application No. 60/479,502, filed on Jun. 17, 2003.

(51) Int. Cl.
*A61K 31/70* (2006.01)
*C07H 15/16* (2006.01)
*C07H 17/04* (2006.01)

(52) U.S. Cl. .............. 514/24; 536/16.1; 536/16.2; 536/16.3; 536/16.4; 536/16.5

(58) Field of Classification Search ......... 536/16.1, 536/16.2, 16.3, 16.4, 16.5; 514/24
See application file for complete search history.

(56) References Cited

U.S. PATENT DOCUMENTS

| | | | |
|---|---|---|---|
| 2,851,463 A | 9/1958 | Hinman et al. |
| 2,928,844 A | 3/1960 | De Boer et al. |
| 3,086,912 A | 4/1963 | Bergy et al. |
| 3,255,174 A | 6/1966 | Bannister et al. |
| 3,268,556 A | 8/1966 | Hoeksema |
| 3,282,917 A | 11/1966 | Magerlein |
| 3,361,739 A | 1/1968 | Argoudelis et al. |
| 3,364,197 A | 1/1968 | Hoeksema |
| 3,380,992 A | 4/1968 | Argoudelis et al. |
| 3,435,025 A | 3/1969 | Birkenmeyer |
| 3,475,407 A | 10/1969 | Birkenmeyer |
| 3,496,163 A | 2/1970 | Birkenmeyer et al. |
| 3,502,648 A | 3/1970 | Birkenmeyer et al. |
| 3,509,127 A | 4/1970 | Kagan et al. |
| 3,539,689 A | 11/1970 | Birkenmeyer et al. |
| 3,544,551 A | 12/1970 | Kagan et al. |
| 3,549,615 A | 12/1970 | Birkenmeyer |
| 3,555,007 A | 1/1971 | Magerlein |
| 3,671,647 A | 6/1972 | Argoudelis et al. |
| 3,674,647 A | 7/1972 | Visser |
| 3,692,767 A | 9/1972 | Magerlein |
| 3,702,322 A | 11/1972 | Bannister |
| 3,714,141 A | 1/1973 | Shephard |
| 3,715,346 A | 2/1973 | Magerlein |
| 3,764,672 A | 10/1973 | Argoudelis et al. |
| 3,787,390 A | 1/1974 | Birkenmeyer |
| 3,817,979 A | 6/1974 | Argoudelis et al. |
| 3,833,475 A | 9/1974 | Reusser et al. |
| 3,849,396 A | 11/1974 | Birkenmeyer et al. |
| 3,853,843 A | 12/1974 | Morozwich |
| 3,856,943 A | 12/1974 | Birkenmeyer |
| 3,870,699 A | 3/1975 | Bannister |
| 3,892,729 A | 7/1975 | Birkenmeyer |
| 3,892,730 A | 7/1975 | Birkenmeyer |
| 3,915,954 A | 10/1975 | Bannister |
| 4,031,304 A | 6/1977 | Bannister |
| RE29,558 E | 2/1978 | Bannister |
| 4,271,266 A | 6/1981 | Bergy et al. |
| 4,278,789 A | 7/1981 | Birkenmeyer |
| 4,293,547 A | 10/1981 | Lewis et al. |
| 4,309,533 A | 1/1982 | Birkenmeyer |
| 4,310,660 A | 1/1982 | Birkenmeyer |
| 4,317,903 A | 3/1982 | Hofstetter |

(Continued)

FOREIGN PATENT DOCUMENTS

EP  0161 794  11/1985

(Continued)

OTHER PUBLICATIONS

Alexander, J. et al. (1988) "(Acyloxy)alkyl Carbamates as Novel Bioreversible Prodrugs for Amines: Increased Permeation through Biological Membranes," Journal of Medicinal Chemistry 31(2); 318-22.

(Continued)

*Primary Examiner*—Elli Peselev
(74) *Attorney, Agent, or Firm*—Frank W. Forman; Gregg C. Benson

(57) ABSTRACT

Novel lincomycin derivatives are disclosed. These lincomycin derivatives exhibit antibacterial activity. The compounds of the subject invention may exhibit potent activities against bacteria, including gram positive organisms, and may be useful antimicrobial agents. Methods of synthesis and of use of the compounds are also disclosed.

29 Claims, No Drawings

U.S. PATENT DOCUMENTS

| | | | |
|---|---|---|---|
| 4,383,109 | A | 5/1983 | Argoudelis et al. |
| 4,430,495 | A | 2/1984 | Patt et al. |
| 4,464,466 | A | 8/1984 | Argoudelis et al. |
| 4,568,741 | A | 2/1986 | Livingston |
| 4,710,565 | A | 12/1987 | Livingston et al. |

FOREIGN PATENT DOCUMENTS

| | | |
|---|---|---|
| GB | 1 298 295 | 11/1972 |
| GB | 1 347 598 | 2/1974 |
| WO | WO 89/04672 | 6/1989 |
| WO | WO 99/63937 | 12/1999 |
| WO | WO 2004/016632 | 2/2004 |
| WO | WO 2005/007665 | 1/2005 |
| WO | WO 2005/012320 | 2/2005 |

OTHER PUBLICATIONS

Alexander, J. et al. (1996) "Investigation of (Oxodioxolenyl)methyl Carbanates as Nonchiral Bioreversible Prodrug Moieties for Chiral Amines," Journal of Medicinal Chemistry 39(2): 480-86.

Anonymous (2001). "The Merck Index: Clindamycin," Merck & Co. Monograph No. 2377, XP-002271008, one page.

Anonymous (2001). "The Merck Index: Lincomycin," Merck & Co. Monograph No. 5522, XP-002271009, one page.

International Search Report mailed on May 18, 2004, for PCT Patent Application PCT/US03/25820 filed on Aug. 15, 2003, 6 pages.

Corrected version of International Search Report mailed on Jul. 26, 2004, for International Application PCT/US03/25820 filed on Aug. 15, 2003.

International Search Report mailed on May 6, 2005, for PCT Patent Application PCT/US2004/019497 filed on Jun. 17, 2004, 7 pages.

International Search Report mailed on Aug. 8, 2005, for PCT Patent Application PCT/US2004/019689 filed on Jun. 17, 2004, 21 pages.

Baldwin, J.E. et al. (1989) "Amino Acid Synthesis Using (L)-Pyroglutamic Acid As a Chiral Starting Material," Tetrahedron 45(23): 7459-68.

Baldwin, J.E. et al. (1990) "Stereospecific Synthesis of Dealanylalahopein," Tetrahedron 46 (13/14): 4733-48.

Bannister, B. et al. (1980) "The S-Alkylation of Sulphides by an Activated Carbohydrate Epimine Under Acidic Catalysis: the Formation of α-Acetamido-sulphides. Part 4. Reactions with Dithioacetals and Monothioacetals" Journal of the Chemical Society, Perkins Transactions 1 2:540-552.

Bannister, B. et al. (1987) "The S-Alkylation of Sulphides by an Activated Carbohydrate Epimine Under Acidic Catalysis: the Formation of α-Acetamido-sulphides. Part 5. The Introduction of Functionality into the Sulphide Substituent" J. Chem. Res. 4:701-94.

Bannister, B. et al. (1989) "The S-Alkylation of Sulphides by an Activated Carbohydrate Epimine Under Acidic Catalysis: the Formation of α-Acetamido-sulphides. Part 5. The Introduction of Functionality into the Sulphide Substituent" Journal of Chemical Research 4:90-91.

Birkenmeyer, R.D. et al. (1984) "Synthesis and Antimicrobial Activity of Clindamycin Analogues : Pirlimycin, A Potent Antibacterial Agent," Journal of Medicinal Chemistry 27(2): 216-23.

Bousquet, Y. et al. (1997) "Preparation of Enantiopure 4-Oxygenated Pipeolic Acid Derivatives," Tetrahedron 53(46): 15671-15680.

Bundgaard, H. et al. (1980) "Prodrugs as Drug Delivery Systems IV: N-Mannich bases as Potential Novel Prodrugs for Amides, Ureide, Amines, and Other NH-Acidic Compounds," Journal of Pharmaceutical Sciences 69(1): 44-46.

Deiters, A. et al. (2004) "Synthesis of Oxygen- and Nitrogen-Containing Heterocycles by Ring-Closing Metathesis" Chem. Rev. 104: 2199-2238.

Del Valle, J.R. et al. (2003) "Asymmetric Hydrogenations for the Synthesis of Boc-Protected 4-Alkylprolinols and Prolines," Journal of Organic Chemistry 68(10): 3923-31.

Demange, L. et al. (1998) "Practical Synthesis of the Boc and Fmoc Protected 4-Fluoro and 4-Difluoroprolines from Trans-4-Hydroxyproline," Tetrahedron Letters 39: 11169-72.

Dondoni, A. et al. (1997) "Stereoselective Addition of 2-Furyllithium and 2-Thiazolyllithium to Sugar Nitrones. Synthesis of Carbon-Linked Glycoglycines." Journal of Organic Chemistry 62(16): 5484-96.

Dondini, A. (1994) "Synthesis of N-Benzyl Nitrones" Synthetic Communications 24(18):2537-50.

Flaherty, P. et al. (1996) "Synthesis and Selective Monoamine Oxidase B-Inhibiting Properties of 1-Methyl-2,3,6-Tetrahydropyrid-4-yl Carbomate Derivatives: Potential Prodrugs of (R)- and (S)-Nordeprenyl," Journal of Medicinal Chemistry 39(24): 4756-61.

Fukuyama, T. et al. (1995) "2- and 4-Nitrobenzenesulfonamides: Exceptionally Versatile Means for Preparation of Secondary Amines and Protection of Amines." Tetrahedron Letters 36(36): 6373-74.

Goldstein, B.P. et al. (1995). "Antimicrobial Activity of MDL 63,246, a New Semisynthetic Glycopeptide Antibiotic," Antimicrob. Agents & Chemother. 39(7): 1580-88.

Griffith, W.P. et al. (1990) "TPAP: Tetra-n-propylammonium Perruthenate, A Mild and Convenient Oxidant for Alcohols." Aldrichimica Acta 23(1): 13-19.

Ibatullin, F.M. et al. (2002) "Reaction of 1,2-trans-glycosyl acetates with phosphorus pentachloride: new efficient approach to 1,2-trans-glycosyl chlorides" Tetrahedron Letters 43: 9577-9580.

Jensen, N.P. et al. (1980) "Use of Acetylacetone to Prepare a Prodrug of Cycloserine," Journal of Medicinal Chemistry 23(1): 6-8.

Magerlein, B.J. et al. (1972). "Lincomycin. 14. An Improved Synthesis and Resolution of the Antimalarial Agent, 1'-Demethyl-4'-depropyle-4'(R)-(S)-Pentyclindamycin Hydrochloride (U-24, 729A)," Journal of Medicinal Chemistry 15(12): 1255-59.

Magerlein, B.J. et al. (1969) "Lincomycin. VIII. 4'-Alkyl-1'-demethyl-4'-depropylclindamycins, Potent Antibacterial and Antimalarial Agents" Journal of Medicinal Chemistry 12: 780-84.

Magerlein, B.J. (1967) "Lincomycin. VII. 4'-depropyl-4'ethoxylincomycins" Journal of Medicinal Chemistry 10(6): 1161-63.

Misiek, M. et al. (1973) "Microbiological Properties of a New Cephalosporin, BL-S 339: 7-(Phenylacetimidoyl-aminoacetamido)-3-(2-Methyl-1,3,4-Thiadiazol-5-Ylthiomethyl)Ceph-3-em-4-Carboxylic Acid" Antimicrobial Agents and Chemotherapy 3(1):40-48.

Myers, A.G. et al. (1999) "Greatly Simplified Procedures for the Synthesis of a-Amino Acids by the Direct Alkylation of Pseudoephedrine Glycinamide Hydrate" J. Org. Chem. 64: 3322-27.

Osuch, C. et al. (1956) "The Use of Organolithium Compounds to effect the Alkylation of 2- and 4-Picoline" Journal of the American Chemical Society 78:1723-25.

Sakamoto, F. et al. (1984) "Studies on Prodrugs. II. Preparation and Characterization of (5-Substituted 2-Oxo-1,3-Dioxolen-4-yl)methyl Esters of Ampicillin" Chem. Pharm. Bull. 36(6):2241-48.

Schroeder, W. et al. (1967) "Lincomycin. III. The Structure and Stereochemistry of the Carbohydrate Moiety," Journal of the American Chemical Society 89(10): 2448-53.

Shek, E. et al. (1976) "Improved Delivery Through Biological Membranes. 2. Distribution, Excretion, and Metabolism of N-Methyl-1,6-dihydropyrident-2-Carbaldoxime Hydrochloride A Pro-drug of N-Methylpyridinium-2-Carbalkdoxime Chloride" Journal of Medicinal Chemistry 19(1):108-12.

Shuman, R.T. et al. (1990) "An improved Synthesis of Homoproline and Derivatives," Journal of Organic Chemistry 55: 738-41.

Spizek, J. et al. (2004) "Lincomycin, Cultivation of Producing Strains and Biosynthesis" Appl. Microbiol. Biotechnol. 63:510-19.

Sztaricskai, F. et al. (1996) "Semisynthetic Modification of Antibiotic Lincomycin" J. Antibiotics 49(9): 941-43.

Sztaricskai, F. et al. (1997) "Chemical Synthesis and Structural Study of Lincomycin Sulfoxides and a Sulfone" J. Antibiotics 50(10): 866-73.

Sztaricskai, F. et al. (1999) "Structural Modification of the Lincomycin Antibiotic" J. Antibiotics 52(11): 1050-55.

Watanabe, T. et al. (1982) "Synthesis of a-Amino-cycloheptatriene-1-acetic Acids and Their 7-Acylaminocephalosporin Derivatives" Chemical Pharmaceutical Bulletin 30(7): 2579-82.

Weiss, W.J. et al. (1999) "In vivo Activities of Peptidic Prodrugs of Novel Aminomethyl Tetrahydrofuranyl-1β-Methylcarbapenems" Antimicrobial Agents and Chemotherapy 43(3): 460-64.

Yong, K. et al. (2001) "Studies on the Alkylation of 3-Methyl-3-buten-1-ol Dianion: An Efficient Synthesis of 3-Methylene-1-alkanols Including a San Jose Scale Sex Phereomone" Journal of Organic Chemistry 66(24): 8248-51.

Zhang, R. et al. (1998) "Pseudo-A(1,3) Strain as a Key Conformational Control Element in the Design of Poly-L-Proline Type II Peptide Mimics," Journal of the American Chemical Society 120(16): 3894-3902.

LINCOMYCIN DERIVATIVES POSSESSING ANTIMICROBIAL ACTIVITY

CROSS-REFERENCE TO RELATED APPLICATIONS

This application is a continuation-in-part of U.S patent application Ser. No. 10/777,455, filed Feb. 11, 2004, which is a continuation-in-part of U.S. patent application Ser. No. 10/642,807, filed Aug. 15, 2003, and further claims the benefit under 35 U.S.C. §119(e) of U.S. Provisional Application No. 60/479,296 filed on Jun. 17, 2003 and of U.S. Provisional Application No. 60/479,502, filed on Jun. 17, 2003, the disclosures of which are hereby incorporated by reference in their entirety.

BACKGROUND OF THE INVENTION

1. Field of the Invention

This invention relates to lincomycin derivatives that exhibit antibacterial activity as well as to methods for using such derivatives.

2. State of the Art

Lincomycin is a biosynthetic product that adversely affects growth of various microorganisms, in particular gram positive bacteria. The characteristics and preparation of lincomycin are disclosed in U.S. Pat. No. 3,086,912. A variety of derivatives of lincomycin, which also have antimicrobial activity, have been prepared. These derivatives include, for example, clindamycin, which is described in U.S. Pat. No. 3,496,163.

Lincomycin derivatives remain attractive targets for antibacterial drug discovery. Accordingly, lincomycin derivatives that possess antimicrobial activity are desired as potential antibacterial agents.

SUMMARY OF THE INVENTION

The present invention provides lincomycin derivatives that possess antibacterial activity. In some embodiments, said novel lincomycin derivatives exhibit antibacterial activity against gram positive and anaerobe pathogens. Surprisingly, selected novel lincomycin compounds described herein exhibit atypical potency against *Enterocci* species such as *Enterocci faecium* and *Enterocci faecalis*, and/or against fastidious gram-negative pathogens such as *Haemophilus influenzae*, when compared against known compounds such as clindamycin.

In one of its composition aspects, this invention is directed to a compound of Formula (I):

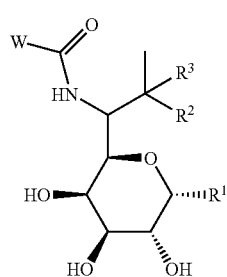

(I)

wherein:

W is a nitrogen-containing ring:

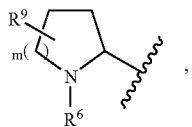

wherein m is 0, 1, 2, or 3; wherein when m is 2, the nitrogen-containing ring may optionally contain a double bond between the 4 and 5 nitrogen-containing ring positions; wherein when m is 3, the nitrogen-containing ring may optionally contain one double bond between either the 4 and 5 nitrogen-containing ring positions or between the 5 and 6 nitrogen-containing ring positions; wherein the nitrogen-containing ring positions are consecutively numbered counterclockwise beginning with "1" at the nitrogen;

$R^1$ is selected from the group consisting of hydrogen, alkyl, substituted alkyl, hydroxyalkyl, alkenyl, substituted alkenyl, alkoxy, substituted alkoxy, cycloalkylalkyl, halo, alkylsulfanyl, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =$NOR^7$ and the other is absent, or one of $R^2$ and $R^3$ is =$CH_2$ and the other is absent;

$R^6$ is selected from the group consisting of hydrogen, alkyl, hydroxyalkyl, cycloalkyl, substituted alkyl, iminomethyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, 5-alkyl-[1,3]dioxol-2-one-4-yl-methyl, 5-alkyl-[1,3]dioxol-2-one-4-yl-methoxy-carbonyl, or —N($R^6$)— fragment is part of the amidine, N-cyanoamidine, N-hydroxyamidine, or N-alkoxyamidine structure;

$R^7$ is H or alkyl;

$R^9$, which can be singly or multiply substituted in the ring on the same or different carbons, is independently selected from the group consisting of hydrogen, alkyl, substituted alkyl, cycloalkyl, substituted cycloalkyl, cycloalkylalkyl, substituted alkenyl, substituted oxygen, substituted nitrogen, halogen, phenyl, substituted phenyl, alkylsulfanyl, substituted alkylsulfanyl, substituted arylsulfanyl, heteroarylsulfanylalkyl, heterocyclicsulfanylalkyl, heteroarylsulfanyl, and heterocyclicsulfanyl, propylidene (=$CHCH_2CH_3$), azido, —$(CH_2)_n$—OH, —$(CH_2)_n$—$NR^4R^5$, and branched chain isomers thereof wherein n is an integer of from 1 to 8 inclusive and $R^4$ and $R^5$ are H or alkyl, alkoxyalkoxy, aryl, substituted aryl, alkenyl, substituted alkenyl, and —$S(O)_q R^{13}$ where q is an integer equal to zero, one or two and $R^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, and wherein not more than one —$S(O)_q R^{13}$ group is present on the nitrogen-containing ring;

or a prodrug and/or pharmaceutically acceptable salt thereof.

In another one of its composition aspects, this invention is directed to a compound of Formula (II):

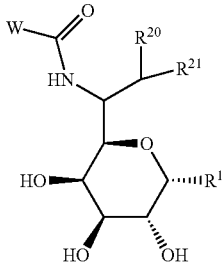

(II)

wherein:
W is a nitrogen-containing ring:

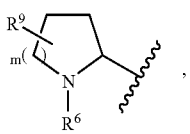

wherein m is 0, 1, 2, or 3; wherein when m is 2, the nitrogen-containing ring may optionally contain a double bond between the 4 and 5 nitrogen-containing ring positions; wherein when m is 3, the nitrogen-containing ring may optionally contain one double bond between either the 4 and 5 nitrogen-containing ring positions or between the 5 and 6 nitrogen-containing ring positions; wherein the nitrogen-containing ring positions are consecutively numbered counterclockwise beginning with "1" at the nitrogen;

$R^1$ is selected from the group consisting of hydrogen, alkyl, substituted alkyl, hydroxyalkyl, alkenyl, substituted alkenyl, alkoxy, substituted alkoxy, cycloalkylalkyl, halo, alkylsulfanyl, and substituted alkylsulfanyl;

$R^{20}$ and $R^{21}$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^{20}$ and $R^{21}$ is =$NOR^7$ and the other is absent, or one of $R^{20}$ and $R^{21}$ is =$CH_2$ and the other is absent, or $R^{20}$ and $R^{21}$ taken together are cycloalkyl, aryl, substituted aryl, heterocyclic, or heteroaryl;

$R^6$ is selected from the group consisting of hydrogen, alkyl, hydroxyalkyl, cycloalkyl, substituted alkyl, iminomethyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, 5-alkyl-[1,3]dioxol-2-one-4-yl-methyl, 5-alkyl-[1,3]dioxol-2-one-4-yl-methoxy-carbonyl, or —N($R^6$)— fragment is part of the amidine, N-cyanoamidine, N-hydroxyamidine, or N-alkoxyamidine structure;

$R^7$ is H or alkyl;

$R^9$, which can be singly or multiply substituted in the ring on the same or different carbons, is independently selected from the group consisting of hydrogen, alkyl, substituted alkyl, cycloalkyl, substituted cycloalkyl, cycloalkylalkyl, substituted alkenyl, substituted oxygen, substituted nitrogen, halogen, phenyl, substituted phenyl, alkylsulfanyl, substituted alkylsulfanyl, substituted arylsulfanyl, heteroarylsulfanylalkyl, heterocyclicsulfanylalkyl, heteroarylsulfanyl, and heterocyclicsulfanyl, propylidene (=$CHCH_2CH_3$), azido, —$(CH_2)_n$—OH, —$(CH_2)_n$—$NR^4R^5$, and branched chain isomers thereof wherein n is an integer of from 1 to 8 inclusive and $R^4$ and $R^5$ are H or alkyl, alkoxyalkoxy, aryl, substituted aryl, alkenyl, substituted alkenyl, and —$S(O)_q$$R^{13}$ where q is an integer equal to zero, one or two and $R^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, and wherein not more than one —$S(O)_qR^{13}$ group is present on the nitrogen-containing ring;

or a prodrug and/or pharmaceutically acceptable salt thereof

In another one of its composition aspects, this invention is directed to a compound of Formula (IA):

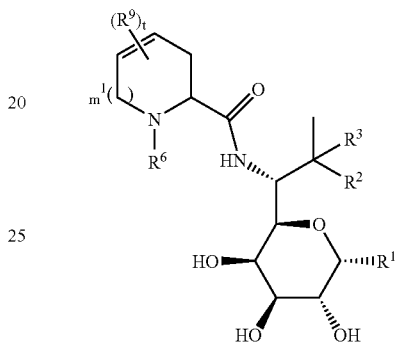

(IA)

wherein:
the

----- represents a bond that may be a double bond or a single bond;

$R^1$ is selected from the group consisting of —S-alkyl, —S-substituted alkyl, hydrogen, alkyl, substituted alkyl, alkenyl, substituted alkenyl, alkoxy, substituted alkoxy and halo;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =$NOR^7$ and the other is absent, or one of $R^2$ and $R^3$ is =$CH_2$ and the other is absent;

$R^6$ is selected from the group consisting of hydrogen, alkyl, substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl,

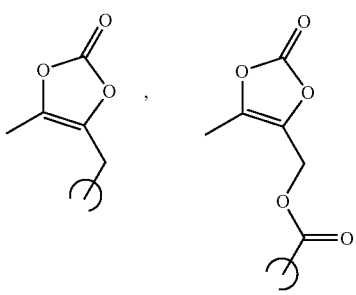

or —N(R⁶)— fragment is part of the amidine, N-cyanoamidine, N-hydroxyamidine, or N-alkoxyamidine structure;

R⁷ is selected from the group consisting of hydrogen and alkyl;

R⁹, which can be singly or multiply substituted in the ring on the same or different carbons, is independently selected from the group consisting of hydrogen, alkyl, substituted alkyl, alkoxyalkoxy, cycloalkyl, substituted cycloalkyl, substituted oxygen, substituted nitrogen, halo, aryl, substituted aryl, alkenyl, substituted alkenyl, and —S(O)$_q$R¹³ where q is an integer equal to zero, one or two and R¹³ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m¹=0–2;

and wherein t=0–3;

or pharmaceutically acceptable salts and/or prodrugs thereof; with the following provisos:

A. that in the compounds of formula (I) when

----- is a single bond, m¹ is zero or one,

R² and R³ are independently hydrogen, alkyl, hydroxy, fluoro, cyanoalkyl or one of R² and R³ is =NOR⁷ and the other is absent, or one of R² and R³ is =CH₂ and the other is absent, R⁶ is hydrogen, alkyl, hydroxyalkyl, —C(O)O-alkylene-cycloalkyl, —C(O)O-alkylene-substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, —C(O)O-heterocyclic, —C(O)O-substituted hetercyclic, —[C(O)O]$_p$-alkylene-heterocycle, —[C(O)O]$_p$-alkylene-substituted heterocycle, where p is zero or one, and R⁷ is selected from the group consisting of hydrogen and alkyl;

R⁹ is hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$—OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl; and then R¹ is not —S-alkyl B. in the compounds of formula (I), when

----- is a single bond,

R¹ and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent, or one of R² and R³ is =CH₂ and the other is absent, with the provisos that both R² and R³ are not hydrogen; when one of R² and R³ is halo, the other is not hydrogen or hydroxy; and when one of R² and R³ is hydroxy, the other is not hydrogen or hydroxy;

R⁶ is selected from the group consisting of hydrogen, alkyl, substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, or —N(R⁶)— fragment is part of the amidine, N-cyanoamidine, N-hydroxyamidine, or N-alkoxyamidine structure;

R⁷ is selected from the group consisting of hydrogen and alkyl; and

R¹ is selected from the group consisting of —S-alkyl, —S-substituted alkyl, hydrogen, alkyl, substituted alkyl, alkenyl, substituted alkenyl, alkoxy, substituted alkoxy and halo;

then at least one of R⁹ is other than hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$—OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl, C. in the compounds of formula (I), when

----- is a single bond,

R² and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent, or one of R² and R³ is =CH₂ and the other is absent, with the provisos that both R² and R³ are not hydrogen; when one of R² and R³ is halo, the other is not hydrogen or hydroxy; and when one of R² and R³ is hydroxy, the other is not hydrogen or hydroxy;

R⁷ is selected from the group consisting of hydrogen and alkyl; and

R¹ is selected from the group consisting of —S-alkyl, —S-substituted alkyl, (heteroaryl)alkyl, hydrogen, alkyl, substituted alkyl, alkenyl, substituted alkenyl, alkoxy, substituted alkoxy and halo;

R⁹ is independently selected from other than hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$—OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl, then R⁶ is selected from the group consisting of substituted alkyl (other than monosubstituted heterocycle or substituted heterocycle),

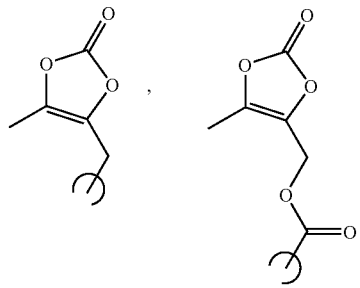

(carboxamido)alkyl, and an —N(R⁶)— fragment that is part of an amidine, N-cyanoamidine, N-hydroxyamidine, or N-alkoxyamidine structure;

wherein, as used in these provisos only, the following specific terms have the following specific meanings:

substituted alkyl refers to alkyl groups wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl), substituted cycloalkyl refers to cycloalkyl substituted with an alkyl group, wherein alkyl is as defined above or a group wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl, substituted oxygen refers to the group —OR$^d$ where R$^d$ is alkyl, haloalkyl, aryl, substituted aryl, heteroaryl, substituted heteroaryl, allkenyl, cycloalkyl, and substituted cycloalkyl, substituted nitrogen or amino refers to the group —NR$^a$R$^b$ wherein R$^a$ and R$^b$ are independently hydrogen, alkyl, haloalkyl, alkenyl, cycloalkyl, substituted cycloalkyl, aryl, substituted aryl, heteroaryl and substituted heteroaryl, substituted aryl refers to an aryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups, and substituted heteroaryl refers to a heteroaryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups.

In another one of its composition aspects, this invention is directed to a compound of Formula (IB):

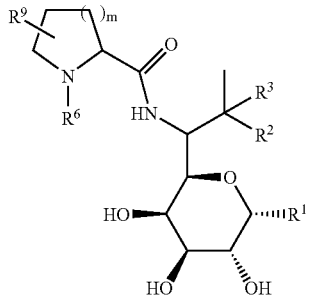

wherein:

R$^1$ is selected from the group consisting of hydrogen, alkyl, substituted alkyl, alkenyl, substituted alkenyl, alkoxy, substituted alkoxy, cycloalkylalkyl, halo, and substituted alkylsulfanyl;

R$^2$ and R$^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R$^2$ and R$^3$ is =NOR$^7$ and the other is absent;

R$^6$ is H, alkyl, or hydroxyalkyl;

R$^7$ is H or alkyl;

R$^9$, which can be singly or multiply substituted in the ring on the same or different carbons, is independently selected from the group consisting of hydrogen, alkyl, substituted alkyl, cycloalkyl, substituted cycloalkyl, substituted oxygen, substituted nitrogen, halogen, phenyl, substituted phenyl, —(CH$_2$)$_n$—OH, —(CH$_2$)$_n$—NR$^4$R$^5$, and branched chain isomers thereof wherein n is an integer of from 1 to 8 inclusive and R$^4$ and R$^5$ are H or alkyl; and m is 1 or 2;

or prodrugs and/or pharmaceutically acceptable salts thereof.

In some embodiments, when the nitrogen-containing ring is saturated,

R$^2$ and R$^3$ are independently hydrogen, hydroxyl, halo, alkoxy, alkylsulfanyl, substituted alkylsulfanyl, alkyl, substituted alkyl, hydroxyalkyl R$^6$ is hydrogen, alkyl, hydroxyalkyl;

R$^9$ is hydrogen, alkyl, substituted alkyl, cycloalkyl, substituted cycloalkyl, substituted oxygen, substituted nitrogen, halo, phenyl, substituted phenyl, —(CH$_2$)$_n$—OH, —(CH$_2$)$_n$NR$^4$R$^5$, and branched isomers thereof wherein n is an integer from 1 to 8 inclusive and R$^4$ and R$^5$ are hydrogen or alkyl; and then R$^1$ is not —S-alkyl.

In some embodiments, when the nitrogen containing ring is saturated, m is 0, 1, 2, or 3, R$^2$ and R$^3$ are independently hydrogen, alkyl, hydroxy, fluoro, cyanoalkyl or one of R$^2$ and R$^3$ is =NOR$^7$ and the other is absent, or one of R$^2$ and R$^3$ is =CH$_2$ and the other is absent, R$^6$ is hydrogen, alkyl, hydroxyalkyl, —C(O)O-alkylene-cycloalkyl, —C(O)O-alkylene-substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, —C(O)O-heterocyclic, —C(O)O-substituted hetercyclic, —[C(O)O]$_p$-alkylene-heterocycle, —[C(O)O]$_p$-alkylene-substituted heterocycle, where p is zero or one, and R$^7$ is selected from the group consisting of hydrogen and alkyl;

R$^9$ is hydrogen, alkyl, substituted alkyl, alkoxyalkoxy, cycloalkyl, substituted cycloalkyl, substituted oxygen, substituted nitrogen, halo, phenyl, substituted phenyl, —(CH$_2$)$_n$—OH, —(CH$_2$)$_n$NR$^4$R$^5$, -alkylene-R$^a$ where R$^a$ is selected from monofluorophenyl or monochlorophenyl, and branched isomers thereof wherein n is an integer from 1 to 8 inclusive and R$^4$ and R$^5$ are hydrogen or alkyl; and then R$^1$ is not —S-alkyl.

In some embodiments, when the nitrogen containing ring is saturated, m is one or two, R$^2$ and R$^3$ are independently hydrogen, alkyl, hydroxy, fluoro, cyanoalkyl or one of R$^2$ and R$^3$ is =NOR$^7$ and the other is absent, or one of R$^2$ and R$^3$ is =CH$_2$ and the other is absent, R$^6$ is hydrogen, alkyl, hydroxyalkyl, —C(O)O-alkylene-cycloalkyl, —C(O)O-alkylene-substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, —C(O)O-heterocyclic, —C(O)O-substituted hetercyclic, —[C(O)O]$_p$-alkylene-heterocycle, —[C(O)O]$_p$-alkylene-substituted heterocycle, where p is zero or one, and R$^7$ is selected from the group consisting of hydrogen and alkyl;

$R^9$ is hydrogen, alkyl, substituted alkyl, alkoxyalkoxy, cycloalkyl, substituted cycloalkyl, substituted oxygen, substituted nitrogen, halo, phenyl, substituted phenyl, —$(CH_2)_n$OH, —$(CH_2)_nNR^4R^5$, -alkylene-$R^a$ where $R^a$ is selected from monofluorophenyl or monochlorophenyl, and branched isomers thereof wherein n is an integer from 1 to 8 inclusive and $R^4$ and $R^5$ are hydrogen or alkyl; and then $R^1$ is not —S-alkyl.

In some embodiments, when the nitrogen-containing ring is saturated, $R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =$NOR^7$ and the other is absent, or one of $R^2$ and $R^3$ is =$CH_2$ and the other is absent, with the provisos that both $R^2$ and $R^3$ are not hydrogen; when one of $R^2$ and $R^3$ is halo, the other is not hydrogen or hydroxy; and when one of $R^2$ and $R^3$ is hydroxy, the other is not hydrogen or hydroxy;

$R^6$ is selected from the group consisting of hydrogen, alkyl, substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, (carboxamido)alkyl, (carbamoyl)alkyl, or —N($R^6$)— fragment is part of the amidine, N-cyanoamidine, N-hydroxyamidine, or N-alkoxyamidine structure;

$R^7$ is selected from the group consisting of hydrogen and alkyl; and $R^1$ is selected from the group consisting of —S-alkyl, —S-substituted alkyl, hydrogen, alkyl, substituted alkyl, alkenyl, substituted alkenyl, alkoxy, substituted alkoxy and halo;

then at least one of $R^9$ is other than hydrogen, alkyl, substituted alkyl, alkoxyalkoxy, cycloalkyl, substituted cycloalkyl, substituted oxygen, substituted nitrogen, halo, phenyl, substituted phenyl, —$(CH_2)_n$—OH, —$(CH_2)_n$ $NR^4R^5$, -alkylene-$R^a$ where $R^a$ is selected from monofluorophenyl or monochlorophenyl, and branched isomers thereof wherein n is an integer from 1 to 8 inclusive and $R^4$ and $R^5$ are hydrogen or alkyl, In some embodiments, when the nitrogen-containing ring is saturated, $R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =$NOR^7$ and the other is absent, or one of $R^2$ and $R^3$ is =$CH_2$ and the other is absent, with the provisos that both $R^2$ and $R^3$ are not hydrogen; when one of $R^2$ and $R^3$ is halo, the other is not hydrogen or hydroxy; and when one of $R^2$ and $R^3$ is hydroxy, the other is not hydrogen or hydroxy;

$R^7$ is selected from the group consisting of hydrogen and alkyl; and $R^1$ is selected from the group consisting of —S-alkyl, —S-substituted alkyl, (heteroaryl)alkyl, hydrogen, alkyl, substituted alkyl, alkenyl, substituted alkenyl, alkoxy, substituted alkoxy and halo;

$R^9$ is independently selected from other than hydrogen, alkyl, substituted alkyl, alkoxyalkoxy, cycloalkyl, substituted cycloalkyl, substituted oxygen, substituted nitrogen, halo, phenyl, substituted phenyl, —$(CH_2)_n$—OH, —$(CH_2)_nNR^4R^5$, -alkylene-$R^a$ where $R^a$ is selected from monofluorophenyl or monochlorophenyl, and branched isomers thereof wherein n is an integer from 1 to 8 inclusive and $R^4$ and $R^5$ are hydrogen or alkyl, then $R^6$ is selected from the group consisting of substituted alkyl (other than monosubstituted heterocycle or substituted heterocycle),

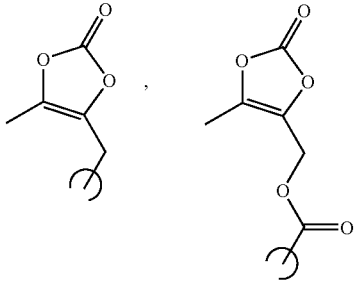

(carboxamido)alkyl, and an —N($R^6$)— fragment that is part of an amidine, N-cyanoamidine, N-hydroxyamidine, or N-alkoxyamidine structure.

When used in these provisos above only, the following specific terms have the following specific meanings:

substituted alkyl refers to alkyl groups wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl), substituted cycloalkyl refers to cycloalkyl substituted with an alkyl group, wherein alkyl is as defined above or a group wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl, substituted oxygen refers to the group —$OR^d$ where $R^d$ is alkyl, haloalkyl, aryl, substituted aryl, heteroaryl, substituted heteroaryl, allkenyl, cycloalkyl, and substituted cycloalkyl, substituted nitrogen or amino refers to the group —$NR^aR^b$ wherein $R^a$ and $R^b$ are independently hydrogen, alkyl, haloalkyl, alkenyl, cycloalkyl, substituted cycloalkyl, aryl, substituted aryl, heteroaryl and substituted heteroaryl, substituted aryl refers to an aryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups, and substituted heteroaryl refers to a heteroaryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups.

In some embodiments, both $R^2$ and $R^3$ are not hydrogen. In some embodiments, when one of $R^2$ and $R^3$ is halo, the other is not hydrogen or hydroxy. In some embodiments, when one of $R^2$ and $R^3$ is hydroxy, the other is not hydrogen or hydroxy.

In one embodiment, m is 0

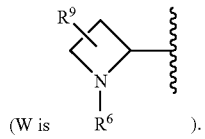

(W is $R^6$ ).

In another embodiment, m is 1

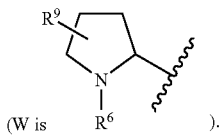

(W is R⁶ ).

In one embodiment, m is 2. In another embodiment, m is 2, and the nitrogen-containing ring is saturated

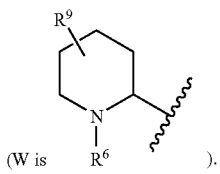

(W is R⁶ ).

In another embodiment, m is 2, and the nitrogen-containing ring contains a double bond between the 4 and 5 nitrogen-containing ring positions

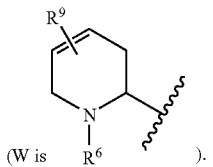

(W is R⁶ ).

In one embodiment, m is 3. In another embodiment, m is 3, and the nitrogen-containing ring is saturated

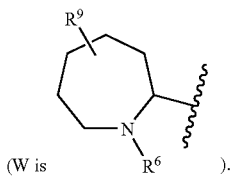

(W is R⁶ ).

In another embodiment, m is 3, and the nitrogen-containing ring contains a double bond between the 4 and 5 nitrogen-containing ring positions

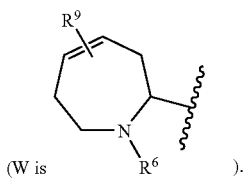

(W is R⁶ ).

In another embodiment, m is 3, and the nitrogen-containing ring contains a double bond between the 5 and 6 nitrogen-containing ring positions

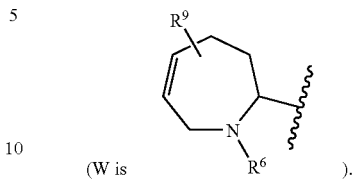

(W is R⁶ ).

In one embodiment, the nitrogen-containing ring is saturated.

In a preferred embodiment, this invention provides compounds wherein the nitrogen-containing ring in the Formulas described above is selected from

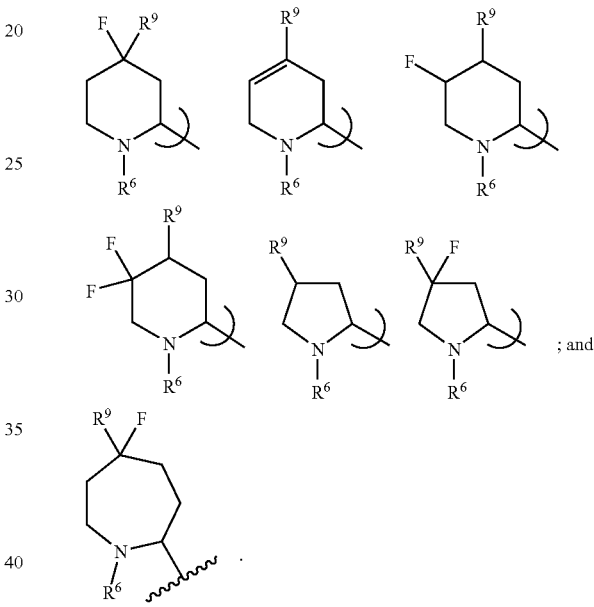

In one embodiment, R¹ is selected from the group consisting of hydrogen, alkyl, substituted alkyl, alkenyl, substituted alkenyl, alkoxy, substituted alkoxy, halo, alkylsulfanyl, and substituted alkylsulfanyl. In one embodiment, R¹ is selected from the group consisting of hydrogen, alkyl, substituted alkyl, hydroxyalkyl, alkenyl, substituted alkenyl, alkoxy, substituted alkoxy, cycloalkylalkyl, halo, and substituted alkylsulfanyl. In one embodiment, R¹ is selected from the group consisting of hydrogen, alkyl, substituted alkyl, hydroxyalkyl, alkoxy, cycloalkylalkyl, alkylsulfanyl, and substituted alkylsulfanyl. In one embodiment, R¹ is selected from the group consisting of hydrogen, alkyl, substituted alkyl, hydroxyalkyl, alkoxy, cycloalkylalkyl, and substituted alkylsulfanyl. In a preferred embodiment, R¹ is selected from the group consisting of hydrogen, —S-methyl, —S-iso-propyl, —S-tert-butyl, propyl, 2,2,2-trifluoro-ethyl-sulfanyl, 2-ethoxy-eth-1-yl, butoxy, 2-hydroxy-ethyl, 3-hydroxy-propyl, hydroxy-methyl, 2-(methyl-sulfanyl)-ethyl, and cyclopropyl-methyl. In another preferred embodiment, R¹ is selected from the group consisting of hydrogen, —S-iso-propyl, —S-tert-butyl, propyl, 2,2,2-trifluoro-ethyl-sulfanyl, 2-ethoxy-eth-1-yl, butoxy, 2-hydroxy-ethyl, 3-hydroxy-propyl, hydroxy-methyl, 2-(methyl-sulfanyl)-ethyl, and cyclopropyl-methyl. In another preferred embodiment, R¹ is —S-methyl. Preferred R¹ groups may be found in Tables I, II and III. In some embodiments, $R^1$ is not —S-alkyl. In some embodiments, $R^1$ is not —S-methyl. In other embodiments, $R^1$ is not —S-substituted alkyl.

In other embodiments, $R^1$ is preferably —$SR^0$ where $R^0$ is preferably $C_{1-4}$alkyl, and more preferably methyl, 2-hydroxyethyl, or 2-ethyl salicylate. In another embodiment, $R^1$ is preferably hydrogen, alkyl, substituted alkyl or 2,2,2-trifluoroethylsulfanyl. More preferably, $R^1$ is hydrogen, propyl, 2-ethoxyethyl or 2,2,2-trifluoroethylsulfanyl.

In one embodiment, $R^2$ and $R^3$ are independently selected from the group consisting of hydrogen, alkyl, hydroxy, and halo. In a preferred embodiment, $R^2$ and $R^3$ are independently selected from the group consisting of hydrogen, methyl, hydroxy, and chloro. In another preferred embodiment, $R^2$ and $R^3$ are hydrogen and hydroxy. In another preferred embodiment, $R^2$ and $R^3$ are hydrogen and chloro. In another preferred embodiment, $R^2$ and $R^3$ are hydrogen and methyl. Preferred $R^2$ and $R^3$ groups may be found in Tables I, II and III.

In one embodiment, $R^{20}$ and $R^{21}$ are independently alkyl or alkenyl, or $R^{20}$ and $R^{21}$ taken together are cycloalkyl, aryl, substituted aryl, heterocyclic, or heteroaryl. In one embodiment, one of $R^{20}$ and $R^{21}$ is H and the other is alkyl or alkenyl. In a preferred embodiment, one of $R^{20}$ and $R^{21}$ is H and the other is ethyl or ethenyl. In another embodiment, $R^{20}$ and $R^{21}$ taken together are cycloalkyl or aryl. In a preferred embodiment, $R^{20}$ and $R^{21}$ taken together are cyclopropyl, cyclopentyl, phenyl, or 4-chloro-phenyl. Preferred $R^{20}$ and $R^{21}$ groups may be found in Tables I, II and III. In one embodiment, when one of $R^{20}$ and $R^{21}$ is hydrogen, then the other is not hydrogen, alkyl, hydroxy, cyano, alkylsulfanyl, or substituted alkylsulfanyl.

In one embodiment, $R^6$ is selected from the group consisting of hydrogen, alkyl, cycloalkyl, hydroxyalkyl, substituted alkyl, iminomethyl, —C(O)O-substituted alkyl, 5-alkyl-[1,3]dioxol-2-one-4-yl-methyl, and 5-alkyl-[1,3]dioxol-2-one-4-yl-methoxy-carbonyl. In another embodiment, $R^6$ is selected from hydrogen and alkyl. In one embodiment, $R^6$ is selected from the group consisting of 1H-imidazol-2-yl-methyl; 2-[HC(O)]-eth-1-yl; 2-amino-eth-1-yl; 2-hydroxyethyl; 2-methoxy-eth-1-yl; 5-methyl-2-oxo-[1,3]dioxol-4-yl-methoxy-carbonyl; 5-methyl-2-oxo-[1,3]dioxol-4-yl-methyl; aminocarbonylmethyl; aminocarbonylethyl; cyanomethyl; cyclopropyl; hydrogen; iminomethyl; methyl; and methoxycarbonylmethyl. In one embodiment, $R^6$ is selected from the group consisting of 1H-imidazol-2-yl-methyl; 2-hydroxyethyl; 5-methyl-2-oxo-[1,3]dioxol-4-yl-methoxy-carbonyl; 5-methyl-2-oxo-[1,3]dioxol-4-yl-methyl; aminocarbonylmethyl; cyanomethyl; cyclopropyl; hydrogen; iminomethyl; and methyl. In a preferred embodiment, $R^6$ is selected from the group consisting of 1H-imidazol-2-yl-methyl; 2-[HC(O)]-eth-1-yl; 2-amino-eth-1-yl; 2-hydroxyethyl; 2-methoxy-eth-1-yl; aminocarbonylmethyl; aminocarbonylethyl; cyanomethyl; cyclopropyl; hydrogen; iminomethyl; methyl; and methoxycarbonylmethyl. In a preferred embodiment, $R^6$ is hydrogen or methyl. In another preferred embodiment, $R^6$ is selected from the group consisting of: 5-methyl-[1,3]dioxol-2-one-4-yl-methyl and 5-methyl-[1,3]dioxol-2-one-4-yl-methoxy-carbonyl. Preferred $R^6$ groups may be found in Tables I, II and III.

In another embodiment, $R^9$ is selected from the group consisting of alkyl, substituted alkyl, cycloalkyl, cycloalkylalkyl, substituted alkenyl, alkylsulfanyl, substituted alkylsulfanyl, substituted arylsulfanyl, heteroarylsulfanylalkyl, heterocyclicsulfanylalkyl, halogen, propylidene (=$CHCH_2CH_3$), azido, substituted oxygen, heteroarylsulfanyl, and heterocyclicsulfanyl. In another embodiment, $R^9$ is selected from the group consisting of alkyl, substituted alkyl, cycloalkyl, cycloalkylalkyl, substituted alkenyl, alkylsulfanyl, substituted alkylsulfanyl, substituted arylsulfanyl, heteroarylsulfanylalkyl, heterocyclicsulfanylalkyl, halogen, propylidene (=$CHCH_2CH_3$), and azido. In a preferred embodiment, $R^9$ is alkyl. In another preferred embodiment, $R^9$ is halogen.

In another embodiment, $R^9$ is selected from the group consisting of (2-fluorocyclopropyl)methoxy; (3-fluoropropoxy)methyl; 1H-pyrrolylmethyl; 2-(4-ethylthiazol-2-yl)-eth-1-yl; 2-(4-methylthiazol-2-yl)-eth-1-yl; 2-(5-ethyl-isoxazol-3-yl)-eth-1-yl; 2,2,2-trifluoroethyl-sulfanyl; 2,2-difluoroethoxymethyl; 2-[1,3]dithiolan-2-yl-eth-1-yl; 2-chlorophenyl-methylsulfanyl; 2-cyclobutylethyl; 2-cyclobutylidene-ethyl; 2-cyclopropylethyl; 2-mercaptoethoxyethyl-sulfanyl; 2-fluoroethoxy; 2-propoxyethyl; 3-(1H-[1,2,3]triazole)-prop-1-yl; 3-(3-fluoropropoxy)propyl; 3-(cyclohexyloxy)propyl; 3-(difluoromethylsulfanyl)propyl; 3-(ethylthio)propyl; 3-(furan-2-ylmethylsulfanyl)-prop-1-yl; 3,3,3-trifluoroprop-1-yl-sulfanyl; 3,3,3-trifluoropropoxy; 3,3-difluoroallyl; 3,3-difluorobutyl; 3,3-difluoropropyl; 3-[(cyclopropyl)methoxy]propyl; 3-cyanoprop-1-yl; 3-cyclohexyloxypropyl; 3-cyclopropylpropyl; 3-ethoxyiminoprop-1-yl; 3-ethylsulfanylprop-1-yl; 3-fluoropropoxy; 3-fluoropropoxymethyl; 3-fluoropropyl; 3-imidazol-1-yl-prop-1-yl; 3-mercaptopropylsulfanyl; 3-methoxyimino-prop-1-yl; 3-methylbut-1-yl-sulfanyl; 3-methylbutyl; 3-pyridin-4-yl-allyl; 3-pyridin-4-yl-propyl; 3-pyrrolidin-2-onyl-prop-1-yl; 3-thiophen-2-ylsulfanyl-prop-1-yl; 4-(methoxy)butyl; 4,4-difluorobutyl; 4,4-difluoropentyl; 4-fluorobutoxy; 5,5-difluoropentyl; azido; butoxy; butyl; butylsulfanyl; chloro; cyclobutylmethyl; cyclohexylmethyl; cyclopropyl; cyclopropylmethyl; ethyl; ethylsulfanyl; fluoro; isobutyl; methyl; m-methylbenzylsulfanyl; n-butylsulfanyl; o,p-dichlorobenzylsulfanyl; pentoxy; pentyl; p-fluorobenzylsulfanyl; p-fluorophenylsulfanyl; p-methylbenzylsulfanyl; propoxy; propyl; propylidene (=$CHCH_2CH_3$); p-trifluoromethoxybenzyl-sulfanyl; pyrazin-2-yl-methyl-sulfanyl; pyridin-2-yl-methyl-sulfanyl; pyridin-4-yl-sulfanyl; and thiophen-2-yl-methylsulfanyl.

In another embodiment, $R^9$ is selected from the group consisting of 2-(4-methylthiazol-2-yl)-eth-1-yl; 2-(5-ethyl-isoxazol-3-yl)-eth-1-yl; 2-[1,3]Dithiolan-2-yl-eth-1-yl; 2-cyclobutylethyl; 2-cyclobutylidene-ethyl; 2-cyclopropylethyl; 3-(difluoromethylsulfanyl)-prop-1-yl; 3-(furan-2-ylmethylsulfanyl)-prop-1-yl; 3,3,3-trifluoroprop-1-yl-sulfanyl; 3,3-difluoroallyl; 3,3-difluoro-propyl; 3-cyanoprop-1-yl; 3-cyclopropyl-propyl; 3-ethoxyiminoprop-1-yl; 3-ethylsulfanylprop-1-yl; 3-Imidazol-1-yl-prop-1-yl; 3-methoxyimino-prop-1-yl; 3-methylbut-1-yl-sulfanyl; 3-methylbutyl; 3-pyridin-4-yl-allyl; 3-pyridin-4-yl-propyl; 3-thiophen-2-ylsulfanylprop-1-yl; 4-propyl; azido; butyl; butylsulfanyl; cyclobutylmethyl; cyclopropyl; cyclopropylmethyl; ethyl; ethylsulfanyl; fluoro; methyl; n-butylsulfanyl; o,p-dichlorobenzylsulfanyl; pentyl; p-fluorophenylsulfanyl; p-methylbenzylsulfanyl; propyl; propylidene (=$CHCH_2CH_3$); pyrazin-2-yl-methyl-sulfanyl; and thiophen-2-yl-methylsulfanyl. In one embodiment, at least one $R^9$ group is other than hydrogen.

In a preferred embodiment, $R^9$ is propyl. Preferred $R^9$ groups may be found in Tables I, II and III.

In one embodiment, Z is selected from the group consisting of hydrogen, phosphate, and palmitate. In one embodiment, Z is hydrogen. In another embodiment, Z is phosphate. In another embodiment, Z is palmitate.

The compounds of this invention also include prodrugs of Formulas (I), (II), (IA), and (IB). Such prodrugs include the compounds of Formulas (I), (II), (IA), and (IB) where $R^6$ or one of the hydroxy groups on the sugar are modified to include a substituent selected from phosphate, palmitate or

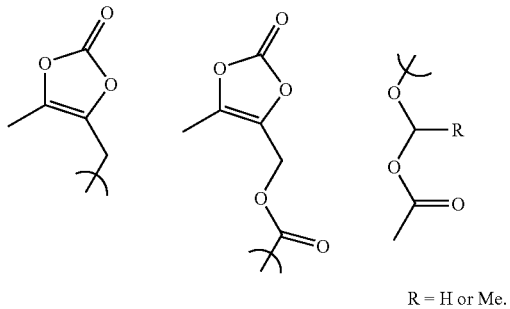

R = H or Me.

Preferred prodrugs include the compounds of Formulas (I), (II), (IA), and (IB) where $R^6$ or one of the hydroxy groups on the sugar are modified to include a substituent selected from

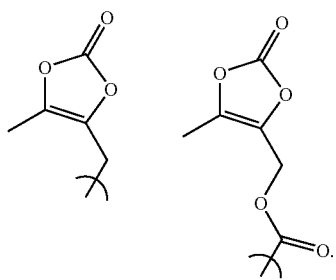

Preferred compounds of formulas (I), (II), (IA), and (IB) have a minimum inhibition concentration of 32 μg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*.

In one embodiment, the compounds of formulas (I), (II), (IA), and (IB) have a minimum inhibition concentration of 4 μg/mL or less against at least one of the organisms selected from the group consisting of *Haemophilus influenzae* and *Moraxella catarrhalis*. In one embodiment, the compounds of formulas (I), (II), (IA), and (IB) have a minimum inhibition concentration of 4 μg/mL or less against at least one of the organisms selected from the group consisting of *Enterococcus faecali* and *Enterococcus faecium*. In one embodiment, the compounds of formulas (I), (II), (IA), and (IB) have a minimum inhibition concentration of 4 μg/mL or less against at least one of the organisms selected from the group consisting of the Gram negative organisms *Haemophilus influenzae* VHIN1003 and *Haemophilus influenzae* VHIN1004.

In another aspect of the invention are pharmaceutical compositions comprising a pharmaceutically acceptable carrier and a therapeutically effective amount of a compound described herein.

In another aspect of the invention are methods for the treatment of a microbial infection in a mammal comprising administering to the mammal a therapeutically effective amount of a compound described herein. In one embodiment, the microbial infection being treated is caused by one or more of the following pathogens: *H. influenzae, M catarrhalis, E. faecalis*, and *E. faecium*. The compound administered may be formulated into a pharmaceutical composition as described herein. The compound may be administered to the mammal orally, parenterally, transdermally, topically, rectally, or intranasally in a pharmaceutical composition. In one embodiment, the compound may be administered in an amount of from about 0.1 to about 100 mg/kg body weight/day.

Lincomycin derivatives within the scope of this invention include those of Formula I as set forth in Table I as follows, wherein the nitrogen-containing ring positions are consecutively numbered counterclockwise beginning with "1" at the nitrogen, i.e.,

TABLE 1

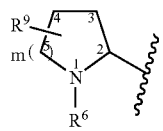

| Ex. # | $R^2/R^3$ | $R^6$ | $R^9$ | m | = | $R^1$ |
|---|---|---|---|---|---|---|
| 1 | H/Me | H | 4-(3,3-difluoroallyl) | 1 | S | SMe |
| 2 | H/Me | H | 4-(3-pyridin-4-yl-allyl) | 1 | S | SMe |
| 3 | H/Me | H | 4-(3-pyridin-4-yl-propyl) | 1 | S | SMe |
| 4 | H/OH | H | 4-n-butylsulfanyl | 1 | S | SMe |
| 5 | H/OH | H | 4-ethylsulfanyl | 1 | S | SMe |
| 6 | H/OH | H | 4-ethylsulfanyl | 1 | S | SMe |
| 7 | H/Cl | H | 4-ethylsulfanyl | 1 | S | SMe |
| 8 | H/Cl | H | 4-ethylsulfanyl | 1 | S | SMe |
| 9 | H/OH | H | 4-(p-methylbenzylsulfanyl) | 1 | S | SMe |
| 10 | H/OH | H | 4-(p-fluorophenylsulfanyl) | 1 | S | SMe |
| 11 | H/OH | H | 4-(3,3,3-trifluoroprop-1-yl-sulfanyl) | 1 | S | SMe |
| 12 | H/OH | H | 4-(3-methylbut-1-yl-sulfanyl) | 1 | S | SMe |
| 13 | H/OH | H | 4-(o,p-dichlorobenzylsulfanyl) | 1 | S | SMe |
| 14 | H/OH | H | 4-(thiophen-2-yl-methylsulfanyl) | 1 | S | SMe |
| 15 | H/OH | H | 4-(pyrazin-2-yl-methyl-sulfanyl) | 1 | S | SMe |
| 16 | H/Me | H | 4-(o,p-dichlorobenzylsulfanyl) | 1 | S | SMe |
| 17 | H/Me | H | 4-butylsulfanyl | 1 | S | SMe |

TABLE 1-continued

| Ex. # | R²/R³ | R⁶ | R⁹ | m | = | R¹ |
|---|---|---|---|---|---|---|
| 18 | H/OH | H | 4-azido | 1 | S | SMe |
| 19 | H/Me | H | 4-[3-(furan-2-ylmethylsulfanyl)-prop-1-yl] | 2 | S | SMe |
| 20 | H/Me | H | 4-(3-Imidazol-1-yl-prop-1-yl) | 2 | S | SMe |
| 21 | H/Me | H | 4-(3-thiophen-2-ylsulfanylprop-1-yl) | 2 | S | SMe |
| 22 | H/Me | H | 4-(3-ethylsulfanylprop-1-yl) | 2 | S | SMe |
| 23 | H/Me | H | 4-(3-cyanopropyl-1-yl) | 2 | S | SMe |
| 24 | H/Cl | H | 4-[3-(difluoromethylsulfanyl)-prop-1-yl] | 2 | S | SMe |
| 25 | H/Me | H | 4-[3-(difluoromethylsulfanyl)-prop-1-yl] | 2 | S | SMe |
| 26 | H/Me | H | 4-(2-[1,3]Dithiolan-2-yl-eth-1-yl) | 2 | S | SMe |
| 28 | H/Me | H | 4-[2-(4-methylthiazol-2-yl)-eth-1-yl] | 2 | S | SMe |
| 29 | H/Me | H | 4-(3-methoxyimino-prop-1-yl) | 2 | S | SMe |
| 30 | H/Me | H | 4-(3-ethoxyiminoprop-1-yl) | 2 | S | SMe |
| 31 | H/Me | H | 4-[2-(5-ethyl-isoxazol-3-yl)-eth-1-yl] | 2 | S | SMe |
| 32 | H/Cl | H | 4-propyl/4-fluoro | 2 | S | SMe |
| 33 | H/Cl | H | 4-propyl/4-fluoro | 2 | S | SMe |
| 34 | H/OH | H | 4-propyl/4-fluoro | 1 | S | SMe |
| 35 | H/Cl | H | 4-butyl/4-fluoro | 1 | S | SMe |
| 36 | H/Cl | H | 4-ethyl/4-fluoro | 2 | S | SMe |
| 37 | H/Me | H | 4-(propylidene) (=CHCH₂CH₃) | 2 | S | SMe |
| 38 | H/Me | H | 4-propyl | 2 | D | SMe |
| 39 | H/Cl | H | 4-propyl | 2 | D | SMe |
| 40 | H/Me | amino-carbonyl-methyl | 4-pentyl | 1 | S | SMe |
| 41 | H/Me | Cyano-methyl | 4-pentyl | 1 | S | SMe |
| 42 | H/Me | 1H-imidazol-2-yl-methyl | 4-pentyl | 1 | S | SMe |
| 43 | H/Me | HN=CH— | 4-pentyl | 1 | S | SMe |
| 44 | H/Me | Me | 4-propyl | 1 | S | S-iPr |
| 45 | H/Me | H | 4-propyl | 2 | S | S-iPr |
| 46 | H/Me | Me | 4-propyl | 1 | S | S-tBu |
| 47 | H/Me | H | 4-propyl | 2 | S | S-tBu |
| 48 | H/Cl | 5-methyl-[1,3]dioxol-2-one-4-yl-methyl | 5-propyl | 3 | S | SMe |
| 49 | H/Cl | 5-methyl-[1,3]dioxol-2-one-4-yl-methoxy-carbonyl | 5-propyl | 3 | S | SMe |
| 50 | H/Cl | H | 5-methyl | 3 | S | SMe |
| 51 | H/Cl | H | 5-ethyl | 3 | S | SMe |
| 52 | H/Cl | H | 5-cyclopropylmethyl | 3 | S | SMe |
| 53 | H/Cl | H | 5-cyclopropyl | 3 | S | SMe |
| 54 | H/Cl | H | 4-methyl/5-ethyl | 3 | S | SMe |
| 55 | H/Cl | H | 4-ethyl/5-methyl | 3 | S | SMe |
| 56 | H/Cl | H | 5-ethyl/6-methyl | 3 | S | SMe |
| 57 | H/Cl | H | 4-propyl | 3 | S | SMe |
| 58 | H/Cl | H | 5-propyl/5-fluoro | 3 | S | SMe |
| 59 | H/Cl | H | 4-propyl | 2 | D | SMe |
| 60 | H/Me | H | 4-butyl | 2 | D | SMe |
| 61 | H/Cl | 2-hydroxyethyl | 4-propyl/4-fluoro | 2 | S | SMe |
| 62 | H/Cl | H | 4-butyl/4-fluoro | 2 | S | SMe |
| 63 | H/Cl | H | 4-(2-cyclobutylethyl) | 2 | S | SMe |
| 64 | H/Cl | H | 4-(cyclopropylmethyl) | 1 | S | SMe |
| 65 | H/Cl | H | 4-(cyclopropylmethyl) | 2 | S | SMe |
| 66 | H/Me | H | 4-(2-cyclobutylidene-ethyl) | 1 | S | SMe |
| 67 | H/Cl | H | 4-(2-cyclobutylidene-ethyl) | 1 | S | SMe |
| 68 | H/Cl | H | 4-(2-cyclobutyl-ethyl) | 1 | S | SMe |
| 69 | H/Cl | H | 4-(cyclobutylmethyl) | 2 | S | SMe |
| 70 | H/Cl | H | 5-propyl | 3 | D 4,5 | SMe |
| 71 | H/Cl | H | 4-(2-cyclopropyl-ethyl) | 1 | S | SMe |
| 72 | H/Cl | H | 4-cyclopropylmethyl/4-fluoro | 2 | S | SMe |
| 73 | H/Cl | H | 5-propyl | 3 | S | SMe |
| 74 | H/Cl | H | 5-propyl | 3 | S | SMe |
| 75 | H/Me | Cyclopropyl | 5-propyl | 3 | S | SMe |
| 76 | H/Cl | H | 4-butyl | 2 | D | SMe |
| 77 | H/Me | H | 5-propyl | 3 | S | S-iPr |
| 78 | H/Me | H | 5-propyl | 3 | S | S-tBu |
| 80 | H/Cl | H | 3-cyclopropylmethyl | 0 | S | SMe |
| 81 | H/Cl | H | 3-(2-cyclobutylethyl) | 0 | S | SMe |
| 82 | H/Cl | H | 3-(2-cyclopropylethyl) | 0 | S | SMe |
| 83 | H/Cl | H | 3-(3-cyclopropyl-propyl) | 0 | S | SMe |
| 84 | H/Cl | H | 3-propyl | 0 | S | SMe |
| 85 | H/Cl | H | 3-butyl | 0 | S | SMe |
| 86 | H/Cl | 2-hydroxy-ethyl | 3-butyl | 0 | S | SMe |

TABLE 1-continued

| Ex. # | R²/R³ | R⁶ | R⁹ | m | = | R¹ |
|---|---|---|---|---|---|---|
| 87 | H/Cl | H | 3-pentyl | 0 | S | SMe |
| 88 | H/Cl | H | 3-(3-methylbutyl) | 0 | S | SMe |
| 89 | H/Cl | H | 3-(3,3-difluoro-propyl) | 0 | S | SMe |
| 90 | H/Cl | Me | 3-butyl | 0 | S | SMe |
| — | H/Me | H | (2-fluorocyclopropyl)methoxy | 2 | S | SMe |
| — | H/OH | H | 4-(p-trifluoromethoxybenzyl-sulfanyl) | 1 | S | SMe |
| — | H/Cl | H | 2-(3-fluoropropoxy)methyl/fluoro | 2 | S | SMe |
| — | H/Cl | H | 2-(propoxy)ethyl/fluoro | 2 | S | SMe |
| — | H/Cl | H | 2,2-difluoroethoxymethyl | 2 | S | SMe |
| — | H/Cl | H | 2,2-difluoroethoxymethyl/fluoro | 2 | S | SMe |
| — | H/Cl | H | 2-fluoroethoxy | 2 | D | SMe |
| — | H/Cl | H | 2-fluoroethoxy/fluoro | 2 | S | SMe |
| — | H/Cl | H | 3-(3-fluoropropoxy)propyl/fluoro | 2 | S | SMe |
| — | H/Cl | H | 3-(cyclohexyloxy)propyl | 2 | D | SMe |
| — | H/Cl | H | 3-(cyclohexyloxy)propyl/fluoro | 2 | S | SMe |
| — | H/Me | H | 3-(difluoromethylsulfanyl)propyl | 2 | S | SMe |
| — | H/Cl | H | 3-(ethylthio)propyl/fluoro | 2 | S | SMe |
| — | H/Cl | H | 3,3,3-trifluoropropoxy | 2 | S | SMe |
| — | H/Cl | H | 3,3,3-trifluoropropoxy/fluoro | 2 | S | SMe |
| — | H/Cl | H | 3,3-difluorobutyl/fluoro | 2 | S | SMe |
| — | H/Cl | H | 3,3-difluoropropyl | 2 | D | SMe |
| — | H/Cl | H | 3,3-difluoropropyl/fluoro | 2 | S | SMe |
| — | H/Cl | H | 3-[(cyclopropyl)methoxy]propyl | 2 | D | SMe |
| — | H/Cl | H | 3-[(cyclopropyl)methoxy]propyl/Fluoro | 2 | S | SMe |
| — | H/Cl | H | 3-fluoropropoxy | 2 | D | SMe |
| — | H/Cl | H | 3-fluoropropoxy/fluoro | 2 | S | SMe |
| — | H/Cl | H | 3-fluoropropyl/fluoro | 2 | S | SMe |
| — | H/Me | H | 4-(1H-Pyrrolylmethyl) | 2 | S | SMe |
| — | H/OH | H | 4-(2,2,2-trifluoroethyl-sulfanyl) | 1 | S | SMe |
| — | H/OH | H | 4-(2-chlorophenyl-methylsulfanyl) | 1 | S | SMe |
| — | H/OH | H | 4-[2-(2-mercapto-ethoxy)-ethylsulfanyl] | 1 | S | SMe |
| — | H/Me | H | 4-(3-cyclohexyloxypropyl) | 2 | S | SMe |
| — | H/OH | H | 4-(3-mercaptopropylsulfanyl) | 1 | S | SMe |
| — | H/Me | H | 4-(3-pyrrolidin-2-onyl-prop-1-yl) | 2 | S | SMe |
| — | H/Cl | H | 4-(methoxy)butyl/fluoro | 2 | S | SMe |
| — | H/OH | H | 4-(m-methylbenzylsulfanyl) | 1 | S | SMe |
| — | H/OH | H | 4-(p-fluorobenzylsulfanyl) | 1 | S | SMe |
| — | H/OH | H | 4-(pyridin-2-yl-methyl-sulfanyl) | 1 | S | SMe |
| — | H/OH | H | 4-(pyridin-4-yl-sulfanyl) | 1 | S | SMe |
| — | H/Cl | H | 4,4-difluorobutyl | 2 | D | SMe |
| — | H/Cl | H | 4,4-difluorobutyl/fluoro | 2 | S | SMe |
| — | H/Cl | H | 4,4-difluoropentyl | 2 | D | SMe |
| — | H/Cl | H | 4,4-difluoropentyl/fluoro | 2 | S | SMe |
| — | H/Me | H | 4-[2-(4-ethylthiazol-2-yl)-eth-1-yl] | 2 | S | SMe |
| — | H/Me | H | 4-{3-(1H-[1,2,3]triazole)-prop-1-yl} | 2 | S | SMe |
| — | H/Cl | H | 4-fluorobutoxy | 2 | S | SMe |
| — | H/Cl | H | 4-fluorobutoxy/fluoro | 2 | S | SMe |
| — | H/Me | Amino-carbonyl-ethyl | 4-pentyl | 1 | S | SMe |
| — | H/Me | 2-methoxy-eth-1-yl | 4-pentyl | 1 | S | SMe |
| — | H/Me | 2-[HC(O)]-eth-1-yl | 4-pentyl | 1 | S | SMe |
| — | H/Me | 2-amino-eth-1-yl | 4-pentyl | 1 | S | SMe |
| — | H/Me | Methoxy carbonyl methyl | 4-pentyl | 1 | S | SMe |
| — | H/Cl | H | 5,5-difluoropentyl | 2 | D | SMe |
| — | H/Cl | H | 5,5-difluoropentyl/fluoro | 2 | S | SMe |
| — | H/Cl | H | Butoxy | 2 | D | SMe |
| — | H/Cl | H | butoxy/fluoro | 2 | S | SMe |
| — | H/Cl | H | Butyl | 2 | D | SMe |
| — | H/Cl | H | butyl/fluoro | 2 | S | SMe |
| — | H/Cl | H | Cyclohexylmethyl | 2 | D | SMe |
| — | H/Cl | H | cyclohexylmethyl/fluoro | 2 | S | SMe |
| — | H/Cl | H | Ethyl | 2 | D | SMe |
| — | H/Cl | H | Isobutyl | 2 | D | SMe |
| — | H/Cl | H | isobutyl/fluoro | 2 | S | SMe |
| — | H/Cl | H | pentoxy/fluoro | 2 | S | SMe |
| — | H/Cl | H | Pentyl | 2 | D | SMe |
| — | H/Cl | HN=CH— | pentyl/fluoro | 1 | S | SMe |
| — | H/Cl | H | Propoxy | 2 | D | SMe |
| — | H/Cl | H | Propoxy/fluoro | 2 | S | SMe |
| — | H/Cl | HN=CH— | Propyl | 2 | S | SMe |
| — | H/Cl | HN=CH— | Propyl | 2 | D | SMe |

TABLE 1-continued

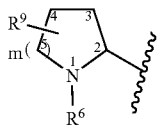

| Ex. # | R²/R³ | R⁶ | R⁹ | m | = | R¹ |
|---|---|---|---|---|---|---|
| — | H/Cl | H | propyl/chloro | 2 | S | SMe |
| — | H/Cl | Me | propyl/chloro | 2 | S | SMe |
| — | H/Cl | Me | propyl/fluoro | 2 | S | SMe |
| — | H/Cl | HN=CH— | propyl/fluoro | 2 | S | SMe |
| — | H/Me | H | 2-(3-fluoropropoxy)methyl | 2 | S | SMe |
| — | H/Me | H | 2-(propoxy)ethyl | 2 | S | SMe |
| — | H/Me | H | 2,2-difluoroethoxymethyl/fluoro | 2 | S | SMe |
| — | H/Me | H | 2-fluoroethoxy | 2 | S | SMe |
| — | H/Me | H | 3-(3-fluoropropoxy)propyl | 2 | S | SMe |
| — | H/Me | H | 3,3,3-trifluoropropoxy | 2 | S | SMe |
| — | H/Me | H | 3,3-difluoropropyl/fluoro | 2 | S | SMe |
| — | H/Me | H | 3-[(cyclopropyl)methoxy]propyl | 2 | S | SMe |
| — | H/Me | H | 3-fluoropropoxy | 2 | S | SMe |
| — | H/Me | H | 3-fluoropropyl/fluoro | 2 | S | SMe |
| — | H/Me | H | 4-(methoxy)butyl | 2 | S | SMe |
| — | H/Me | H | 4,4-difluoropentyl | 2 | S | SMe |
| — | H/Me | H | 4-fluorobutoxy | 2 | S | SMe |
| — | H/Me | 9H-fluoren-9-yl-methoxy carbonyl | 4-propyl | 2 | S | SMe |
| — | H/Me | Ethoxy carbonyl | 4-propyl | 2 | S | SMe |
| — | H/Me | phenyloxy-carbonyl | 4-propyl | 2 | S | SMe |
| — | H/Me | 5-methyl-2-oxo-[1,3](dioxol-4-ylmethyl | 4-propyl | 2 | S | SMe |
| — | H/Me | 5-methyl-2-oxo-[1,3]dioxol-4-ylmethoxy carbonyl | 4-propyl | 2 | S | SMe |
| — | H/Me | H | 4-propyl/4-fluoro | 2 | S | SMe |
| — | H/Me | H | 4-propyl/4-fluoro | 1 | S | SMe |
| — | H/Me | H | butyl/fluoro | 2 | S | SMe |
| — | H/Me | H | ethyl/fluoro | 2 | S | SMe |
| 107 | H/Me | H | 4-Pentyl | 1 | S | Propyl |
| 108 | H/Me | H | 4-Propyl | 2 | S | Propyl |
| 109 | H/Me | H | 4-Propyl | 2 | S | 2,2,2-Trifluoro-Ethyl-sulfanyl |
| 110 | H/Me | H | 4-Pentyl | 1 | S | 2-Ethoxy-eth-1-yl |
| 111 | H/Me | 2-Hydroxy-ethyl | 4-Pentyl | 1 | S | Propyl |
| 112 | H/Me | H | 4-Pentyl | 1 | S | H |
| 113 | H/Me | H | 4-pentyl | 1 | S | Butoxy |
| 114 | H/Me | Me | 4-butyl | 1 | S | propyl |
| 119 | H/Me | 5-methyl-2-oxo-[1,3]dioxol-4-ylmethyl | 4-pentyl | 1 | S | propyl |
| 120 | H/Me | 5-methyl-2-oxo-[1,3]dioxol-4-yl-methoxy-carbonyl | 4-pentyl | 1 | S | Propyl |
| 121 | H/Me | 5-methyl-2-oxo-[1,3]dioxol-4-yl-methyl | 4-propyl | 1 | S | Propyl |
| 122 | H/Me | 5-methyl-2-oxo-[1,3]dioxol-4-yl-methoxy-carbonyl | 4-propyl | 1 | S | Propyl |
| 123 | H/Me | H | 4-propyl | 1 | S | 2-hydroxy-ethyl |
| 124 | H/Me | H | 4-propyl | 1 | S | 3-hydroxy-propyl |
| 125 | H/Me | H | 4-propyl | 1 | S | Hydroxyl-methyl |
| 126 | H/Me | H | 4-propyl | 1 | S | 2-(Methyl-sulfanyl)-ethyl |
| 127 | H/Me | H | 4-propyl | 1 | S | Cyclo-propyl-methyl |

In Table I, unless otherwise noted, the R⁹ substituents are substituted at the 4-position, when m is 0 or 1.

Additional lincomycin derivatives within the scope of this invention include those of formula II as set forth in Table II as follows, wherein the nitrogen-containing ring positions are numbered as in Formula (I).

TABLE 1I

| Ex. # | R²⁰/R²¹ | R⁶ | R⁹ | m | = | R¹ |
|---|---|---|---|---|---|---|
| 91 | R²⁰/R²¹ = cyclopropyl | Me | 4-propyl | 1 | S | SMe |
| 92 | R²⁰/R²¹ = Cyclopropyl | H | 4-propyl | 2 | S | SMe |
| 93 | R²⁰/R²¹ = Cyclopropyl | H | 5-propyl | 3 | S | SMe |
| 94 | R²⁰/R²¹ = phenyl | H | 4-propyl | 2 | S | SMe |
| 95 | R²⁰/R²¹ = phenyl | Me | 4-propyl | 1 | S | SMe |
| 96 | R²⁰/R²¹ = Cyclopentyl | H | 4-propyl | 2 | S | SMe |
| 97 | R²⁰/R²¹ = Cyclopentyl | Me | 4-propyl | 1 | S | SMe |
| 98 | R²⁰/R²¹ = Cyclopentyl | H | 5-propyl | 3 | S | SMe |
| 99 | H/ethyl | H | 5-propyl | 3 | S | SMe |
| 100 | H/ethenyl | Me | 4-propyl | 1 | S | SMe |
| 101 | H/ethenyl | H | 4-propyl | 2 | S | SMe |
| 102 | H/ethyl | H | 4-propyl | 2 | S | SMe |
| 103 | R²⁰/R²¹ = 4-Chloro-phenyl | Me | 4-propyl | 1 | S | SMe |
| 104 | R²⁰/R²¹ = 4-Chloro-phenyl | H | 4-propyl | 2 | S | SMe |
| 105 | H/ethyl | Me | 4-propyl | 1 | S | SMe |
| 106 | R²⁰R²¹ = 4-chloro-phenyl | H | 5-propyl | 3 | S | SMe |

Additional lincomycin derivatives within the scope of this invention include those of formula III as set forth in Table III as follows:

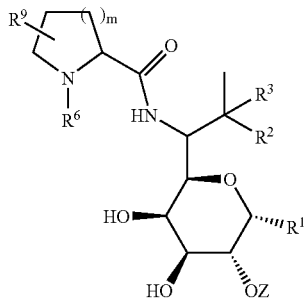

(III)

wherein the nitrogen-containing ring positions are numbered as in Formula (I).

TABLE III

| Ex No. | $R^1$ | Z | $R^2/R^3$ | $R^6$ | $R^9$ | m |
|---|---|---|---|---|---|---|
| 115 | Propyl | —P(=O)(OH)$_2$ | H/Me | H | 4-pentyl | 1 |
| 116 | Propyl | —C(O)(CH$_2$)$_{14}$—CH$_3$ | H/Me | H | 4-pentyl | 1 |
| 117 | Propyl | —P(=O)(OH)$_2$ | H/Me | H | 4-propyl | 1 |
| 118 | Propyl | —C(O)(CH$_2$)$_{14}$—CH$_3$ | H/Me | H | 4-propyl | 1 |

In Tables I, II, and III above, the following abbreviations are used:
S=single bond
D=double bond
D4,5=double bond between 4 and 5 nitrogen-containing ring positions
Me=methyl
Pr=propyl
Bu=butyl
i=iso-
t=tert- As used below, these compounds are named based on amine derivatives but, alternatively, these compounds could have been named based on 1-thio-L-threo-α-D-galacto-octopyranoside derivatives.

Preferred compounds within the scope of this invention include the following compounds:
4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;
4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;
4-(3-Pyridin-4-yl-propyl)-pyrrolidine-2-carboxylic acid [2-methyl-1-(3,4,5-trihydroxy-methylsulfanyl-tetrahydro-pyran-2-yl)-propyl]-amide;
4-Butylsulfanyl-pyrrolidine-2-carboxylic acid [2-hydroxy-1-(3,4,5-trihydroxy-6-methylsulfanyl-tetrahydro-pyran-2-yl)-propyl]-amide;
4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide;
4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide;
4-Ethylsulfanyl-pyrrolidine-2-carboxylic acid [2-chloro-1-(3,4,5-trihydroxy-6-methylsulfanyl-tetrahydro-pyran-2-yl)-propyl]-amide;
4-Ethylsulfanyl-pyrrolidine-2-carboxylic acid [2-chloro-1-(3,4,5-trihydroxy-6-methylsulfanyl-tetrahydro-pyran-2-yl)-propyl]-amide;
4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(4-Fluoro-phenylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(3,3,3-Trifluoro-propylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(3-Methyl-butylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(2,4-Dichloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;
4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;
4-Butylsulfanyl-pyrrolidine-2-carboxylic acid [2-methyl-1-(3,4,5-trihydroxy-6-methylsulfanyl-tetrahydro-pyran-2-yl)-propyl]-amide;
4-Azido-pyrrolidine-2-carboxylic acid [2-hydroxy-1-(3,4,5-trihydroxy-6-methylsulfanyl-tetrahydro-pyran-2-yl)-propyl]-amide;
4-[3-(Furan-2-ylmethylsulfanyl)-prop-1-yl]-piperidine-2-carboxylic acid [2-methyl-1-(3,4,5-trihydroxy-6-methylsulfanyl-tetrahydro-pyran-2-yl)-propyl]-amide;
4-(3-Imidazol-1-yl-prop-1-yl)-piperidine-2-carboxylic acid [2-methyl-1-(3,4,5-trihydroxy-6-methylsulfanyl-tetrahydro-pyran-2-yl)-propyl]-amide;
4-[3-(Thiophen-2-ylsulfanyl)-prop-1-yl]-piperidine-2-carboxylic acid [2-methyl-1-(3,4,5-trihydroxy-6-methylsulfanyl-tetrahydro-pyran-2-yl)-propyl]-amide;
4-(3-Ethylsulfanyl-prop-1-yl)-piperidine-2-carboxylic acid [2-methyl-1-(3,4,5-trihydroxy-6-methylsulfanyl-tetrahydro-pyran-2-yl)-propyl]-amide;
4-(3-Cyano-prop-1-yl)-piperidine-2-carboxylic acid [2-methyl-1-(3,4,5-trihydroxy-6-methylsulfanyl-tetrahydro-pyran-2-yl)-propyl]-amide;
4-(3-Difluoromethylsulfanyl-prop-1-yl)-piperidine-2-carboxylic acid [2-chloro-1-(3,4,5-trihydroxy-6-methylsulfanyl-tetrahydro-pyran-2-yl)-propyl]-amide;
4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide;
4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;
4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;
4-(3-Methoxyimino-prop-1-yl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-prop-1-yl)-piperidine-2-carboxylic acid [2-methyl-1-(3,4,5-trihydroxy-6-methylsulfanyl-tetrahydro-pyran-2-yl)-propyl]-amide;

4-[2-(5-Ethyl-isoxazol-3-yl)-ethyl]-piperidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-butyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-ethyl-piperidine-2-carboxylic acid [2-chloro-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Methyl-4-propyl-pyrrolidine-2-carboxylic acid [2-methyl-1-(3,4,5-trihydroxy-6-isopropylsulfanyl-tetrahydro-pyran-2-yl)-propyl]-amide;

4-Propyl-piperidine-2-carboxylic acid [2-methyl-1-(3,4,5-trihydroxy-6-isopropylsulfanyl-tetrahydro-pyran-2-yl)-propyl]-amide;

1-Methyl-4-propyl-pyrrolidine-2-carboxylic acid [1-(6-tert-butylsulfanyl-3,4,5-trihydroxy-tetrahydro-pyran-2-yl)-2-methyl-propyl]-amide;

4-Propyl-piperidine-2-carboxylic acid [1-(6-tert-butylsulfanyl-3,4,5-trihydroxy-tetrahydro-pyran-2-yl)-2-methyl-propyl]-amide;

1-(5-Methyl-2-oxo-[1,3]dioxol-4-ylmethyl)-5-propyl-azepane-2-carboxylic acid [2-chloro-1-(3,4,5-trihydroxy-6-methylsulfanyl-tetrahydro-pyran-2-yl)-propyl]-amide;

2-[2-Chloro-1-(3,4,5-trihydroxy-6-methylsulfanyl-tetrahydro-pyran-2-yl)-propylcarbamoyl]-5-propyl-azepane-1-carboxylic acid 5-methyl-2-oxo-[1,3]dioxol-4-ylmethyl ester;

5-Methyl-azepane-2-carboxylic acid [2-chloro-1-(3,4,5-trihydroxy-6-methylsulfanyl-tetrahydro-pyran-2-yl)-propyl]-amide;

5-Ethyl-azepane-2-carboxylic acid [2-chloro-1-(3,4,5-trihydroxy-6-methylsulfanyl-tetrahydro-pyran-2-yl)-propyl]-amide;

5-Cyclopropylmethyl-azepane-2-carboxylic acid [2-chloro-1-(3,4,5-trihydroxy-6-methylsulfanyl-tetrahydro-pyran-2-yl)-propyl]-amide;

5-Cyclopropyl-azepane-2-carboxylic acid [2-chloro-1-(3,4,5-trihydroxy-6-methylsulfanyl-tetrahydro-pyran-2-yl)-propyl]-amide;

5-Ethyl-4-methyl-azepane-2-carboxylic acid [2-chloro-1-(3,4,5-trihydroxy-6-methylsulfanyl-tetrahydro-pyran-2-yl)-propyl]-amide;

4-Ethyl-5-methyl-azepane-2-carboxylic acid [2-chloro-1-(3,4,5-trihydroxy-6-methylsulfanyl-tetrahydro-pyran-2-yl)-propyl]-amide;

5-Ethyl-6-methyl-azepane-2-carboxylic acid [2-chloro-1-(3,4,5-trihydroxy-6-methylsulfanyl-tetrahydro-pyran-2-yl)-propyl]-amide;

4-Propyl-azepane-2-carboxylic acid [2-chloro-1-(3,4,5-trihydroxy-6-methylsulfanyl-tetrahydro-pyran-2-yl)-propyl]-amide;

5-Fluoro-5-propyl-azepane-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide;

4-Butyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Fluoro-1-(2-hydroxy-ethyl)-4-propyl-pyrrolidine-2-carboxylic acid [2-chloro-1-(3,4,5-trihydroxy-6-=methylsulfanyl-tetrahydro-pyran-2-yl)-propyl]-amide;

4-Butyl-4-fluoro-piperidine-2-carboxylic acid [2-chloro-1-(3,4,5-trihydroxy-6-methylsulfanyl-tetrahydro-pyran-2-yl)-propyl]-amide;

4-(2-Cyclobutyl-ethyl)-piperidine-2-carboxylic acid [2-chloro-1-(3,4,5-trihydroxy-6-methylsulfanyl-tetrahydro-pyran-2-yl)-propyl]-amide;

4-Cyclopropylmethyl-pyrrolidine-2-carboxylic acid [2-chloro-1-(3,4,5-trihydroxy-6-methylsulfanyl-tetrahydro-pyran-2-yl)-propyl]-amide;

4-Cyclopropylmethyl-piperidine-2-carboxylic acid [2-chloro-1-(3,4,5-trihydroxy-6-methylsulfanyl-tetrahydro-pyran-2-yl)-propyl]-amide;

4-(2-Cyclobutylidene-ethyl)-pyrrolidine-2-carboxylic acid [2-methyl-1-(3,4,5-trihydroxy-6-methylsulfanyl-tetrahydro-pyran-2-yl)-propyl]-amide;

4-(2-Cyclobutylidene-ethyl)-pyrrolidine-2-carboxylic acid [2-chloro-1-(3,4,5-trihydroxy-6-methylsulfanyl-tetrahydro-pyran-2-yl)-propyl]-amide;

4-(2-Cyclobutyl-ethyl)-pyrrolidine-2-carboxylic acid [2-chloro-1-(3,4,5-trihydroxy-6-methylsulfanyl-tetrahydro-pyran-2-yl)-propyl]-amide;

4-Cyclobutylmethyl-piperidine-2-carboxylic acid [2-chloro-1-(3,4,5-trihydroxy-6-methylsulfanyl-tetrahydro-pyran-2-yl)-propyl]-amide;

5-Propyl-2,3,6,7-tetrahydro-1H-azepine-2-carboxylic acid [2-chloro-1-(3,4,5-trihydroxy-6-methylsulfanyl-tetrahydro-pyran-2-yl)-propyl]-amide;

4-(2-Cyclopropyl-ethyl)-pyrrolidine-2-carboxylic acid [2-chloro-1-(3,4,5-trihydroxy-6-methylsulfanyl-tetrahydro-pyran-2-yl)-propyl]-amide;

4-Cyclopropylmethyl-4-fluoro-piperidine-2-carboxylic acid [2-chloro-1-(3,4,5-trihydroxy-6-methylsulfanyl-tetrahydro-pyran-2-yl)-propyl]-amide;

5-Propyl-azepane-2-carboxylic acid [2-chloro-1-(3,4,5-trihydroxy-6-methylsulfanyl-tetrahydro-pyran-2-yl)-propyl]-amide;

1-Cyclopropyl-5-propyl-azepane-2-carboxylic acid [2-methyl-1-(3,4,5-trihydroxy-6-methylsulfanyl-tetrahydro-pyran-2-yl)-propyl]-amide;
4-Butyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide;
5-Propyl-azepane-2-carboxylic acid [2-methyl-1-(3,4,5-trihydroxy-6-isopropylsulfanyl-tetrahydro-pyran-2-yl)-propyl]-amide;
5-Propyl-azepane-2-carboxylic acid [1-(6-tert-butylsulfanyl-3,4,5-trihydroxy-tetrahydro-pyran-2-yl)-2-methyl-propyl]-amide;
3-Cyclopropylmethyl-azetidine-2-carboxylic acid [2-chloro-1-(3,4,5-trihydroxy-6-methylsulfanyl-tetrahydro-pyran-2-yl)-propyl]-amide;
3-(2-Cyclobutyl-ethyl)-azetidine-2-carboxylic acid [2-chloro-1-(3,4,5-trihydroxy-6-methylsulfanyl-tetrahydro-pyran-2-yl)-propyl]-amide;
3-(2-Cyclopropyl-ethyl)-azetidine-2-carboxylic acid [2-chloro-1-(3,4,5-trihydroxy-6-methylsulfanyl-tetrahydro-pyran-2-yl)-propyl]-amide;
3-(3-Cyclopropyl-propyl)-azetidine-2-carboxylic acid [2-chloro-1-(3,4,5-trihydroxy-6-methylsulfanyl-tetrahydro-pyran-2-yl)-propyl]-amide;
3-Propyl-azetidine-2-carboxylic acid [2-chloro-1-(3,4,5-trihydroxy-6-methylsulfanyl-tetrahydro-pyran-2-yl)-propyl]-amide;
3-Butyl-azetidine-2-carboxylic acid [2-chloro-1-(3,4,5-trihydroxy-6-methylsulfanyl-tetrahydro-pyran-2-yl)-propyl]-amide;
3-Butyl-1-(2-hydroxy-ethyl)-azetidine-2-carboxylic acid [2-chloro-1-(3,4,5-trihydroxy-6-methylsulfanyl-tetrahydro-pyran-2-yl)-propyl]-amide;
3-Pentyl-azetidine-2-carboxylic acid [2-chloro-1-(3,4,5-trihydroxy-6-methylsulfanyl-tetrahydro-pyran-2-yl)-propyl]-amide;
3-(3-Methyl-butyl)-azetidine-2-carboxylic acid [2-chloro-1-(3,4,5-trihydroxy-6-methylsulfanyl-tetrahydro-pyran-2-yl)-propyl]-amide;
3-(3,3-Difluoro-propyl)-azetidine-2-carboxylic acid [2-chloro-1-(3,4,5-trihydroxy-6-methylsulfanyl-tetrahydro-pyran-2-yl)-propyl]-amide;
3-Butyl-1-methyl-azetidine-2-carboxylic acid [2-chloro-1-(3,4,5-trihydroxy-6-methylsulfanyl-tetrahydro-pyran-2-yl)-propyl]-amide;
1-Methyl-4-propyl-pyrrolidine-2-carboxylic acid [cyclopropyl-(3,4,5-trihydroxy-6-methylsulfanyl-tetrahydro-pyran-2-yl)-methyl]-amide;
4-Propyl-piperidine-2-carboxylic acid [cyclopropyl-(3,4,5-trihydroxy-6-methylsulfanyl-tetrahydro-pyran-2-yl)-methyl]-amide;
5-Propyl-azepane-2-carboxylic acid [cyclopropyl-(3,4,5-trihydroxy-6-methylsulfanyl-tetrahydro-pyran-2-yl)-methyl]-amide;
4-Propyl-piperidine-2-carboxylic acid [phenyl-(3,4,5-trihydroxy-6-methylsulfanyl-tetrahydro-pyran-2-yl)-methyl]-amide;
1-Methyl-4-propyl-pyrrolidine-2-carboxylic acid [phenyl-(3,4,5-trihydroxy-6-methylsulfanyl-tetrahydro-pyran-2-yl)-methyl]-amide;
4-Propyl-piperidine-2-carboxylic acid [cyclopentyl-(3,4,5-trihydroxy-6-methylsulfanyl-tetrahydro-pyran-2-yl)-methyl]-amide;
1-Methyl-4-propyl-pyrrolidine-2-carboxylic acid [cyclopentyl-(3,4,5-trihydroxy-6-methylsulfanyl-tetrahydro-pyran-2-yl)-methyl]-amide;
5-Propyl-azepane-2-carboxylic acid [cyclopentyl-(3,4,5-trihydroxy-6-methylsulfanyl-tetrahydro-pyran-2-yl)-methyl]-amide;
5-Propyl-azepane-2-carboxylic acid [1-(3,4,5-trihydroxy-6-methylsulfanyl-tetrahydro-pyran-2-yl)-butyl]-amide;
1-Methyl-4-propyl-pyrrolidine-2-carboxylic acid [1-(3,4,5-trihydroxy-6-methylsulfanyl-tetrahydro-pyran-2-yl)-but-3-enyl]-amide;
4-Propyl-piperidine-2-carboxylic acid [1-(3,4,5-trihydroxy-6-methylsulfanyl-tetrahydro-pyran-2-yl)-but-3-enyl]-amide;
4-Propyl-piperidine-2-carboxylic acid [1-(3,4,5-trihydroxy-6-methylsulfanyl-tetrahydro-pyran-2-yl)-butyl]-amide;
1-Methyl-4-propyl-pyrrolidine-2-carboxylic acid [(4-chloro-phenyl)-(3,4,5-trihydroxy-6-methylsulfanyl-tetrahydro-pyran-2-yl)-methyl]-amide;
4-Propyl-piperidine-2-carboxylic acid [(4-chloro-phenyl)-(3,4,5-trihydroxy-6-methylsulfanyl-tetrahydro-pyran-2-yl)-methyl]-amide;
1-Methyl-4-propyl-pyrrolidine-2-carboxylic acid [1-(3,4,5-trihydroxy-6-methylsulfanyl-tetrahydro-pyran-2-yl)-butyl]-amide;
5-Propyl-azepane-2-carboxylic acid [(4-chloro-phenyl)-(3,4,5-trihydroxy-6-methylsulfanyl-tetrahydro-pyran-2-yl)-methyl]-amide;
4-Pentyl-pyrrolidine-2-carboxylic acid [2-methyl-1-(3,4,5-trihydroxy-6-propyl-tetrahydro-pyran-2-yl)-propyl]-amide;
4-Propyl-piperidine-2-carboxylic acid [2-methyl-1-(3,4,5-trihydroxy-6-propyl-tetrahydro-pyran-2-yl)-propyl]-amide;
4-Propyl-piperidine-2-carboxylic acid {2-methyl-1-[3,4,5-trihydroxy-6-(2,2,2-trifluoro-ethylsulfanyl)-tetrahydro-pyran-2-yl]-propyl}-amide;
4-Pentyl-pyrrolidine-2-carboxylic acid [1-(6-ethoxyethyl-3,4,5-trihydroxy-tetrahydro-pyran-2-yl)-2-methyl-propyl]-amide;
1-(2-Hydroxy-ethyl)-4-pentyl-pyrrolidine-2-carboxylic acid [2-methyl-1-(3,4,5-trihydroxy-6-propyl-tetrahydro-pyran-2-yl)-propyl]-amide;
4-Pentyl-pyrrolidine-2-carboxylic acid [2-methyl-1-(3,4,5-trihydroxy-tetrahydro-pyran-2-yl)-propyl]-amide;
4-Pentyl-pyrrolidine-2-carboxylic acid [1-(6-butoxy-3,4,5-trihydroxy-tetrahydro-pyran-2-yl)-2-methyl-propyl]-amide;
4-Butyl-1-methyl-pyrrolidine-2-carboxylic acid [2-methyl-1-(3,4,5-trihydroxy-6-propyl-tetrahydro-pyran-2-yl)-propyl]-amide;
Phosphoric acid mono-(4,5-dihydroxy-6-{2-methyl-1-[(4-pentyl-pyrrolidine-2-carbonyl)-amino]-propyl}-2-propyl-tetrahydro-pyran-3-yl) ester;
Hexadecanoic acid 4,5-dihydroxy-6-{2-methyl-1-[(4-pentyl-pyrrolidine-2-carbonyl)-amino]-propyl}-2-propyl-tetrahydro-pyran-3-yl ester;
Phosphoric acid mono-(4,5-dihydroxy-6-{2-methyl-1-[(4-propyl-pyrrolidine-2-carbonyl)-amino]-propyl}-2-propyl-tetrahydro-pyran-3-yl) ester;
Hexadecanoic acid 4,5-dihydroxy-6-{2-methyl-1-[(4-propyl-pyrrolidine-2-carbonyl)-amino]-propyl}-2-propyl-tetrahydro-pyran-3-yl ester;
1-(5-Methyl-2-oxo-[1,3]dioxol-4-ylmethyl)-4-pentyl-pyrrolidine-2-carboxylic acid [2-methyl-1-(3,4,5-trihydroxy-6-propyl-tetrahydro-pyran-2-yl)-propyl]-amide;
2-[2-Methyl-1-(3,4,5-trihydroxy-6-propyl-tetrahydro-pyran-2-yl)-propylcarbamoyl]-4-pentyl-pyrrolidine-1-carboxylic acid 5-methyl-2-oxo-[1,3]dioxol-4-ylmethyl ester;

1-(5-Methyl-2-oxo-[1,3]dioxol-4-ylmethyl)-4-propyl-pyrrolidine-2-carboxylic acid [2-methyl-1-(3,4,5-trihydroxy-6-propyl-tetrahydro-pyran-2-yl)-propyl]-amide;

2-[2-Methyl-1-(3,4,5-trihydroxy-6-propyl-tetrahydro-pyran-2-yl)-propylcarbamoyl]-4-propyl-pyrrolidine-1-carboxylic acid 5-methyl-2-oxo-[1,3]dioxol-4-ylmethyl ester;

4-Propyl-pyrrolidine-2-carboxylic acid {2-methyl-1-[3,4,5-trihydroxy-6-(2-hydroxy-ethyl)-tetrahydro-pyran-2-yl]-propyl}-amide;

4-Propyl-pyrrolidine-2-carboxylic acid {2-methyl-1-[3,4,5-trihydroxy-6-(3-hydroxy-propyl)-tetrahydro-pyran-2-yl]-propyl}-amide;

4-Propyl-pyrrolidine-2-carboxylic acid [2-methyl-1-(3,4,5-trihydroxy-6-hydroxymethyl-tetrahydro-pyran-2-yl)-propyl]-amide;

4-Propyl-pyrrolidine-2-carboxylic acid {2-methyl-1-[3,4,5-trihydroxy-6-(2-methylsulfanyl-ethyl)-tetrahydro-pyran-2-yl]-propyl}-amide;

4-Propyl-pyrrolidine-2-carboxylic acid [1-(6-cyclopropylmethyl-3,4,5-trihydroxy-tetrahydro-pyran-2-yl)-2-methyl-propyl]-amide;

or a prodrug and/or a pharmaceutically acceptable salt thereof.

Additional compounds within the scope of this invention include:

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Fluoro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;

4-Butylsulfanyl-pyrrolidine-2-carboxylic acid [2-methyl-1-(3,4,5-trihydroxy-6-methylsulfanyl-tetrahydro-pyran-2-yl)-propyl]-amide;

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide;

1-(2-Methoxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Formylamino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Amino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Cyclohexyloxy-propyl)-piperidine-2-carboxylic acid [2-methyl-1-(3,4,5-trihydroxy-6-methylsulfanyl-tetrahydro-pyran-2-yl)-propyl]-amide;

{2-[2-Methyl-1-(3,4,5-trihydroxy-6-methylsulfanyl-tetrahydro-pyran-2-yl)-propylcarbamoyl]-4-pentyl-pyrrolidin-1-yl}-acetic acid methyl ester;

1-Methylcarbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-[3-(Furan-2-ylmethylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(Thiophen-2-ylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(2-Oxo-pyrrolidin-1-yl)-propyl]-piperidine-2-carboxylic acid [2-methyl-1-(3,4,5-trihydroxy-6-methylsulfanyl-tetrahydro-pyran-2-yl)-propyl]-amide;

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide;

4-[2-(4-Ethyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Ethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-propyl)-piperidine-2-carboxylic acid [2-methyl-1-(3,4,5-trihydroxy-6-methylsulfanyl-tetrahydro-pyran-2-yl)-propyl]-amide;

4-Pyrrol-1-ylmethyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

4-(3-Cyano-propyl)-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

4-(2-[1,2,3]Triazol-1-yl-ethyl)-piperidine-2-carboxylic acid [2-methyl-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-Pentyl-pyrrolidine-2-carboxylic acid [1-(6-ethoxymethyl-3,4,5-trihydroxy-tetrahydro-pyran-2-yl)-2-methyl-propyl]-amide;

or a prodrug and/or a pharmaceutically acceptable salt thereof.

Additional compounds of the invention include:

phosphoric acid mono-(6-{2-chloro-1-[(5-propyl-azepane-2-carbonyl)-amino]-propyl}-4,5-dihydroxy-2-methylsulfanyl-tetrahydro-pyran-3-yl) ester;

phosphoric acid mono-(6-{2-chloro-1-[(5-fluoro-5-propyl-azepane-2-carbonyl)-amino]-propyl}-4,5-dihydroxy-2-methylsulfanyl-tetrahydro-pyran-3-yl) ester;

phosphoric acid mono-(6-{2-chloro-1-[(5-cyclopropylmethyl-azepane-2-carbonyl)-amino]-propyl}-4,5-dihydroxy-2-methylsulfanyl-tetrahydro-pyran-3-yl) ester;

phosphoric acid mono-(6-{2-chloro-1-[(4-fluoro-4-propyl-piperidine-2-carbonyl)-amino]-propyl}-4,5-dihydroxy-2-methylsulfanyl-tetrahydro-pyran-3-yl) ester;

hexadecanoic acid 6-{2-chloro-1-[(5-propyl-azepane-2-carbonyl)-amino]-propyl}-4,5-dihydroxy-2-methylsulfanyl-tetrahydro-pyran-3-yl ester;

hexadecanoic acid 6-{2-chloro-1-[(5-fluoro-5-propyl-azepane-2-carbonyl)-amino]-propyl}-4,5-dihydroxy-2-methylsulfanyl-tetrahydro-pyran-3-yl ester;

hexadecanoic acid 6-{2-chloro-1-[(5-cyclopropylmethyl-azepane-2-carbonyl)-amino]-propyl}-4,5-dihydroxy-2-methylsulfanyl-tetrahydro-pyran-3-yl ester; and hexadecanoic acid 6-{2-chloro-1-[(4-fluoro-4-propyl-piperidine-2-carbonyl)-amino]-propyl}-4,5-dihydroxy-2-methylsulfanyl-tetrahydro-pyran-3-yl ester.

Additional compounds of the invention include:

2-[2-chloro-1-(3,4,5-trihydroxy-6-methylsulfanyl-tetrahydro-pyran-2-yl)-propylcarbamoyl]-5-propyl-azepane-1-carboxylic acid 5-methyl-2-oxo-[1,3]dioxol-4-ylmethyl ester 2-[2-chloro-1-(3,4,5-trihydroxy-6-methylsulfanyl-tetrahydro-pyran-2-yl)-propylcarbamoyl]-5-fluoro-5-propyl-azepane-1-carboxylic acid 5-methyl-2-oxo-[1,3]dioxol-4-ylmethyl ester;

5-fluoro-1-(5-methyl-2-oxo-[1,3]dioxol-4-ylmethyl)-5-propyl-azepane-2-carboxylic acid [2-chloro-1-(3,4,5-trihydroxy-6-methylsulfanyl-tetrahydro-pyran-2-yl)-propyl]-amide;

5-cyclopropylmethyl-1-(5-methyl-2-oxo-[1,3]dioxol-4-yl-methyl)-azepane-2-carboxylic acid [2-chloro-1-(3,4,5-trihydroxy-6-methylsulfanyl-tetrahydro-pyran-2-yl)-propyl]-amide;

2-[2-chloro-1-(3,4,5-trihydroxy-6-methylsulfanyl-tetrahydro-pyran-2-yl)-propylcarbamoyl]-5-cyclopropylmethyl-azepane-1-carboxylic acid 5-methyl-2-oxo-[1,3]dioxol-4-ylmethyl ester;

2-[2-chloro-1-(3,4,5-trihydroxy-6-methylsulfanyl-tetrahydro-pyran-2-yl)-propylcarbamoyl]-4-fluoro-4-propyl-piperidine-1-carboxylic acid 5-methyl-2-oxo-[1,3]dioxol-4-ylmethyl ester; and 4-fluoro-1-(5-methyl-2-oxo-[1,3]dioxol-4-ylmethyl)-4-propyl-piperidine-2-carboxylic acid [2-chloro-1-(3,4,5-trihydroxy-6-methylsulfanyl-tetrahydro-pyran-2-yl)-propyl]-amide.

The compounds, prodrugs and pharmaceutically acceptable salts thereof, as defined herein, may have activity against bacteria, protozoa, fungi, and/or parasites.

In another aspect, this invention provides pharmaceutical compositions comprising a pharmaceutically acceptable carrier and a therapeutically effective amount of the compounds defined herein. The pharmaceutical compositions of the present invention may further comprise one or more additional antibacterial agents. In one embodiment, one or more of the additional antibacterial agents may be active against gram negative bacteria. In one embodiment, one or more of the additional antibacterial agents may be active against gram positive bacteria. In another embodiment, at least one of the antibacterial agents may be active against both gram negative and gram positive bacteria.

In one of its method aspects, this invention is directed to a method for the treatment of a microbial infection in a mammal comprising administering to the mammal a therapeutically effective amount of a compound of this invention. The compound of this invention may be administered to the mammal orally, parenterally, transdermally, topically, rectally, or intranasally in a pharmaceutical composition.

In another of its method aspects, this invention is directed to a method for the treatment of a microbial infection in a mammal comprising administering to the mammal a pharmaceutical composition comprising a therapeutically effective amount of a compound of this invention. The pharmaceutical compositions of the present invention may further comprise one or more additional antibacterial agents. In one embodiment, one or more of the additional antibacterial agents may be active against gram negative bacteria. In one embodiment, one or more of the additional antibacterial agents may be active against gram positive bacteria. The pharmaceutical composition may be administered to the mammal orally, parenterally, transdermally, topically, rectally, or intranasally.

In a preferred embodiment, the microbial infection being treated is a gram positive infection. In another embodiment, the infection may be a gram negative infection. In a further embodiment, the infection may be a mycobacteria infection, a mycoplasma infection, or a chlamydia infection.

In yet another aspect, the present invention provides novel intermediates and processes for preparing the compounds described herein.

DETAILED DESCRIPTION OF THE INVENTION

As described above, this invention relates to lincomycin derivatives that exhibit antibacterial activity, in particular gram positive antibacterial activity. In some embodiments, said novel lincomycin derivatives exhibit antibacterial activity against gram positive and anaerobe pathogens. Surprisingly, selected novel lincomycin compounds described herein exhibit atypical potency against *Enterocci* species such as *Enterocci faecium* and *Enterocci faecalis*, and/or against fastidious gram-negative pathogens such as *Haemophilus influenzae*, when compared against known compounds such as clindamycin. However, prior to describing this invention in further detail, the following terms will first be defined.

It must be noted that as used herein and in the appended claims, the singular forms "a," "an," and "the" include plural references unless context clearly dictates otherwise. Thus, for example, a reference to "a pharmaceutically acceptable carrier" includes a plurality of such carriers; a reference to "an additional antibacterial agent" is a reference to one or more agents and to equivalents thereof known to those skilled in the art, and so forth.

Definitions

Unless otherwise stated, the following terms used in the specification and claims have the meanings given below:

"Acyl" means the group —C(O)$R^{14}$ wherein $R^{14}$ is hydrogen, alkyl, substituted alkyl, alkenyl, substituted alkenyl, alkynyl, aryl, substituted aryl, heteroaryl, substituted heteroaryl, heterocyclic or substituted heterocyclic.

"Acylamino" refers to —N$R^a$C(O)$R^{14}$ where $R^a$ and $R^{14}$ are as defined above.

"Alkenyl" means a linear unsaturated monovalent hydrocarbon radical of two to eight carbon atoms or a branched monovalent hydrocarbon radical of three to eight carbon atoms containing at least one double bond, (—C=C—) and preferably from 1–2 double bonds. Examples of alkenyl groups include, but are not limited to, allyl, vinyl, 2-butenyl, and the like.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" means a linear saturated monovalent hydrocarbon radical of one to eight carbon atoms or a branched saturated monovalent hydrocarbon radical of three to eight carbon atoms. Examples of alkyl groups include, but are not limited to, groups such as methyl, ethyl, n-propyl, isopropyl, n-butyl, iso-butyl, sec-butyl, t-butyl, n-pentyl, and the like.

"Alkylene" means a linear divalent hydrocarbon group of one to eight carbon atoms or a branched divalent hydrocarbon group of three to eight carbon atoms. Examples of alkylene groups include, but are not limited to, methylene, ethylene, 2-methylpropylene, and the like.

"Alkylsulfanyl" refers to the group "alkyl-S—" wherein alkyl is as defined herein which includes, by way of example, methylsulfanyl, butylsulfanyl, and the like.

"Alkynyl" means a linear monovalent hydrocarbon radical of two to eight carbon atoms or a branched monovalent hydrocarbon radical of three to eight carbon atoms containing at least one triple bond, (—C≡C—), and preferably a single triple bond. Examples of alkynyl groups include, but are not limited to, ethynyl, propynyl, 2-butynyl, and the like.

"Amino" or "substituted nitrogen" refers to the group "—N$R^aR^b$" wherein $R^a$ and $R^b$ are independently hydrogen, alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic or where $R^a$ and $R^b$ are tethered together with the nitrogen atom to which they are bound to form a heterocyclic ring.

"Aminoacyl" refers to —C(O)N$R^aR^b$.

"Aminocarbonylalkyl" means a group "—$R^c$C(O)N$R^aR^b$" where $R^c$ is an alkylene and $R^a$ and $R^b$ are as defined above.

"Aryl" means a monovalent monocyclic or bicyclic aromatic carbocyclic group of 6 to 14 ring atoms. Examples include, but are not limited to, phenyl, naphthyl, and anthryl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl. Representative aryl groups with fused rings include, but are not limited to, 2,5-dihydro-benzo[b]oxepine, 2,3-dihydrobenzo[1,4]dioxane, chroman, isochroman, 2,3-dihydrobenzofuran, 1,3-dihydroisobenzofuran, benzo[1,3]dioxole, 1,2,3,4-tetrahydroisoquinoline, 1,2,3,4-tetrahydroquinoline, 2,3-dihydro-1Hindole, 2,3-dihydro1H-isoindole, benzimidazole-2-one, 2-H-benzoxazol-2-one, and the like.

"Carboxy" means the group "C(O)OH."

"Cyanoalkyl" refers to an alkyl substituted with one or more cyano (—CN) groups provided that no more than a single cyano group is present on the same carbon atom. Examples of cyanoalkyl groups include, for example, cyanomethyl, 2-cyanoethyl, 2-cyanopropyl, and the like.

"Cycloalkyl" means a cyclic saturated hydrocarbon group of 3 to 8 ring atoms. Examples of cycloalkyl groups include, but are not limited to, cyclopropyl, cyclobutyl, cyclopentyl, cyclohexyl, and the like.

"Cycloalkylalkyl" means a group —$R^cR^d$ where $R^c$ is an alkylene group and $R^d$ is a cycloalkyl group, as defined above. Examples include, but are not limited to, cyclopropylmethylene, cyclohexylethylene, and the like.

"Halo" or "Halogen" means fluoro, chloro, bromo, or iodo.

"Haloalkyl" means an alkyl substituted with one or more, preferably one to 6, of the same or different halo atoms. Examples of haloalkyl groups include, for example, trifluoromethyl, 3-fluoropropyl, 2,2-dichloroethyl, and the like.

"Heteroaryl" means a monovalent monocyclic or bicyclic aromatic radical of 5 to 10 ring atoms containing one, two, or three ring heteroatoms selected from N, O, or S, the remaining ring atoms being C.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, oxygen or $S(O)_q$ (where q is zero, one or two) within the ring wherein, in fused ring systems, one or more of the rings can be aryl or heteroaryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Hydroxy" means the group —OH.

"Hydroxyalkyl" refers to an alkyl substituted with one or more —OH groups provided that no more, than a single hydroxy (—OH) group is present on the same carbon atom. Examples of hydroxyalkyl groups include, for example, hydroxymethyl, 2-hydroxyethyl, 2-hydroxypropyl, and the like.

"Mammal" refers to all mammals including humans, livestock, and companion animals.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth metal ion, or an aluminum ion; or coordinates with an organic base such as ethanolamine, diethanolamine, triethanolamine, N-methylglucamine, and the like.

"Pro-drugs" mean any compound which releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxy, sulfhydryl, or amino group, respectively. Examples of prodrugs include, but are not limited to, esters (e.g., acetate, formate, palmitate, and benzoate derivatives), carbamates (e.g., N,N-dimethylaminocarbonyl) of hydroxy functional groups in compounds of the subject invention, and the like. Preferred prodrug substituents include the following substituents attached to the N-position of the five or six member nitrogen containing heterocycle: phosphate, palmitate or

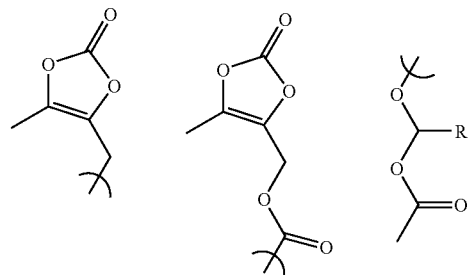

R = H or Me.

"Substituted alkyl" means an alkyl group, as defined above having 1–3 independently selected substitutents selected from the group consisting of cyano, a halogen (i.e., Cl, Br, F, or I), acyl, substituted oxygen, hydroxy, alkylsulfanyl, substituted alkylsulfanyl, cycloalkyl, substituted cycloalkyl, aminocarbonylalkyl, carboxy, —C(O)H, —C(O)OR$^{15}$ (where R$^{15}$ is alkyl, substituted alkyl, alkenyl, substituted alkenyl, alkynyl, substituted alkynyl, aryl, substituted aryl, heteroaryl, substituted heteroaryl and the like), —C(O)NR$^a$R$^b$, substituted nitrogen, =N—OR$^7$ where R$^7$ is hydrogen or alkyl, —SH, —S(O)$_q$R$^{16}$ [where q is zero, one or two, and R$^{16}$ is alkyl, haloalkyl, aryl, heteroaryl, heterocyclic and alkyl substituted with aryl, heteroaryl, cycloalkyl and heterocyclic], aryl, substituted aryl, heteroaryl, substituted heteroaryl, heterocyclic and substituted heterocyclic. Examples of substituted alkyl groups include, but are not limited to, 1-fluoroethyl, 1-chloroethyl, 2-fluoroethyl, 2-chloroethyl, 1-bromopropyl, 2-iodopropyl, 1-chlorobutyl, 4-flurobutyl, 4-chlorobutyl, 2-ethoxyeth-1-yl, —$CH_2$—$S(O)_2CH_3$, and the like.

"Substituted alkenyl" means an alkenyl group, as defined above, in which one or more of the hydrogen atoms, and preferably 1 to 3 hydrogen atoms, has been replaced by substituents as defined for substituted alkyl.

"Substituted alkynyl" means an alkynyl group, as defined above, in which one or more of the hydrogen atoms, and preferably 1 to 3 hydrogen atoms, has been replaced by substituents as defined for substituted alkyl.

"Substituted alkylsulfanyl" refers to the group —S-substituted alkyl where substituted alkyl is as defined above, which includes, by way of example, 2-hydroxyethylsulfanyl, and the like.

"Substituted alkoxy" refers to the group —O-substituted alkyl where substituted alkyl is as defined above.

"Substituted aryl" means an aryl ring substituted with one or more substituents, preferably one to three substituents selected from the group consisting of alkyl, substituted alkyl, alkylsulfanyl, substituted alkylsulfanyl, alkenyl, substituted alkenyl, alkynyl, substituted alkynyl, halo, alkoxy, substituted alkoxy, acyl, amino, acylamino, acylamino, cycloalkyl, substituted cycloalkyl, cycloalkylalkyl, heteroaryl, substituted heteroaryl, heterocyclic, substituted heterocyclic, hydroxy, carboxy, —$C(O)OR^{15}$, —$C(O)NR^aR^b$, cyano, nitro and sulfanylalkyl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl.

"Substituted cycloalkyl" means a cycloalkyl substituted with an alkyl group or a group as defined above for substituted alkyl. Representative examples include, but are not limited to, 2-cyclopropylethyl, 3-cyclobutylpropyl, 4-cyclopentylbutyl, 4-cyclohexylbutyl, and the like.

"Substituted heteroaryl" means a heteroaryl ring substituted with one or more substituents, preferably one to three substituents selected from the group defined above for substituted aryl.

"Substituted heterocyclic" refers to heterocycle groups that are independently substituted with from 1 to 3 of the same substituents as defined for substituted cycloalkyl.

"Substituted oxygen" refers to the group "—O—$R^d$" wherein $R^d$ is alkyl, substituted alkyl, alkenyl, substituted alkenyl, cycloalkyl, substituted cycloalkyl, aryl, substituted aryl, heteroaryl, substituted heteroaryl, heterocyclic or substituted heterocyclic.

"Substituted phenyl" refers to phenyl groups having from 1 to 3 substituents selected from the group defined for substituted aryl.

"Sulfanylalkyl" refers to an alkyl substituted with one or more —SH groups provided that if two thiol groups are present they are not both on the same carbon atom. Examples of sulfanylalkyl groups include, for example, sulfanylmethyl, 2-sulfanylethyl, 2-sulfanylpropyl, and the like.

"Therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

The compounds of the present invention are generally named according to the IUPAC or CAS nomenclature system. Abbreviations that are well known to one of ordinary skill in the art may be used (e.g. "Ph" for phenyl, "Me" for methyl, "Et" for ethyl, "h" for hour or hours and "rt" for room temperature).

Unless defined otherwise, all technical and scientific terms used herein have the same meanings as commonly understood by one of ordinary skill in the art to which this invention belongs.

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, and pharmacology, within the skill of the art. Such techniques are explained fully in the literature.

General Synthetic Schemes

Compounds of this invention can be made by the methods depicted in the reaction schemes shown below.

The starting materials and reagents used in preparing these compounds are either available from commercial suppliers such as Toronto Research Chemicals (North York, ON Canada), Aldrich Chemical Co. (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

As it will be apparent to those skilled in the art, conventional protecting groups may be necessary to prevent certain functional groups from undergoing undesired reactions.

Suitable protecting groups for various functional groups, as well as suitable conditions for protecting and deprotecting particular function groups are well known in the art. For example, numerous protecting groups are described in T. W. Greene and G. M. Wuts, *Protecting Groups in Organic Synthesis*, Second Edition, Wiley, New York, 1991, and references cited therein.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

The compounds of this invention will typically contain one or more chiral centers. Accordingly, if desired, such compounds can be prepared or isolated as pure stereoisomers. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Preparation of Compounds of the Invention

In general, to prepare the compounds of formula (I) of the present invention, an appropriately 7-substititued lincosamine intermediate and an appropriately substituted pyrrolidinyl, piperidyl, azetindinyl, or azepane carboxylic acid are condensed under reactive conditions, preferably in an inert organic solvent, in the presence of a coupling reagent and an organic base. This reaction can be performed with any number of known coupling reagents, such as O-(7-azabenzotriazol-1-yl)-N,N,N',N'-tetramethyluronium hexafluorophosphate (HATU), 1-hydroxybenzotriazole hydrate (HOBT) with carbodiimides, isobutyl chloroformate, and the like. Suitable organic bases include diisopropylethylamine (DIEA), triethylamine (TEA), pyridine, N-methyl morpholine, and the like. Suitable inert organic solvents which can be used include, for example, N,N-dimethylformamide, acetonitrile, dichloromethane, and the like. This reaction is typically conducted using an excess of carboxytic acid to lincosamine at temperatures in the range of about 0° C. to about 50° C. The reaction is continued until completion, which typically occurs in from about 2 to 12 hours.

Appropriately 7-substititued lincosamine intermediates, as defined in the present invention (i.e., $R^2/R^3$), are synthesized by methods well known to those of skill in the art from methyl 6-amino-6,8-dideoxy-1-thio-erythro-α-D-galacto-octopyranoside, which can be prepared as described by Hoeksema, H. et. al. *Journal of the American Chemical Society,* 1967, 89 2448–2452. Illustrative syntheses for 7-substituted lincosamine intermediates are shown below in Schemes 1–6.

Additional appropriately 7-substititued lincosamine intermediates, as defined in the present invention (i.e., $R^2/R^3$), are synthesized by methods well known to those of skill in the art from methyl 6-amino-6,8-dideoxy-1-thio-erythro-α-D-galacto-octopyranoside as disclosed in U.S. Pat. No. 3,086,912 (R2=OH, R3=H), U.S. Pat. No. 3,496,136, U.S. Pat. No. 3,502,646 or preferably European Pat. No. 0161794 (R2=Halogen, R3=H), U.S. Pat. No. 3,179,565 (R2=SR, R3=H), U.S. Pat. No. 3,544,551 (R2=SH, R3=H).

Appropriately substituted pyrrolidinyl or piperidyl carboxylic acid intermediates, as defined in the present invention (i.e., $R^9$), are also synthesized by methods well known to those of skill in the art from prolines and pyridines. The prolines and pyridines that can be used in the synthesis of the carboxylic acid intermediates of the present invention include, for example, 4-oxoproline and 4-substituted pyridines. The prolines and pyridines used in the synthesis are commercially available from vendors such as Aldrich and Sigma. Alternatively, these prolines and pyridines can be prepared by methods well known in the art. Illustrative syntheses for appropriately substituted pyrrolidinyl or piperidyl carboxylic acid intermediates are shown below in Schemes 7–12.

Scheme 1 below illustrates a general synthesis of a lincosamine internediate 1c wherein P is an N-protecting group, preferably either Cbz or Boc, and $R^1$ is as defined for formula (I).

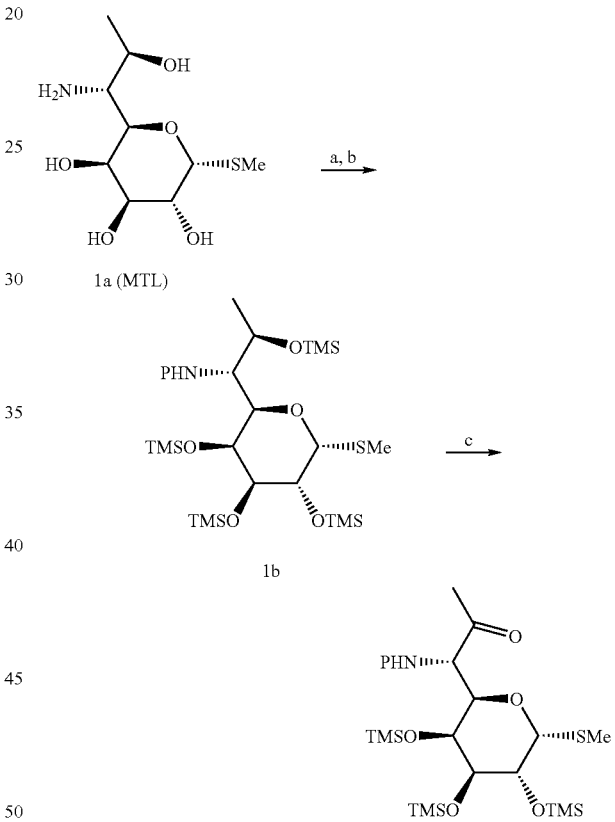

(a) N-Protection (Boc, Cbz); (b) O-silyl protection (TMS); (c) Swern oxidation.

As shown in Scheme 1, methyl 6-amino-6,8-dideoxy-1-thio-erythro-α-D-galacto-octopyranoside 1a is prepared as described by Hoeksema, H. et. al. *Journal of the American Chemical Society,* 1967, 89, 2448–2452. The amino functional group and the hydroxy functional groups of the product 1a are then protected with suitable protecting groups. Suitable N-protecting groups (P) can be formed by the addition of di-t-butyldicarbonate, N-(benzyloxycarbonyloxy) succinimide, and the like. The hydroxy groups can be protected as silyl ethers. The hydroxy group can be converted to trimethylsilyl (TMS) ethers by reaction with N,O-bis-(trimethylsilyl)-trifluoroacetamide in the presence of an appropriate organic base such as triethylamine or trimethylsilyl chloride in the presence of an organic base such as triethylamine. The N-protection is typically accomplished before the O-protection. Chromatography of the crude product on silica after evaporation of the solvent provides the protected product 1b.

The 7-O-trimethylsilyl group of 1b is chemoselectively deprotected and oxidized to provide the 7-keto-lincosamine derivative 1c. This selective transformation is performed by addition of the protected product 1b to dimethylsulfoxide and oxalyl chloride in an inert organic solvent such as dichloromethane followed by an appropriate organic base such as triethylamine. Alternatively, the transformation may be performed by addition of 1b to dimethyl sulfoxide and an appropriate activating agent such as trifluoroacetic anhydride in an inert organic solvent. The reaction is typically conducted at temperatures in the range of approximately −70° C. The resulting reaction mixture is stirred at the low temperature and is then allowed to warm to approximately −50° C. The reaction is maintained at this second temperature for approximately 1 h to 3 h. To the reaction mixture is added a suitable organic base, such as TEA, pyridine, and the like. The reaction mixture is appropriately worked up to provide the product 1c. The general class of conditions used in the transformation of 1b to 1c is known in the art as Swern oxidation conditions.

Scheme 2 below illustrates a general synthesis of a lincosamine intermediate 2b wherein P is an N-protecting group, preferably either Cbz or Boc, $R^3$ is hydrogen, $R^{2'}$ is consistent with $R^2$ as defined for formula (I), and $R^1$ is as defined for formula (I).

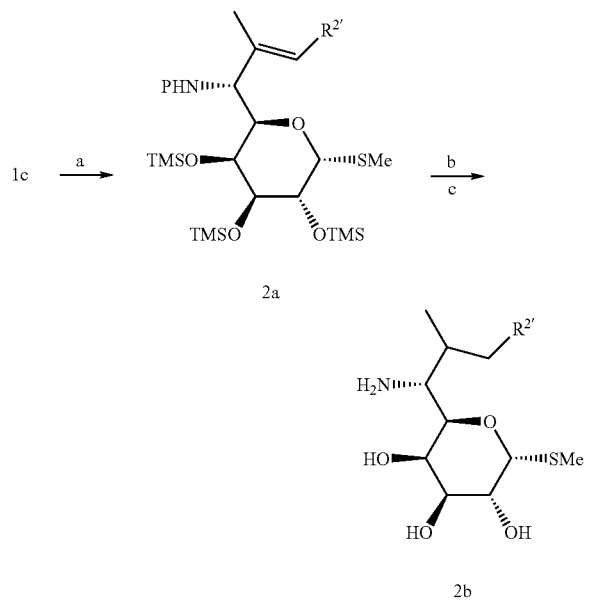

(a) Wittig olefination ($R^{2'}CH_2Ph_3^+X^-$ or $R^{2'}CH_2PO(OEt)_2$, base, solvent); (b) $H_2$/Pd; (c) Global de-protection As shown in Scheme 2, a keto-lincosamine intermediate 1c is reacted to form an alkene using the Wittig or Horner-Wadsworth-Emmons reaction. In this reaction, a suitable phosphonium salt or phosphonate is deprotonated using a strong base to form a phosphorus ylide. Suitable phosphonium salts which can be used are alkyltriphenylphosphonium halides, which can be prepared by the reaction of triphenylphosphine and an alkyl halide. Suitable phosphorous compounds include, for example, methyltriphenylphosphonium bromide, diethyl(cyanomethyl)phosphonate and the like. Suitable strong bases which can be used to form the ylide include organolithium reagents, potassium tert-butoxide, and the like. The formation of the phosphorus ylide is typically conducted under an inert atmosphere, such as $N_2$, in an inert organic solvent such as toluene, THF, or the like, at low temperatures.

After formation of the phosphorus ylide, the product 1c is added to the reaction. The reaction conveniently can be performed at temperatures between −40° C. and room temperature and is stirred until completion, typically 1 to 4 hours. The resulting organic solution is worked-up and chromatography of the crude product on silica provides the alkene product 2a.

The product 2a is then hydrogenated to provide the saturated product 2b. The hydrogenation is typically performed in a polar organic solvent such as methanol, ethanol, and the like, using 10% Palladium on carbon in a Parr bottle. The bottle is purged, and charged with $H_2$ to approximately 50 to 70 psi and shaken until completion, typically approximately 12 to 24 h. The resulting reaction mixture is filtered, e.g., through celite, and rinsed with a polar organic solvent such as methanol. The organic solution is worked up by transferring to a resin funnel containing dry, washed Dowex 50w-400x $H^+$ form and shaken. After washing the resin with methanol and water, the product 2b is eluted from the resin by washing with 5% TEA in MeOH. The product can also be purified by silica gel column chromatography.

Scheme 3 illustrates a general synthesis of a lincosamine intermediate 3b wherein P is an N-protecting group, preferably either Cbz or Boc, one of $R^2$ or $R^3$ is alkyl and the other is —OH, and $R^1$ is as defined for formula (I).

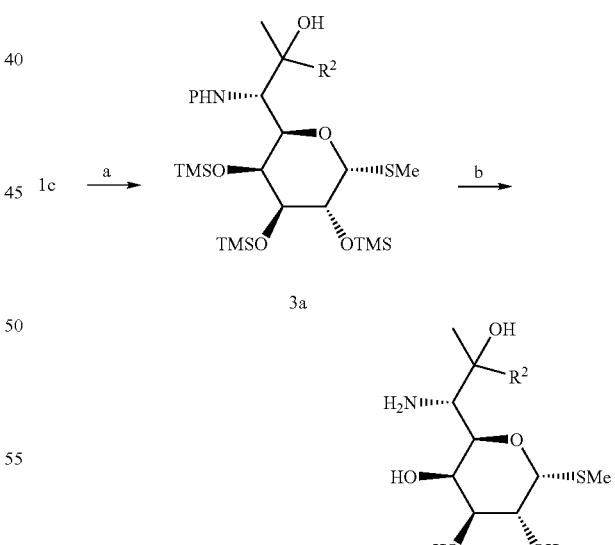

(a) $R^2M$ (carbon nucleophile); (b) (i) TMS de-protection ($H^+$ or $F^-$) and (ii) N-deprotection As shown in Scheme 3, suitable carbon nucleophiles are added to 7-ketolincosamine intermediate 1c in suitable inert organic solvents to provide 7-hydroxy lincosamine intermediate 3b. Suitable carbon nucleophiles include methylmagnesium chloride, diethyl zinc, sodium acetylide, and the like, and suitable inert organic solvents which can be used include THF, diethyl ether, toluene, and the like. The reaction is typically conducted at reduced temperatures, approximately at 0° C., for about 3 to 5 h. The reaction is then quenched with a saturated aqueous acidic solution, such as saturated aqueous $NH_4Cl/H_2O$. The quenched mixture is then worked up and can be purified by chromatography to provide the product 3b.

Scheme 4 below illustrates a general synthesis of a lincosamine intermediate 4b wherein P is a N-protecting group, preferably Boc, $R^1$ is as defined for formula (I), and $R^2/R^3$ is an oxime ($=NOR^7$), wherein $R^7$ is as defined for formula (I).

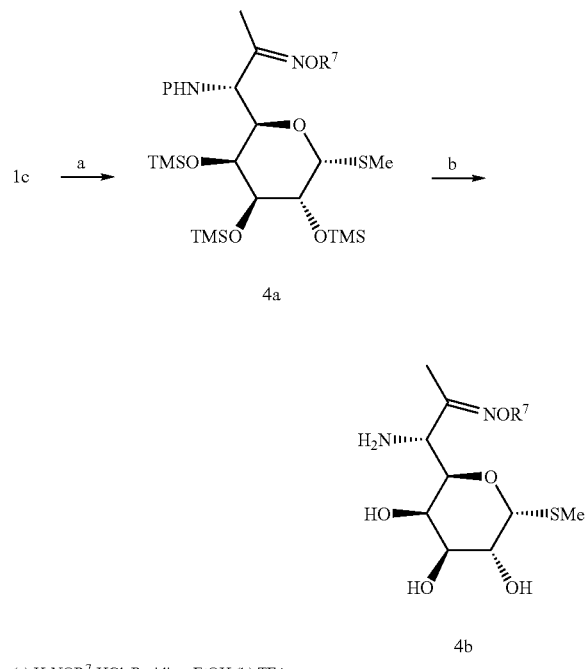

(a) $H_2NOR^7$·HCl, Pyridine, EtOH (b) TFA

As shown in Scheme 4, the lincosamine intermediate 1c is converted to the oxime by stirring in the presence of a suitable reagent such as O-trimethylsilylhydroxylamine, O-alkylhydroxylamine hydrochloride (for example, O-methylhydroxylamine hydrochloride), and the like. The reaction is typically conducted in a polar organic solvent such as methanol. The reaction conveniently can be conducted at rt in approximately 8 to 24 h. The solvent is removed to provide the N-protected product 4a.

Removal of the protecting group can be carried out with acids, such as triflouoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product 4b.

Scheme 5 below illustrates a general synthesis of a lincosamine intermediate 5b wherein $R^2$ and $R^3$ are both fluorine, P is an N-protecting group, preferably Cbz or Boc, and $R^1$ is as defined for formula (I).

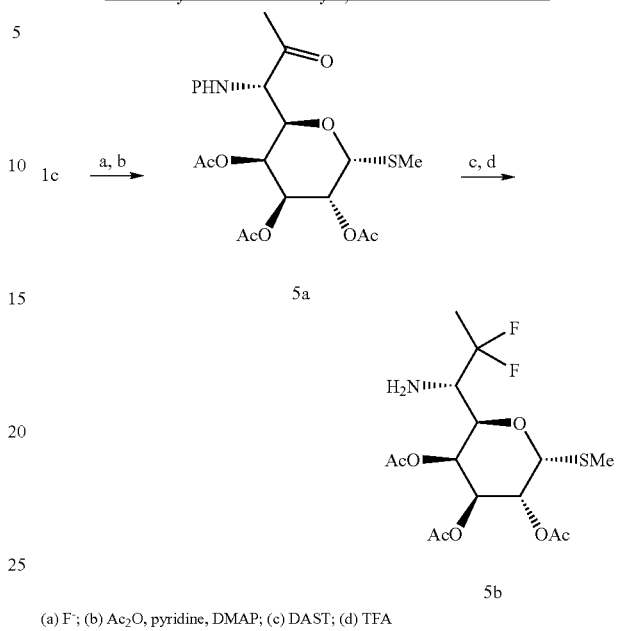

(a) $F^-$; (b) $Ac_2O$, pyridine, DMAP; (c) DAST; (d) TFA

As shown in Scheme 5, the lincosamine intermediate 1c is contacted with a suitable fluoride in an inert organic solvent. Suitable fluorides which can be used include tetrabutylammonium fluoride, Amberlite resin A-26 $F^-$ form, HF.pyridine and the like. Suitable inert organic solvents include THF, acetonitrile, dichloromethane, dioxane, and the like. The reaction conveniently can be conducted at rt in about 1 to 2 h. The product (not shown) can be purified on a silica gel column.

The O-protecting groups on the product obtained from the column are converted by contact with acetic anhydride and dimethylaminopyridine (DMAP) in a suitable mixture of an inert organic solvent and an organic base, such as, for example, dichloromethane and pyridine. The reaction conveniently can be conducted at rt in approximately 6 to 12 hours. The product can be purified on silica gel column to provide product 5a.

The product 5a is contacted with a suitable fluorinating reagent and then the N-protecting group is removed to provide the product 5b. Suitable fluorinating reagents which can be used include, for example, dimethylaminosulfurtrifluoride, [bis(2-methoxyethyl)-amino]sulfurtrifluoride, and the like. The reaction is typically conducted in an inert organic solvent such as dichloromethane, ethylacetate, THF, and the like at room temperature in approximately 6 to 12 h.

Removal of the protecting group can be carried out with acids, such as triflouoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product 5b.

Scheme 6 below illustrates a general synthesis of a lincosamine intermediate 6b wherein P is a N-protecting group, preferably trifluoroacyl, one of $R^2$ and $R^3$ is hydrogen and the other is Cl, Br or I, and $R^1$ is as defined for formula (I).

Scheme 6. General synthesis of 7-deoxy-7-halolincosamines 6b.

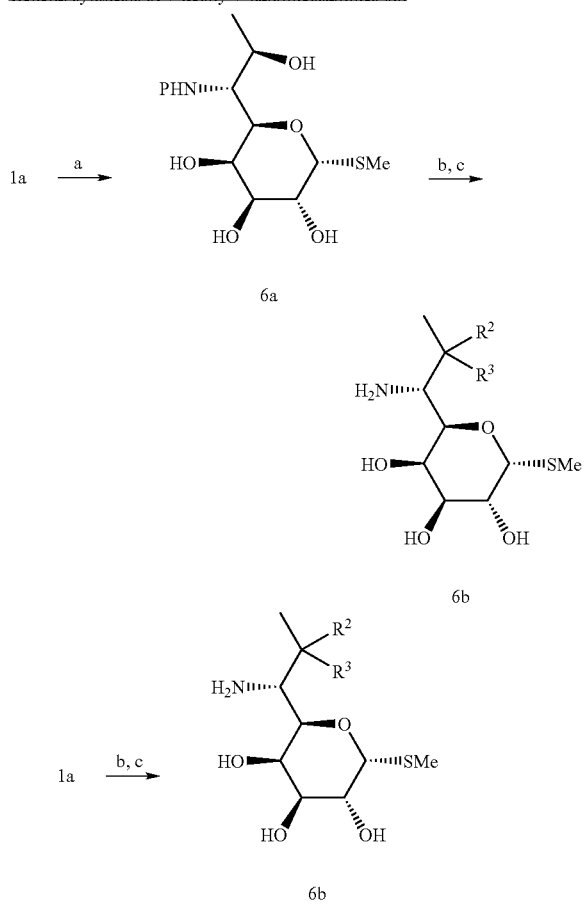

(a) Methyltrifluoracetate, triethyamine; (b) Halogenating reagent (i.e. PPh$_3$X$_2$ where X = Cl, Br, I or preferably a 1-N-(halomethylene)piperidine salt); (c) aqueous base (i.e. KOH, ammonia).

As shown in Scheme 6, lincosamine intermediate 1a is N-protected with a suitable trifluoroacylating reagent in the presence of base in a suitable organic solvent. Suitable trifluoroacylating reagents include methyltrifluoroacetate, ethyl trifluorothioacetate, trifluoroacetic anhydride and the like. Suitable organic solvents include methanol, THF, acetonitrile, dichloromethane, dioxane, and the like. The reaction conveniently can be conducted at ambient temperature in about 2 to 4 h. Protected lincosamide intermediate 6a may be purified by crystallization or used crude in the subsequent reactions.

Halogenation of the 7-position of protected intermediate 6a is accomplished by contact with a suitable Rydon reagent as described by Magerlein, B. J.; Kagen, F. *Journal of Medicinal Chemistry*, 1969, 12, 780–784 or an amidehalide salt as disclosed in European Pat. No. 0161794. Suitable Rydon reagents include triphenylphosphene dichloride, triphenylphosphene dibromide and the like in an inert organic solvent such as acetonitrile, dichloromethane, dichloroethane, or toluene. Suitable haloamide salt reagents include 1-N-(Chloromethylene)-piperidine chloride 1-N-(Chloromethylene)-N-methylmethaninium chloride and the like in inert organic solvents such as acetonitrile, dichloromethane, dichloroethane, or toluene. The reaction is typically conducted at temperatures ranging from approximately 24° C. to 70° C., for 16 to 24 h with an excess of halogenating reagent. Hydrolysis of the halogenated product adducts (not shown) and removal of the protecting group in aqueous base provides 7-deoxy-7-halolincosamide intermediate 6b. Suitable bases are NaOH, KOH and concentrated ammonia in water or admixtures of water with miscible organic solvent such as methanol, acetonitrile, tetrahydrofuran, dioxane and the like. The reaction is typically conducted under conditions that precipitate the crude 7-deoxy-7-halolincosamide intermediate 6b. 7-deoxy-7-halolincosamide intermediate 6b may be purified by crystallization from an appropriate solvent or solvent system.

Alternately 1c may be directly halogenated as disclosed in U.S. Pat. No. 3,496,136 or U.S. Pat. No. 3,502,646 by contact with a suitable Rydon reagent or amidehalide salt as disclosed in European Pat. No. 0161794. Hydrolysis of the halogenated product adduct (not shown) in aqueous base provides 7-deoxy-7-halolincosamide intermediate 6b.

Scheme 7 below illustrates a general synthesis of trans R$^{9'''}$-proline intermediates 7d, wherein R$^{9'''}$ is alkyl or substituted alkyl.

Scheme 7. General synthesis of trans-alkylprolines 7d.

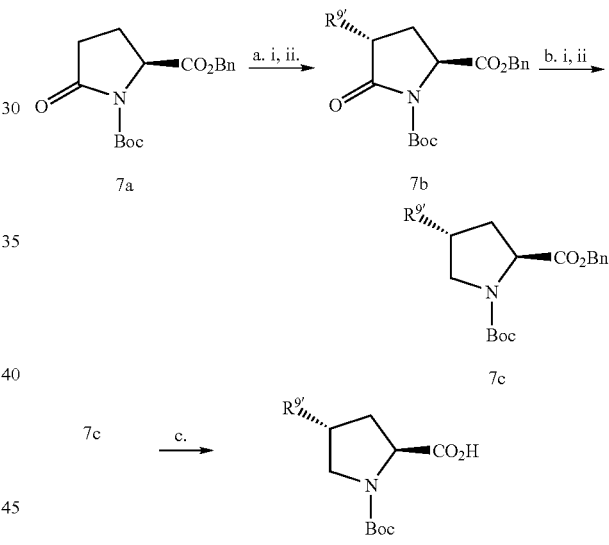

(a) (i) LiHMDS, THF -78° C., (ii) bromoalkene; (b) (i) LiBHEt$_3$, THF -78° C., (ii) BF$_3$•OEt$_2$, Et$_3$SiH; (c) H$_2$ Pd/C.

As shown in Scheme 7, a protected 5-oxoproline 7a is enolated with a suitable base and then alkylated with a suitable alkylating agent in an inert organic solvent to provide a lactam 7b (wherein R$^{9'}$ is alkenyl), as described in the literature procedure by Zhang, R.; et. al. *Journal of the American Chemical Society*, 1998, 120, 3894–3902. Compound 7a is commercially available from vendors such as Bachem. Alternatively, 7a can be prepared by methods well known in the art. Suitable basic enolating agents include LiHMDS, LiN(iPr)$_2$, and the like, and suitable alkylating agents include allylic and benzylic bromides, for example, 4-bromo-2-methyl-2-butene and cis-1-bromo-2-pentene, allylbromide, and the like.

The lactam 7b is reduced using a suitable reducing agent to provide a pyrrolidine 7c, wherein R$^{9'}$ is alkenyl. The reduction is preformed by a two-step sequence involving Superhydride® reduction of the lactam to the hemiaminal and the subsequent reduction of the hemiaminal. Suitable reducing agents that can be used include $Et_3SiH/BF_3 \cdot OEt_2$, $Et_3SiH/TiCl_4$, and the like.

The pyrrolidine 7c is then hydrogenated to simultaneously remove the unsaturation in the $R^{9'}$ substituent and remove the benzyl protecting group from the carboxylic acid to provide the product 7d. The hydrogenation is typically performed in a polar organic solvent such as methanol, ethanol, and the like, using 10% Palladium on carbon in a Parr bottle. The bottle is purged, and charged with $H_2$ to approximately 50 to 70 psi and shaken until completion, typically approximately 5 to 24 h. The reaction mixture is filtered, e.g., through a celite pad, and washed with a polar organic solvent, such as methanol. Evaporation of the combined washings and filtrate affords the product 7d, wherein $R^{9'''}$ is an alkyl or substituted alkyl.

Scheme 8 below illustrates a general synthesis of trans-$R^9$-proline intermediates 8b and 8c, wherein $R^{9'}$ is alkenyl or substituted alkenyl and $R^{9'''}$ is alkyl or substituted alkyl.

Scheme 8.
General synthesis of trans-$R^9$-substituted prolines 8b, wherein $R^{9'}$ is alkenyl and $R^{9'''}$ is the saturated form of $R^{9'}$, and 8c, wherein $R^{9'}$ is alkenyl or substituted alkenyl.

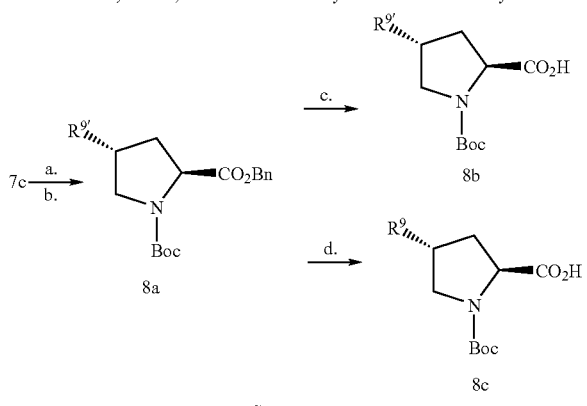

(a) i.O$_3$, DCM, -78° C., ii.DMS; (b) $R^9CH_2P^+Ph_3$ salt, Base; (c) H$_2$, Pd/C; (d) Aq. LiOH, THF.

As shown in Scheme 8, the product 7c is ozonized to provide the aldehyde which is then treated under Wittig conditions to provide 8a. The ozonolysis reaction is typically conducted in an anhydrous inert organic solvent, such as dichloromethane, dioxane, THF, and the like, at low temperatures, e.g., −78° C., followed by quenching of the reaction with a reducing agent such as DMS, Ph$_3$P.

The aldehyde is reacted with a suitable phosphonium salt in the presence of a strong base in an inert organic solvent. Suitable phosphonium salts which can be used include, for example, fluorobenzyl phosphonium chloride, 4-chlorobenzyl phosphonium chloride, dibromofluoromethane and triphenylphosphine, and the like. Suitable bases which can be used include potassium t-butoxide, organolithium reagents, and activated zinc. Suitable organic solvents which can be used include toluene, THF, dimethylacetamide, and the like. The reaction is typically conducted in an inert atmosphere, such as under nitrogen, with vigorous stirring. The reaction is typically conducted at rt to approximately 110° C. for 1 to 2 h. The resulting reaction mixture is appropriately worked-up and can be purified by chromatography to provide 8b.

The intermediate 8b is then hydrogenated to provide the product 8c. The hydrogenation is typically performed in a polar organic solvent such as methanol, ethanol, and the like, using 10% Palladium on carbon in a Parr bottle. The bottle is purged, and charged with $H_2$ to approximately 40 to 70 psi and shaken until completion, typically approximately 4 to 24 h. The reaction mixture is filtered, e.g., through a celite pad and washed several times with a polar organic solvent, such as methanol. Evaporation of the combined washings and filtrate affords the product 8c, wherein $R^{9'''}$ is an alkyl or substituted alkyl and corresponds to the saturated form of product 8b.

Alternately, intermediate 8b may be saponified by methods well known to those of skill in the art by contact with aqueous alkali and a miscible organic co-solvent to provide $R^{9'}$ unsaturated amino acid intermediate 8c.

Scheme 9 below illustrates a general synthesis of a proline intermediate 9d wherein $R^9$ is as defined for formula (I).

Scheme 9.
General synthesis of cis-$R^9$ or trans-$R^9$ substituted cyclic amino acids 9d

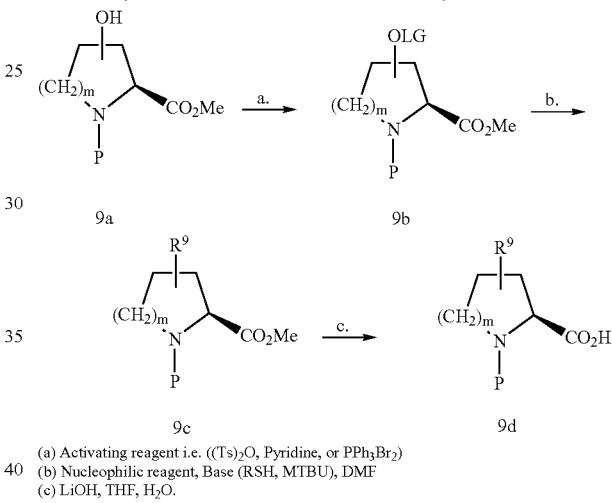

(a) Activating reagent i.e. ((Ts)$_2$O, Pyridine, or PPh$_3$Br$_2$)
(b) Nucleophilic reagent, Base (RSH, MTBU), DMF
(c) LiOH, THF, H$_2$O.

Scheme 10 below illustrates a general synthesis, as described in Shuman, R. T.; Journal of Organic Chemistry. 1990, 55, 741–750, of substituted pyridine carboxylic acid intermediates 10b, wherein $R^9$ is as defined for formula (I).

Scheme 10
General synthesis of substituted pyridin-2-yl carboxylic acids 10b.

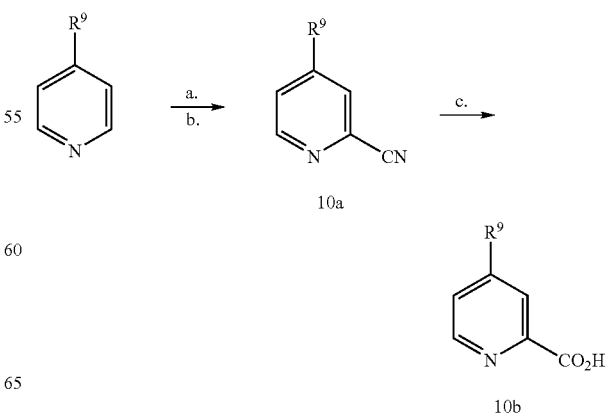

As shown in Scheme 10, an appropriately substituted pyridine is contacted with a suitable oxidizing agent in an inert organic solvent. The appropriately substituted pyridine starting materials are commercially available from vendors such as Aldrich and Sigma. Alternatively, these pyridines can be prepared by methods well known in the art. Suitable oxidizing agents that can be used include hydrogen peroxide, MCPBA, and the like. The reaction is typically conducted at reflux for 6 to 12 h. The reaction mixture is then contacted with a suitable cyanide reagent to provide the cyano-substituted pyridine 10a. Suitable cyanide reagents that can be used include trimethylsilyl cyanide, HCN, and the like. Suitable inert organic solvents include dichloromethane, dioxane, THF, and the like. The reaction conveniently can be conducted at rt in approximately 6 to 12 h. The reaction mixture is worked up to provide the cyano-substituted pyridine 10a.

The cyano-substituted pyridine 10a is then hydrolyzed to provide the pyridin-2-yl carboxylic acid 10b by contact with a suitable acid. Suitable acids for hydrolyzing the cyano group to the carboxylic acid include hydrochloric acid, aqueous sulfuric acid, and the like. The reaction is typically conducted at reflux in 6 to 12 h.

Scheme 11 below illustrates a general synthesis of pyridine and piperidine intermediates, wherein $R^9$ is as defined for formula (I).

Scheme 11
General synthesis of 4-substituted intermediates 11c, 11d, and 11e.

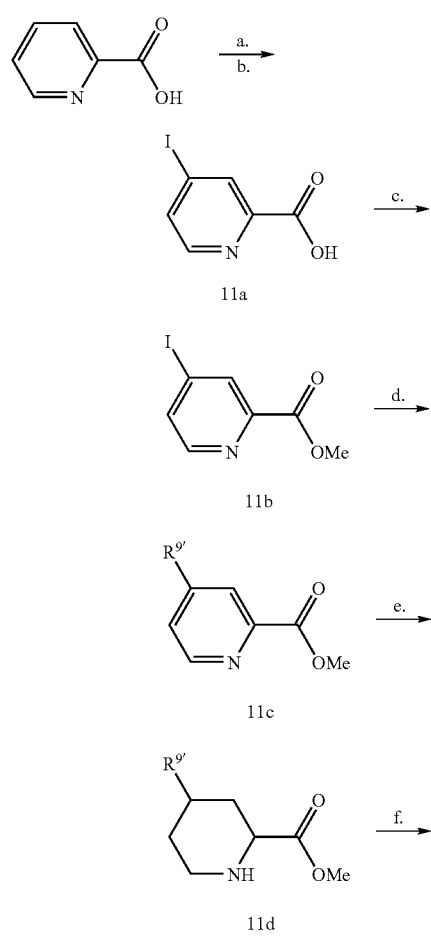

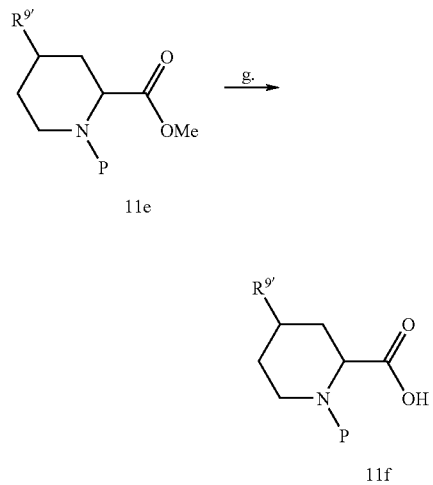

(a) SOCl$_2$, MeOH (not shown) (b) HI, H$_3$PO$_3$, (c) MeOH, H$_2$SO$_4$ (cat.), (d) Pd(OAc)$_2$, CuI, PPh$_3$R$^9$ alkyne (e) PtO$_2$, H$_2$, H$^+$ (f) N-protection reagent (i.e.(Boc)$_2$O, CbzCl ect.) base (g) Aq. LiOH, Dioxane.

Scheme 12 below illustrates a general synthesis of a proline intermediate 12d wherein $R^9$ is as defined for formula (I).

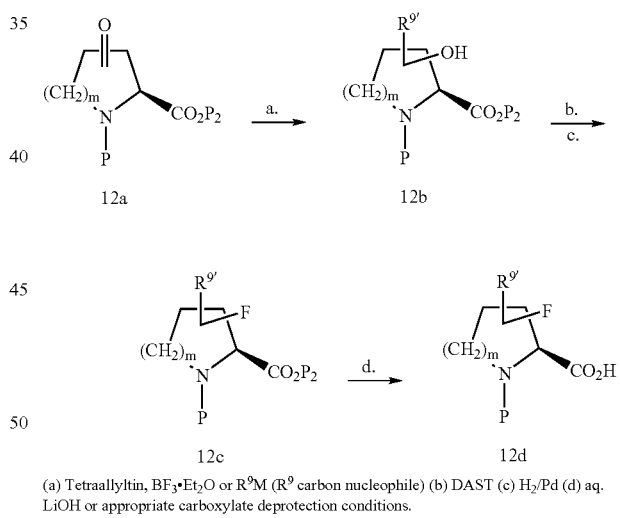

(a) Tetraallyltin, BF$_3$•Et$_2$O or R$^9$M (R$^9$ carbon nucleophile) (b) DAST (c) H$_2$/Pd (d) aq. LiOH or appropriate carboxylate deprotection conditions.

As shown in Scheme 12, the ketoproline 12a is allylated to form a hydroxy allyl proline, whose hydroxy functionality is subsequently replaced by fluorine. Hydrogenation of the allyl double bond provides the fluoro alkyl proline 12c, which is deprotected to form 12d.

Scheme 13 below illustrates the coupling reaction of a lincosamine intermediate, prepared as described above in Schemes 1–6, and a pyrrolidinyl or piperidyl carboxylic acid, prepared as described above in Schemes 7–12, wherein $R^1$, $R^2$, $R^3$, $R^6$, and $R^9$ are as defined for formula (I) and $P^1$ is a suitable O-protecting group and $P^2$ is a suitable N-protecting group.

Scheme 13. General coupling and deprotection methods.

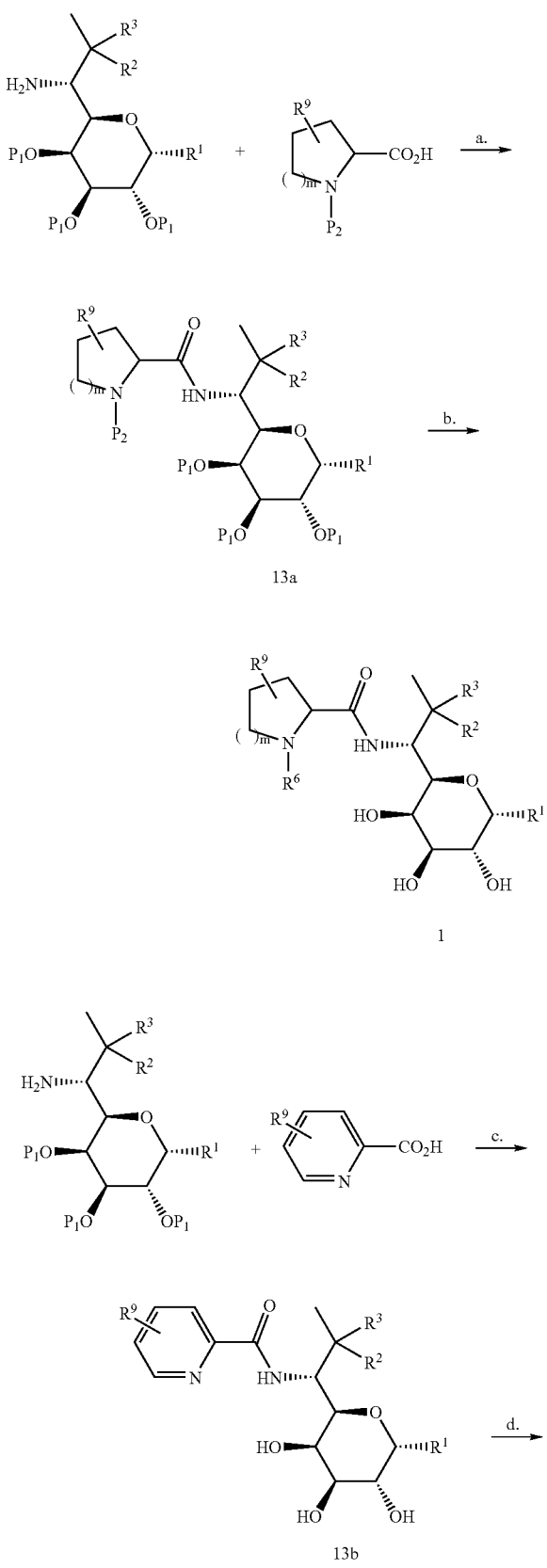

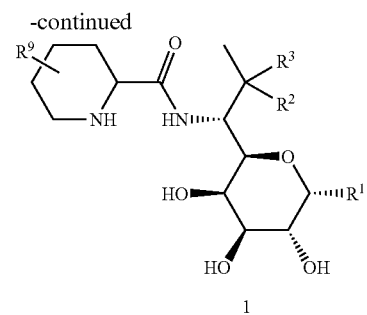

As shown in Scheme 13, an appropriately 7-substitiitued lincosamine intermediate (prepared, for example, according to any one of Schemes 1–6) and an appropriately substituted pyrrolidinyl or piperidyl carboxylic acid (prepared, for example, according to any one of Schemes 7–9 or 11–12) are condensed under reactive conditions, preferably in an inert organic solvent, in the presence of a coupling reagent and an organic base. This reaction can be performed with any number of known coupling reagents, such as O-(7-azabenzotriazol-1-yl)-N,N,N',N'-tetramethyluronium hexafluorophosphate (HATU), 1-hydroxybenzotriazole hydrate (HOBT) with carbodiimides, isobutylchloroformate, and the like. Suitable organic bases include diisopropylethylamine (DIEA), triethylamine (TEA), pyridine, N-methyl morpholine, and the like. Suitable inert organic solvents which can be used include, for example, N,N-dimethylformamide, acetonitrile, dichloromethane, and the like. This reaction is typically conducted using an excess of carboxylic acid to lincosamine at temperatures in the range of about 0° C. to about 50° C. The reaction is continued until completion, which typically occurs in from about 2 to 12 hours.

Removal of the protecting groups can be carried out with acids, such as trifluoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product.

Also as shown in Scheme 13, an appropriately 7-substitiitued lincosamine intermediate (prepared, for example, according to any one of Schemes 1–6) and an appropriately substituted pyridin-2-yl carboxylic acid (prepared, for example, according to Scheme 10) are condensed under reactive conditions, preferably in an inert organic solvent, in the presence of a coupling reagent and an organic base, as described above.

The pyridine 13b is hydrogenated to provide the piperidyl product. The hydrogenation is typically performed in a polar organic solvent such as methanol, ethanol, and the like, using Platinum (IV) oxide in the presence of an acid such as HCl, acetic acid, and the like, in a Parr bottle. The bottle is purged, and charged with $H_2$ to approximately 40 to 70 psi and shaken until completion, typically approximately 24 h. The reaction mixture is filtered, e.g. through a celite pad, and washed several times with a polar organic solvent such as methanol. Evaporation of the combined washings and filtrate affords the piperidyl product.

The coupling of pyridine carboxylic acids and lincosamines to provide pyridine 13b followed by reduction to the piperidyl product may also be conducted as described in Birkenmeyer, R. D; et al; *Journal of Medicinal Chemistry* 1984, 27, 216–223.

Scheme 14 below illustrates the coupling reaction of a lincosanine intermediate, prepared as described above in Schemes 1–6, and a pyrrolidinyl or piperidyl carboxylic acid, prepared as described above in Schemes 7–12, wherein $R^1$, $R^2$, $R^3$, and $R^9$ are as defined for formula (I) and P is a suitable N-protecting group. The coupling reactions described herein may also be used to coupling azetidinyl and azepane carboxylic acids.

Scheme 15 illustrates general synthetic methods for building protected 1-allylic intermediates 15b, 15c, 15e, 15f. where $R^2$, $R^3$, $R^9$ are as defined for formula (I) and $P_1$ and $P_2$ indicate suitable N- and O-protecting groups, respectively.

Scheme 14.
General synthesis of 4-thioetherlincosamides 14c.

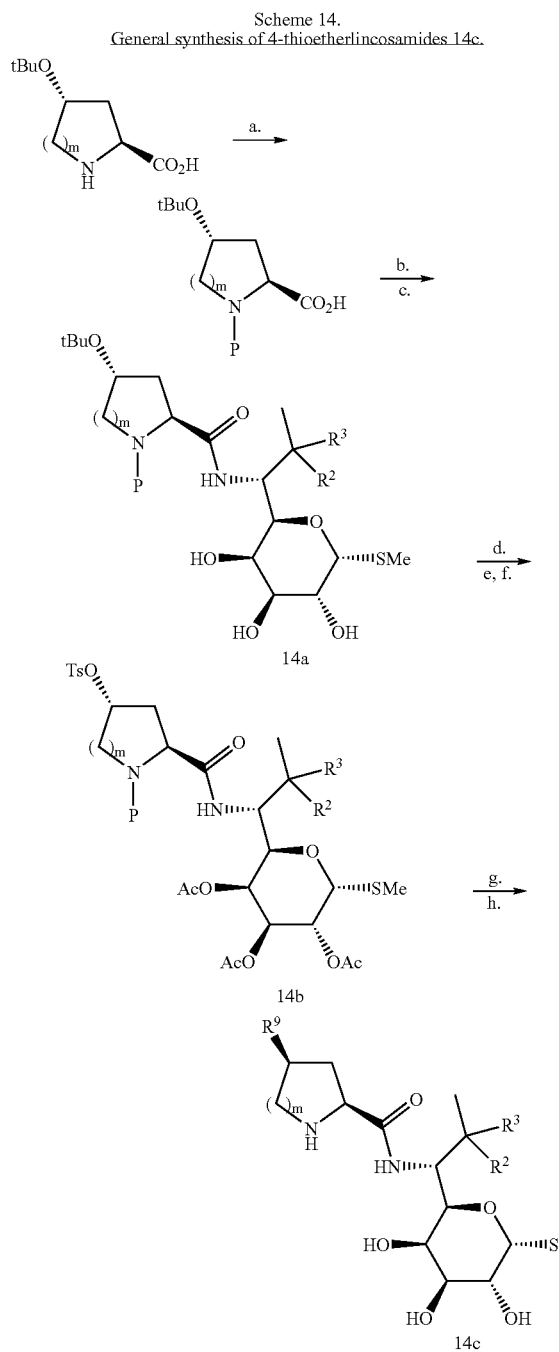

(a) (TEA, CF₃COOEt) (b) MTL, BSTFA, TEA, HATU (c) Dowex H⁺ Resin MeOH. (d) (Ac)₂O, pyridine, DMAP (e) TFA, DMS, DCE, H₂O (f) (Ts)₂O, Pyridine, DCM (g) R⁹H, MTBU (wherein R⁹ is selected such that an alkylsulfanyl or substituted alkylsulfanyl substituent is introduced; a sulfoxide or sulfone substituent is also within the scope of the invention and may be obtained by conventional oxidizing methods well known in the art (h) MeONa, MeOH.

Scheme 15.
General synthesis of building protected 1-allylic intermediates 15b, 15c, 15e, 15f.

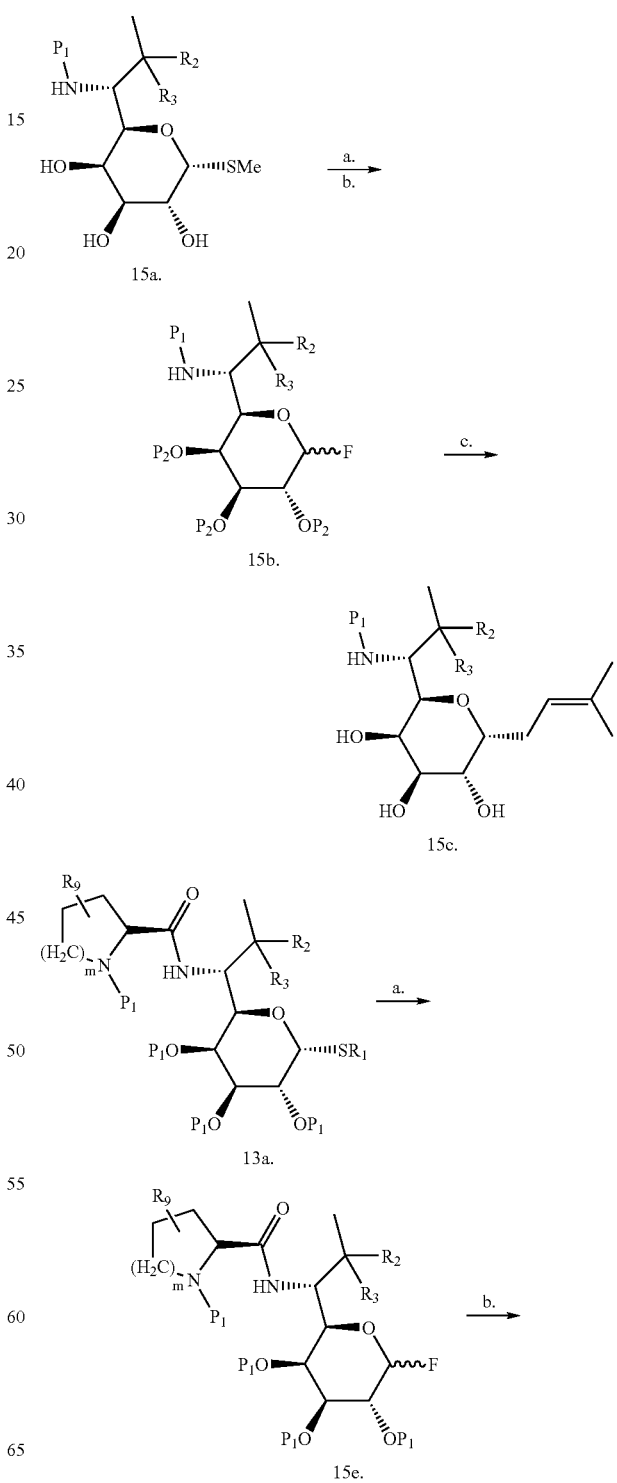

-continued

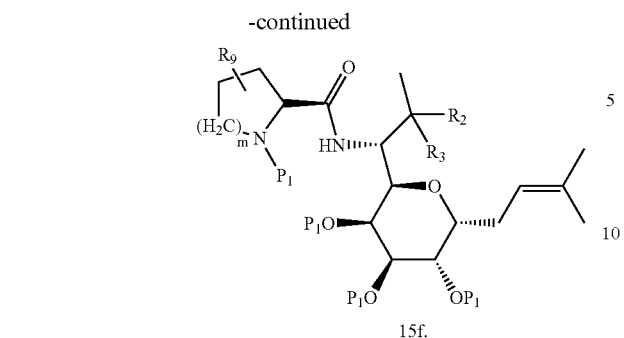

15f.

(a) DAST, NBS
(b) BF$_3$·Et$_2$O, CH$_3$CN, TMS, CH$_2$CH=CH$_2$.

In scheme 15, P$_1$ and P$_2$ are preferentially differentially removable protecting groups. Displacement of the methylsulfanyl (methylsulfanyl) group by a fluoro substituent is accomplished by contact with DAST in the presence of N-bromosuccinimide (NBS) and in suitable solvent such as dichloromethane (DCM) which provides for compounds 15b and 15e.

In turn, the fluoro group is displaced to form the allyl substituent by contact with trimethylallylsilane in the presence of the trifluoroborate diethyl ether complex. Subsequent removal of the Boc (t-butoxycarbonyl) protecting group with trifluoroacetic acid (TFA) provides for the deprotected product. Alternatively, conventional defluorination of the 1-des(methylsulfanyl)-1-fluoro-2,3,4-tri-O-benzyl-7-deoxy-7-methyllincosamine leads to the 1-des(methylsulfanyl)-2,3,4-tri-O-benzyl-7-deoxy-7-methyllincosamine (i.e., R$^1$ is hydrogen).

Conventional amide coupling of the carboxyl group of N-Boc-4-pentyl-proline with 1-des(methylsulfanyl)-1-allyl-2,3,4-tri-O-benzyl-7-deoxy-7-methyllincosamine, in the presence of a coupling promoter such as O-(7-azabenzotriazol-1-yl)-N,N,N',N'-tetramethyluronium hexafluorophosphate (HATU) in dimethylformamide (DMF) and triethylamine (TEA) leads to compounds 15c and 15f. The allyl group of compounds 15c and 15f provides a ready source for numerous modifications at the 1-position of the lincosamine group.

Scheme 16 illustrates general synthetic methods for building, wherein R$^1$ is alkylsulfanyl, substituted alkylsulfanyl, R$^2$, R$^3$, R$^9$ are as defined for formula (I) and P$_1$ and P$_2$ indicate suitable N- and O-protecting groups, respectively.

Scheme 16. Displacement of Fluoro by Sulfanyl Moiety

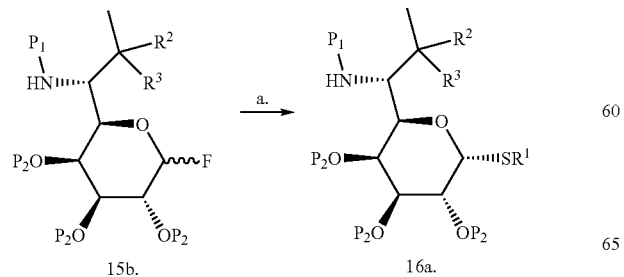

15b.                16a.

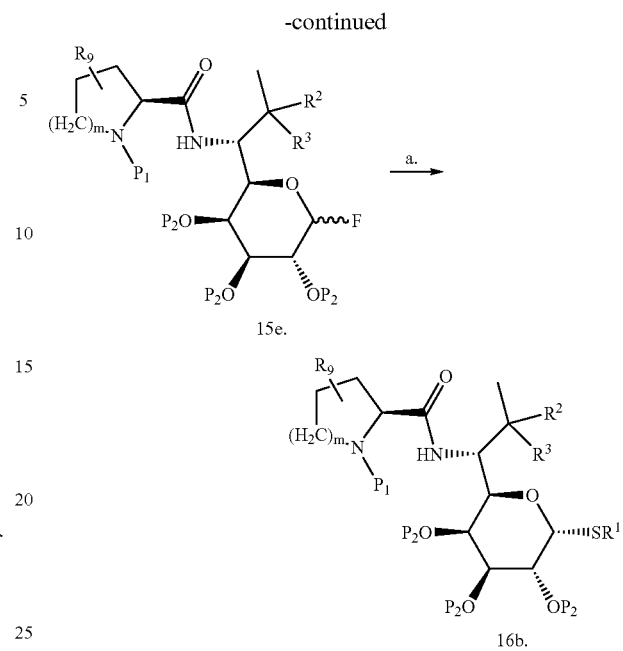

15e.

16b.

Scheme 16 illustrates that nucleophilic displacement of the 1-fluoro group by a suitable sulfanyl moiety can be accomplished either on the lincosame moiety to form compound 16a or on the coupled lincosamine derivative to form compound 16b. The nucleophilic displacement occurs using conventional techniques well known in the art.

Scheme 17 illustrates general synthetic methods for building alcohol and ether substituents at the 1-position, wherein R$^2$, R$^3$, R$^9$ are as defined for formula (I), P$_1$ and P$_2$ indicate suitable N- and O-protecting groups, respectively, and R is hydrogen, alkyl, substituted alkyl, aryl, substituted aryl, heteroaryl, or substituted heteroaryl.

Scheme 17
General synthesis of alcohol and ether 1-position lincosamine derivatives

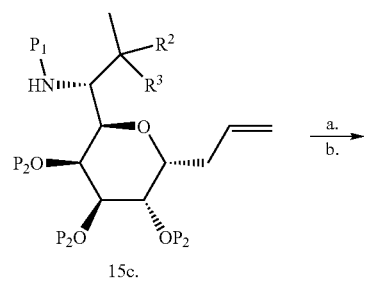

15c.

17c.

-continued

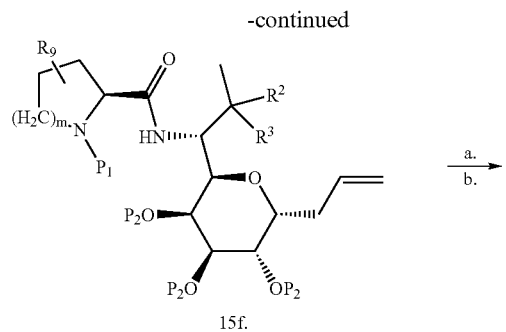
15f.

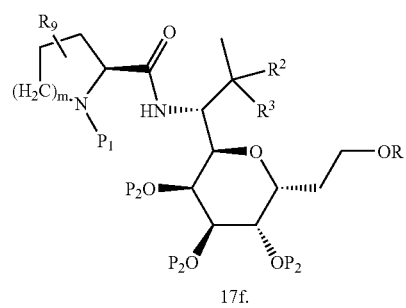
17f.

(a) i.O₃-78° C. to 0° C., ii. NaBH₄ (b) RX, Base wherein R may be selected from the group consisting of hydrogen, alkyl, substituted alkyl, aryl, substituted aryl, heteroaryl, and substituted heteroaryl.

Scheme 17 illustrates that the 1-(dessulfanylmethyl)-1-allyl-lincosamine derivative can be oxidized to the corresponding aldehyde which is reduced to the primary alcohol by conventional methods such as ozonolysis followed by reduction with sodium borohydride preferably in a protic solvent such as methanol. Subsequently, the primary alcohol is contacted with an appropriate base such as sodium hydride and a suitable alkyl halide to form the ether derivative as either the lincosamine entity or as the coupled lincosamine derivative to provide for compounds 17c and 17f respectively.

Scheme 18 illustrates deprotection schemes for 15f, 16b, and 17f, wherein $R^2$, $R^3$, $R^9$ are as defined for formula (I), P is a suitable N-protecting groups, and $R^1$ is consistent with schemes 15, 16, and 17, respectively.

Scheme 18.

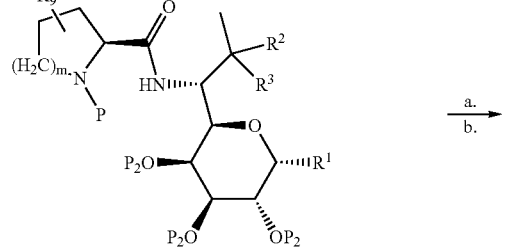
15f, 16b, 17b

-continued

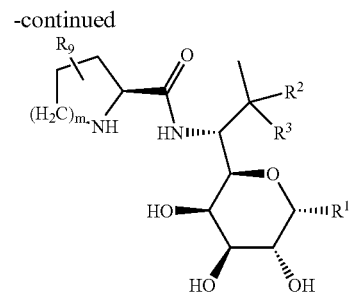
1.

Scheme 18 illustrates that conventional deprotection leads to compounds of formula (I).

Scheme 19 below illustrates the alkylation of nitrogen of the pyrrolidinyl or piperidyl ring, wherein $R^6$ is alkyl or hydroxyalkyl and $R^1$, $R^2$, $R^3$, and $R^9$ are as defined for formula (I).

Scheme 19

General synthesis of 1'-N-substituted lincosamides. (a) alkylating agents

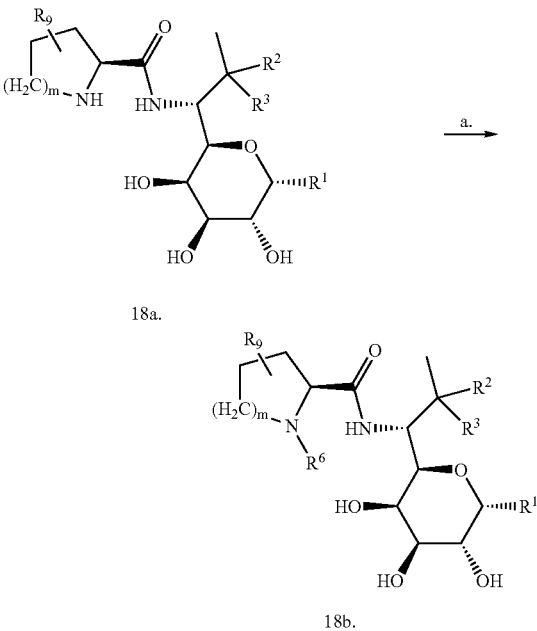

(a) alkylating agents

As shown in Scheme 19, the lincosamine 18a can be N-substituted by contact with an alkylating agent in the presence of a suitable base to provide a product 18b. Suitable alkylating agents that can be used include epoxides, alkyl bromides, and the like. Suitable bases that can be used include potassium carbonate, cesium carbonate triethylamine, and the like. The alkylation reaction is typically conducted in a polar organic solvent such as methanol or DMF. The alkylation reaction is typically conducted at low temperatures in the range of 0° C. to −10° C. for 10 to 20 h.

In Scheme 20, $R^2$, $R^3$, $R^6$ and $R^9$ are as defined for formula (I), $P_2$ is a suitable O-protecting group.

Scheme 20.

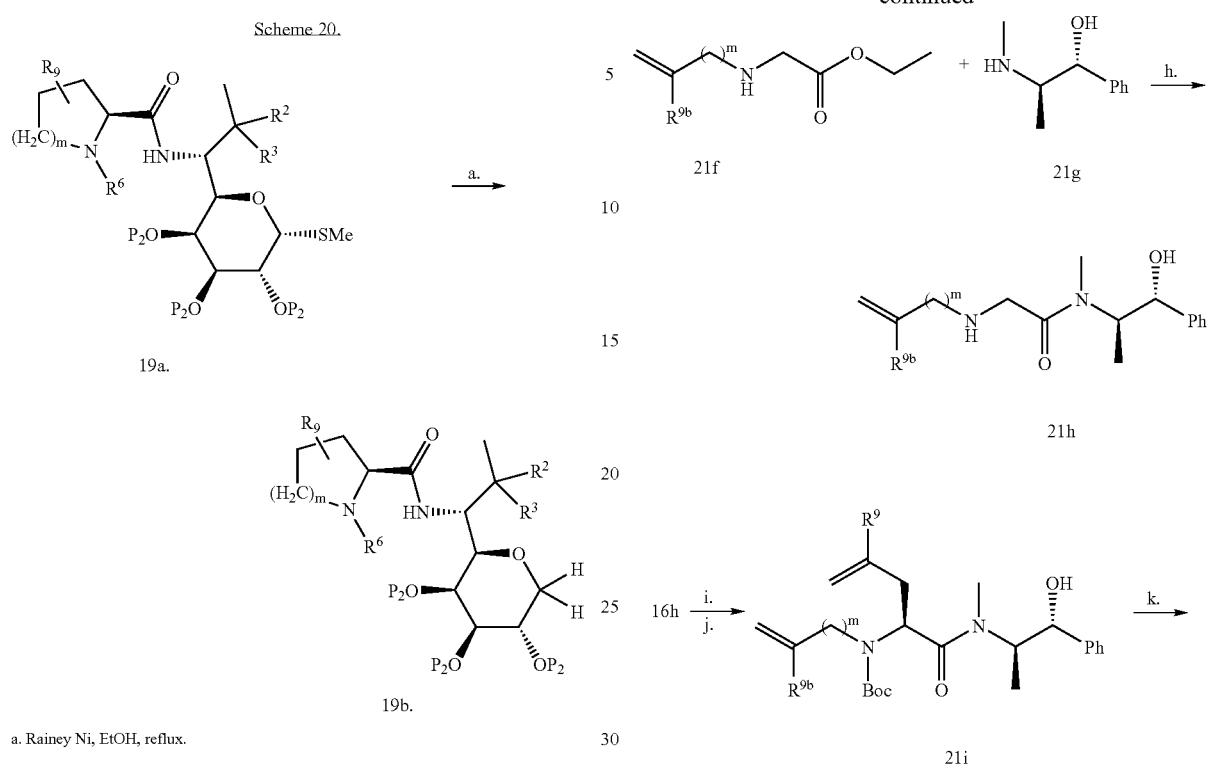

a. Rainey Ni, EtOH, reflux.

Scheme 21 below illustrates a versatile synthetic sequence allowing the synthesis of unsaturated N-protected amino acids 21k ring, wherein m and $R^9$ are as defined for formula (I).

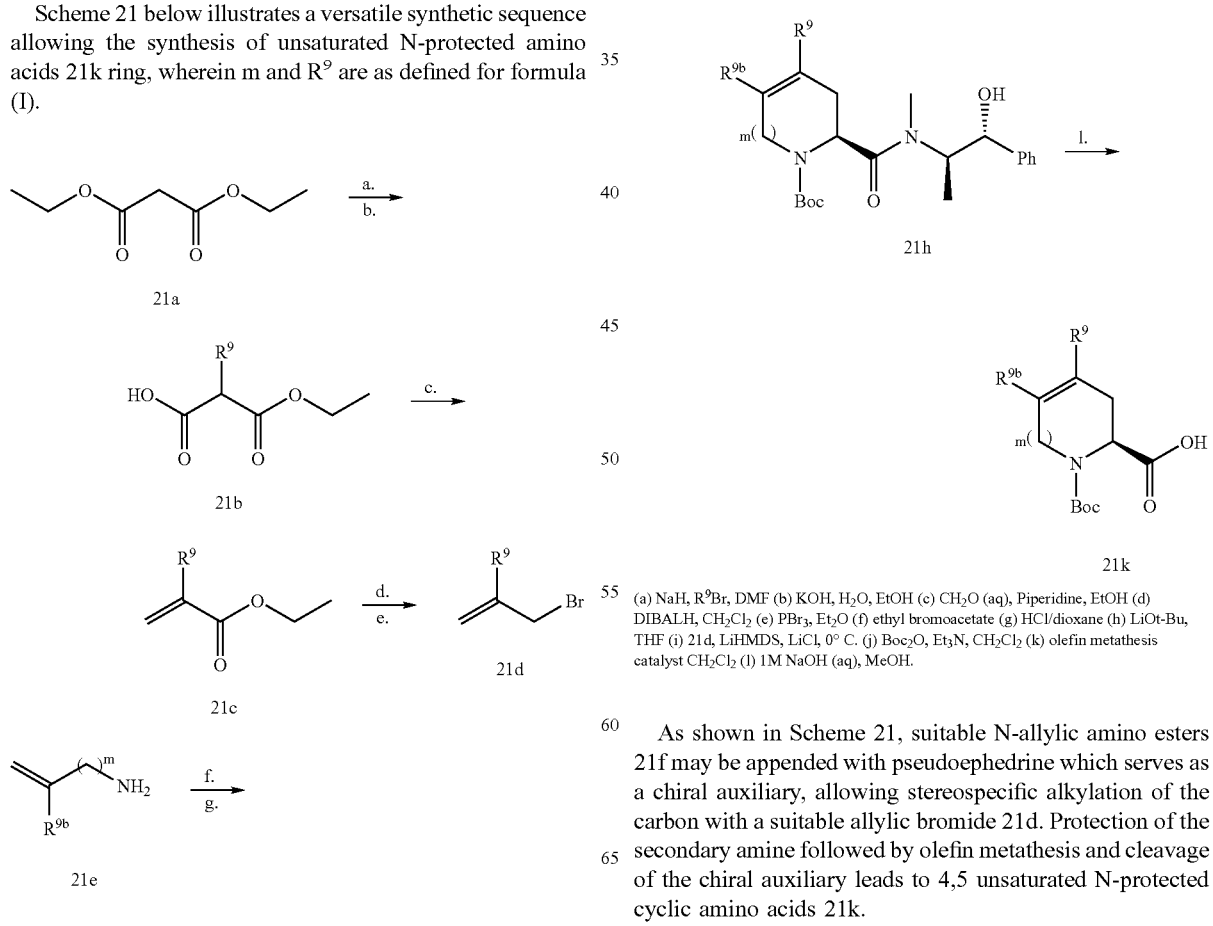

(a) NaH, $R^9$Br, DMF (b) KOH, $H_2O$, EtOH (c) $CH_2O$ (aq), Piperidine, EtOH (d) DIBALH, $CH_2Cl_2$ (e) $PBr_3$, $Et_2O$ (f) ethyl bromoacetate (g) HCl/dioxane (h) LiOt-Bu, THF (i) 21d, LiHMDS, LiCl, 0° C. (j) $Boc_2O$, $Et_3N$, $CH_2Cl_2$ (k) olefin metathesis catalyst $CH_2Cl_2$ (l) 1M NaOH (aq), MeOH.

As shown in Scheme 21, suitable N-allylic amino esters 21f may be appended with pseudoephedrine which serves as a chiral auxiliary, allowing stereospecific alkylation of the carbon with a suitable allylic bromide 21d. Protection of the secondary amine followed by olefin metathesis and cleavage of the chiral auxiliary leads to 4,5 unsaturated N-protected cyclic amino acids 21k.

Scheme 22.

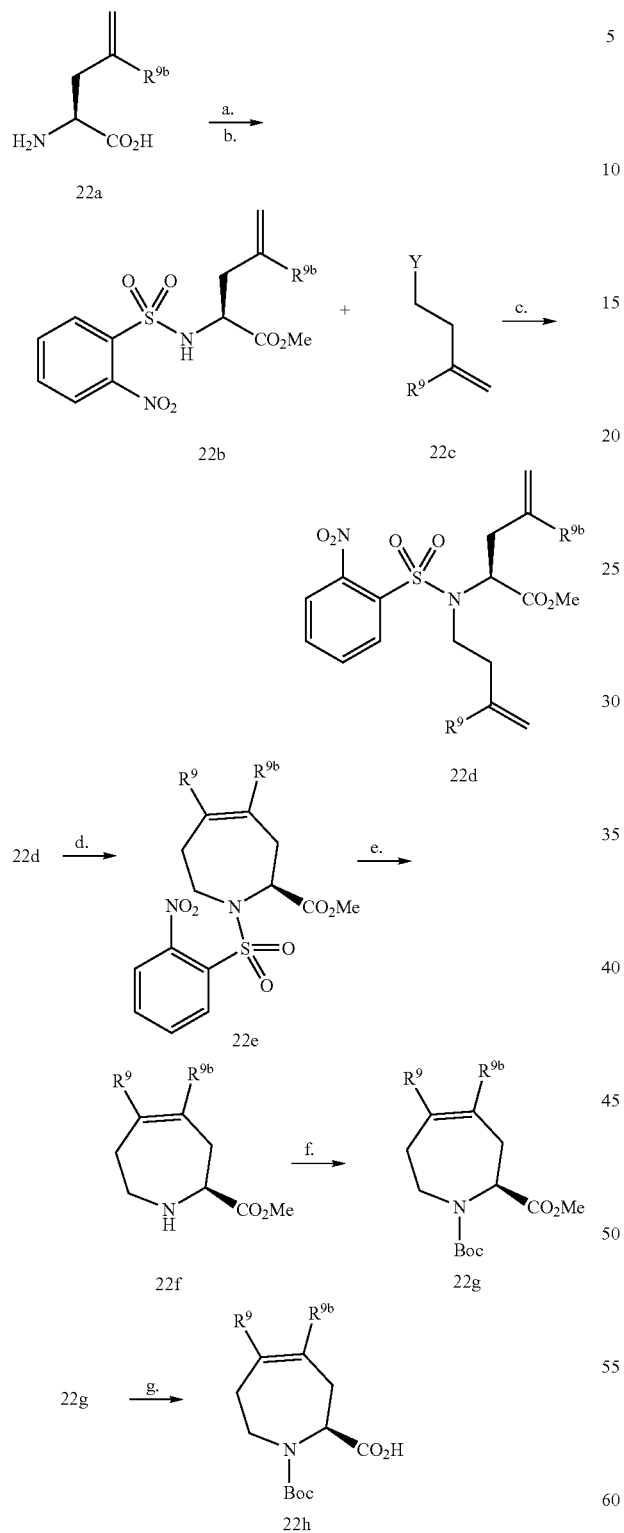

a. H+, MeOH b. 2-nitrobenzenesulfonyl chloride, 2,4,6-collidine, dichloroethane
c. Cs$_2$CO$_3$, TBABr, DMF, 22c (Y = Br, or OTs) or c. by Mitsunobu alkylation PPh$_3$, Diisopropylazidodicarboxylate, 22c (Y = OH) d. Benzylidene[1,3-bis(2,4,6-trimethylphenyl)-2-imidazolidinylidene] dichloro-(tricyclohexylphosphine)ruthenium e. organic base (7-methyl,1,5,7-triazabicyclo[4.4.0]dec-5-ene), thiophenol f. (Boc)$_2$O, TEA g. Aq. LiOH, Dioxane.

Scheme 23. General synthesis of C6 lincosamine derivatives.

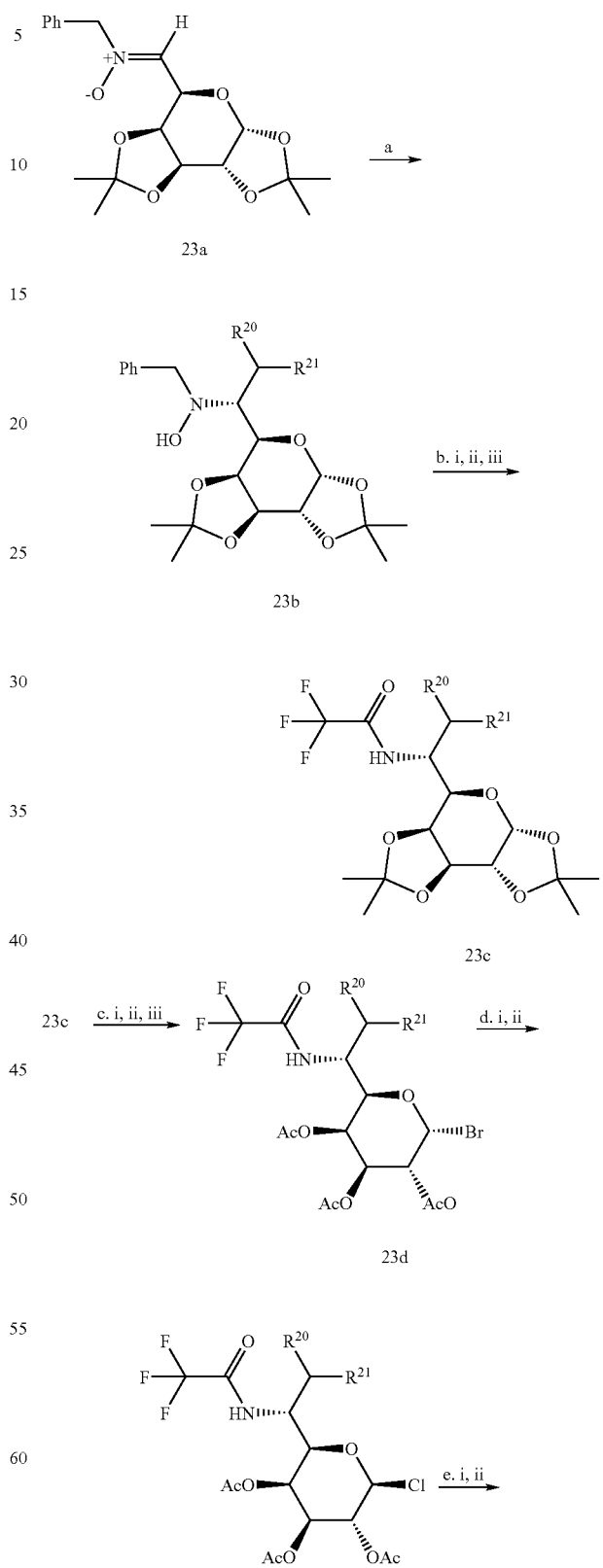

63

-continued

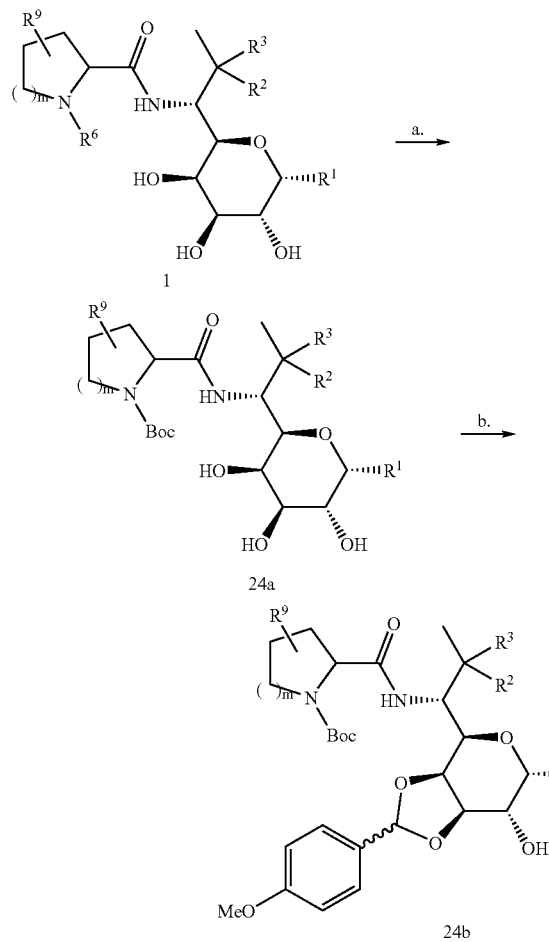

(a) $R^{20}+R^{21}$ Metal, $Et_2AlCl$, $Et_2O$; (b) (i) MsCl, $Et_3N$, $CH_2Cl_2$, (ii) Girard's reagent T, MeOH, (iii) Trifluoroacetic anhydride, 2,6-lutidine, $CH_2Cl_2$; (c) (i) TFA, $H_2O$, (ii) $Ac_2O$, $Et_3N$, DMAP, $CH_2Cl_2$, (iii) HBr, AcOH, $CH_2Cl_2$; (d) (i) AcOAg, AcOH,(ii) $PCl_5$, $BF_3$•$OEt_2$, $CH_2Cl_2$; (e) (i) MeSNa, HMPA, DMF, (ii) $Ac_2O$, $Et_3N$, DMAP, $CH_2Cl_2$; (f) NaOH, $H_2O$, MeOH.

Scheme 24. General synthesis of 2-substituted esters.

64

-continued

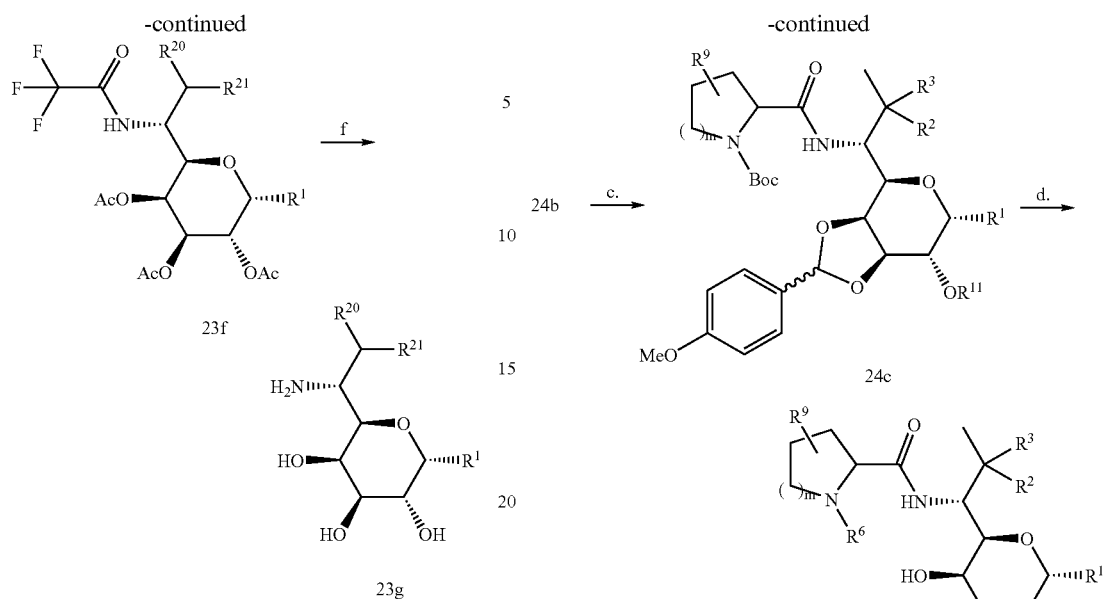

a. $(Boc)_2O$, aq. $KHCO_3$ THF b. p-anisaldehyde dimethyl acetal, PPTS, c. $R^{11}$ acylating agent, base d. TFA, DCE, water.

Scheme 25. General synthesis of trans-alkylazetidine carboxylic acids.

(a) (i) LDA, THF, 0° C., (ii) bromoalkane or bromoalkene; (b) $TMSCHN_2$, MeOH, 23° C.; (c) (i) $TMSCHN_2$, MeOH, 23° C., (ii) $H_2$, Pd/C, EtOAc, 23° C.; (d) $Et_3N$•3HF, THF, 23° C.; (e) $LiAlH_4$, THF, 68° C.; (f) $Boc_2O$, $CH_2Cl_2$, 23° C.; (g) $RuCl_3$•$xH_2O$, $NaIO_4$, acetone, $H_2O$, 23° C.

Scheme 26.
General synthesis of trans-alkylazetidine carboxylic acids via aldehyde.

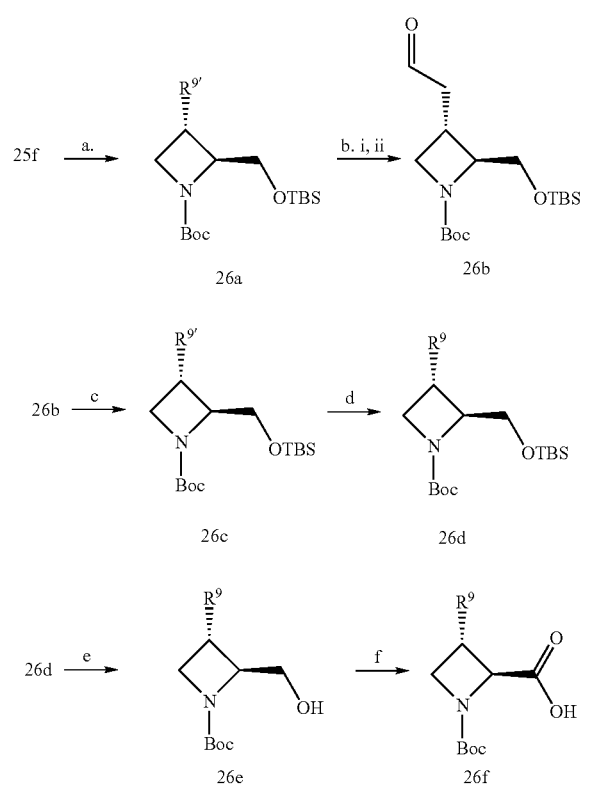

(a) TBSCl, imidazole, DMF, 23° C.; (b) (i) ozone, CH$_2$Cl$_2$, -78° C., (ii) PPH$_3$; (c) olefination, R$_1$R$_2$CHP=Ph$_3$X$^-$, base, solvent; (d) H$_2$, Pd/C, EtOAc, 23° C. or KO$_2$CN=NCO$_2$K, AcOH, dioxane, 23° C.; (e) TBAF, THF, 23° C.; (f) RuCl$_3$·xH$_2$O, NaIO$_4$, acetone, H$_2$O, 23° C.

Scheme 27.
General synthesis of racemic cis 4-substitued intermediates 27a and resolution to provide 2S, 4R, R$^9$ intermediates 27b

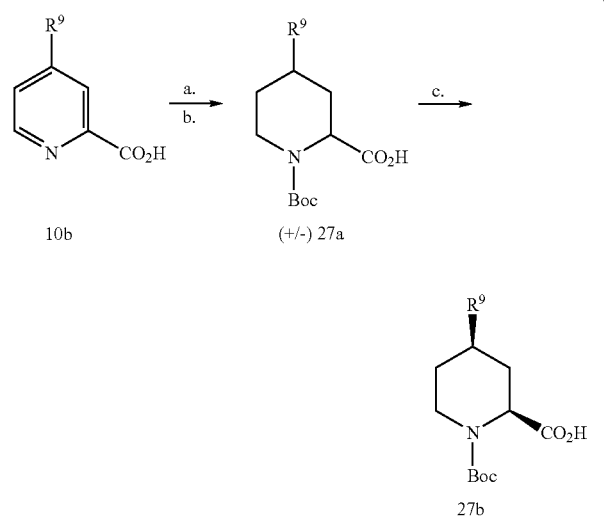

(a) PtO$_2$, H$_2$, H$^+$ (b) (Boc)$_2$O, $^-$OH (c) i. chiral amine, recrystallization ii. H$^+$.

Scheme 28. General synthesis of 2-substituted esters.

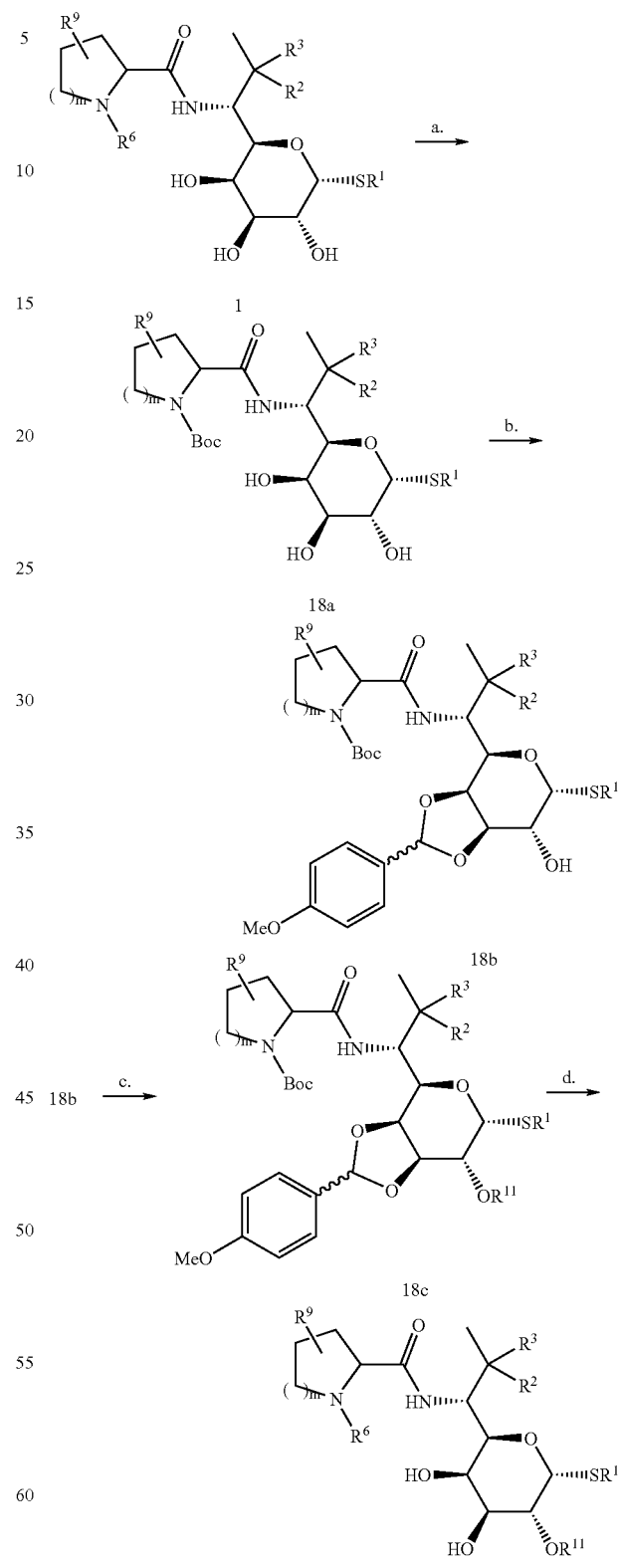

a. (Boc)$_2$O, aq. KHCO$_3$ THF b. p-anisaldehyde dimethyl acetal, PPTS, c. R$^{11}$acylating agent, base d. TFA, DCE, water.

Pharmaceutical Formulations

When employed as pharmaceuticals, the compounds of the subject invention are usually administered in the form of pharmaceutical compositions. These compounds can be administered by a variety of routes including oral, parenteral, transdermal, intravenous, intramuscular, topical, rectal, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of the subject invention above associated with one or more pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, which is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An intravenous formulation may be prepared as follows:

| Ingredient | Quantity |
| --- | --- |
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

In general, the compounds of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (the concentration of the test compound which achieves a half-maximal inhibition of symptoms) as determined in cell culture. Such information can be used to more accurately determine useful doses in humans. Levels in plasma may be measured, for example, by high performance liquid chromatography.

Utility

The compounds, prodrugs and pharmaceutically acceptable salts thereof, as defined herein, have activity against at least one of a variety of bacteria, protozoa, fungi, and parasites. By way of example, the compounds, prodrugs and pharmaceutically acceptable salts thereof may be active against gram positive and gram negative bacteria. The compounds, prodrugs and pharmaceutically acceptable salts thereof may be active against a variety of fungi, including fungi from the genus *Mucor* and *Candida*, e.g., *Mucor racemosus* or *Candida albicans*. The compounds, prodrugs and pharmaceutically acceptable salts thereof may be active against a variety of parasites, including malaria and cyptosporidium parasite.

The compounds of the subject invention may exhibit activity against at least one of a variety of bacterial infections, including, for example, gram positive infections, gram negative infections, mycobacteria infections, mycoplasma infections, and chlamydia infections.

Since the compounds of the subject invention may exhibit potent activities against a variety of bacteria, such as gram positive bacteria, the compounds of the present invention may be useful antimicrobial agents and may be effective against at least one of a number of human and veterinary pathogens, including gram positive bacteria. The Gram positive organisms against which the compounds of the present invention may be effective include, for example, *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*, and the like.

The compounds of the subject invention may be combined with one or more additional antibacterial agents. One or more of the additional antibacterial agents may be active against gram negative bacteria. One or more of the additional antibacterial agents may be active against gram positive bacteria. The combination of the compounds of the subject invention and the one or more additional antibacterial agents may be used to treat a gram negative infection. The combination of the compounds of the subject invention and the one or more additional antibacterial agents may be used to treat a gram positive infection. The combination of compounds of the subject invention and the one or more additional antibacterial agents may also be used to treat a mycobacteria infection, mycoplasma infection, or chlamydia infection.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," 3rd ed., published 1993 by the National Committee for Clinical Laboratory standards, Villanova, Pa., USA.

The amount administered to the mammalian patient will vary depending upon what is being administered, the purpose of the administration, such as prophylaxis or therapy, the state of the patient, the manner of administration, and the like. One in example, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 to about 11, more preferably from about 5 to about 9 and most preferably from about 7 to about 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 mg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

7-methylMTL=1-methylsulfanyl-7-deoxy-7-methyllincosamine
Ac=acetyl
apt=apparent triplet
Aq=aqueous
atm=atmospheres
Bn=benzyl
Boc=tert-butoxycarbonyl protecting group
br s=broad singlet
BSTFA=N,O-bis(trimethylsilyl)trifluoroacetamide
$^{13}$C NMR=$^{13}$carbon nuclear magnetic resonance
Cbz=carbonyloxybenzyloxy protecting group
$CDCl_3$=deuterated chloroform
$CD_3OD$=deuterated methanol
$CD_3SOCD_3$=deuterated dimethylsulfoxide
cfu=colony forming units
$D_2O$=deuterated water
d=doublet
DAST=dimethylaminosulfurtrifluoride
dd=doublet of doublets
dddd=doublet of doublets of doublet of doublets
DIBALH=Diisobutylaluminum hydride
dt=doublet of triplets
DCE=dicholoroethane
DCM=dichloromethane
DIEA=diisopropylethylamine
DMAP=dimethylaminopyridine
DMF=dimethylformamide
DMS=dimethyl sulfide
DMSO=dimethyl sulfoxide
DPPA=diphenylphosphoryl azide
$ED_{50}$=dose therapeutically effective in 50% of the population
equiv=equivalents
ESMS=electrospray mass spectrometry
Et=ethyl
EtOAc=ethyl acetate
$Et_2O$=diethyl ether
g=grams
h=hours
HATU=O-(7-azabenzotriazol-1-yl)-N,N,N',N'-tetramethyluronium hexafluorophosphate
HOBT=1-hydroxybenzotriazole hydrate
$^1$H NMR=Hydrogen Nuclear Magnetic Resonance spectroscopy
HPLC=high pressure liquid chromatography
Hz=hertz
$IC_{50}$=concentration of the test compound which achieves a half-maximal inhibition of symptoms
J=coupling constant in hertz
L=liters
$LD_{50}$=dose lethal to 50% of the population
LiHMDS=lithium hexamethyldisilazide
m=multiplet
M=molar
MCPBA=3-Chloroperoxybenzoic acid
Me=methyl
MeCN=acetonitrile
MeOH=methanol
mg=milligrams
MHB=Mueller Hinton broth
MHz=megahertz
MIC=minimum inhibitory concentration
min=minutes
mL=milliliters
mm=millimeter
mmHg=millimeters mercury
mmol=millimol
MS(ESPOS)=mass spectrometry by positive mode electrospray ionization
MS(ESNEG)=Mass Spectrometry by negative mode electrospray ionization
MTBU=7-methyl-1,5,7-triazabicyclo-[4.4.0]dec-5-ene
MTL=1-methylsulfanyllincosamine (methyl 6-amino-6,8-dideoxy-1-thio-erythro-α-D-galacto-octopyranoside)
N=normal
NBS N-bromosuccinimide
NMR=nuclear magnetic resonance
OBz=benzyloxy protecting group
OtBu=tert-butoxy
Pd/C=palladium/carbon
pg=picograms
Ph=phenyl
Pro=L-proline
psi=pounds per square inch
q=quartet
q.v.=quantitative
$R_f$=Retention factor
rt=room temperature
s=singlet
sat.=saturated
t=triplet
TCI=TCI America
TEA=triethylamine
TFA=trifluoroacetic acid
THF=tetrahydrofuran
TLC=thin layer chromatography
TMS trimethylsilyl
Ts=tosyl
μg=micrograms
μL=microliters
μM=micromolar
v/v=volume by volume Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; the term "RSP" indicates that the compound or reagent is commercially available from RSP Amino Acid Analogs, Inc., 106 South St., Hopkinton, Mass. 01748, USA, and the term "TCI" indicates that the compound or reagent is commercially available from TCI America, 9211 North Harborgate St., Portland, Oreg., 97203, OR, USA; the term "Toronto" indicates that the compound or reagent is commercially available from Toronto Reasearch Chemicals, Inc., 2 Brisbane Rd., New York, ON, Canada M3J2J8; the term "Alfa" indicates that the compound or reagent is commercially available from Johnson Matthey Catalog Company, Inc. 30 Bond Street, Ward Hill, Mass. 01835-0747; and the term "Nova Biochem" indicates that the compound or reagent is commercially available from Nova-Biochem USA, 10933 North Torrey Pines Road, P.O. Box 12087, La Jolla Calif. 92039-2087.

In the examples below, all temperatures are in degrees Celsius (unless otherwise indicated) and the following general procedures are used to prepare the compounds as indicated.

General Procedures

Method A

Methyl 6-amino-6,8-dideoxy-1-thio-erythro-α-D-galacto-octopyranoside 1a (MTL) was prepared as described by Hoeksema, H. et. al. *Journal of the American Chemical Society*, 1967, 89, 2448–2452. N-(Benzyloxycarbonyloxy)succinimide (5.8 g 23.1 mmol) and 1a (5.0 g, 19.7 mmol) were suspended in pyridine (40 mL) and stirred under $N_2$ atmosphere for 36 h. The reaction mixture was cooled to 0° C. and then bis-N,O-trifluoroacetamide (15.7 mL, 59.0 mmol) was added by syringe over 2 min. The reaction mixture was allowed to warm to rt and stirred for 42 h. Toluene (100 mL) was added and the reaction mixture was evaporated to dryness. The residue was taken up in ethyl acetate (400 mL). The organic solution was washed quickly with 10% citric acid (200 mL), $H_2O$ (3×100 mL), saturated $NaHCO_3$ (100 mL), and brine (2×100 mL), and dried over $Na_2SO_4$ and evaporated to dryness. Chromatography of the crude product on silica 10% EtOAc/hexanes containing 0.2% TEA after co-evaporation from toluene (100 mL) and cyclohexane (2×100 mL) provided the protected product 1b (P=Cbz, R1=SMe) (7.2 g, 54%) as a colorless oil: $^1$H NMR (300 MHz, $CD_3SOCD_3$) δ 7.34–7.31 (m, 5), 7.05 (d, J=8.2, 1), 5.19 (d, J=5.8, 1), 5.01 (d, J=1.6, 2), 3.99 (apt dt, J=5.5, 9.3, 9.3, 2), 3.93–3.86 (m, 3), 3.49 (dd, J=2.5, 9.6, 1), 2.01 (s, 3), 1.03 (d, J=6.3, 3), 0.10 (s, 9), 0.09 (s, 9), 0.04 (m, 18).

To dimethylsulfoxide (413 μL, 5.82 mmol) in DCM (1.5 mL) cooled to −72° C. was added oxalyl chloride 2 M in DCM (1.49 mL, 2.98 mmol) over 1 min. After 25 min the protected product 1b (1.92 g, 2.84 mmol) in DCM (4.0 mL) was added by cannula. The resulting reaction mixture was stirred 25 min and then allowed to warm to −50° C. (dry ice acetonitrile) and maintained at this temperature for 2 h. To the reaction mixture was added TEA (1.29 mL, 3.30 mmol). After 25 min the reaction mixture was diluted with EtOAc (300 mL). The resulting organic solution was washed quickly with 5% citric acid (300 mL), $H_2O$ (2×300 mL), saturated $NaHCO_3$ (100 mL), brine (100 mL) dried over $Na_2SO_4$ and evaporated to dryness with the aid of toluene (100 mL) to provide the product 1c. The product 1c (P=Cbz, R1=SMe) was obtained as a colorless crystalline solid after co-evaporation with n-pentane and removal of residual solvent under high vacuum (1.60 g, 94%): $^1$H NMR (300 MHz, $CDCl_3$) δ 7.37–7.33 (m, 5), 5.60 (m, 1), 5.21 (d, J=5.2, 1), 5.17 (d, J=12.4, 1), 5.08 (d, J=12.4, 1), 4.74 (m, 1), 4.16–4.12 (m, 2), 3.87 (d, J=2.2, 1), 3.69 (dd, J=2.5, 9.3, 1), 2.01 (br s, 3), 1.90 (s, 3), 0.19 (s, 9), 0.16 (s, 9), 0.15 (s, 9).

Method B

The Boc-protected product 1c (P=Boc, $R^1$=SMe) may be prepared in general as outlined below. To 1a (MTL) (Dried at 50° C. high vacuum) (21.8 g, 86 mmol) suspended in methanol (200 mL) and TEA (26 mL) was cooled to 0° C. on ice, di-t-butyldicarbonate (57.0 g, 0.26 mol) was added. The reaction mixture was then stirred over night at room temperature. To the reaction mixture was added toluene (100 mL) solvents were removed to a total volume of 100 mL leaving a thick suspension to which was added cyclohexane (300 mL). The resulting solid precipitate was triturated then filtered and washed with cyclohexane, ether, and pentane and dried to constant weight. The crude Boc-protected product was used without further purification (87%): TLC $R_f$=0.75 (10% MeOH/DCM); MS (ESPOS): 354 [M+H]$^+$; $^1$H NMR (300 MHz, $CD_3OD$) δ 0.14 (d, J=6.3, 3), 1.43 (s, 9), 2.07 (s, 3), 3.55 (dd, J=3.3, 10.43, 1), 3.84–4.08 (m, 3), 4.10–4.15 (m, 2), 5.25 (d, J=5.5, 1).

To N-Boc-1-methylthiolincosamide (240 mg, 0.68 mmol) in DMF (5 mL), BSTFA (0.52 mL, 2.0 mmol) and triethylamine (0.14 mL, 1.42 mmol) was added at 0° C. and then left stirred at room temperature over night. DMF was removed and the crude product was quickly passed through a silica gel column (pretreated with 2% triethylamine in ethyl acetate) eluting with 10% ethyl acetate in hexanes 1b (P=Boc, R1=SMe) (350 mg, 95%). To oxalyl chloride (0.16 mL, 0.78 mmol) in dichloromethane (5 mL) at −60° C., dimethylsulfoxide (0.22 mL, 0.78 mmol) was added slowly and then left stirred for 15 min. After which, 1b (370 mg, 0.65 mmol) in dichloromethane (5 mL) was added slowly. The reaction mixture was left stirred for 45 min, during which the reaction temperature was increased to −40° C. Triethylamine (0.70 mL, 3.25 mmol) was then added and the stirring continued for further 15 min at −40° C. It was then extracted with dichloromethane (100 mL) and washed with 10% citric acid (50 mL). The residue obtained on removal of solvent was then purified on silica gel column using 10% ethyl acetate in hexanes as eluent 1c (P=Boc, R1=SMe) as a colorless oil (289 mg, 78%): TLC: Rf=0.60 (10% EtOAc/hexanes); MS (ESPOS): 590 [M+Na]+; 1H NMR (300 MHz, CDCl3) δ 0.11 (s, 18), 0.17 (s, 18), 1.40 (s, 9), 1.84 (s, 3), 2.26 (s, 3), 3.63 (dd, J=2.7, 9.34, 1), 3.82 (d, J=1.9, 1), 4.01–4.12 (m, 2), 5.15 (d, J=5.5, 1).

Method C

Triphenylphosphonium bromide (3.29 g, 9.20 mmol) and potassium tert-butoxide (715 mg, 6.4 mmol) under $N_2$ atmosphere were suspended in toluene (31 mL) with vigorous stirring. After 4.0 h protected product 1c (P=Cbz, R1=SMe) (1.40 g, 2.36 mmol) in toluene (20 mL) was added by cannula. The resulting reaction mixture was stirred 2 h and then diluted with EtOAc (250 mL). The resulting organic solution was washed quickly with $H_2O$ (2×100 mL), brine (1×100 mL) dried over $Na_2SO_4$ and evaporated to dryness. Chromatography of the crude product on silica 6% EtOAc/hexanes containing 0.2% TEA gave the alkene product 2a (P=Cbz, R1=SMe, $R^{2'}$=H) as a colorless oil that crystallized after co-evaporation from toluene and cyclohexane (0.65 g, 46%): $^1$H NMR (300 MHz, $CDCl_3$) δ 7.35–7.27 (m, 5), 6.36 (d, J=7.1, 1), 5.24 (d, J=5.5, 1), 5.08 (m, 4), 4.34 (m, 1), 4.16 (m, 2), 3.88 (d, J=2.2, 1), 3.61 (dd, J=2.2, 9.3, 1), 2.20 (s, 3), 1.79 (s, 3), 0.17–0.13 (m, 27).

The product 2a (P=Cbz, R1=SMe, $R^{2'}$=H) (490 mg, 0.82 mmol) in ethanol (50 mL) was added to 10% Palladium on carbon (degusa wet form 50% w/w water) (700 mg) in a parr bottle. The bottle was purged, and charged with $H_2$ to 65 psi and shaken 24 h. The reaction mixture was filtered through celite, rinsed with methanol. The organic solution was transferred to a resin funnel containing dry, washed Dowex® 50w-400x H$^+$ form (0.8 g) and shaken 10 min. After washing the resin with methanol three times and water two times, the saturated product 2b was eluted from the resin by washing with 5% TEA in MeOH (35 mL×10 min×5). The combined filtrate was evaporated to dryness, co-evaporated from EtOH twice and lyophilized from 1:1 MeCN/H$_2$O to give the product 2b (R$^{2'}$=H) as a colorless powder (198 mg, 96%): $^1$H NMR (300 MHz, D$_2$O) δ 5.17 (d, J=5.8, 1), 3.97–3.84 (m, 3), 3.52 (dd, J=3.0, 10.0, 1), 2.82 (dd, J=4.4, 8.5, 1), 1.94 (s, 3), 1.89–1.81 (m, 1), 0.82 (d, J=6.9, 3), 0.72 (d, J=6.9, 3); MS (ESPOS): 252.2 [M+H]$^+$, (ESNEG): 250.4 [M−H]$^−$.

Method D

In the alternative, when a Boc-protecting group is used in Scheme 1 (P=Boc), methyltriphenyl-phosphonium bromide (12 g, 33.6 mmol) and potassium t-butoxide (3 g, 26.7 mmol) were taken in THF (70 mL) at 0° C., and stirred at rt for 4 h. Then Boc-protected product 1c (P=Boc, R1=SMe) (4.7 g, 8.2 mmol) in THF (30 mL) was added and stirred at rt for 2 h. After which it was extracted with EtOAc (300 mL), washed with brine (100 mL) and dried over sodium sulfate. The crude alkene product 2a (P=Boc, R1=SMe, R$^{2'}$=H) was purified on silica gel column chromatography using 10% EtOAc in Hexane as eluent (4.1 g, 87.6%): TLC: R$_f$=0.5 (10% of EtOAc in Hexane): $^1$H NMR (300 MHz, CD$_3$OD) δ 7.24 (m, 2), 5.22 (d, J=5.7, 1), 4.21 (m, 1), 4.09 (m, 2), 3.87 (d, J=2.4, 1), 3.60 (dd, J=2.7, 9.3, 1), 1.99 (s, 3), 1.76 (s, 3), 1.43 (s, 9); MS (ESPOS): 444 [M−2TMS+Na]$^+$.

To the product 2a (P=Boc, R1=SMe, R$^{2'}$=H) in methanol (30 mL), Dowex® H$^+$ resin (1 g) was added and stirred at rt for 1 h. The resin was filtered and the product obtained on removal of solvent (2.4 g, 6.8 mmol,) was taken in MeOH (30 mL), Pd/C (2.5 g) was added and hydrogenated at 55 psi overnight. The crude product obtained on filtering and removal of solvent was purified on silica gel column chromatography using 10% MeOH in DCM to provide Boc-protected 7-Methyl MTL as a white solid (2.06 g, 86%): TLC R$_f$=0.5 (10% of MeOH in DCM); $^1$H NMR (300 MHz, CD$_3$OD) δ 5.23 (d, J=5.4, 1), 4.11 (m, 1), 3.97 (d, J=10.2, 1), 3.84 (m, 1), 3.52 (m, 1), 2.08 (s, 3), 1.44 (s, 9), 1.14 (m, 1), 0.93 (d, J=6.9, 3), 0.85 (d, J=6.9, 3); MS (ESPOS): 351 [M+H]$^+$.

To Boc-protected 7-Methyl MTL (150 mg, 0.43 mmol) in dichloroethane (6 mL), dimethylsulfide (0.16 mL, 2.5 mmol) was added, followed by TFA (2 mL), water (0.16 mL) and stirred at rt for 1 h. The solvent was removed to obtain the crude product 2b (R$^1$=SMe, P=Boc, R$^{2'}$=H). After purification on silica gel column chromatography using 30% MeOH in DCM as eluent, the product 2b (R$^{2'}$=H) was obtained identical in all respects to the material obtained from Method C.

Method E

Sodium hydride (80 mg, 3.3 mmol) under N$_2$ atmosphere was suspended in THF (4 mL) with vigorous stirring. The suspension was cooled to −30° C. and diethyl(cyanomethyl)phosphonate (805 μL, 5.0 mmol) was added. After 30 min, protected product 1c (P=Cbz, R1=SMe) (1.0 g, 1.7 mmol) in THF (3 mL) was added by cannula. The resulting reaction mixture was stirred 4 h and then diluted with EtOAc (250 mL). The resulting organic solution was washed quickly with saturated aqueous NaHCO$_3$ (1×100 mL), brine (1×50 mL) dried over Na$_2$SO$_4$ and evaporated to dryness. Chromatography of the crude product on silica 6% EtOAc/hexanes to 10% EtOAc/hexanes containing 0.2% TEA gave the protected alkene product 2a (P=Cbz, R1=SMe, R$^{2'}$=CN) as a colorless oil (0.38 g, 37%): MS (ESPOS): 625.5 [M+H]$^+$, MS (ESNEG): 659.5 [M+Cl]$^−$.

The product 2a (P=Cbz, R$^1$=SMe, R$^{2'}$=CN) (180 mg, 0.29 mmol) in ethanol (15 mL) was added to 10% Palladium on carbon (degusa wet form 50% w/w water) (300 mg) in a Parr bottle and concentrated HCl (29 μL) was added. The bottle was purged, and charged with H$_2$ to 65 psi and shaken 24 h. The reaction mixture was filtered through celite, rinsed with methanol. The organic solution was transferred to a resin funnel containing dry, washed Dowex® 50w-400x H$^+$ form (1 g) and shaken 10 min. After washing the resin with methanol twice and water, the saturated product 2b (R$^1$=SMe, R$^{2'}$=CN) was eluted from the resin by washing with 5% TEA in MeOH (20 mL×20 min×3) and MeCN (20 mL×20 min). The combined organic filtrate was evaporated to dryness lyophilized from 1:1 MeCN/H$_2$O to give the product 2b (R$^1$=SMe, R$^{2}$=CH$_2$CN) as a colorless solid (70 mg, 91%): MS (ESNEG): 275.3 [M−H]$^−$.

Method F

To the protected product 1c (P=Cbz, R$^1$=SMe) (0.75 g, 1.3 mmol) in THF (7.3 mL) was added MeMgCl 3 M (Aldrich) in THF (7.0 mL 2.1 mmol) at 0° C. Over 30 min the reaction mixture was warmed to 4° C. and after 4 h the reaction mixture was quenched with 1:3 saturated aqueous NH$_4$Cl/H$_2$O (10 mL). The quenched mixture was diluted to 100 mL with water and extracted with DCM (4×50 mL). The combined organic phase was dried and evaporated. The residue was dissolved in 1:2:4 H$_2$O/HOAc/THF (100 mL) and stirred 20 h, and then evaporated with the aid of toluene (2×100 mL). Chromatography (10:1 to 10:2 DCM/MeOH) gave product 3a (P=Cbz, R$^1$=SMe, R$^{2''}$=Me) (153 mg, 31%): MS (ESNEG): 399.5 [M−H]$^−$.

3a (P=Cbz, R$^1$=SMe, R$^{2''}$=Me) (79 mg, 0.2 mmol) in ethanol (10 mL) was added to 10% Palladium on carbon (degusa wet form 50% w/w water) (400 mg) in a Parr bottle. The bottle was purged, and charged with H$_2$ to 65 psi and shaken 6 h. The reaction mixture was filtered through celite, rinsed with methanol. The combined filtrate was evaporated to dryness and lyophilized from 1:1 MeCN/H$_2$O to give the product 3b (R$^1$=SMe, R$^{2''}$=Me) as a colorless powder (42 mg, 80%): $^1$H NMR (300 MHz, D$_2$O) δ 5.33 (d, J=5.8, 1), 4.83–4.06 (m, 3), 3.65–3.60 (m, 1), 3.06–3.03 (m, 1), 2.18 (s, 3), 1.30 (s, 3), 1.23 (s, 3); MS (ESPOS): 268.4 [M+H], MS (ESNEG): 266.2 [M−H]$^−$.

Method G

To the Boc-protected product 1c (P=Boc, R$^1$=SMe) (100 mg, 0.18 mmol) in methanol (3 mL), O-trimethylsilylhydroxylamine (0.10 mL, 0.88 mmol) was added and stirred at rt overnight. The solvent was removed to obtain the crude Boc-protected product 4a (R$^1$=SMe, R$^7$=H). To the crude product 4a (95 mg, 0.15 mmol), 30% triflouoroacetic acid in dichloroethane (10 mL) and dimethyl sulfide (0.5 mL) were added and stirred for 1 h. The solvent was removed and the product 4b (R$^1$=SMe, R$^7$=H) was taken as such for the next step.

TLC: R$_f$=0.35 (10% MeOH/DCM); MS (ESPOS): 267 (M+H); $^1$H NMR (300 MHz, CD$_3$OD) δ 1.96 (s, 3), 2.09 (s, 3), 3.58 (dd, J=3.3, 10.2, 1), 3.90 (s, 1), 4.11 (dd, J=5.7, 10.20, 1), 4.19 (d, J=5.4, 1), 4.50 (d, J=5.1, 1), 5.36 (d, J=5.7, 1).

Method H

To the Boc-protected product 1c (P=Boc, R$^1$=SMe) (100 mg, 0.176 mmol) in methanol (4 mL) and water (1 mL), O-alkylhydroxylamine hydrochloride (for example, O-methylhydroxylamine hydrochloride) (60 mg, 0.70 mmol) and sodium acetate (57 mg, 0.70 mmol) were added and heated at 80° C. for 3 h and then stirred at rt overnight. The solvent was removed under high vacuum to obtain the crude Boc-protected product 4a (R1=SMe, R7=Me). The crude product 4a was taken in 30% trifluoroacetic acid in dichloroethane (10 mL), dimethylsulfide (0.5 mL) and stirred for 1 h at rt. The solvent was removed and the residue was kept under high vacuum for 1 h and the product 4b (R1=SMe, R7=Me) was taken as such for the next step: TLC Rf=0.63 (10% MeOH/DCM); MS (ESPOS): 281 [M+H]+; 1H NMR (300 MHz, CD3OD) δ 1.95 (s, 3), 2.08 (s, 3), 3.60 (dd, J=3.3, 10.2, 1), 3.92 (s, 3), 4.13 (dd, J=4.8, 10.2, 1), 4.49 (d, J=1.2, 1), 5.38 (d, J=5.4, 1).

Method I

To the Boc-protected product 1c (P=Boc, $R^1$=SMe) (500 mg, 0.88 mmol) in THF (10 mL), tetrabutylammonium fluoride (2.5 mmol, 1 M in THF) was added and the reaction mixture was stirred at rt for 1 h. The solvent was removed and the residue was purified on silica gel column using 5% methanol in dichloromethane as eluent. The product (111 mg, 0.31 mmol) obtained from the column was then taken in a mixture of dichloromethane (3 mL) and pyridine (3 mL) to which acetic anhydride (0.5 mL, 10.6 mmol) and dimethylaminopyridine (80 mg, 1.7 mmol) were added and stirred at rt overnight. The solvent was removed and the crude product was purified on silica gel column using 30% ethyl acetate in hexanes as eluent to provide 5a (P=Boc, $R^1$=SMe) (58 mg, 38%): TLC $R_f$=0.73 (50% EtOAc/hexanes); $^1$H NMR (300 MHz, CDCl$_3$) δ 1.38 (s, 9), 1.91 (s, 3), 1.98 (s, 3), 2.07 (s, 3), 2.18 (s, 3), 4.33 (m, 1), 4.72 (m, 1), 4.94 (m, 1), 5.21 (m, 2), 5.45 (s, 1), 5.57 (m, 1); MS (ESPOS): 500 [M+Na]$^+$.

To product 5a (P=Boc, $R^1$=SMe) (158 mg, 0.331 mmol) in DCM (5 mL), dimethylaminosulfurtrifluoride (732 μL, 3.31 mmol) was added and stirred overnight. More DCM was added and the organic portion was washed with sodium bicarbonate. The residue obtained on removal of solvent was purified on silica gel column chromatography using 20% ethyl acetate in hexanes as eluent (100 mg, 60%) to provide the protected product (P=Boc, $R^1$=SMe). The Boc-protected product was taken up in 30% trifluoroacetic acid in dichloroethane and dimethylsulfide and stirred for 1 h at rt. The solvent was removed to provide the product 5b ($R^1$=SMe): TLC $R_f$=0.63 (40% MeOH/hexanes); $^1$H NMR (300 MHz, CDCl$_3$) δ 1.40 (s, 9), 1.69 (t, J=18.9, 3), 1.98 (s, 3), 2.08 (s, 6), 2.13 (s, 3), 4.22–4.30 (m, 1), 4.53 (dd, J=10.9, 25.3, 1), 5.16–5.28 (m, 2), 5.52 (s, 1), 5.63 (d, J=5.2, 1); MS (ESPOS): 522 [M+Na]$^+$.

Method J

Preparation of Compound 6a (P=TFA).

To a 1 L round bottom flask was added dry 1a MTL ($R^1$=SMe) (dried at 50° C. under vacuum over night) (20 g, 0.079 mol), anhydrous methanol (200 mL), triethylamine (8.77 g, 0.087 mol), and methyl trifluoroacetate (127.3 g, 0.99 mol). The reaction mixture was stirred at rt for 4 h, after which the solvent was evaporated to dryness to yield the protected MTL 6a ($R^1$=SMe, P=TFA) (26.2 g, 95%), which was taken as such for the next step.

Chloromethylene Piperidinium HCl (Scheme 6, Reagent b)

To a 3 L 3 necked round bottom flask fitted with a mechanical stirrer, glass stir rod (large Teflon paddle) under a nitrogen atmosphere, was added diethyl ether (anhydrous, 1.8 L) and N-formylpiperidine (35.6 g, 0.315 mol). The reaction mixture was cooled to 0° C. and triphosgene (31.2 g, 0.105 mol) was added in at least 5 portions over the course of 2 hours, maintaining 0° C. and vigorous stirring. The reaction mixture was then allowed to warm to rt (1 hr) to ensure complete reaction of triphosgene and then cooled again to 0° C. The reaction mixture was then filtered under a stream of nitrogen or argon (very hygroscopic, stench) and washed with cold diethyl ether (2×100 mL). The white crystals obtained were then dried in vacuum to give chloromethylenepiperidium HCl (46.4 g, 95%).

TFA Protected 7-Cl MTL.

To a 3 L, 3 neck round bottom flask, under a nitrogen atmosphere, fitted with a mechanical stirrer, glass stir rod, Teflon paddle, and a reflux condensor, was added chloromethylene piperidinium HCl (44.4 g, 0.286 mol) and dichloroethane (anhydrous, 1 L). The resulting slurry was stirred vigorously and the temperature was brought to 0° C. To the stirring reaction mixture was added the crude 6a ($R^1$=SMe, P=TFA) (20 g, 0.057 mol) over a period of 1 minute. The reaction mixture was stirred for 1 hr and then the temperature was raised to 65° C., during this process the reaction was seen to turn to a clear solution. The reaction mixture was then stirred at 65° C. for a period of 18 h. The reaction mixture was then cooled to 0° C. and then poured rapidly into a 4 L Erlenmeyer fitted with a mechanical stirrer, to which had been added water (1 L) and NaOH (22.9 g, 0.57 mol,) cooled to 0° C. The reaction mixture was then allowed to stir for a period of 30 min and then the pH was adjusted to 10.5 (pH paper) with concentrated HCl (added over a period of 5 min while pH was checked after each HCl addition, if pH is reduced below 10.5 it is acceptable to simply add NaOH to adjust to 10.5. This pH adjusted mixture is then stirred for a period of 2 hours while allowing the reaction to come to rt. The pH was then adjusted to pH 7 with more concentrated HCl and then allowed to stir overnight, or until the product is seen to be free of the adduct formed by the chlorinating agent and the sugar OH functionality. The reaction mixture was then evaporated to dryness with the aid of high vacuum attached to a rotary evaporator (co-evaporating with solvents such as toluene can be used to facilitate this process). To the resulting solid was then added a mixture of 10% methanol/DCM, and stirred for a period of 1 hour to free the product from the salts. The mixture was then filtered and the filtrate was evaporated to dryness to yield syrup containing the product and N-formyl piperidine. The majority of the N-formyl piperidine can be removed by triturating the mixture with hexanes and decanting the hexane from the product oil several times. The crude reaction product was then chromatographed using 10% methanol/DCM to yield the purified TFA protected 7-Cl MTL (21.1 g, 75%).

6b ($R^1$=SMe, $R^2$=Cl, $R^3$=H).

To a 500 mL 3-neck round bottom flask fitted with a mechanical stirrer was added the purified TFA protected 7-Cl MTL (20 g, 0.054 mol) in a minimal amount of methanol (10 mL), followed by 1 M NaOH, (250 mL) at 0° C. The reaction mixture was then stirred at 0° C. (the mixture was seen at first to form an intractable sticky solid that eventually went into solution and the pure product crystals were seen to form soon after) for 12 hr with periodic harvesting of the pure product crystals to prevent hydrolysis of the 7-chloro functionality, and washed with a minimal amount of cold water, followed by cold methanol to furnish 7-Cl MTL 6b ($R^1$=SMe, $R^2$=Cl, $R^3$=H) as a colorless solid (10 g, 50%).

Method K

Enolization (LiHMDS) and alkylation of 7a with 4-bromo-2-methyl-2-butene afforded a mixture of diastereomers of the lactam 7b ($R^{9'}$=2-methyl-2-butene) (61%) according to the literature procedure by Zhang, R.; et. al., *Journal of the American Chemical Society.* 1998, 120, 3894–3902. Compound 7a is commercially available from vendors such as Bachem. Alternatively, 7a can be prepared by methods well known in the art, for an example see Baldwin J. E.; et al.; *Tetrahedron,* 1989, 45, 7449–7468.

The lactam 7b was reduced to the pyrrolidine 7c ($R^{9'}$=2-methyl-2-butene) (70%) by the two-step sequence involving superhydride® reduction of the lactam to the hemiaminal and the subsequent reduction of the hemiaminal with $Et_3SiH/BF_3.OEt_2$. The pyrrolidine 7c (778 mg, 2.08 mmol), 10% palladium on carbon (230 mg), in anhydrous methanol (25 mL) was subjected to Parr hydrogenolysis at 50 psi for 5 h. The reaction mixture was filtered through a celite pad and washed several times with methanol. The combined washings and filtrate were evaporated to dryness, affording, without further purification, a colorless oil 7d ($R^{9''}$=2-methyl-2-butane): TLC $R_f$=0.3 [Solvent system: DCM/hexanes/MeOH (6:5:1)]; MS (ESNEG): 284.5 $[M-H]^-$.

Method L

To a stirred solution of 7a (9.47 g, 29.7 mmol, 1 equiv) in anhydrous THF at −78° C. under $N_2$ was added a 1 M solution of LiHMDS in THF (33 mmol, 33 mL, 1.1 equiv) followed by cis-1-bromo-2-pentene (4.21 mL, 35.6 mmol, 1.2 equiv), afforded a mixture of diastereomers of the lactam 7b (R9'=2-pentene) (43.2%) after silica gel purification. The lactam 7b (3.96 g, 10.22 mmol) was reduced to the pyrrolidine 7c (R9'=2-pentene) by the two-step sequence involving superhydride® reduction of the lactam to the hemiaminal, at −78° C. in anhydrous THF, and the subsequent reduction of the hemiaminal with Et3SiH/BF3OEt2 in anhydrous DCM at −78° C., affording 7c (R9'=2-pentene) (71%) after silica gel purification. The pyrrolidine 7c (2.71 g, 7.26 mmol) and 10% palladium on carbon (560 mg) in anhydrous methanol (30 mL) was subjected to Parr hydrogenolysis at 50 psi for 5 h. The reaction mixture was filtered through a celite pad and washed several times with methanol. The combined washings and filtrate were evaporated to dryness, affording, without further purification, a colorless oil 7d (R9=pentyl) (1.68 g, 80%); TLC: Rf=0.3 [Solvent system: DCM:hexanes:MeOH (6:5:1)]. MS (ESNEG): 284.5 $[M-H]^-$.

Method M 8a ($R^{9'}$=3,3-difluoroprop-2-ene).

Ozonolysis treatment of 7c ($R^{9'}$=2-methyl-2-butene) in anhydrous dichloromethane, followed by treatment with DMS at −78° C., followed by slow warming to rt afforded a terminal aldehyde 8a (77%), which was used in the next step without further purification.

To a solution of aldehyde 8a from the above reaction (407 mg, 1.17 mmol, 1 equiv) in dimethylacetamide (0.25 mL) at 0° C. was added dibromodifluoromethane (0.21 mL, 2.34 mmol, 2 equiv). To the stirred mixture was added a solution of triphenylphosphine (0.61 g, 2.34 mmol, 2 equiv) in dimethyl acetamide (0.5 mL) over a period of 20 minutes under nitrogen. The reaction mixture was warmed to rt and stirred for 30 minutes, then was added to an activated zinc (0.25 g, 3.82 mmol, 3.3 equiv) with the aid of dimethylacetamide (0.3 mL). The resulting reaction mixture was stirred at 110° C. for 1 h and cooled to rt and filtered with the aid of dimethylacetamide (7 mL). The filtrate was poured into an ice water (100 mL) and extracted with ether (150 mL). The ether layer was washed with brine, dried and concentrated. The residue was purified by chromatography to give a clear oil 8a ($R^{9'}$=3,3-difluoroprop-2-ene) (182 mg, 41%): MS (ESPOS): 282.4 [M Boc+H]$^+$.

8c ($R^{9'}$=3,3-difluoroprop-2-ene). To a solution of 8a (84.1 mg, 0.22 mmol, 1 equiv) in THF (3 mL) and water (1 mL) was added lithium hydroxide monohydrate (46.3 mg, 1.10 mmol, 5 equiv). The reaction mixture was stirred at rt overnight. THF was removed under vacuum. The residue was taken up in ethyl acetate (50 mL), partitioned with 10% citric acid (20 mL). The organic layer was washed with water (1×), brine (1×), dried and concentrated to provide 8c ($R^{9'}$=3,3-difluoroprop-2-ene) as a clear glass (56 mg, 87%): MS (ESPOS): 192.3 $[M-Boc+H]^+$; MS (ESNEG): 290.3 $[M-H]-$.

8b ($R^{9''}$=3,3-difluoropropane). The saturated product of Scheme 8 may be obtained by hydrogenation methods described, for example, in method K for 7d.

Method N 9b (P=Boc, m=1, LG=Ts).

To a solution of N-Boc-(2S,4R)-4-hydroxyproline methylester (Bachem) 9a (P=Boc, m=1) (5 g, 20.4 mmol, 1 equiv) and DMAP (0.25 g, 2.04 mmol, 0.1 equiv) in DCM (80 mL) was added toluenesulfonic anhydride (8.65 g, 26.5 mmol, 1.3 equiv). The reaction mixture was cooled to 0° C. and pyridine (6.59 mL, 81.5 mmol, 4 equiv) was added. The mixture was stirred at 0° C. for 30 minutes and then at rt overnight. The solution was concentrated to dryness. The residue was taken up in ethyl acetate (400 mL), washed with 10% aq. citric acid (2×400 mL), sat. aq. $NaHCO_3$ (400 mL) and brine, and dried over $Na_2SO_4$ and concentrated to yield a yellow syrup 9b (P=Boc, m=1, LG=Ts) (8.44 g, 100%): HPLC (Method RV-1), C18 3.5 μm, 4.6 30 mm Column; gradient eluent 2%–98% MeCN over 5 min; 1.5 ml/min): Rt=3.096.

9c (P=Boc, m=1, $R^9$=2,4-dichlorobenzylsulfide).

To a solution of tosylate 9b (P=Boc, m=1, LG=Ts) (1.02 g, 2.55 mmol, 1 equiv) in dry DMF (7.6 mL) under $N_2$ was added 2,4-dichlorobenzylthiol (1.48 g, 7.66 mmol, 3 equiv), followed by the addition of MTBU (0.55 mL, 3.83 mmol, 1.5 equiv). The reaction mixture was stirred at rt overnight and concentrated to dryness. The residue was taken up in ethyl acetate (100 mL), washed with 10% citric acid (50 mL) and brine, and concentrated. The residue was purified by chromatography to provide a clear syrup, 9c (P=Boc, m=1, $R^9$=4-(2,4-dichlorobenzyl sulfide) (1.0 g). MS (ESPOS): 320.2 [M−Boc+]+; MS (ESNEG): 418.4 $[M-H]^-$.

To a solution of methyl ester 9c (P=Boc, m=1, $R^9$=2,4-dichlorobenzylsulfide) (1.0 g, 2.38 mmol, 1 equiv) in THF (9 mL) and water (3 mL) was added lithium hydroxide (0.5 g, 11.9 mmol, 5 equiv). The reaction mixture was stirred at rt overnight. THF was removed under vacuum. The residue was partitioned between ethyl acetate (150 mL) and 10% citric acid (100 mL). The organic layer was washed with water (1×), brine (1×), dried over $Na_2SO_4$ and evaporated to give a clear syrup, 9d (P=Boc, m=1, $R^9$=2,4-dichlorobenzylsulfide) (1.0 g): MS (ESPOS): 306.3 $[M-Boc+H]^+$; MS (ESNEG): 404.2 $[M-H]^-$.

Method O

4-Propylpyridine-2-carboxylic acid 10b ($R^9$=n-propyl).

To 4-propylpyridine (TCI) (2.5 g, 20 mmol), 30% hydrogenperoxide (2.4 g) was added and refluxed overnight. The solvent was removed and the resulting residue was taken in DCM (30 mL). Trimethylsilyl cyanide (2.6 g, 26 mmol) was added to the above solution followed by dimethyl carbamyl chloride (2.8 g, 26 mmol) and left stirred at room temperature overnight. Potassium carbonate (10%, 100 mL) was added. The organic layer was separated, dried over sodium sulfate and then concentrated to obtain 4-propyl-2-cyanopyridine (2.5 g, 93%). It was then refluxed in hydrochloric acid (6N, 60 mL) for overnight. The 4-propylpyridinecarboxylic acid 10b ($R^9$=nPr) was obtained after crystallization from acetonitrile (2.0 g, 71%): MS (ESPOS): 166 [M+H]; $^1$H NMR (300 MHz, CD$_3$OD) δ 8.75 (dd, J=9.0, 3.0, 1), 8.42 (s, 1), 8.08 (dd, J=9.0, 3.0, 1), 3.00 (t, J=7.5, 2), 1.82 (m, 2), 1.05 (t, J=7.2, 3).

4-Propyl-(3-phenyl)pyridine-2-carboxylic acid 10b ($R^9$=4-propyl-(3-phenyl)).

To 4-propyl-(3-phenyl)pyridine-N-Oxide (1 g, 4.69 mmol) in dichloromethane (10 mL) trimethylsilyl cyanide (1.3 mL, 10 mmol) and dimethylcarbamyl chloride (1 mL, 10 mmol) was added and stirred at room temperature for 24 hours. Aqueous potassium carbonate (10%, 10 mL) was added and extracted with dichloromethane (100 mL). The crude product obtained on removal of solvent was taken in hydrochloric acid (6N, 30 mL) and refluxed for 24 hours. Removal of acid followed by crystallization of the crude product from acetonitrile resulted in acid 10b (1 g, 86%): MS (EPOS): 240 [M−1]; $^1$H NMR (300 MHz, CD$_3$OD) δ 2.03–2.17 (m, 2), 2.74 (t, J=7.2, 2), 3.04 (t, J=7.8, 2), 7.16–7.38 (m, 5), 8.07 (d, J=4.2, 1), 8.40 (s, 1), 8.71 (d, J=5.7, 1).

Method P

4-Chloropicolinic acid methyl ester

A mixture of picolinic acid (20 g, 162 mmol, 1 equiv) and sodium bromide (33.43 g, 325 mmol, 2 equiv) in thionyl chloride (81 mL) was refluxed for 5 h. The solvent was removed under vacuum. Absolute methanol (160 mL) was added and the mixture was stirred at rt for 30 minutes. The solvent was evaporated, and the residue was taken up in 5% sodium bicarbonate and extracted with ethyl acetate (3×). The organic layers were combined and dried over MgSO$_4$ and evaporated. The residue was purified by chromatography to afford 4-chloropicolinic acid methyl ester (19.9 g, 72%) as a white solid: $^1$H NMR (300 MHz, CDCl$_3$) δ 8.63 (d, J=5.4, 1), 8.13 (d, J=2.1, 1), 7.48 (dd, J=2.0, 5.3, 1), 4.00 (s, 3).

4-Iodopicolinic acid 11a.

A mixture of 4-chloropicolinic acid methyl ester (2.4 g, 14.1 mmol), 57% hydriodic acid (13.3 mL) and 50% aqueous hypophosphorous acid (0.66 mL) was stirred at 85° C. for 2 h and then was stirred at 107° C. overnight. The mixture was cooled to 95° C. At this temperature were added in 30 minutes 10 M sodium hydroxide aqueous solution (4.2 mL), followed by the addition of water (15.2 mL). The mixture was cooled to rt and stirred at rt for 1 h. The precipitate was filtered, washed with cold water and dried under high vacuum overnight to give a yellow solid 11a, 4-Iodopicolinic acid (3.5 g, 66%): $^1$H NMR (300 MHz, DMSO d$_6$) δ 8.39 (d, J=5.1, 1), 8.35 (d, J=1.8, 1), 8.07 (dd, J=1.7, 5.2, 1); MS (ESPOS): 250.2 [M+H]$^+$.

4-Iodopicolinic acid methyl ester 11b.

To a solution of 4-iodopicolinic acid 11a (7.0 g, 18.6 mmol) in MeOH (70 mL) at 23° C. was added concentrated sulfuric acid (350 μL), and the reaction mixture was refluxed for 48 h. The reaction mixture was cooled to room temperature and concentrated to yield the desired product 4-iodopicolinic acid methyl ester 11b (4.4 g, 90%) as a yellow oil; $^1$H NMR (300 MHz, CDCl$_3$) δ 8.52 (t, J=0.6, 1.5, 1), 8.40 (d, J=5.1, 1), 7.86–7.88 (dd, J=0.6, 5.1, 1), 4.02 (s, 3); MS (ESPOS): 263.9 [M+H]; 285.9 [M+Na].

4-[3-(tert-Butyl-dimethyl-silanyloxy)-prop-1-ynyl]-pyridine-2-carboxylic acid methyl ester 11c ($R^{9'}$=tert-butyl-dimethyl-silanyloxy).

To a dry flask was added 11b (5.41 g, 20.6 mmol, 1 equiv), triphenylphosphine (431.5 mg, 1.65 mmol, 0.08 equiv), copper (I) iodide (313.4 mg, 1.65 mmol, 0.08 equiv), palladium acetate (184.5 mg, 0.82 mmol, 0.04 equiv) and triethylamine (74 mL). The mixture was degassed with nitrogen, followed by addition of t-butyldimethyl(2-propynyloxy)silane (Aldrich) (8.34 mL, 41.14 mmol, 2 equiv). The mixture was stirred at rt for 3 h. The solvent was removed under vacuum to give a dark residue. The residue was purified by chromatography to give ester 11c ($R^{9'}$=3-(tert-butyl-dimethyl-silanyloxy)-prop-1-ynyl) (6.07 g, 97%) as a brown oil: $^1$H NMR (300 MHz, CDCl$_3$) δ 8.67 (dd, J=0.8, 5.0, 1), 8.09 (m, 1), 7.43 (dd, J=1.7, 5.0, 1), 4.54 (s, 2), 3.99 (s, 3), 0.92 (s, 9), 0.14 (s, 6). MS (ESPOS): 306.5 [M+H]+.

4-[3-(tert-Butyl-dimethyl-silanyloxy)-propyl]-piperidine-2-carboxylic acid methyl ester 11d ($R^{9'}$=3-(tert-Butyl-dimethyl-silanyloxy)-propyl).

To a mixture of 11c ($R^{9'}$=3-(tert-butyl-dimethyl-silanyloxy)-prop-1-ynyl) (6.05 g, 19.8 mmol, 1 equiv) in MeOH (60 mL), water (60 mL) and acetic acid (1.14 mL, 19.8 mmol, 1 equiv) was added platinum oxide (2.0 g). The mixture was purged and charged with hydrogen (50 psi) and shaken at rt for overnight. The platinum oxide was removed by filtration and the filtrate was concentrated to give the product 11d ($R^{9'}$=3-(tert-Butyl-dimethyl-silanyloxy)-propyl) (5.0 g, 80%): MS (ESPOS): 316.6 [M+H]+.

4-[3-(tert-Butyl-dimethyl-silanyloxy)-propyl]-piperidine-1,2-dicarboxylic acid 1-tert-butyl ester 2-methyl ester 11e ($R^{9'}$=3-(tert-Butyl-dimethyl-silanyloxy)-propyl, P=Boc).

To the 11d ($R^{9'}$=3-(tert-Butyl-dimethyl-silanyloxy)-propyl) (4.99 g, 15.8 mmol, 1 equiv) in methanol (60 mL) were added triethylamine (4.42 mL, 31.7 mmol, 2 equiv) and di-t-butyldicarbonate (4.7 mL, 20.6 mmol, 1.3 equiv). The mixture was stirred at rt overnight. The solvent was removed under vacuum. The residue was purified by chromatography to give carbamate 11e ($R^{9'}$=3-(tert-Butyl-dimethyl-silanyloxy)-propyl, P=Boc) (2.75 g, 42%) as a clear syrup: $^1$H NMR (300 MHz, CDCl$_3$) δ 4.28 (t, J=6.6, 1), 3.70 (s, 3), 3.55 (t, J=6.3, 2), 3.55–3.48 (m, 1), 3.40–3.30 (m, 1), 2.00–1.92 (m, 1), 1.82–1.69 (m, 2), 1.64–1.20 (m, 6), 1.41 (s, 9), 0.86 (s, 9), 0.01 (s, 6); MS (ESPOS): 316.6 [M+H−Boc]+.

4-[3-(tert-Butyl-dimethyl-silanyloxy)-propyl]-piperidine-1,2-dicarboxylic acid 1-tert-butyl ester 11f ($R^{9'}$=3-(tert-Butyl-dimethyl-silanyloxy)-propyl, P=Boc).

To a mixture of 11e ($R^{9'}$=3-(tert-Butyl-dimethyl-silanyloxy)-propyl, P=Boc) (2.75 g, 6.63 mmol, 1 equiv) in THF (12 mL) and water (4 mL) was added lithium hydroxide monohydrate (306 mg, 7.29 mmol, 1.1 equiv). The mixture was stirred at rt overnight. Additional lithium hydroxide monohydrate (834 mg, 19.89 mmol, 3 equiv) was added and the mixture was stirred at rt for 5 hr. THF was removed under vacuum. The aqueous layer was taken up in ethyl acetate, partitioned with 10% citric acid. The organic layer was washed with water (1×), brine (1×), dried and concentrated to give a yellow syrup which was purified by chromatography to provide the desired acid 11f ($R^{9'}$=3-(tert-Butyl-dimethyl-silanyloxy)-propyl, P=Boc) (1.83 g, 69%) as a colorless syrup: $^1$H NMR (300 MHz, CDCl$_3$) δ 4.26 (t, J=6.9, 1), 3.57 (t, J=6.5, 2), 3.53–3.44 (m, 1), 3.43–3.33 (m, 1), 2.05–1.96 (m, 1), 1.82–1.68 (m, 2), 1.64–1.45 (m, 3), 1.42 (s, 9), 1.37–1.27 (m, 3), 0.86 (s, 9), 0.02 (s, 6). MS (ESPOS): 424.7 [M+Na]+.

Method Q (2S,4R)-N-Boc-4-hydroxyproline methylester.

To a stirred solution of (2S,4R)-4-hydroxyproline (Bachem) (25 g, 108 mmol) in methanol (50 mL) at 0° C. was added trimethylsilyldiazomethene (24.6 g, 216 mmol). The mixture was stirred at 0° C. for 1 h. The residue obtained on removal of solvent was purified by column chromatography using 50% ethyl acetate in hexanes to obtain (2S,4R)-N-Boc-4-hydroxyproline methylester (27 g, 100%) as a colorless oil: $^1$H NMR (300 MHz, CDCl$_3$) δ 4.47 (m, 1), 4.39 (m, 1), 3.70 (s, 3), 3.60 (m, 2), 2.27 (m, 1), 2.05 (m, 1), 1.38 (s, 9); MS (ESPOS): 268 (M+Na).

(2S,4R)-N-Boc-4-ketoproline methylester 12a (P=Boc, P$_2$=Me, m=1).

To oxalyl chloride (15 g, 118 mmol) in DCM (15 mL) at −78° C., DMSO (18.6 mL, 236 mmol) was added slowly over 15 minutes. After the completion of addition, (2S,4R)-N-Boc-4-hydroxyproline methylester (26.5 g, 108 mmol) in DCM (100 mL) was added dropwise and stirred at −78° C. for 20 min, then triethylamine (54.6 g, 540 mmol) was added and left stirred for 2 h. The reaction mixture was then washed with 10% aq. HCl (200 mL). The organic layer was separated and dried over sodium sulfate. The crude product obtained on removal of solvent was purified by silica gel column chromatography using 50% EtOAc in hexanes to obtain 12a (P=Boc, P2=Me, m=1)-(20 g, 78%) as a brown solid: $^1$H NMR (300 MHz, CDCl$_3$) δ 4.80 (m, 1), 3.88 (d, J=8.7, 2), 3.77 (s, 3), 2.98 (m, 1), 2.58 (m, 1), 1.45 (s, 9); MS (ESPOS): 244 (M+H).

N-Boc-4-hydroxy-4-allylproline methylester 12b (P=Boc, P$_2$=Me, m=1, R$^9$=allyl).

To a stirred solution of 12a (P=Boc, P$_2$=Me) (1 g, 4.11 mmol) in THF (10 mL), tetraallyltin (1.08 mL, 4.52 mmol) in dry THF was added, then cooled to 0° C. before borontrifluoride etherate (0.520 mL, 4.11 mmol) was added slowly. The mixture was stirred at 0° C. for 1 h and then at room temperature for an additional 2 h. Potassium fluoride (360 mg in 5 mL water) and celite (1 g) was added and the reaction mixture was stirred for an hour. The reaction mixture was filtered and concentrated to dryness. The residue was dissolved in DCM (200 mL) and washed with water (100 mL) and brine (100 mL), dried over MgSO$_4$ and evaporated to dryness. The residue obtained was purified by silica gel column chromatography using 50% EtOAc in hexanes to obtain 12b (P=Boc, P$_2$=Me, m=1, R$^9$=allyl) (0.94 g, 80%) as a colorless oil: $^1$H NMR (300 MHz, CDCl$_3$) δ 5.87 (m, 1), 5.19 (m, 2), 4.34 (m, 1), 3.75 (d, J=4.8, 3), 3.50 (m, 3), 2.37 (m, 1), 2.21 (m, 1), 1.39 (d, J=12.9, 9); MS (ESPOS): 308 [M+Na]+.

N-Boc-4-fluoro-4-allylproline methylester 12c (P=Boc, P$_2$=Me, m=1, R$^9'$=allyl).

To a stirred solution of DAST (1.06 g, 6.58 mmol) in DCM (10 mL) at −78° C., 12b (P=Boc, P$_2$=Me, R$^9$=allyl) (940 mg, 3.3 mmol) in dry DCM (10 mL) was added slowly. The mixture was then stirred at −78° C. for 1 h, then at −10° C. for an additional 1 h. DCM (50 mL) was added, quenched with NH$_4$Cl (10%, 150 mL), the organic layer was separated, dried over sodium sulfate and evaporated to dryness. The residue was purified by silica gel column chromatography using 5% EtOAc in hexanes as eluent to provide the desired product 12c (P=Boc, P$_2$=Me, m=1, R$^9$=allyl) (330 mg, 34%) as a colorless oil: $^1$H NMR (300 MHz, CDC$_{13}$) δ 5.82 (m, 1), 5.12 (m, 2), 4.43 (m, 1), 3.66 (s, 3), 3.47 (m, 1), 2.37 (m, 1), 2.43 (m, 4), 1.37 (dd, J=4.5, 13.8, 9); MS (ESPOS): 310 [M+Na]+.

N-Boc-4-fluoro-4-propylproline methyl ester 12c (P=Boc, P$_2$=Me, m=1, R$^9$=propyl).

To a solution of 12c (P=Boc P$_2$=Me, m=1, R$^9$=allyl)(0.33 g, 1.15 mmol) in MeOH (15 mL) was added 10% Pd/C (40 mg). The reaction mixture was stirred at room temperature under hydrogen (30 atm) for 3 hr. The catalyst was filtered through celite and washed with methanol. The filtrate was concentrated to give the desired protected amino acid ester 12c (P=Boc, P$_2$=Me, R$^9$=propyl) (0.33 g, 100%) as a clear oil: $^1$H NMR (300 MHz, CDCl3) δ 4.43 (m, 1), 3.71 (m, 4), 3.47 (m, 1), 2.51 (m, 1), 1.98 (m, 5), 1.40 (dd, J=5.1, 13.8, 9), 0.93 (J=7.8, 3); MS (ESPOS): 190 [M−Boc]+.

N-Boc-4-fluoro-4-propylproline 12d (P=Boc, R$^9$=propyl, m=1).

To a solution of the methyl ester 12d (330 mg, 1.15 mmol) in THF (12 mL) and water (4 mL), was added lithium hydroxide monohydrate (60 mg, 1.38 mmol). The reaction mixture was stirred at room temperature overnight. THF was removed, the residue was taken up in ethyl acetate (50 mL), washed with 10% citric acid (100 mL) and brine (20 mL). Concentration of organic portion afforded the desired protected amino acid 12e (P=Boc, R$^9$=propyl, m=1) (310 mg, 100%) as a white solid: $^1$H NMR (300 MHz, CD$_3$OD) δ 4.43 (m, 1), 3.71 (m, 6), 2.51 (m, 2), 1.98 (m, 3), 1.45 (m, 9), 0.96 (m, 3); MS (ESNEG): 274 [M−1]

Method R (2S,4R)-N-Trifluoroacyl-4-tertbutyloxyproline.

To a solution of 4-tertbutyloxyproline (Bachem) (5.0 g, 27 mmol, 1 equiv) and TEA (11.2 mL, 80 mmol, 3 equiv) dry MeOH (30 mL) was added ethyl trifluoroacetate (4.8 mL, 40 mmol, 1.5 equiv). The mixture was stirred at 24° C. overnight. The solution was concentrated to dryness, dissolved in DCM (200 mL) and the organic phase washed with aq. 0.2 M KHSO4 (2×100 mL) and brine (1×100 mL), dried over MgSO4 and evaporated to dryness. The resulting residue was titurated with cyclohexane and pentane to provide the product (2S,4R)-N-Trifluoroacyl-4-tertbutyloxyproline as a light yellow powder (5.5 g, 72%).

14a (P=CF$_3$CO, m=1, R$^2$=H, R$^3$=OH).

To a solution of MTL 1a (1.32 g, 5.3 mmol, 1 equiv) in dry DMF (16 mL) at 0° C. was added triethylamine (2.20 mL, 15.9 mmol, 3 equiv), followed by bis-(trimethylsilyl) trifluoroacetamide (2.81 mL, 10.6 mmol, 2.0 equiv). The reaction mixture was stirred at 0° C. for 10 minutes, and then was stirred at rt for 50 minutes. To the reaction mixture were added (2S,4R)-N-Trifluoroacyl-4-tertbutyloxyproline (1.8 g, 6.3 mmol, 1.2 equiv), HATU (3.02 g, 8.0 mmol, 1.5 equiv). The reaction mixture was stirred for 3 h. The reaction mixture was evaporated to dryness, taken up in ethyl acetate (500 mL), washed with 10% citric acid (100 mL), water (100 mL), half sat. aqueous NaHCO$_3$ (200 mL) and brine. The organic layer was dried over Na$_2$SO$_4$ and evaporated to give a yellow syrup, which was dissolved in MeOH (100 mL). Dried Dowex® H+ form resin (500 mg) was added and the resulting suspension was stirred for 50 min, filtered, and evaporated to dryness to give a yellow solid (2.89 g). Purification of the product by silica chromatography DCM/hexanes/MeOH 6:5:1 to 7:2:1 provided product 14a (P=CF$_3$CO, m=1, R$^2$=H, R$^3$=OH) as a colorless solid (1.7 g, 51%).

14b (P=CF$_3$CO, m=1, R$^2$=H, R$^3$=OAc).

To a solution of 14a (P=CF$_3$CO, m=1, R$^2$=H, R$^3$=OH) (1.63 g, 3.1 mmol), pyridine (3 mL, 30 mmol,) and DMAP (38 mg, 0.31 mmol) in dry DCM (10 mL) at 0° C. was added acetic anhydride (3 mL, 31 mmol). The reaction temperature was allowed to rise to 24° C. over 1 h and stirred 48 h. The reaction mixture was diluted with chloroform (200 mL) and the organic phase washed with Aq. 10% acetic acid (3×200 mL), 10% citric acid (200 mL) half sat. aq. NaHCO$_3$ (200 mL) and brine (1×100 mL), dried over Na$_2$SO$_4$ and evaporated to give the peracylated intermediate 14b (P=CF$_3$CO, m=1, R$^2$=H, R$^3$=OAc) (2.14 g, 99%) as colorless crystals.

To a solution of the above per-acylated intermediate 14b (P=CF3CO, m=1, R2=H, R3=OAc) (2.1 g, 3.1 mmol) in DCE (64 mL) with methylsulfide (1.4 mL) were added trifluoroacetic acid (21 mL) and water (1.4 mL). The reaction mixture was stirred at rt for 1 h. The solvent was removed under vacuum and co-evaporated with DCE twice. The residue was purified by chromatography 5% MeOH in DCM to provide the intermediate alcohol (1.6 g, 83%) as a colorless solid which was taken to the next step without characterization.

14b (P=CF$_3$CO, m=1, R$^2$=H, R$^3$=OAc).

To a solution of the above 4-alcohol intermediate (1.5 g, 2.38 mmol, 1 equiv) and DMAP (29 mg) in DCE (9.5 mL) was added p-toluenesulfonic anhydride (1.01 g, 3.09 mmol, 1.3 equiv). The reaction mixture was cooled to 0° C. and pyridine (0.77 mL, 9.52 mmol, 4 equiv) was added. The reaction mixture was stirred at 0° C. for 30 minutes then at rt overnight. The reaction mixture was concentrated to dryness. The residue was taken up in ethyl acetate (200 mL), washed with 10% citric acid (2×200 mL), sat. NaHCO$_3$ (200 mL) and brine, and dried over Na$_2$SO$_4$ and concentrated to yield a yellow syrup which was purified by chromatography 4:1 hexanes/EtOAc to provide the p-toluenesulfonic ester product 14b (P=CF$_3$CO, m=1, R$^2$=H, R$^3$=OAc) (1.7 g, 92%) as a colorless solid.

Method S

Diethyl n-propylmalonate.

To a suspension of sodium hydride (60% dispersion in mineral oil, 12.6 g, 315 mmol, 1.05 equiv) in DMF (300 mL) at 23° C. was added a solution of diethyl malonate (45.5 mL, 300 mmol, 1 equiv) in DMF (100 mL) via cannula over the course of 10 min. The addition caused a mild exotherm and H$_2$ gas evolution was observed, cooling was not necessary. Following the addition, the reaction was stirred for 45 min at 23° C. then treated with 1-bromopropane (27.3 mL, 300 mmol, 1 equiv). The reaction was stirred at 23° C. for 25 min, then heated to 65° C. for 3 h, then stirred at 23° C. overnight. The reaction mixture was added to 1.0 N HCl (1 L) then extracted with diethyl ether (700 mL). The ether extracts were washed with H$_2$O (400 mL), brine (200 mL), dried (MgSO$_4$), filtered and concentrated to give 65.1 g of product as a clear oil. $^{13}$C NMR revealed approximately 4:1 mono:bis-alkylated product. The product diethyl n-propylmalonate was used without further purification: $^1$H NMR (300 MHz, CDCl$_3$) 4.18 (q, J=6.9 Hz, 4H), 3.32 (t, J=7.8 Hz, 1H), 1.91–1.79 (m, 2H), 1.41–1.25 (m, 2H), 1.25 (t, J=6.9 Hz, 6H), 0.92 (t, J=7.5 Hz, 3H); $^{13}$C NMR (300 MHz, CDCl$_3$) (*denotes signal due to minor product of bis-alkylation)? 169.6, 61.2, 60.9*, 51.8, 34.4*, 30.7, 20.5, 17.3*, 14.4*, 14.0, 13.7.

Ethyl n-propylmalonate 21b (R$^9$=n-propyl).

To a solution of diethyl n-propylmalonate (contaminated by approximately 20% diethyl bis(n-propyl)malonate, 65.0 g, 273 mmol, 1 equiv) in EtOH (500 mL) at 23° C. was added a solution of 1.0 M KOH (273 mL, 273 mmol, 1 equiv). Following the addition, the reaction was heated to 80° C. (internal temperature) for 4 h. After cooling to 23° C. EtOH was removed in vacuo. The residual mixture was partitioned between diethyl ether (400 mL) and H$_2$O (200 mL). The layers were separated and the ether layer was extracted with saturated aqueous NaHCO$_3$ (100 mL). The aqueous NaHCO$_3$ layer was combined with the original aqueous layer and this solution was acidified to pH 1 with 1.0 N HCl, then extracted with EtOAc (2×600 mL). The EtOAc extracts were dried (MgSO$_4$), filtered and concentrated to give 21b (R$^9$=n-propyl) 41.3 g (237 mmol, 79% for 2 steps) of pure product as a clear oil: $^1$H NMR (300 MHz, CDCl3) 4.43 (q, J=7.2 Hz, 2H), 3.60 (t, J=7.5 Hz, 1H), 2.18–2.02 (m, 2), 1.66–1.50 (m, 2H), 1.49 (t, J=7.2 Hz, 3H), 1.15 (t, J=7.5 Hz, 3H).

Ethyl n-propylacrylate 21c (R$^9$=n-propyl).

To a solution of ethyl n-propylmalonate (41.3 g, 237 mmol, 1 equiv) in EtOH (500 mL) at 23° C. was added piperidine (28.1 mL, 284 mmol, 1.2 equiv) followed by aqueous formaldehyde (37%, 88 mL). Following the addition, the reaction was refluxed for 29 h. After cooling to 23° C., the mixture was partitioned between diethyl ether (500 mL) and 1.0 N HCl (800 mL). The layers were separated and the aqueous layer was extracted with diethyl ether (500 mL). The combined organic layers were washed with H$_2$O (500 mL), brine (300 mL), dried (MgSO$_4$), filtered and concentrated (rotovap only, product is potentially volatile). The product was vacuum distilled (bp 70° C. at 15 mmHg) to give 16.4 g 21c (R$^9$=n-propyl) (115 mmol, 49%) of the desired product: $^1$H NMR shows contamination with unidentified material; the product was used in the subsequent step without further purification: $^1$H NMR (300 MHz, CDCl$_3$) 6.12 (s, 1H), 5.50 (s, 1H), 4.19 (q, J=7.2 Hz, 2H), 2.23 (t, J=7.5 Hz, 2H), 1.55–1.42 (m, 2H), 1.24 (t, J=7.2 Hz, 3H), 0.92 (t, J=7.5 Hz, 3H).

2-Propyl-prop-2-en-1-ol.

To a solution of 21c (R$^9$=n-propyl) (16.4 g, 115 mmol, 1 equiv) in CH$_2$Cl$_2$ (500 mL) at 78° C. was added DIBALH (1.0 M in hexanes, 403 mL, 403 mmol, 3.5 equiv) via cannula over the course of 20 min. Following the addition, the reaction was stirred at 78° C. for 30 min, then allowed to warm to 55° C. over the course of 60 min. Once the reaction bath temperature had reached 55° C., EtOAc (15 mL) was added to quench excess DIBALH. After stirring for 5 min the quenched reaction mixture was added slowly via cannula to a stirred mixture of 1:1 saturated aqueous sodium potassium tartrate:saturated aqueous NaHCO$_3$ (1 L) at 23° C. The biphasic mixture was stirred for 1 h then the layers were separated. The aqueous layer was extracted with diethyl ether (500 mL). The combined organic layers were dried (MgSO$_4$), filtered and concentrated (rotovap only, product is potentially volatile). The product was vacuum distilled (bp 100–120° C. at 15 mmHg) to give 7.58 g (75.8 mmol, 66%) of the desired product 2-Propyl-prop-2-en-1-ol as a clear oil: $^1$H NMR (300 MHz, CDCl3) 5.22 (s, 1H), 5.06 (s, 1H), 4.27 (s, 2H), 2.24 (t, J=7.5 Hz, 2H), 1.75–1.60 (m, 2H), 1.12 (t, J=6.9 Hz, 3H).

2-Bromomethyl-pent-1-ene 21d (R$^9$=n-propyl).

To a solution of n-propyl allyl alcohol (7.58 g, 75.8 mmol, 1 equiv) in Et$_2$O (65 mL) at 0° C. was added pyridine (0.58 mL). A solution of PBr$_3$ (4.28 mL, 45.5 mmol, 0.6 equiv) in Et$_2$O (20 mL) was then added via cannula over the course of 15 min. Following the addition, the reaction was stirred at 0°

C. for 75 min, then the cold reaction mixture was added slowly to stirred ice-cold saturated aqueous NaHCO$_3$ (500 mL). The resulting biphasic mixture was extracted with diethyl ether (250 mL). The organic extracts were washed with saturated aqueous NaHCO$_3$ (2×100 mL), brine (100 mL), 1.0 N HCl (100 mL), brine (100 mL), dried (MgSO$_4$), filtered and concentrated (rotovap at 0° C., product is volatile). The product was purified via flash column chromatography on silica gel using pentane as eluent to give 5.97 g (36.8 mmol, 49%) of the desired product 21d (R$^9$=n-propyl) as a clear oil: $^1$H NMR (300 MHz, CDCl$_3$) 5.16 (s, 1H), 4.95 (s, 1H), 3.97 (s, 2H), 2.19 (t, J=7.5 Hz, 2H), 1.56–1.43 (m, 2H), 0.93 (t, J=7.8 Hz, 3H).

N-Allylglycine ethyl ester.

To a solution of allylamine 21e (R$^{9b}$=H, m=1) (50 mL, 666 mmol, 2 equiv) in Et$_2$O (167 mL) at 0° C. was added ethyl bromoacetate (36.9 mL, 333 mmol, 1 equiv). White precipitate and an exothermic reaction were observed immediately upon addition; the exotherm caused the solvent to boil for approximately 2 min. Following the addition, the reaction was stirred for 2.5 h, then the ice-water bath was removed and the reaction was stirred at 23° C. overnight. After 15 h at 23° C. the reaction mixture was filtered through a glass frit to remove the precipitated allylamine hydrobromide salt byproduct. The collected solid was washed with Et$_2$O (200 mL), then the combined filtrates were concentrated. The product was vacuum distilled (bp 48–55° C. at 1.0 mm Hg) to give 35.5 g (249 mmol, 75%) of the desired product N-Allylglycine ethyl ester as a yellow oil: $^1$H NMR (300 MHz, CDCl$_3$) 5.93–5.79 (m, 1H), 5.22–5.08 (m, 2H), 4.18 (q, J=7.2 Hz, 2H), 3.39 (s, 2H), 3.29–3.23 (m, 2H), 1.27 (t, J=7.2 Hz, 3H); MS (ESPOS): 144.1 [M+H]+.

N-Allylglycine ethyl ester hydrochloride 21f (R$^{9b}$=H, m=1).

To a solution of N-allylglycine ethyl ester (10.0 g, 70.0 mmol, 1 equiv) in Et$_2$O (260 mL) and hexane (1.3 L) at 23° C. was slowly added 4.0 M HCl in dioxane (16.6 mL, 66.5 mmol, 0.95 equiv) over the course of 35 min via addition funnel. Following the addition the suspension was stirred a further 40 min, then the product was isolated via filtration through a glass frit, washing with hexane (200 mL). The collected white solid was transferred to a flask and placed under vacuum (0.5 mm Hg) for 1 h to give 11.5 g of the desired product as a white solid. The reaction was repeated on the same scale to yield a total of 22.73 g (127 mmol, 90%) of the desired amine hydrochloride 21f (R$^{9b}$=H, m=1) as a white solid: $^1$H NMR (300 MHz, DMSO-d6) 9.50 (s, 2H), 5.95–5.81 (m, 1H), 5.49–5.37 (m, 2H), 4.21 (q, J=7.2 Hz, 2H), 3.92 (s, 2H), 3.59 (d, J=6.6 Hz, 2H), 1.24 (t, J=7.2 Hz, 3H); MS (ESPOS): 144.1 [M+H]+.

Pseudoephedrine N-allylglycinamide 21h (R$^{9b}$=H, m=1).

To a flask containing 21f (R$^{9b}$=H). (20.3 g, 113 mmol, 1.3 equiv) and (1R,2R)-pseudoephedrine 21g (14.4 g, 86.9 mmol, 1 equiv) was added THF (130 mL). The resulting mixture was stirred vigorously for 20 minutes at 20° C. to give a uniform slurry, then treated with solid lithium-tert-butoxide (9.74 g, 122 mmol, 1.4 equiv) added in a single portion. The reaction was stirred at 20° C. for 2 d, after which time analysis revealed both starting materials were still present. The incomplete reaction was treated with H$_2$O (200 mL), then THF was removed in vacuo. The resulting aqueous solution was extracted with CH$_2$Cl$_2$ (2 150 mL), then saturated with NaCl and further extracted with CH$_2$Cl$_2$ (2 100 mL). The organic extracts were dried (K$_2$CO$_3$), filtered and concentrated. The crude product was purified via flash column chromatography on silica gel using 2:2:96 MeOH/Et$_3$N/CH$_2$Cl$_2$ as eluent to give 18 g of product. This material was still substantially contaminated with N-allylglycine ethyl ester, this was removed with gentle heating (60° C.) under vacuum (1.0 mmHg) for 15 h to give 14.88 g (56.8 mmol, 65%) of the desired glycinamide product 21h (R$^{9b}$=H, m=1) as a viscous oil: $^1$H NMR (300 MHz, CDCl$_3$) (Spectrum shows rotamers) 7.41–7.24 (m, 5H), 6.00–5.80 (m, 1H), 5.29–5.07 (m, 2H), 4.64–4.44 (m, 1H), 3.96–3.84 (m, 0.5H), 3.63 (d, J=13.8 Hz, 0.5H), 3.45–3.21 (m, 4H), 2.95 (s, 1.5H), 2.78 (s, 1.5H), 1.11 (d, J=6.9 Hz, 1.5H), 0.98 (d, J=6.9 Hz, 1.5H); MS (ESPOS): 263.2 [M+H]+. HPLC (Symmetry C18, 3.5 μm particle size, 100 Å pore size, 4.6 mm diameter 30 mm length, 2%–98% MeCN in H2O w/0.1% TFA over 10 min, 2 mL/min flow rate): Rt=3.10 min.

Alkylation of pseudoephedrine N-allylglycinamide.

To a flask containing LiCl (flame dried in vacuo, 3.14 g, 74.1 mmol, 4 equiv) at 0° C. was added a solution of pseudoephedrine N-allylglycinamide 21h (R$^{9b}$=H, m=1) (4.85 g, 18.5 mmol, 1 equiv) in THF (50 mL). The resulting mixture was stirred at 0° C. for 25 min, then treated with a solution of LiHMDS (1.0 M in THF, 37.0 mL, 37 mmol, 2 equiv) added slowly via cannula over the course of 40 min. Following the addition of LiHMDS, the enolate solution was stirred at 0° C. for a further 30 min, then allylic bromide (3.00 g, 18.5 mmol, 1 equiv) was added dropwise via syringe over the course of 30 sec. The reaction was stirred at 0° C. for a further 90 min then quenched with H$_2$O (200 mL) and extracted with CH$_2$Cl$_2$ (3×150 mL). The organic extracts were dried (K$_2$CO$_3$), filtered and concentrated to give 8.0 g of yellow oil. A small portion of the crude product was purified via flash column chromatography on silica gel using (3:2:95 MeOH/Et$_3$N/CH$_2$Cl$_2$) as eluent to provide an analytically pure sample of product. The remaining material was used without any purification in the subsequent step: $^1$H NMR (300 MHz, CDCl$_3$) (Spectrum shows rotamers) 7.40–7.24 (m, 5H), 5.90–5.76 (m, 1H), 5.20–5.02 (m, 2H), 4.92–4.75 (m, 2H), 4.66–4.45 (m, 2H), 4.20–4.00 (m, 1H), 3.62 (t, J=6.3 Hz, 1H), 3.34–3.16 (m, 1H), 3.05–2.94 (m, 2H), 2.84 (s, 3H), 2.55 (q, J=7.2 Hz, 1H), 2.22–1.80 (m, 5H), 1.58–1.36 (m, 3H), 1.11 (d, J=6.9 Hz, 2H), 1.04 (t, J=7.2 Hz, 1H), 0.96 (d, J=6.9 Hz, 1H), 0.89 (t, J=7.2 Hz, 2H); MS (ESPOS): 345.0 [M+H]+. HPLC (Symmetry C18, 3.5 μm particle size, 100 Å pore size, 4.6 mm diameter 30 mm length, 2%–98% MeCN in H$_2$O w/0.1% TFA over 10 min, 2 mL/min flow rate): Rt=4.28 min.

Boc-protection of diene amino amide 21i (R$^9$=n-propyl, R$^{9b}$=H, m=1).

To a solution of amine (crude from previous step, 8.0 g, approximately 18 mmol, 1 equiv) in CH$_2$Cl$_2$ (100 mL) at 23° C. was added triethylamine (2.83 mL, 20 mmol, 1.1 equiv) followed by (Boc)$_2$O (8.07 g, 37 mmol, 2 equiv). The resulting mixture was stirred at 23° C. for 13.5 h, then concentrated. The crude product was purified via gradient flash column chromatography on silica gel (column packed 5.5 cm diameter 17 cm height) eluting first with 25% EtOAc/hexanes (1 L), then 30% EtOAc/hexanes (600 mL), then 40% EtOAc/hexanes (400 mL). This provided 21i (R$^9$=n-propyl, R$^{9b}$=H, m=1). 5.20 g (11.7 mmol, 65% over 2 steps) of pure product. Some mixed fractions also containing minor amounts of product were discarded: $^1$H NMR (300 MHz, CDCl3) (Spectrum shows rotamers) 7.52–7.24 (m, 5H), 5.90–5.62 (m, 1H), 5.44 (t, J=6.9 Hz, 0.5H), 5.20–4.96 (m, 2.5H), 4.77 (d, J=13.2 Hz, 2H), 4.68–4.35 (m, 2H), 4.00–3.55 (m, 1H), 3.79 (d, J=5.7 Hz, 1H), 2.91 (s, 1H), 2.87 (s, 2H), 2.52–2.29 (m, 2H), 2.10–1.96 (m, 2H), 1.54–1.35 (m, 9H), 1.13–1.00 (m, 2H), 0.96–0.86 (m, 3H); MS (ESPOS): 467.3 [M+Na]+. HPLC (Symmetry C18, 3.5 μm particle size, 100 Å pore size, 4.6 mm diameter 30 mm length, 2%–98% MeCN in H$_2$O w/0.1% TFA over 10 min, 2 mL/min flow rate): Rt=6.85 min.

Ring-closing diene metathesis 21j ($R^9$=n-propyl, $R^{9b}$=H, m=1).

To a solution of diene 21i ($R^9$=n-propyl, $R^{9b}$=H) (5.20 g, 11.7 mmol, 1 equiv) in CH$_2$Cl$_2$ (700 mL) at 23° C. was added benzylidene [1,3-bis(2,4,6-trimethylphenyl)-2-imidazolidinylidene]dichloro-(tricyclohexylphosphine)ruthenium (Grubbs 2nd generation catalyst, 320 mg, 0.38 mmol, 0.03 equiv). The reaction was refluxed for 2 h, then cooled to 23° C. and concentrated. The resulting product was first purified via flash column chromatography on silica gel (40% EtOAc in hexanes as eluent) to give the desired product still slightly contaminated with unidentified material. The product was then dissolved in hot hexanes (100 mL), and allowed to crystallize over the course of 2 days. The crystallized product was isolated via filtration through a glass frit, washing with ice-cold hexane (100 mL), providing 3.425 g of the desired tetrahydropyridine (8.23 mmol, 70%): The mother liquor was concentrated to give 0.57 g of brown oil which was again subjected to flash column chromatography on silica gel (40–50% EtOAc in hexanes as eluent) to give a further 392 mg (0.94 mmol, 8%) of desired product 21j ($R^9$=n-propyl, $R^{9b}$=H, m=1): $^1$H NMR (300 MHz, CDCl$_3$) (spectrum shows rotamers) 7.50–7.25 (m, 5H), 5.52–5.26 (m, 1H), 5.05–4.96 (m, 1H), 4.63–4.35 (m, 2H), 4.30–3.58 (m, 3H), 2.91 (s, 3H), 2.50–2.34 (m, 1H), 2.20–1.94 (m, 3H), 1.46 (s, 7H), 1.41 (s, 2H), 1.19–1.01 (m, 2H), 0.94–0.85 (m, 3H); MS (ESPOS): 439.3 [M+Na]+. HPLC (Symmetry C18, 3.5 μm particle size, 100 Å pore size, 4.6 mm diameter 30 mm length, 2%–98% MeCN in H2O w/0.1% TFA over 10 min, 2 mL/min flow rate): Rt=6.29 min.

Cleavage of pseudoephedrine auxiliary 21k ($R^9$=n-propyl, $R^{9b}$=H, m=1).

To a solution of amide 21j ($R^9$=n-propyl, $R^{9b}$=H, m=1) (3.42 g, 8.22 mmol, 1 equiv) in MeOH (170 mL) at 23° C. was added 1.0 M aqueous NaOH (41.1 mL, 41.1 mmol, 5 equiv). The reaction was refluxed for 24 h (oil-bath temperature at 100° C.), then cooled to 23° C. and concentrated via rotary evaporation to remove most of the MeOH. The resulting aqueous solution was transferred to a separatory funnel, diluted with H$_2$O (100 mL) and extracted with Et$_2$O (100 mL). The ether extract was washed with 0.5 M aqueous NaOH (70 mL) then discarded. The combined basic aqueous layers were acidified to pH 2 with 1.0 N HCl, then extracted with EtOAc (2 200 mL). The organic extracts were dried (MgSO$_4$), filtered and concentrated to give 2.46 g of the desired Boc-protected amino acid 21k ($R^9$=n-propyl, $R^{9b}$=H, m=1): $^1$H NMR (300 MHz, CDCl$_3$) (Spectrum shows rotamers) 5.36 (d, J=22.8 Hz, 1H), 5.09 (d, J=4.8 Hz, 0.5H), 4.90 (br s, 0.5H), 4.14–3.97 (m, 1H), 3.83–3.67 (m, 1H), 2.57–2.37 (m, 2H), 1.98 (t, J=7.2 Hz, 2H), 1.48 (s, 6H), 1.47–1.35 (m, 2H), 1.46 (s, 3H), 0.86 (t, J=7.2 Hz, 3H); MS (ESPOS): 292.1 [M+Na]+; MS (ESNEG): 268.2 [M–H]–.

Method T

To anhydrous MeOH (20 mL) at 0° C. was added dropwise SOCl$_2$ (1.58 mL, 21.6 mmol) the solution was stirred at 0° C. for 10 minuets then solid L-2-amino-4-pentenioc acid 22a ($R^{9b}$=H) (Aldrich) (1.0 g, 8.7 mmol) was added. The reaction mixture was stirred 48 h at ambient temperature, solvents were removed under vacuum. Purification was carried by silica gel column chromatography (10% MeOH/DCM) provide L-2-amino-4-pentenioc acid methyl ester 22b ($R^{9b}$=H) (0.95 g, 85%).

To a solution of L-2-amino-4-pentenioc acid methyl ester in dichloroethane (32 mL) at 0° C. was added 2,4,6-collidine (2.3 mL, 19.1 mmol, 2.2 equiv) and solid 2-nitrobenzenesulfonyl chloride. The reaction was stirred for 3 h at r.t. The solvent was removed under vacuum and the residue was distributed between EtOAc (200 mL) and saturated aqueous NH$_4$Cl. The organic layer was washed with 1.0 M aq. KHSO$_4$, saturated aq. NaHCO$_3$, brine, and dried (MgSO$_4$), and concentrated to give a residue that was purified by column chromatography on silica (gradient 10 to 20% EtOAc/hexanes) to give the desired product 22b ($R^{9b}$=H) 0.70 g (26%) as a yellow oil.

$^1$H NMR (300 MHz, CDCl$_3$) δ 8.10–8.06 (m, 1), 7.95–7.92 (m, 1), 7.76–7.73 (m, 2), 6.08 (d, J=8.2, 1), 5.74–5.60 (m, 1), 5.17–5.12 (m, 2), 4.33–4.26 (m, 1), 3.52 (s, 3), 2.58 (dd, J=6.0, 6.0, 1), 3.44–3.30 (m, 2), 2.25–2.10 (m, 2), 2.11 (s, 3), 2.00–1.88 (m, 1), 1.86–1.70 (m, 1), 1.44–1.25 (m, 6), 0.98–0.88 (m, 9H).

MS (ESNEG): 313.0 [M–H]$^-$.

To a stirred suspension of sulfonamide 22b ($R^{9b}$=H) (685 mg, 2.18 mmol), Cs$_2$CO$_3$ (710 mg, 2.18 mmol), and tetrabutylammonium bromide (702 mg, 2.18 mmol), in DMF (5.0 mL) was added a solution of 3-methylenehex-1-yl-toluenesulfonate 22c ($R^9$=propyl) (702 mg, 2.61 mmol; prepared as described by Kelvin H. Yong et al. *Journal of Organic Chemistry*, 2001, 66, 8248) in DMF (1.0 mL), the reaction mixture was heated to 60° C. overnight. The reaction solvent was removed by evaporation, the resulting residue taken up in EtOAc and washed with 10% aqueous citric acid and brine, the organic phase was dried over MgSO$_4$ concentrated to give a residue that was purified by column chromatography on silica (17%–20% EtOAc/hexanes) to give the desired product 22d ($R^9$=propyl, $R^{9b}$=H), (0.38 g, 42%) as an oil.

MS (ESPOS): 433 [M+Na]$^+$.

To a solution of 22d ($R^9$=propyl, $R^{9b}$=H) (0.38 g, 0.92 mmol) in anhydrous DCM (40 mL) was added benzylidene [1,3-bis(2,4,6-trimethylphenyl)-2-imidazolidinylidene] dichloro(tricyclohexylphosphine)ruthenium (23.3 mg, 0.0276 mmol) the resulting reaction mixture was refluxed under N$_2$ for 2.5 hrs, cooled to room temperature and concentrated. The product was purified by flash column chromatography on silica gel (35% ethyl acetate/hexanes) to give the desired compound 22e ($R^9$=propyl, $R^{9b}$=H) (0.29 g, 81%).

MS (ESPOS): 383 [M+Na]$^+$.

To a stirred solution of thiophenol (183 μL, 1.79 mmol) and 7-methyl-1,5,7-triazabicyclo-[4,4,0]dec-5-ene (214 μL, 1.49 mmol) in anhydrous DMF (3 mL) was added a solution of alkene 22e ($R^9$=propyl, $R^{9b}$=H) (228 mg, 0.596 mmol) in anhydrous DMF (3.0 mL) via a canula the resulting reaction mixture was stirred under N$_2$ for one hour then concentrated to a residue. The residue was taken up in ether, stirred with 1N aqueous HCl (15.0 mL) for 5 min. The aqueous phase was washed with ether then made basic with solid potassium carbonate. The resulting basic aqueous phase was extracted with ether three times. The combined organic layer was washed with brine, dried with anhydrous sodium sulfate, and concentrated, cooled to 0° C. and treated with 2M HCl in ether (0.8 mL) was added and the resulting mixture was stirred for 5 min and then evaporated to dryness to give the desired product 22f ($R^9$=propyl, $R^{9b}$=H) as the hydrochloride salt (144 mg, 103%).

MS (ESPOS): 198 [M+H]$^+$.

To a solution of amine 22f ($R^9$=propyl, $R^{9b}$=H) (143 mg, 0.61 mmol) in anhydrous dichrolomethane (2.0 mL) was added triethylamine (170 µL, 1.22 mmol) and di-t-butyldicarbonate (350 mg, 1.6 mmol). The resulting reaction mixture was stirred over night at room temperature under $N_2$ then evaporated to dryness and purified by flash column chromatography on silica gel using 20% ethylacetate in hexanes as an eluent to give the desired compound 22g ($R^9$=propyl, $R^{9b}$=H) (176 mg, 86%).

MS (ESPOS): 320 [M+Na]$^+$.

To a solution of ester 22g ($R^9$=propyl, $R^{9b}$=H) (175 mg, 0.59 mmol) in dioxane/water (6:1) (4 mL) was added 1 M aqueous lithium hydroxide (0.65 mL, 0.648 mmol). The resulting reaction mixture was stirred over night at room temperature under $N_2$ and the solvent was removed under reduced pressure. The residue was taken up in water washed with ether. The aqueous layer was acidified with 10% citric acid and extracted with ether. The organic layer was washed with brine, dried with sodium sulfate, and evaporated to dryness to give the desired protected cyclic amino acid 22h ($R^9$=propyl, $R^{9b}$=H) (175 mg, 105%).

MS (ESNEG): 292 [M−H]$^−$.

General Method U

To a solution of nitrone 23a (prepared as described by Dondoni et al, *Synthetic Communications*, 1994, 24, 2537–2550) (5.96 g, 16.4 mmol, 1 equiv) in $Et_2O$ (200 mL) at 23° C. was added a solution of $Et_2AlCl$ (1.0 M in heptane, 16.4 mL, 16.4 mmol, 1 equiv). The reaction was stirred for 15 min at 23° C. then cooled to −78° C. and treated with a solution of cyclopropylmagnesium bromide (0.5 M in THF, 99 mL, 49 mmol, 3 equiv) added via cannula over the course of 25 min. After stirring for a further 1.7 h at −78° C. the reaction was quenched at low temperature with 1.0 M aqueous NaOH (80 mL). The resulting mixture was stirred at 23° C. for 25 min, then transferred to a separatory fimnel and the layers separated. The organic layer was washed with brine (100 mL, using gentle agitation to avoid formation of an emulsion). The original aqueous layer was extracted with $Et_2O$ (3×150 mL), washing each extract with brine (100 mL). The combined organic layers were dried ($MgSO_4$), filtered and concentrated to give 5.89 g (14.5 mmol, 89%) of the desired product 23b ($R^{20}+R^{21}$=cyclopropane) as a white solid. This material was used without further purification.

MS (ESPOS): 406.0 [M+H]

To a solution of hydroxylamine 23b ($R^{20}+R^{21}$=cyclopropane) (5.89 g, 14.5 mmol, 1 equiv) and $Et_3N$ (12.2 mL, 87.3 mmol, 6 equiv) in $CH_2Cl_2$ (200 mL) at 0° C. was added methanesulfonyl chloride (2.25 mL, 29.1 mmol, 2 equiv). The reaction was stirred for 20 min at 0° C., then at 23° C. for a further 25 min, then added to 1.0 M aqueous NaOH:brine (1:1, 200 mL). The layers were separated, the aqueous layer was extracted with $CH_2Cl_2$ (2×50 mL), then the combined organics were dried ($MgSO_4$), filtered and concentrated. The resulting residue was dissolved in 1:1 EtOAc:hexane (200 mL) and washed with $H_2O$ (150 mL), saturated aqueous $NaHCO_3$ (200 mL), brine (150 mL), dried ($MgSO_4$), filtered and concentrated to give 5.95 g of brown oil of which the major component is the desired imine.

MS (ESPOS): 388.2 [M+H]

To a solution of crude imine (5.95 g) in MeOH (150 mL) at 23° C. was added Girard's reagent T (2.84 g, 16.9 mmol, 1.1 equiv). After stirring for 70 min the solution was concentrated. The residue was partitioned between EtOAc (150 mL) and 1:1:1 $H_2O$:brine:saturated aqueous $NaHCO_3$ (150 mL). The layers were separated, the aqueous layer was extracted with EtOAc (150 mL). The combined organics were dried ($MgSO_4$), filtered and concentrated to give 4.70 g of yellow oil of which the major component is the desired amine.

MS (ESPOS): 300.0 [M+H]$^+$.

To a solution of crude amine (4.70 g) and 2,6-lutidine (7.31 mL, 62.9 mmol, 4 equiv) in $CH_2Cl_2$ (200 mL) at 0° C. was added trifluoroacetic anhydride (3.28 mL, 23.6 mmol, 1.5 mmol). The reaction was stirred at 0° C. for 1 h, then at 23° C. for 3 h, then quenched with $H_2O$ (100 mL). The quenched reaction mixture was stirred for 10 min then partitioned between 1:1 EtOAc:hexanes (300 mL) and brine (200 mL). The layers were separated, the organic layer was washed with 1.0 N HCl, (300 mL), saturated aqueous $NaHCO_3$ (300 mL), brine (200 mL), dried ($MgSO_4$), filtered and concentrated. The product was purified using flash column chromatography on silica gel using 25% EtOAc in hexanes as eluent to provide 4.50 g of the desired trifluoroacetamide 23c ($R^{20}+R^{21}$=cyclopropane) (11.3 mmol, 78% from hydroxylamine).

MS (ESPOS): 418.0 [M+Na]$^+$

To a solution of diacetonide 23c ($R^{20}+R^{21}$=cyclopropane) (4.50 g, 11.3 mmol, 1 equiv) at 23° C. was added aqueous TFA (80%, 100 mL, precooled to 0° C.). The reaction was stirred at 23° C. for 35 min then concentrated to provide 3.87 g of white solid of which the major component is the desired deprotected galactose.

MS (ESPOS): 338.1 [M+Na]$^+$

To a solution of crude galactose (3.65 g, 11.6 mmol, 1 equiv) and $Et_3N$ (16.1 mL, 116 mmol, 10 equiv) in $CH_2Cl_2$ (130 mL) at 23° C. was added $Ac_2O$ (7.65 mL, 81.1 mmol, 7 equiv) followed by DMAP (141 mg, 1.2 mmol, 0.1 equiv). The reaction was stirred at 23° C. for 2 h, then quenched with MeOH (5 mL). The quenched reaction mixture was stirred for 5 min then diluted with $Et_2O$ (300 mL). The resulting solution was washed with $H_2O$ (2×300 mL), 1.0 N HCl (300 mL), saturated aqueous $NaHCO_3$ (300 mL), brine (300 mL), dried ($MgSO_4$), filtered and concentrated to provide 5.07 g of acetylated product as a mixture of both alpha/beta and pyranose/furanose isomers.

MS (ESPOS): 506.1 [M+Na]$^+$.

To a solution of peracetate isomers (5.07 g) in $CH_2Cl_2$ (150 mL) at 0° C. was added a solution of HBr in acetic acid (33%, 30 mL). The reaction was stirred at 0° C. for 30 min then warmed to 23° C. After stirring a further 3.5 h, the reaction mixture was diluted with $CH_2Cl_2$ (50 mL), washed with ice-water (2×300 mL), ice-cold 50% saturated aqueous $NaHCO_3$ (2×300 mL), ice-cold 50% saturated brine (300 mL), dried ($MgSO_4$) filtered and concentrated to provide 4.33 g of the α-bromide 23d ($R^{20}+R^{21}$=cyclopropane) (8.60 mmol, 76% from diacetonide). This material was used without further purification.

To a solution of bromide 23d ($R^{20}+R^{21}$=cyclopropane) (4.33 g, 8.60 mmol, 1 equiv) in AcOH (100 mL) at 23° C. was added AgOAc (1.44 g, 8.60 mmol, 1 equiv). After stirring for 45 min at 23° C., the reaction mixture was diluted with $CH_2Cl_2$ (350 mL) and washed with $H_2O$ (2×400 mL), ice-cold 50% saturated aqueous $NaHCO_3$ (3×300 mL), brine (400 mL), dried ($MgSO_4$), filtered and concentrated to give 3.76 g (7.78 mmol, 91%) of the desired β-acetate as a white foam. This material was used without further purification.

MS (ESPOS): 506.1 [M+Na]

To a solution of β-acetate (3.76 g, 7.78 mmol, 1 equiv) in $CH_2Cl_2$ (50 mL) at 23° C. was added $PCl_5$ (1.70, 8.17 mmol, 1.05 equiv) followed by BF$_3$.OEt$_2$ (50 µL). After stirring for 1 h the reaction was diluted with CH$_2$Cl$_2$ (300 mL) and washed with ice-cold brine (500 mL), ice-cold 50% saturated aqueous NaHCO$_3$ (2×500 mL), ice-cold brine (500 mL), dried (MgSO$_4$), filtered and concentrated to give 3.72 g of the desired β-chloride 23e (R$^{20}$+R$^{21}$=cyclopropane). The product was used without further purification.

MS (ESNEG): 458.2 [M−H]

To a solution of galactosyl chloride 23e (R$^{20}$+R$^{21}$=cyclopropane) (3.72 g, 8.10 mmol, 1 equiv) in DMF (30 mL) and HMPA (7.5 mL) at 23° C. was added MeSNa (1.70 g, 24.3 mmol, 3 equiv). After stirring for 35 min at 23° C., the reaction mixture was partitioned between Et$_2$O (150 mL) and 1:1 H$_2$O/brine (70 mL). The layers were separated, the aqueous layer was re-extracted with Et$_2$O (150 mL). The combined organics were dried (MgSO$_4$), filtered and concentrated. The residue was dissolved in CH$_2$Cl$_2$ (130 mL) and treated with Et$_3$N (11.3 mL, 81.0 mmol, 10 equiv), Ac$_2$O (5.35 mL, 56.7 mmol, 7 equiv), and DMAP (99 mg, 0.81 mmol, 0.1 equiv). After stirring for 1 h at 23° C. the reaction was quenched with MeOH (3.0 mL). The quenched reaction mixture was stirred for 10 min then partitioned between Et$_2$O (200 mL) and H$_2$O (200 mL). The layers were separated, the organic layer was washed with 1.0 M aqueous HCl (200 mL), saturated aqueous NaHCO$_3$ (200 mL), brine (100 mL), dried (MgSO$_4$), filtered and concentrated. The crude product was purified via flash column chromatography on silica gel using 30% EtOAc in hexane as eluent to give 2.03 g (4.30 mmol, 53%) of the desired product 23f (R$^{20}$+R$^{21}$=cyclopropane, R$^1$=SMe) as a white solid.

$^1$H NMR (300 MHz, CDCl$_3$) β 6.52 (br d, J=9.3 Hz, 1H), 5.65 (d, J=5.4 Hz, 1H), 5.56 (dd, J=0.9, 3.0 Hz, 1H), 5.27 (dd, J=5.4, 11.1 Hz, 1H), 5.20 (dd, J=3.0, 10.5 Hz, 1H), 4.43 (dd, J=0.9, 7.5 Hz, 1H), 3.66 (q, J=9.0 Hz, 1H), 2.15 (s, 3H), 2.08 (s, 3H), 2.07 (s, 3H), 1.98 (s, 3H), 0.94–0.78 (m, 1H), 0.70–0.61 (m, 1H), 0.57–0.33 (m, 3H); MS (ESPOS): 493.9 [M+Na]; MS (ESNEG): 470.2 [M−H]$^−$.

To a solution of triacetyl trifluoroacetamide 23f (R$^{20}$+R$^{21}$=cyclopropane, R$^1$=SMe) (2.03 g, 4.30 mmol, 1 equiv) in MeOH (35 mL) at 23° C. was added 1.0 M aqueous NaOH (43 mL, 43 mmol, 10 equiv). The reaction was stirred for 100 min, then acidified to pH 2 with 1.0 M aqueous HCl (48 mL). The resulting solution was concentrated to dryness in vacuo, then the residue was dissolved/suspended in EtOH (40 mL) and filtered through a medium porosity glass frit to remove NaCl. The solid was washed with EtOH (2×20 mL). The combined filtrate was treated with Amberlite IRA400 (OH$^−$ form) resin (60 mL resin bed in MeOH), transferring the resin with MeOH (2×20 mL). The resulting mixture was stirred at 23° C. for 1 h then filtered. The resin was washed with MeOH (3×100 mL), CH$_3$CN (100 mL). The combined filtrate was concentrated to give 1.04 g of the desired galactoside 23 g (R$^{20}$+R$^{21}$=cyclopropane, R$^1$=SMe) as a white solid (4.19 mmol, 97%). The product was used without further purification.

$^1$H NMR (300 MHz, CD$_3$OD) β 5.28 (d, J=5.7 Hz, 1H), 4.13–4.06 (m, 2H), 3.97 (d, J=6.6 Hz, 1H), 3.59 (dd, J=3.3, 9.9 Hz, 1H), 2.33 (dd, J=6.9, 9.0 Hz, 1H), 2.05 (s, 3H), 0.91–0.77 (m, 1H), 0.58–0.43 (m, 2H), 0.39–0.31 (m, 1H), 0.28–0.19 (m, 1H); MS (ESPOS): 272.0 [M+Na]; MS (ESNEG): 248.2 [M−H].

General Method V

Following the general method in Scheme 24, to a solution of the compound 1 hydrochloride (9.90 mmol, 1 equiv) in THF (70 mL) at 23° C. was added H$_2$O (70 mL) followed by KHCO$_3$ (12.9 mmol, 1.3 equiv) followed by (Boc)$_2$O (12.9 mmol, 1.3 equiv). After stirring for 5 h, the reaction mixture was partitioned between brine (200 mL) and EtOAc (300 mL). The organic layer was separated and washed with brine (150 mL), and dried (MgSO$_4$). Solvent was removed under vacuum and the crude product purified using Biotage® column chromatography system (40+M cartridge, 40 mm ID×150 mm) using a linear gradient (75% EtOAc/hexanes-100% EtOAc) over 1.2 L total eluent at 50 mL/min to give of the carbamate 24a (8.91 mmol, 90%).

To a solution of carbamate 24a (15.9 mmol, 1 equiv) in benzene (300 mL) at 23° C. was added p-anisaldehyde dimethyl acetal (4.06 mL, 23.8 mmol, 1.5 equiv), followed by PPTS (199 mg, 0.79 mmol, 0.05 equiv). The reaction mixture was heated to reflux. After 4 h a second portion of p-anisaldehyde dimethyl acetal (2.0 mL, 11.7 mmol, 0.74 equiv) was added. After a further 17 h a third portion of p-anisaldehyde dimethyl acetal (2.0 mL, 11.7 mmol, 0.74 equiv) was added. Following the final addition the reaction was refluxed a further 3 h then cooled to 23° C. and partitioned between EtOAc (300 mL) and H$_2$O (300 mL). The organic layer was washed with 50% saturated aqueous NaHCO$_3$ (300 mL), brine (150 mL), dried (MgSO$_4$), filtered and concentrated. The crude product was purified via silica gel flash column chromatography using 40% EtOAc in hexane as eluent to give acetal 24b (11.3 mmol, 71%).

To a solution of alcohol 24b (4.82 mmol, 1 equiv) in trimethyl phosphate (60 mL) at 0° C. was added pyridine (3.90 mL, 48.2 mmol, 10 equiv), followed by POCl$_3$ (0.88 mL, 9.65 mmol, 2 equiv) added over the course of 60 sec. Other acylating reagents such as acid anhydrides (R$^{11}$CO)$_2$O or acid chlorides R$^{11}$COCl in the presence of an appropriate base may be used in this step to provide different R$^{11}$ acyl substituents. Following the addition, the reaction was maintained at 0° C. for 2 h, then triethylammonium bicarbonate buffer (1.0 M, pH 8.5, 40 mL) was added carefully to quench the reaction. H$_2$O (60 mL) was then added, and the resulting mixture was stirred at 0° C. for 30 min then warmed to 23° C. After stirring the quenched reaction mixture for 2 h at 23° C., volatiles were removed in vacuo with aid of gentle heating in water bath (40–45° C.). The resulting crude product was azeotropically dried by co-evaporation with DMF (3×100 mL), then toluene (150 mL, bath temperature=40–45° C.) to provide of white solid. The crude product 24c (R$^{11}$=PO(OH)$_2$) was substantially contaminated with triethylammonium salts, but was carried forward without purification.

To a solution of the protected phosphate 24c (R$^{11}$=PO(OH)$_2$) prepared as described above (crude from previous step, approximately 4.8 mmol) in 1,2-dichloroethane (600 mL) at 0° C. was added H$_2$O (25 mL) followed by TFA (200 mL). Following the additions, the reaction was maintained at 0° C. for 5 min then warmed to 23° C. After stirring for 25 min at 23° C., volatiles were removed in vacuo to give 16.2 g of oil. The crude product was dissolved in 1:1 H$_2$O/MeOH (70 mL), filtered and the resulting solution was purified by preparative HPLC (Waters Nova-Pak® HR C$_{18}$, 6 µm particle size, 60 Å pore size, 40 mm ID×200 mm, 5–60% acetonitrile in H$_2$O w/0.1% AcOH over 30 min, 75 mL/min flow rate) to give the desired 2-phosphate 5 (R$^{11}$=PO(OH)$_2$) (3.10 mmol, 64% from free alcohol) as a white solid.

Method W

To a solution of β-lactam 25a (2.92 g, 12.8 mmol) 1 equiv; prepared from benzyl (S)-(−)-4-oxo-2-azetidine-carboxylate (Aldrich) as described by Baldwin et al, *Tetrahedron,* 1990, 46, 4733 in THF (30 mL) at 0° C. was added a solution of LDA (2.0 M, 14.0 mL, 28.1 mmol, 2.2 equiv) via syringe pump over 20 min. The reaction was stirred at 0° C. for 30 min. crotyl bromide (85%, 2.89 mL, 28.1 mmol, 2.2 equiv) was added dropwise over ca. 1.5 min, and the mixture was stirred for 2 h at 0° C., and then partitioned between 1.0 M aqueous $KHSO_4$ (100 mL) and EtOAc (100 mL). The organic layer was separated and washed with 1.0 M aqueous $KHSO_4$ (100 mL), brine (100 mL), dried ($MgSO_4$), filtered and concentrated to give 25b ($R^{9'}$=2-butenyl) 3.65 g (100%) of greenish yellow solid. This material was used without further purification.

MS (ESNEG): 282.2 [M−H]⁻.

Trimethylsilyldiazomethane (2.0 M in $Et_2O$, 25.0 mL, 50 mmol, 3.9 equiv) was slowly added to a solution of acid 25b ($R^{9'}$=2-butenyl) (3.65 g, 12.9 mmol, 1 equiv) in methanol (70 mL) at 0° C. Solvent was removed under vacuum to give 3.53 g (11.9 mmol, 92%) of the desired ester product as a yellow oil. This material was used in the subsequent reaction without further purification.

To a solution of alkene 25c ($R^{9'}$=2-butenyl) (3.53 g, 11.9 mmol, 1 equiv) in EtOAc (40 mL) at 23° C. was added Pd/C (10 wt. %, 482 mg). The reaction vessel was charged with hydrogen (balloon), and the mixture stirred vigorously. After 2.5 h, the reaction mixture was filtered through a pad of Celite. Celite was washed, with EtOAc (200 mL) and the filtrate was concentrated to provide 3.51 g (11.7 mmol, 99%) of 25c ($R^9$=butyl) as a yellow oil. This material was used without further purification.

MS (ESPOS): 300.4 [M+H]⁺.

To a solution of N-TBS β-lactam 25c ($R^9$=butyl) (3.51 g, 11.7 mmol, 1 equiv) in THF (50 mL) at 23° C. was added $Et_3N \cdot 3HF$ (0.95 mL, 5.85 mmol, 0.5 equiv). After stirring for 60 min at 23° C., the reaction mixture was partitioned between 90% saturated brine (150 mL) and EtOAc (200 mL). The organic layer was separated and washed with brine (150 mL), dried ($MgSO_4$), filtered and concentrated. The product was purified via flash column chromatography on silica gel using 50% EtOAc in hexane as eluent to give 1.48 g (8.0 mmol, 68%) of 25d ($R^9$=butyl) as a clear oil.

MS (ESPOS): 578.3 [3M+H]⁺.

To a solution of β-lactam 25d ($R^9$=butyl) (2.06 g, 11.1 mmol, 1 equiv) in THF (150 mL) at 23° C. was added a solution of $LiAlH_4$ (1.0 M in THF, 22.9 mL, 22.9 mmol, 2.06 equiv) via syringe over the course of 2 min. After stirring for 10 min at 0° C., the reaction was warmed to 23° C., stirred for 15 min, and then refluxed for 3 h. The mixture was then cooled to 0° C. and quenched via careful addition of $H_2O$ (1.0 mL), followed by 15% aqueous NaOH (1.0 mL), and then $H_2O$ (2.5 mL). The resulting suspension was stirred at 23° C. for 1.5 h, diluted with $Et_2O$ (250 mL), and filtered through Celite, washing with $Et_2O$ (250 mL). The filtrate was concentrated to furnish 1.42 g of the desired product 25e ($R^9$=butyl) (9.93 mmol, 89%) as a clear oil. The product was used without further purification.

MS (ESPOS): 287.4 [2M+H]⁺.

To a solution of amino alcohol 25e ($R^9$=butyl) (1.41 g, 9.86 mmol, 1 equiv) in dichloromethane (50 mL) at 23° C. was added $Boc_2O$ (2.59 g, 11.9 mmol, 1.2 equiv). After stirring for 2 h at 23° C., the reaction mixture was concentrated. The product was purified via flash column chromatography on silica gel using 33% EtOAc in hexane as eluent to give 1.53 g (6.31 mmol, 64%) 25f ($R^9$=butyl) as a clear oil.

MS (ESPOS): 266.0 [M+Na]⁺.

To a solution of $NaIO_4$ (8.81 g, 41.2 mmol, 10 equiv) in $H_2O$ (60 mL) at 23° C. was added $RuCl_3 \cdot xH_2O$ (350 mg, catalytic amount) followed by a solution of alcohol 25f ($R^9$=butyl) (1.00 g, 4.12 mmol, 1 equiv) in acetone (60 mL). The biphasic mixture was stirred for 30 min at 23° C., then extracted with EtOAc (250 mL), decanting the organic layer. The aqueous residue was extracted with two further portions of EtOAc (2×150 mL). The combined organic extracts were treated with 2-propanol (75 mL) and stirred at 23° C. After stirring for 2 h the mixture was filtered through Celite, washing with EtOAc (300 mL). The filtrate was concentrated to furnish 0.78 g of the desired product 25 g ($R^9$=butyl) (3.04 mmol, 74%) as a dark oil. The product was used without further purification.

MS (ESPOS): 280.0 [M+Na]⁺.

Method X

To a solution of alcohol 25f ($R^{9'}$=2-methyl-2-butenyl) (3.31 g, 13.0 mmol, 1 equiv) in DMF (100 mL) at 23° C. was added imidazole (2.21 g, 32.5 mmol, 2.5 equiv) followed by TBSCl (2.93 g, 19.5 mmol, 1.5 equiv). The reaction was stirred for 35 min and then quenched with MeOH (2.0 mL). After stirring for 5 min, the resulting mixture was partitioned between $Et_2O$ (500 mL) and $H_2O$ (400 mL). The organic layer was separated and washed with $H_2O$ (400 mL), brine (200 mL), dried ($MgSO_4$), filtered and concentrated to give 26a ($R^{9'}$=2-methyl-2-butenyl) 4.13 g (11.2 mmol, 86%) of the desired product as a clear oil.

MS (ESPOS): 392.4 [M+Na]⁺.

A solution of intermediate 26a ($R^{9'}$=2-methyl-2-butenyl) (2.03 g, 5.50 mmol, 1 equiv) in dichloromethane (80 mL) at −78° C. was treated with ozone (1.2 L/min) introduced via a gas dispersion tube until a blue color was observed (20 min). A stream of oxygen (1.2 L/min) was then passed through the reaction mixture to discharge excess ozone. After 15 min, oxygen flow was ceased and $PPh_3$ (2.16 g, 8.25 mmol, 1.5 equiv) was added. The reaction mixture was stirred at −78° C. for 30 min, then at 0° C. for 15 min, and then warmed to 23° C. After stirring for 10 min at 23° C., silica gel was added, and the resulting mixture concentrated to dryness under vacuum to afford a free-flowing powder that was loaded directly onto a silica gel column. Flash column chromatography using 30–33% EtOAc in hexane as eluent gave 1.52 g (4.42 mmol, 80%) of aldehyde 26b as a clear oil.

MS (ESPOS): 398.0 [M+MeOH+Na]⁺.

To a suspension of cyclopropylmethyltriphenylphosphonium bromide (1.22 g, 3.06 mmol, 1.5 equiv) in THF (10 mL) at 0° C. was added a solution of NaHMDS (1.0 M in THF, 3.06 mL, 3.06 mmol, 1.5 equiv) dropwise via syringe over the course of 1 min. The resulting solution was stirred for 20 min at 0° C. then treated with a solution of aldehyde 26b (700 mg, 2.04 mmol, 1 equiv) in THF (3.0 mL; 2×1.0 mL flush) transferred via canula. After 15 min at 0° C. the reaction was warmed to 23° C., stirred for a further 10 min then quenched with saturated $NH_4Cl$ (30 mL). The resulting mixture was partitioned between $Et_2O$ (120 mL) and $H_2O$ (50 mL). The organic layer was separated and washed with brine (50 mL), dried ($MgSO_4$) filtered and concentrated. Flash column chromatography using 10% EtOAc in hexane as eluent gave 588 mg (1.54 mmol, 76%) of 26c ($R^{9'}$=3-cyclopropyl-prop-3-enyl) as a clear oil.

MS (ESPOS): 404.3 [M+Na]⁺.

To a solution of alkene 26c ($R^{9'}$=3-cyclopropyl-prop-3-enyl) (191 mg, 0.50 mmol, 1 equiv) in dioxane (5.0 mL) at 23° C. was added dipotassium azodicarboxylate (973 mg, 5.01 mmol, 10 equiv) followed by slow addition of a solution of AcOH (573 μL, 10.0 mmol, 20 equiv) in dioxane (5.0 mL) over the course of 16 h via syringe pump. Following the completion of the addition the reaction was stirred a further 6 h then filtered through a glass frit with the aid of Et$_2$O (150 mL) to remove precipitate. The resulting solution was washed with saturated aqueous NaHCO$_3$ (2×100 mL), brine (80 mL), dried (MgSO$_4$), filtered and concentrated. The above procedure was repeated three times on the crude material obtained to give complete conversion of the alkene, providing 183 mg (0.48 mmol, 96%) of the saturated product 26d (R$^9$=3-cyclopropyl-propyl) as a clear oil.

MS (ESPOS): 406.0 [M+Na]$^+$.

To a solution of TBS ether 26d (R$^{9'}$=3-cyclopropyl-propyl) (190 mg, 0.50 mmol, 1 equiv) in THF (10 mL) at 23° C. was added a solution of TBAF (1.0 M in THF, 0.55 mL, 0.55 mmol, 1.1 equiv). The resulting solution was stirred for 40 min at 23° C. then partitioned between Et$_2$O (50 mL) and H$_2$O (50 mL). The organic layer was separated and washed with brine (50 mL), dried (MgSO$_4$), filtered and concentrated to give 133 mg (0.50 mmol, 100%) of 26e (R$^9$=3-cyclopropyl-propyl)as a clear oil.

MS (ESPOS): 290.2 [M+Na]$^+$.

Catalytic Ruthenium oxidation of 26e to the desired carboxylic acid product 26f (R$^9$=3-cyclopropyl-propyl) was conducted as described in the previos examples.

MS (NEG): 282 [M−H]$^-$.

Method Y

Synthesis of racemic 27a (R$^9$=n-propyl). A solution of 10b (R$^9$=n-propyl) (22 g, 0.13 mol) in methanol (30 mL) concentrated HCl (10 mL) was added platinum(IV)oxide (5 g). The reaction mixture was hydrogenated at 50 psi for 16 h, the catalyist was removed by filtration through celite® and the filtrate evaporated to driness The crude pipecolic acid was used without further purification.

The crude pipecolic acid residue 19 g was dissolved in acetonitrile (200 mL), tetramethylammonium hydroxide.5H$_2$O (33 g) was added and the reaction mixture stirred 30 minuets, di-t-butyl pyrocarbonate (39 g, 0.46 mol) was added and the reaction mixture stirred at room temperature for 72 h. Additional tetramethylammonium hydroxide.5H$_2$O (8 g) and di-t-butyl pyrocarbonate (9 g) was added and the reaction mixture stirred 24 h. The reaction solvent was remover invaccuo and the resulting oil was diluted with water (200 mL) and washed with ether (200 mL). The aqueous portion was acidified to pH 3–4 with solid citric acid and then extracted with ethyl acetate (3×200 mL). The combined organic layers were dried over MgSO$_4$, filtered and the solvent removed to furnish 27a (R$^9$=n-propyl) (19 g, 77%) as a yellow oil that crystallized on standing.

$^1$H NMR (300 MHz, CD$_3$OD) δ 4.31 (m, 1), 3.60 (m, 1), 3.33 (m, 1), 2.01 (m, 4), 1.24 (m, 14), 0.89 (t, J=5.7, 3); MS (ESNEG): 270 [M−1]$^-$.

The racemic a mixture 27a (R$^9$=n-propyl) is diluted with acetonitrile (5 volumes) and S-α-methylbenzyl amine (0.5 eq) the mixture is heated to reflux and allowed to cool with seeding. The mixture is allowed to stand overnight. The first crop of salt formed is then filtered and put aside until the final recrystallisation.

The liquors from the filtration are concentrated in vacuo and then taken up in DCM (4 volumes), the DCM is then washed with 1M citric acid (2/3 volume of DCM). The DCM is then separated, dried over magnesium sulfate, filtered and concentrated in vacuo. The 2R,4S enantiomer enriched free acid is taken up in 5 volumes of acetonitrile and 0.85 eq. of R-α-methylbenzyl amine was added and the mixture is heated to reflux and allowed to cool with seeding. The mixture is allowed to stand overnight. The salt formed is then filtered and put aside (the ee of the salt is generally 85–90%).

The process to obtain the second crop of 2S,4R salt is identical to that of the previous paragraph except that the R-α-methylbenzyl amine is replaced with S-α-methylbenzyl amine. The second crop salt formed is then filtered (generally has an ee of around 80–90%) and put aside until the final recrystallisation.

The liquors from the filtration (2S,4R salt formation liquors, 2$^{nd}$ crop) are concentrated in vacuo. The salt is broken by the method described previously. At this stage the impurities have been concentrated to such a level that salt formation is not possible. The free acid is subjected to column chromatography (30%EtOAc/Hexane) and this removes the unwanted impurities. The column used a 10:1 weight to weight ratio of silica to compound. Also the compound was absorbed onto 3 equivalents (wt:wt) of silica.

The free acid from the column (which is enriched with the 2R,4S enantiomer) is diluted with acetonitrile (5 volumes) and R-α-methylbenzyl amine is added and the recrystalization repeaas The salt break and formation of the 2S,4R salt is identical to that described previously. The third crop of salt formed generally has an ee of 80–90%.

The 3 crops of 2S,4R salt are combined and diluted with acetonitrile (7 volumes). The mixture is heated to reflux at which point all the salt dissolves. The mixture is then allowed to cool to rt and stand overnight with seeding. The salt that has precipitated out of solution is filtered. The salt shows an ee of approximately 97%. The process is repeated to give a salt with an ee of greater than 99%. The salt is taken up in DCM (4 volumes) and washed twice with 1M citric acid (approximately 2/3 volume of DCM) dried over magnesium sulfate, filtered and concentrated in vacuo. This process gives 77% of the theoretical yield of the 2S,4R enantiomer. as an amber oil 98% ee.

Method Z

The conditions below are representative of the general coupling and deprotection scheme depicted in method Z where P$^1$=H and P$^2$=carboxylic acid-t-butyl ester (Boc).

To a solution of azetedine acid 25f (R$^9$=butyl) (52 mg, 0.20 mmol, 1 equiv), 7-Cl MTL 6b (R$^2$=H, R$^3$=Cl) (58 mg, 0.20 mmol, 1 equiv) and HBTU (84 mg, 0.22 mmol, 1.1 equiv) in DMF (2.0 mL) at 23° C. was added DIPEA (88 μL, 0.51 mmol, 2.5 equiv). After stirring for 12 h at 23° C., DMF was removed in vacuo then the residue was partitioned between EtOAc (100 mL) and 1:1 brine: 10% aqueous citric acid (100 mL). The organic layer was separated and washed with 1:1 brine/saturated aqueous NaHCO$_3$ (100 μL), brine (50 mL), dried (MgSO$_4$), filtered and concentrated to furnish 82 mg (0.17 mmol, 84%) 13a (R$^2$=H, R$^3$=Cl, R$^9$=butyl, P$^1$=H, P$^2$=carboxylic acid-t-butyl ester, m=0) as a glassy solid which was used without purification in the next step.

To a solution of carbamate 13a (R$^2$=H, R$^3$=Cl, R$^9$=butyl, P$^1$=H, P$^2$=carboxylic acid-t-butyl ester, m=0) (82 mg, 0.17 mmol, 1 equiv) in 1,2-dichloroethane (10 mL) at 23° C. was added H$_2$O (0.40 mL) followed by TFA (4.0 mL). After stirring for 20 min at 23° C., toluene (50 mL) was added and the resulting solution was concentrated to dryness. The residue was purified by semi-preparative HPLC (Waters Nova-Pak® HR $C_{18}$, 6 μm particle size, 60 Å pore size, 20 mm ID×100 mm, 5–60% acetonitrile in $H_2O$ w/0.1% HCl over 30 min, 20 mL/min flow rate) to give 41 mg of title compound 3-Butyl-azetidine-2-carboxylic acid [2-chloro-1-(3,4,5-trihydroxy-6-methylsulfanyl-tetrahydro-pyran-2-yl)-propyl]-amide as a white solid.

$^1$H NMR (300 MHz, $CD_3OD$) δ 5.30 (d, J=6.0 Hz, 1H), 4.64 (d, J=7.8 Hz, 1H), 4.63–4.52 (m, 2H), 4.29 (d, J=10.2 Hz, 1H), 4.07 (dd, J=5.7, 10.2 Hz, 1H), 4.00 (t, J=6.6 Hz, 1H), 3.82 (d, J=3.3 Hz, 1H), 3.75 (dd, J=8.4, 9.9 Hz, 1H), 3.56 (dd, J=3.3, 10.2 Hz, 1H), 2.92–2.76 (m, 1H), 2.14 (s, 3H), 1.90–1.67 (m, 2H), 1.45 (d, J=6.6 Hz, 3H), 1.44–1.24 (m, 4H), 0.93 (t, J=6.9 Hz, 3H); MS (ESPOS): 411.0 [M+H]$^+$.

Method AA

To pyridine-2-carboxylic acid 10b (0.5 mmol) in DMF (2 mL) lincosamine as defined in general coupling scheme 13 (0.5 mmol) was added, followed by HBTU (214 mg, 0.55 mmol) and DIEA (132 mg, 1 mmol). The reaction mixture is stirred at room temperature for 2 hr. The solvent was removed, and purification of the crude material was carried out by silica gel column chromatography to obtain compound 13b To a solution of the pyridine 13b (0.46 mmol) in water (10 mL), AcOH (3 mL) and MeOH (2 mL), was added $PtO_2$ (200 mg) and the resulting reaction mixture shaken under 55 psi hydrogen overnight, or for an extended period at lower hydrogen pressure. Residual catalyst was removed by filtration through celite, and the solvent was removed to obtain the crude product. Purification was carried out by silica gel column chromatography using MeOH in DCM to obtain lincosamide analogs of type 1 as defined in scheme 13.

In general silica chromatography readily separates the cis-2S diastereomer from the undesired isomer. In some cases separation of the isomers requires semi-preparative HPLC. A representative set of conditions is as follows: (Waters Nova-Pak® HR $C_{18}$ column, 6 μm particle size, 60 Å pore size, 20 mm ID×100 mm, 5–60% acetonitrile 0.1% AcOH/$H_2O$ 0.1% AcOH over 30 min, 20 mL/min flow rate.

Method AB

Synthesis of [2-Methyl-1-(3,4,5-tris-benzyloxy-6-methylsulfanyl-tetrahydro-pyran-2-yl)-propyl]-carbamic acid tert-butyl ester, 15b step a ($P_1$=Boc, $P_2$=Bn, $R^2$=Me, $R^3$=H), (intermediate not shown). To a rapidly stirred solution of 2a (P=Boc, $R^1$=Me, $R^2$=H) in benzene (40 mL) (2 g, 5.7 mmol) was added 50% aquious KOH (12.8 mL) tetrabutylammonium bisulfate (0.67 g) and benzyl bromide (6.77 mL, 57.0 mmol) under $N_2$ atmosphere were suspended with vigorous stirring. After 3.5 h benzyl amine (6.0 mL) was added and the reaction mixture stirred an additional 20' then toluene (300 mL) was added and the organic layer washed, $H_2O$ (2×100 mL), 2M $KHSO_4$ (3×100 mL), sat. aq. $NaHCO_3$ (1×100 mL), brine (1×100 mL) dried over $MgSO_4$ and evaporated to dryness. Chromatography of the crude product on silica 10% EtOAc/Hexanes to 15% EtOAc/Hexanes product 15b, step a, 2-Methyl-1-(3,4,5-tris-benzyloxy-6-methylsulfanyl-tetrahydro-pyran-2-yl)-propyl]-carbamic acid tert-butyl ester as a colorless foam (2.6 g, 72%); MS (ESPOS): 522.8 [M+H−Boc]$^+$.

Synthesis of [2-Methyl-1-(3,4,5-tris-benzyloxy-6-fluoro-tetrahydro-pyran-2-yl)-propyl]-carbamic acid tert-butyl ester, 15b ($P_1$=Boc, $P_2$=Bn, $R^2$=Me, $R^3$=H), step b. To a stirred solution cooled to −16° C. of the above intermediate 2-Methyl-1-(3,4,5-tris-benzyloxy-6-methylsulfanyl-tetrahydro-pyran-2-yl)-propyl]-carbamic acid tert-butyl ester (1.54 g, 2.5 mmol) in DCM (25 mL) was added DAST (0.599 mL, 4.46 mmol) under $N_2$ atmosphere were suspended with vigorous stirring. After 5 minutes solid NBS (0.599 mL, 4.46 mmol) was added over 5 minuets and the reaction mixture stirred an additional 45' then DCM (300 mL) was added and the organic layer washed with sat. aq. $NaHCO_3$ (1×100 mL), dried over $MgSO_4$ and evaporated to dryness. Chromatography of the crude product on silica 15% to 30% $Et_2O$/Hexanes product, a mixture of 1-α and β Fluorinated [2-Methyl-1-(3,4,5-tris-benzyloxy-6-fluoro-tetrahydro-pyran-2-yl)-propyl]-carbamic acid tert-butyl ester 15b ($P_1$=Boc, $P_2$=Bn, $R^2$=Me, $R^3$=H), was isolated as a colorless oil (0.85 g, 58%); TLC (20% $Et_2O$/Hexanes) $R_f$ isomer 1=0.2, $R_f$ isomer 1=0.05. $^{19}$F NMR ($CDCl_3$) δ isomer 1: −132.78, −132.96, isomer 2: −145.05, −145.13, −145.23, −145.31, HPLC $C_{18}$ 3.5 μm, 4.6×30 mm Column; gradient eluent 2%–98% MeCN over 10 min; 1.5 mL/min): Retention time=7.93 min, 7.98 min; MS (ESPOS): 494.7 [M+H−Boc]$^+$; MS (ESNEG): 592.7 [M−H]$^+$.

Synthesis of 2-Methyl-1-(6-allyl-3,4,5-tris-benzyloxy-tetrahydro-pyran-2-yl)-propylamine, 15c ($P_1$=H, $P_2$=Bn, $R^1$=Allyl, $R^2$=Me, $R^3$=H). To a stirred solution cooled to −32° C. of the above intermediate 15b (831 g, 2.5 mmol) in DCM (30 mL) under $N_2$ atmosphere was added allyltrimethylsilane (1.12 mL, 7.0 mmol). After 10 minutes $BF_3.Et_2O$ (0.36 mL, 2.8 mmol) was added over 2 minuets and the reaction mixture stirred an additional 1.5 h then then warmed to 0° C. for 30 minuets. To the reaction mixture was added water (1 mL) and TFA (15 mL), the reaction mixture was allowed to warm to RT stirred 1 h and evaporated to driness. The residue was dissolved in $Et_2O$ (200 mL) washed with 1M aq. $K_2CO_3$ (50 mL) and brine dried over $Na_2SO_4$ and evaporated to dryness the product 15c ($P_1$=H, $P_2$=Bn, $R^1$=Allyl, $R^2$=Me, $R^3$=H) was isolated as a colorless oil (0.69 g, 96%); TLC (20% EtOAc/Hexanes) $R_f$=0.05; MS (ESPOS): 516.4 [M+H−Boc]$^+$.

2-(1-Amino-2-methyl-propyl)-6-propyl-tetrahydro-pyran-3,4,5-triol. 2-Methyl-1-(6-allyl-3,4,5-tris-benzyloxy-tetrahydro-pyran-2-yl)-propylamine, 15c 160 mg and 100 mg degussa 50% w/w wet 10% palladium/carbon under $N_2$ was suspended in THF (5 mL) and 1M aq. HCl (1 mL) the reaction mixture was stirred 24 h under 1 atm pressure $H_2$. The reaction mixture was filtered through Celite evaporated to driness to provide the product 2-(1-Amino-2-methyl-propyl)-6-propyl-tetrahydro-pyran-3,4,5-triol (60.8 mg 89%) as the HCl salt. TLC ($CHCl_3$: MeOH: 32% aq. AcOH) $R_f$=0.35. MS (ESPOS): 248 [M+H]$^+$.

Method AC

In general the final purification and separation of diastereoisomers of compounds detailed in the following examples may be achieved by semi-preparative HPLC. Final products were purified on a Waters Prep LC 4000® system equipped with a Waters 2487® dual λ absorbance detector set to 214 nm and a S.E.D.E.R.E Sedex 55® evaporative light scattering detector in series. General conditions used for the separation of diastereoisomers follows (Waters Nova-Pak® HR $C_{18}$ column, 6 μm particle size, 60 Å pore size, 20 mm ID×100 mm, 5–60% acetonitrile 0.1% AcOH/$H_2O$ 0.1% AcOH over 30 min, 20 mL/min flow rate. The fractions collected are pooled and lyophylized to driness.

EXAMPLES

The following examples were prepared according to the aforementioned methods.

Example 1

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide

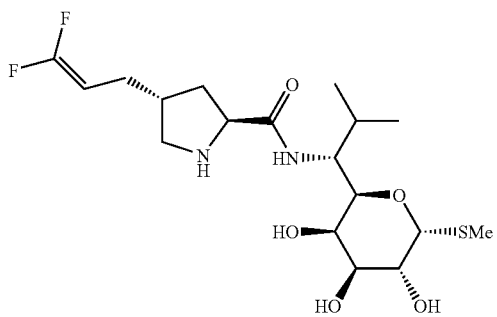

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide. To a solution of 2b ($R^2$=H) (45 mg, 0.18 mmol, 1 equiv) in dry DMF (0.5 mL) at 0° C. was added triethylamine (79.4 µL, 0.57 mmol, 3.2 equiv), followed by bis-(trimethylsilyl)trifluoroacetamide (71.2 µL, 0.27 mmol, 1.5 equiv). The reaction mixture was stirred at 0° C. for 10 minutes, and then was stirred at rt for 50 minutes. The reaction mixture was added to the protected amino acid 8c ($R^9$=3,3-difluoroallyl) prepared in general method M (56 mg, 0.19 mmol, 1.1 equiv) in a 25 mL round bottom flask, followed by the addition of solid HATU (91.2 mg, 0.24 mmol, 1.3 equiv). The reaction mixture was stirred at rt for 3 h. The reaction mixture was evaporated to dryness, taken up in ethyl acetate (60 mL), washed with 10% citric acid (2×40 mL), water (40 mL), half sat. aq. NaHCO$_3$ (40 mL) and brine. The organic layer was dried over Na$_2$SO$_4$ and evaporated to give a yellow syrup.

To a solution of the above crude coupling product in DCM (9 mL) with methylsulfide (0.2 mL) were added trifluoroacetic acid (3 mL) and water (0.2 mL). The reaction mixture was stirred at rt for 1 h. The solvent was removed under vacuum and co-evaporated with toluene twice. The residue was purified by chromatography to provide the title compound 4-(3,3-Difluoroallyl)-pyrrolidine-2-carboxylic acid [2-methyl-1-(3,4,5-trihydroxy-6-methylsulfanyl-tetrahydro-pyran-2-yl)-propyl]-amide (55.6 mg, 73%) as a white solid: $^1$H NMR (300 MHz, CDCl$_3$) δ 7.93 (br s, 1), 5.30 (d, J=4.8, 1), 4.20–4.05 (m, 2), 3.96–3.77 (m, 3), 3.71–3.52 (m, 2), 3.19–3.07 (m, 1), 2.78–2.63 (m, 1), 2.38–2.21 (m, 1), 2.13 (s, 3), 2.20–1.97 (m, 4), 1.94–1.80 (m, 1), 0.92–0.84 (m, 6); MS (ESPOS): 425.5 [M+H]$^+$; MS (ESNEG): 423.5 [M−H]$^-$.

Example 2

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide

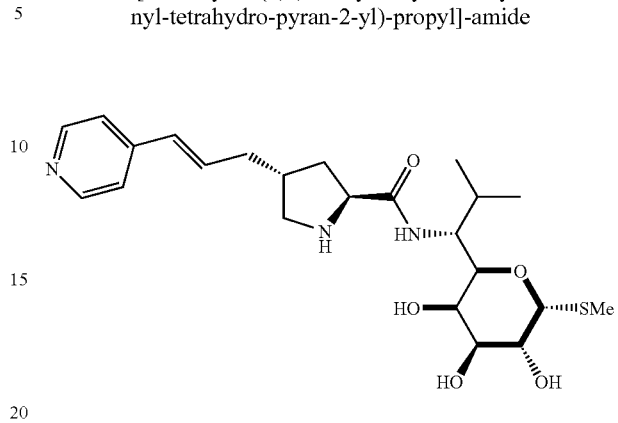

The title compound of example 2, 4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide was prepared according to the procedures described in Example 1 and general Method M using the ylide derived from triphenyl(4-pyridylmethyl)phosphonum chloride in the wittig olefination step depicted in Scheme 8. HPLC: C$_{18}$ 3.5 µm, 4.6×30 mm column; gradient eluent 2%–98% MeCN over 10 min; 1.5 mL/min): R$_t$=2.99 min; MS (ESPOS): 466.4 [M+H]$^+$; MS (ESNEG): 464.2 [M−H]$^-$, 500.3 [M+HCl]$^-$.

Example 3

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide

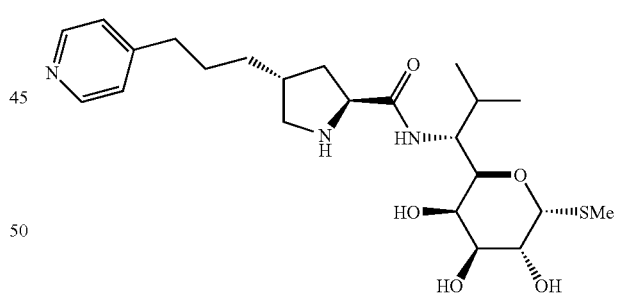

The title compound of example 3, 4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide was prepared according to general Method M using the ylide derived from triphenyl(4-pyridylmethyl) phosphonum chloride in the wittig olefination step depicted in Scheme 8, followed by reductive deprotection to protected aminoacid 8b ($R^9$=3-pyridin-4-yl-propyl, R$_2$=H). The coupling and deprotection procedures described in Example 1 provided the desired final product. HPLC: C$_{18}$ 3.5 µm, 4.6×30 mm column; gradient eluent 2%–98% MeCN over 10 min; 1.5 mL/min): R$_t$=2.99 min; MS (ESPOS): 466.4 [M+H]$^+$; MS (ESNEG): 468.3 [M−H]$^-$, 502.4 [M+HCl]$^-$.

Example 4

4-Butylsulfanyl-pyrrolidine-2-carboxylic acid [2-hydroxy-1-(3,4,5-trihydroxy-6-methylsulfanyl-tetrahydro-pyran-2-yl)-propyl]-amide

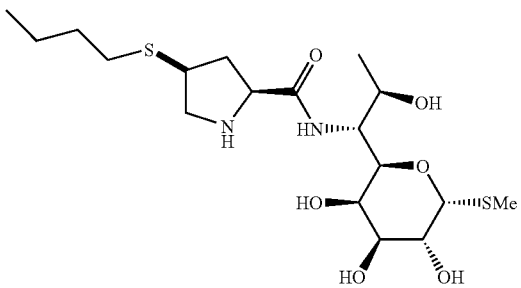

N-Cbz-(2S),(4S)-(n-butylsulfanyl)proline 9d (P=Cbz, m=1, R9=n-butylsulfanyl). The title intermediate was prepared as described in general method N. To a stirred solution of intermediate 9b (P=Cbz, m=1, LG=Ts) (1.34 g, 3.08 mmol) in DMF (10 mL), under $N_2$, was added, 1-butanethiol (0.7 mL, 6.16 mmol, 2 equiv), followed by 7-methyl-1,5,7-triazabicyclo[4.4.0]dec-5-ene (0.7 mL, 4.87 mmol, 1.6 equiv). After the addition, the resulting mixture was stirred at room temperature for 18 h, then partitioned between EtOAc and $H_2O$. The organic layer was separated, washed with brine, dried over $Na_2SO_4$, filtered and evaporated to dryness. The crude residue obtained was chromatographed on silica 3:1 hexanes/EtOAc to give methyl ester 9c (P=Cbz, m=1, $R^9$=n-butylthio) (470 mg, 44%).

Methyl ester 9c was treated with lithium hydroxide (132.7 mg, 3.16 mmol, 2.4 equiv) in 4:1 THF/$H_2O$, overnight. The pH of the reaction solution was adjusted to 3, with aq. 1 M HCl and extracted with EtOAc (3×100 mL). The combined organic phase was dried over $Na_2SO_4$, filtered, evaporated to dryness, to provide the product 9d N-Cbz-(2S),(4S)-(n-butylthio)proline (463 mg, quant.).

To a suspension of MTL 1a (140 mg, 0.56 mmol, 1 equiv) in anhydrous DMF (2 mL), at 0° C. under $N_2$ was added triethylamine (0.3 mL, 2.2 mmol, 3.9 equiv), followed by BSTFA (0.3 mL, 1.1 mmol, 2 equiv). The resulting mixture was stirred at 0° C. for 10 min, then at room temperature for 30 mins, and cooled to 0° C. A solution of protected amino acid N-Cbz-(2S),(4S)-(n-butylthio)proline (215 mg, 0.64 mmol, 1.2 equiv) in anhydrous DMF (1 mL), was added, followed by solid HATU (320 mg, 0.84 mmol, 1.5 equiv), cooling bath removed, and stirred at room temperature for 2 h. After evaporation of the reaction mixture under high vacuum, the residue obtained was diluted with ethyl acetate (150 mL), washed sequentially with 10% citric acid (2×50 mL), 0.5 M sat. aq. $NaHCO_3$ (2×50 mL), brine (50 mL), dried over $Na_2SO_4$, filtered and evaporated to dryness. The per-silylated intermediate obtained was treated with Dowex® 50w-400x $H^+$ form resin (Aldrich)(200 mg) in MeOH (60 mL) for 45 min, filtered, evaporated to dryness, chromatographed on silica (92:8 DCM/methanol) to provide the desired Cbz protected lincosamide (185 mg, 61%).

To a stirred suspension of 10% palladium on carbon (200 mg), in anhydrous EtOH (6 mL), under nitrogen, was added 1,4-cyclohexadiene (2 mL), after 10 min, a solution of the above Cbz protected lincosamide (178 mg, 0.33 mmol) in EtOH (6 mL) was added. The resulting mixture was stirred and heated to reflux overnight. After cooling, the reaction mixture was filtered through a celite pad, washed with ethanol, filtrate and washings evaporated to dryness. The crude residue obtained was chromatographed on silica (90:9:1 DCM/MeOH/conc. ammonium hydroxide) to provide the title compound, which was taken up in 1:1 acetonitrile/water (4 mL), acidified (pH 4) with 1M HCl and lyophilized to provide the HCl salt (35 mg) as a colorless powder: MS (ESPOS): 439.3[M+H]+, 461.2 [M+Na]+.

Example 5

4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide

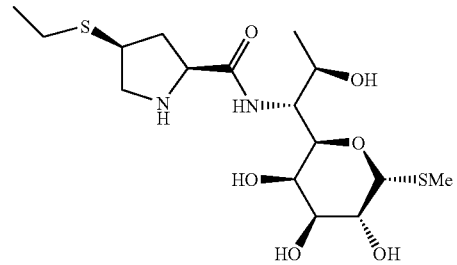

The title compound of example 5 was prepared according to general Method N using sodium ethanethiolate in the displacement step depicted in Scheme 9. The coupling and deprotection procedures described in Example 4 provided the desired final product. MS (ESPOS): 412.6 $[M+H]^+$.

Example 6

4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide

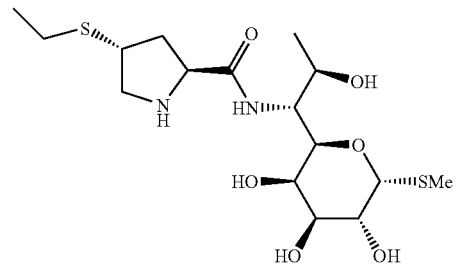

The title compound of example 6 was prepared according to general method N using triphenylphosphoniumdibromide to install a 4-(S) bromide leaving group in 9b (P=Cbz, m=1, LG=Br), sodium ethanethiolate was then used in the displacement step depicted in Scheme 9. The coupling and deprotection procedures described in Example 4 provided the desired final product: MS (ESPOS): 411.6 [M]+.

Example 7

4-Ethylsulfanyl-pyrrolidine-2-carboxylic acid [2-chloro-1-(3,4,5-trihydroxy-6-methylsulfanyl-tetrahydro-pyran-2-yl)-propyl]-amide

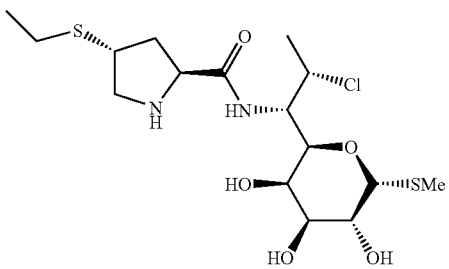

The title compound of example 7, was prepared according to general method N using triphenylphosphoniumdibromide to install a 4-(S) bromide leaving group in 9b (P=Cbz, m=1, LG=Br), sodium ethanethiolate was then used in the displacement step depicted in Scheme 9. The coupling and deprotection procedures described in Example 4 provided the desired final product: MS (ESPOS): 429.1 [M+H]+; MS (ESNEG): 427.6 [M−H]−, 463.6 [M+HCl]−.

Example 8

4-Ethylsulfanyl-pyrrolidine-2-carboxylic acid [2-chloro-1-(3,4,5-trihydroxy-6-methylsulfanyl-tetrahydro-pyran-2-yl)-propyl]-amide

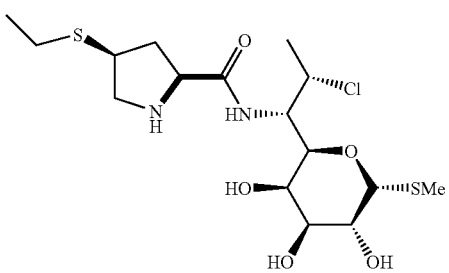

The title compound of example 8 was prepared according to general method N, sodium ethanethiolate was then used in the displacement step depicted in Scheme 9. The coupling and deprotection procedures described in example 4 provided the desired final product. MS (ESPOS): 429.1 [M+H]+.

Example 9

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide

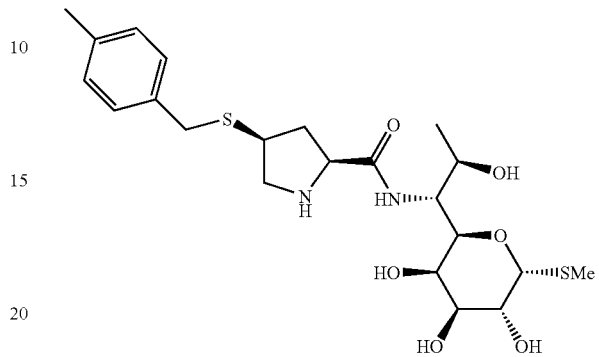

To a solution of tosylate intermediate 14b (P=CF$_3$CO, m=1, R$_2$=H, R$_3$=OAc) prepared in general method R, scheme 14 (73.2 mg, 92 μmol) in dry DMF (300 μL) under N$_2$ was added 4-methylbenzylthiol (Lancaster) (63.5 μL, 0.46 mmol), followed by MTBU (33.6 μL, 0.23 mmol). The reaction mixture was stirred at rt 16 h. The reaction mixture was taken up in MeOH (1.5 mL) 0.5 M NaOMe in MeOH (920 μL, 9.2 mmol) was added and the reaction mixture stirred at room temperature 18 h, then added to Dowex® resin bed (3.3 mL in water). The resin was washed with methanol (5×10 mL) water (1×10 mL) and acetonitrile (2×10 mL) the product was then eluted by washed with 5% conc. NH$_4$OH in MeOH (5×10 mL) and MeCN (1×10 mL). Evaporation of the combined washes and prepartive TLC (95:5 MeOH:0.25M NH$_3$/DCM) to provide the title compound (25.0 mg, 56%) as a colorless solid: MS (ESPOS): 487.3 [M+H]+; HPLC; C$_{18}$ 3.5 μm, 4.6×30 mm column; gradient eluent 2%–98% MeCN over 5 min: R$_t$=1.91 min.

Example 10

4-(4-Fluoro-phenylsulfanyl)-pyrrolidine-2-carboxylic acid [2-hydroxy-1-(3,4,5-trihydroxy-6-methylsulfanyl-tetrahydro-pyran-2-yl)-propyl]-amide

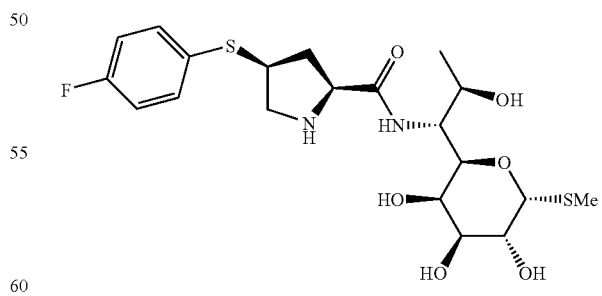

The title compound of example 10 was prepared by the procedure used in example 9 from tosylate intermediate 14b (P=CF$_3$CO, m=1, R$_2$=H, R$_3$=OAc) prepared in general method R, scheme 14. 4-Fluorothiophenol (Aldrich) was the nucleophile used in the displacement step: MS (ESPOS): 477.3 [M+H]+.

Example 11

4-(3,3,3-Trifluoro-propylsulfanyl)-pyrrolidine-2-carboxylic acid [2-hydroxy-1-(3,4,5-trihydroxy-6-methylsulfanyl-tetrahydro-pyran-2-yl)-propyl]-amide

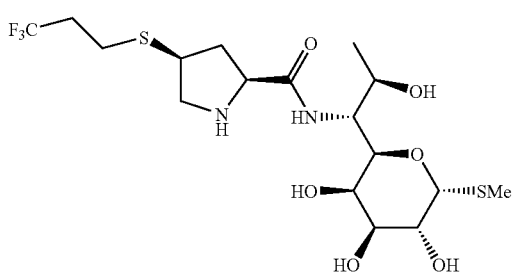

The title compound of example 11 was prepared by the procedure used in example 9 from tosylate intermediate 14b (P=CF$_3$CO, m=1, R$_2$=H, R$_3$=OAc) prepared in general method R, scheme 14. 1,1,1-trifluoropropanethiol (Aldrich) was the nucleophile used in the displacement step. (300 MHz, CDCl$_3$) δ 5.32 (d, J=5.8, 1), 4.43 (dd, J=8.2, 8.2 1), 4.36–4.31 (m, 1), 4.19–4.04 (m, 3), 3.90–3.88 (m, 1), 3.78–3.55 (m, 3), 3.37–3.31 (m, 1), 2.96–2.82 (m, 3), 2.61–2.49 (m, 2), 2.12 (s, 3), 2.07–2.01 (m, 2), 1.14 (d, J=6.6, 3); ($^{19}$F CDCl$_3$) δ −68.8 t; MS (ESPOS): 479.2 [M+H]$^+$, 963.3 [2M+H]$^+$.

Example 12

4-(3-Methyl-butylsulfanyl)-pyrrolidine-2-carboxylic acid [2-hydroxy-1-(3,4,5-trihydroxy-6-methylsulfanyl-tetrahydro-pyran-2-yl)-propyl]-amide

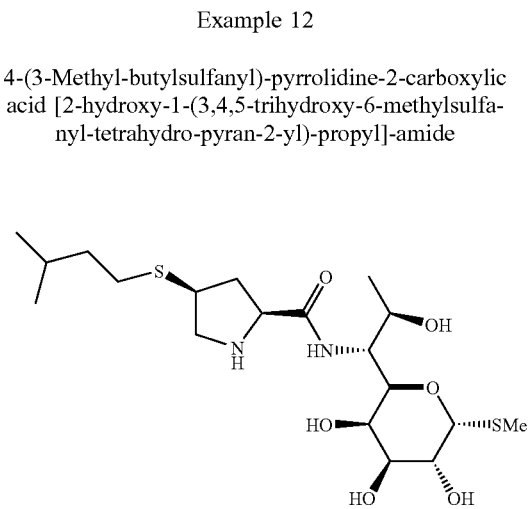

The title compound of example 12 was prepared by the procedure used in example 9 from tosylate intermediate 14b (P=CF$_3$CO, m=1, R$_2$=H, R$_3$=OAc) prepared in general method R, scheme 14. 3-Methylbutanethiol (Aldrich) was the nucleophile used in the displacement step. MS (ESPOS): 453.3 [M+H]$^+$; HPLC: C$_{18}$ 3.5 μm, 4.6×30 mm column; gradient eluent 2%–98% MeCN over 10 min: R$_t$=3.90 min.

Example 13

4-(2,4-Dichloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide

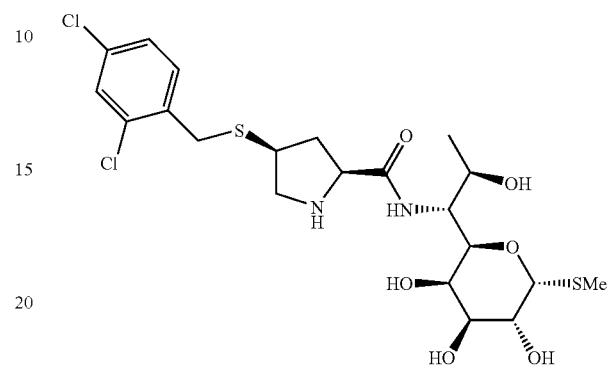

The title compound of example 13 was prepared by the procedure used in example 9 from tosylate intermediate 14b (P=CF$_3$CO, m=1, R$_2$=H, R$_3$=OAc) prepared in general method R, scheme 14. 2,4-Dichlorobenzyl thiol (Maybridge) was the nucleophile used in the displacement step: MS (ESPOS): 541.2 [M]$^+$; HPLC: C$_{18}$ 3.5 μm, 4.6×30 mm column; gradient eluent 2%–98% MeCN over 10 min: R$_t$=4.383 min.

Example 14

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide

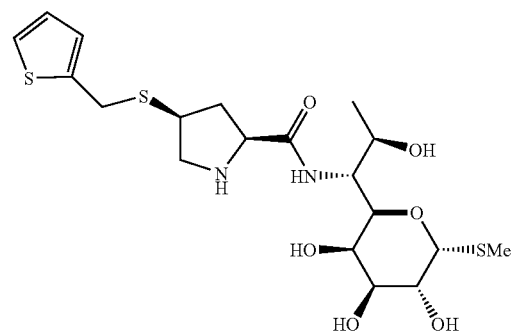

The title compound of example 14 was prepared by the procedure used in example 9 from tosylate intermediate 14b (P=CF$_3$CO, m=1, R$_2$=H, R$_3$=OAc) prepared in general method R, scheme 14. Thiophen-2-yl methanethiol (Aldrich) was the nucleophile used in the displacement step: MS (ESPOS): 479.2 [M+H]$^+$; HPLC: C$_{18}$ 3.5 μm, 4.6×30 mm column; gradient eluent 2%–98% MeCN over 10 min: R$_t$=3.656 min.

Example 15

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide

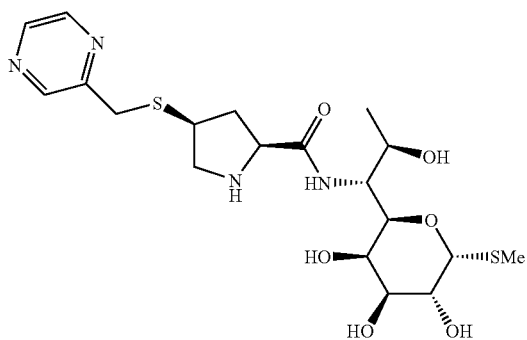

The title compound of example 15 was prepared by the procedure used in example 9 from tosylate intermediate 14b (P=CF$_3$CO, m=1, R$_2$=H, R$_3$=OAc) prepared in general method R, scheme 14. 2-Mercaptomethyl pyrazine (Pyrazine Specialties Inc.) was the nucleophile used in the displacement step. Purification of the title compound of example 15 was performed by preparative TLC (16% methanolic ammonia/dichloromethane) gave the product (9 mg, 15%) of 4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide. MS (ES-POS): 475.5 [M+H]+; 497.4 [M+Na]+.

Example 16

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide

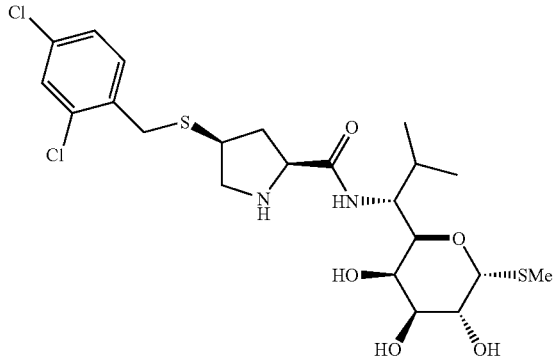

To a solution of 2b (R2'=H) (100 mg, 0.40 mmol, 1 equiv) in dry DMF (1 mL) at 0° C. was added triethylamine (0.18 mL, 1.27 mmol, 3.2 equiv), followed by the addition of Bis(trimethylsilyl)trifluoroacetamide (0.16 mL, 0.60 mmol, 1.5 equiv). The reaction mixture was stirred at 0° C. for 10 minutes, and then was stirred at rt for 50 minutes. To the reaction mixture were added the Boc protected amino acid 9d (P=Boc, m=1, R9=2,4-dichlorobenzylsulfide) prepared in general method N (263 mg, 0.65 mmol, 1.63 equiv), HATU (302 mg, 0.80 mmol, 2 equiv). The reaction mixture was stirred at rt for 3 h. The reaction mixture was evaporated to dryness, taken up in ethyl acetate (150 mL), washed with 10% citric acid (2×80 mL), water (80 mL), half sat. NaHCO$_3$ (80 mL) and brine. The organic layer was dried over Na$_2$SO$_4$ and evaporated to give the desired Boc protected lincosamide as a yellow syrup.

To a solution of the above Boc protected lincosamide in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide a white solid (61 mg). The white solid was purified by preparative thin layer chromatography to give 4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide (47.5 mg, 22%) as a white solid: $^1$H NMR (300 MHz, CDCl$_3$) δ 7.84 (br s, 1), 7.39–7.19 (m, 3), 5.31 (d, J=5.1, 1), 4.09 (dd, J=5.4, 9.9, 1), 3.94–3.76 (m, 4), 3.81 (s, 2), 3.57–3.48 (m, 1), 3.40–3.32 (m, 1), 3.22–3.14 (m, 1), 2.88–2.79 (m, 1), 2.64–2.54 (m, 1), 2.33–2.22 (m, 1), 2.14 (s, 3), 1.93–1.85 (m, 1), 0.92–0.85 (m, 6). MS (ES-POS): 539.4 [M+H]+.

Example 17

4-Butylsulfanyl-pyrrolidine-2-carboxylic acid [2-methyl-1-(3,4,5-trihydroxy-6-methylsulfanyl-tetrahydro-pyran-2-yl)-propyl]-amide

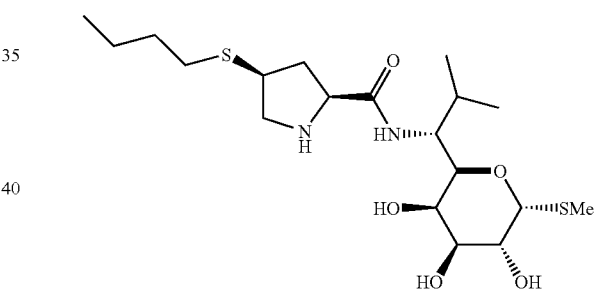

9c (P=Boc, m=1, R$^9$=n-butylsulfide). To a solution of tosylate 9b (P=Boc, m=1) prepared in general method N (1.61 g, 4.03 mmol, 1 equiv) in dry DMF (12 mL) under N$_2$ was added n-butylthiol (1.30 mL, 12.1 mmol, 3 equiv), followed by the addition of 7-methyl-1,5,7-triazabicyclo-[4.4.0]dec-5-ene (MTBU) (0.87 mL, 6.05 mmol, 1.5 equiv). The reaction mixture was stirred at rt overnight and concentrated to dryness. The residue was taken up in ethyl acetate (100 mL), washed with 10% citric acid (50 mL) and brine, and concentrated. The residue was purified by chromatography to provide a clear oil (1.24 g, 97%): $^1$H NMR (300 MHz, CDCl$_3$) δ 4.30 (t, J=8.0, 0.36), 4.23 (t, J=8.1, 0.64), 4.00–3.94 (m, 0.64), 3.87–3.82 (m, 0.36), 3.72 (s, 1.1), 3.71 (s, 1.9), 3.29–3.15 (m, 2), 2.64–2.49 (m, 3), 1.97–1.84 (m, 1), 1.60–1.32 (m, 4), 1.44 (s, 3.2), 1.38 (s, 5.8), 0.93–0.86 (m, 3).

9c (P=Boc, m=1, R9=n-butylsulfide). To a solution of methyl ester 9c (1.24 g, 3.91 mmol, 1 equiv) in THF (15 mL) and water (5 mL) was added lithium hydroxide monohydrate (0.82 g, 19.55 mmol, 5 equiv). The reaction mixture was stirred at rt overnight. THF was removed under vacuum. The residue was partitioned between ethyl acetate (200 mL) and 10% citric acid (100 mL). The organic layer was washed with water (1×), brine (1×), dried over $Na_2SO_4$ and evaporated to give a clear oil 9c (P=Boc, m=1, R9=n-butyl) (1.21 g, 100%): MS (ESPOS): 204.4 [M−Boc+H]$^+$, 326.4 [M+Na]$^+$; MS (ESNEG): 302.3 [M−H]$^−$.

4-Butylsulfanyl-pyrrolidine-2-carboxylic acid [2-methyl-1-(3,4,5-trihydroxy-6-methylsulfanyl-tetrahydro-pyran-2-yl)-propyl]-amide. To a solution of 2b (R2'=H)(75 mg, 0.30 mmol, 1 equiv) in dry DMF (0.8 mL) at 0° C. was added triethylamine (0.13 mL, 0.96 mmol, 3.2 equiv), followed by the addition of bis-(trimethylsilyl)trifluoroacetamide (0.12 mL, 0.45 mmol, 1.5 equiv). The reaction mixture was stirred at 0° C. for 10 minutes, and then was stirred at rt for 50 minutes. To the reaction mixture were added the Boc protected amino acid 9c (P=Boc, m=1, R9=n-Butylsulfide) (147 mg, 0.49 mmol, 1.63 equiv), HATU (227 mg, 0.60 mmol, 2 equiv). The reaction mixture was stirred at rt for 3 h. The reaction mixture was evaporated to dryness, taken up in ethyl acetate (100 mL), washed with 10% citric acid (2×60 mL), water (60 mL), half sat. $NaHCO_3$ (60 mL) and brine. The organic layer was dried over $Na_2SO_4$ and evaporated to give a yellow syrup.

To a solution of the above syrup in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide a white solid, 4-Butylsulfanyl-pyrrolidine-2-carboxylic acid [2-methyl-1-(3,4,5-trihydroxy-6-methylsulfanyl-tetrahydro-pyran-2-yl)-propyl]-amide (95 mg, 73%): $^1$H NMR (300 MHz, $CD_3OD$) δ 5.24 (d, J=6.0, 1), 4.14–4.02 (m, 3), 3.94 (dd, J=7.1, 8.9, 1), 3.82 (d, J=3.3, 1), 3.51 (dd, J=3.3, 10.2, 1), 3.45–3.32 (m, 2), 2.93 (dd, J=6.4, 10.6, 1), 2.71–2.55 (m, 3), 2.23–2.13 (m, 1), 2.10 (s, 3), 1.83–1.72 (m, 1), 1.63–1.52 (m, 2), 1.48–1.38 (m, 2), 0.97–0.88 (m, 9). MS (ESPOS): 437.5 [M+H]$^+$.

Example 18

4-Azido-pyrrolidine-2-carboxylic acid [2-hydroxy-1-(3,4,5-trihydroxy-6-methylsulfanyl-tetrahydro-pyran-2-yl)-propyl]-amide

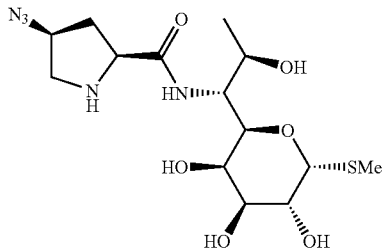

N-Boc-(2S,4R)-4-methanesulfonylproline methylester 9b (P=Boc, m=1, LG=Ms). To N-Boc-(2S,4R)-4-hydroxyproline methylester (Bachem) 9a (P=Boc, m=1), general method N (1 g, 4.0 mmol) in DCM (10 mL), pyridine (1.64 mL, 20.0 mmol), methanesulfonyl chloride (0.631 mL, 5.52 mmol) was added and let stirred for 2 hours at 0° C. and further stirred at room temperature overnight. More DCM (100 mL) was added, washed with HCl (1N, 50 mL) and the organic portion was dried over magnesium sulfate. The mesylate product was obtained on removal of solvent (1.30 g, 100%) and used without further purification.

N-Boc-(2S,4S)-4-Azidoproline methylester 9c (P=Boc, m=1, R9=azide). N-Boc-(2S,4R)-4-methanesulfonylproline methylester was taken in DMF (10 mL) to which sodium azide (1.30 g, 20.0 mmol) was added and heated at 75–80° C. overnight. DMF was removed and the product was extracted with ethyl acetate (100 mL) and washed with water (50 mL). The azide product 9c (P=Boc, m=1, R9=azide) was obtained (0.98 g, 90%) on removal of solvent.

9d (P=Boc, m=1, R9=azide). A stirred solution of 9c (P=Boc, m=1, R9=azide) in THF (10 mL) was treated with lithium hydroxide (300 mg, 7.14 mmol) in water (0.5 mL) overnight. The excess solvent was removed by rotary evaporation and the residue was extracted with ethyl acetate and discarded. The aqueous portion was acidified, extracted with ethyl acetate and dried over magnesium sulfate. Removal of solvent resulted in the protected amino acid N-Boc-(2S,4S)-4-azidoproline 9d (P=Boc, m=1, R9=azide)(0.8 g, 88%): $^1$H NMR (300 MHz, $CD_3OD$) δ 4.34–4.24 (m, 2), 3.73–3.64 (m, 1), 3.39–3.34 (m, 1), 2.61–2.51 (m, 1), 2.16–2.09 (m, 1), 1.46 (s, 3), 1.42 (s, 6); MS (ESNEG): 255 (M−1).

1-(2-(S)-4-(S)-(Azido)-N-pyrrolidin-2-yl-{1-(R)-[2-(S), 3-(S),4-(S),5-(R)-trihydroxy-6-(R)-(methylsulfanyl)tetrahydropyran-2-yl]-2-hydroxy-prop-1-yl}acetamide. To 2b (R9'=H) (200 mg, 0.788 mmol) in DMF (5 mL) at 0° C., triethylamine (0.164 mL, 1.18 mmol) and bis-(trimethylsilyl)trifluoroacetamide (0.93 mL, 3.94 mmol) were added and then left stirring at room temperature overnight. After which, N-Boc-(2S,4S)-4-azidoproline (300 mg, 1.18 mmol) and HATU (444 mg, 1.18 mmol) was added at 0° C. and then left stirring for four hours. At the end, DMF was removed and the residue was taken in ethyl acetate (100 mL) and washed with citric acid (10%, 30 mL), saturated sodium bicarbonate (30 mL) and brine (30 mL). After drying the organic portion with sodium sulfate, the solvent was removed to obtain the crude product which was taken as such for the next deprotection step. To the crude product in dichloroethane 30% trifluoroacetic acid (10 mL) and dimethylsulfide (0.5 mL) was added and the reaction mixture was stirred for an hour. The solvent was removed and the crude product obtained was chromatographed on silica gel column using 20% methanol in DCM to obtain the title compound as a white solid (278 mg, 90%): TLC: $R_f$=0.38 (40% methanol in DCM); $^1$H NMR (300 MHz, $CD_3OD$) δ 4.24 (d, J=5.4, 1), 4.16 (s, 1), 4.03–4.13 (m, 3), 3.95 (d, J=3.6, 1), 3.80 (dd, J=4.5, 9.9, 1), 3.51–3.56 (dd, J=3.3, 10.2, 1), 3.13–3.22 (m, 1), 2.95–3.00 (m, 1), 2.35–2.45 (m, 1), 2.08 (s, 3), 1.93–2.04 (m, 1), 1.29 (t, J=7.2, 1), 0.97 (m, 3); MS (ESPOS): 392 [M+H]+.

Example 19

4-[3-(Furan-2-ylmethylsulfanyl)-prop-1-yl]-piperidine-2-carboxylic acid [2-methyl-1-(3,4,5-trihydroxy-6-methylsulfanyl-tetrahydro-pyran-2-yl)-propyl]-amide

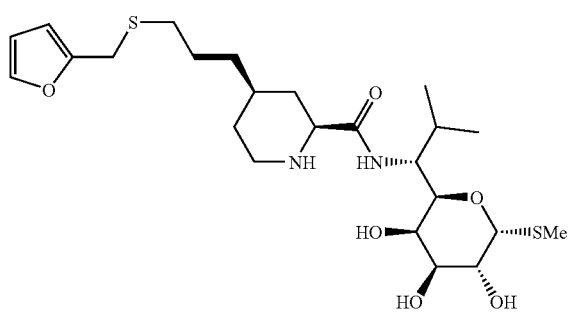

4-(3-Hydroxy-propyl)-2-[2-methyl-1-(3,4,5-trihydroxy-6-methylsulfanyl-tetrahydro-pyran-2-yl)-propylcarbamoyl]-piperidine-1-carboxylic acid tert-butyl ester To a mixture of 2b (R$^{2'}$=H) (532 mg, 1.85 mmol, 1 equiv) in dry DMF (4.5 mL) at 0° C. was added triethylamine (1.28 mL, 9.25 mmol, 5 equiv), followed by the addition of Bis-(trimethylsilyl)trifluoroacetamide (0.74 mL, 2.78 mmol, 1.5 equiv). The reaction mixture was stirred at 0° C. for 10 minutes, and then was stirred at rt for 50 minutes. To the reaction mixture were added the Boc protected amino acid 11f (R$^{9'}$=3-t-butyldimethylsiloxypropyl, P=Boc) prepared in general method P (741 mg, 1.85 mmol, 1.0 equiv) and HATU (886 mg, 2.33 mmol, 1.26 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and concentrated to give a yellow syrup. The residue was taken up into methanol (20 mL) and followed by the addition of Dowex® resin (340 mg). The mixture was stirred at rt for 1 hr and the resin was removed by filtration. The filtrate was concentrated and the residue was purified by column chromatography to give the product 4-(3-hydroxy-propyl)-2-[2-methyl-1-(3,4,5-trihydroxy-6-methylsulfanyl-tetrahydro-pyran-2-yl)-propylcarbamoyl]-piperidine-1-carboxylic acid tert-butyl ester (694 mg, 72%) as a white solid; $^1$H NMR (300 MHz, CDCl$_3$) δ 5.33–5.28 (m, 1), 4.16–3.97 (m, 3), 3.89–3.69 (m, 3), 3.65–3.58 (m, 2), 3.56–3.47 (m, 1), 3.17–3.06 (m, 1), 2.33–2.23 (m, 1), 2.14 (s, 1.5), 2.13 (s, 1.5), 1.94–1.80 (m, 2), 1.67–1.50 (m, 5), 1.45 (s, 9), 1.42–1.23 (m, 2), 0.93–0.82 (m, 6). MS (ESPOS): 521.7 [M+H]$^+$.

2-[2-Methyl-1-(3,4,5-trihydroxy-6-methylsulfanyl-tetrahydro-pyran-2-yl)-propylcarbamoyl]-4-[3-(toluene-4-sulfonyloxy)-propyl]-piperidine-1-carboxylic acid tert-butyl ester To a solution of 4-(3-Hydroxy-propyl)-2-[2-methyl-1-(3,4,5-trihydroxy-6-methylsulfanyl-tetrahydro-pyran-2-yl)-propylcarbamoyl]-piperidine-1-carboxylic acid tert-butyl ester (196 mg, 0.38 mmol, 1 equiv) and p-toluenesulfonic anhydride (123 mg, 0.38 mmol, 1 equiv) in DCM (1.5 mL) at 0° C. was added dropwise triethylamine (63 µL, 0.45 mmol, 1.2 equiv). The reaction mixture was stirred at 0° C. for 5 hr then diluted with ethyl acetate. The organic layer was washed with sat. sodium bicarbonate, brine, dried and concentrated to give a white solid which was purified by chromatography to give 11h (147.5 mg, 58%) as a white solid; $^1$H NMR (300 MHz, CDCl$_3$) δ 7.78–7.74 (m, 2), 7.35–7.31 (m, 2), 5.30 (d, J=5.7, 1), 4.13–4.06 (m, 1), 4.03–3.93 (m, 3), 3.91–3.60 (m, 4), 3.54–3.45 (m, 1), 3.12–3.02 (m, 1), 2.43 (s, 3), 2.32–2.21 (m, 1), 2.121 (s, 1.7), 2.117 (s, 1.3), 1.83–1.73 (m, 2), 1.65–1.59 (m, 4), 1.45 (s, 5), 1.44 (s, 4), 1.37–1.15 (m, 3), 0.93–0.81 (m, 6); MS(ESPOS): 675.9 [M+H]$^+$.

4-[3-(Furan-2-ylmethylsulfanyl)-propyl]-2-[2-methyl-1-(3,4,5-trihydroxy-6-methylsulfanyl-tetrahydro-pyran-2-yl)-propylcarbamoyl]-piperidine-1-carboxylic acid tert-butyl ester To a solution of Boc protected tosylate 2-[2-Methyl-1-(3,4,5-trihydroxy-6-methylsulfanyl-tetrahydro-pyran-2-yl)-propylcarbamoyl]-4-[3-(toluene-4-sulfonyloxy)-propyl]-piperidine-1-carboxylic acid tert-butyl ester (91 mg, 0.13 mmol, 1 equiv) in dry DMF (0.42 mL) under N$_2$ was added furfuryl mercaptan (68 µL, 0.67 mmol, 5 equiv), followed by the addition of 7-methyl-1,5,7-triazabicyclo-[4.4.0]dec-5-ene (MTBU) (48 µL, 0.33 mmol, 2.5 equiv). The reaction mixture was stirred at rt overnight and diluted with DCM, washed with brine (3×), dried and to concentrated. The residue was purified by preparative TLC (8% MeOH/DCM) to provide the desired Boc protected thioether 4-[3-(Furan-2-ylmethylsulfanyl)-propyl]-2-[2-methyl-1-(3,4,5-trihydroxy-6-methylsulfanyl-tetrahydro-pyran-2-yl)-propylcarbamoyl]-piperidine-1-carboxylic acid tert-butyl ester (63.3 mg, 76%) as a clear syrup: MS (ESPOS): 617.9 [M+H]$^+$.

To a solution of the Boc protected thioether 4-[3-(Furan-2-ylmethylsulfanyl)-propyl]-2-[2-methyl-1-(3,4,5-trihydroxy-6-methylsulfanyl-tetrahydro-pyran-2-yl)-propylcarbamoyl]-piperidine-1-carboxylic acid tert-butyl ester in DCM (9 mL) with methyl sulfide (0.2 mL) were added trifluoroacetic acid (3 mL) and water (0.2 mL). The reaction mixture was stirred at rt for 1 h. The solvent was removed under vacuum and co-evaporated with toluene twice. The residue was purified by preparative TLC to provide the title lincosamide product for example 19 (13 mg, 25%) as a white solid; $^1$H NMR (300 MHz, CD$_3$OD) δ 7.39 (dd, J=0.8, 2.0, 1), 6.32 (dd, J=2.1, 3.3, 1), 6.18 (dd, J=0.8, 3.2, 1), 5.24 (d, J=5.7, 1), 4.17 (dd, J=3.2, 10.1, 1), 4.10–4.02 (m, 2), 3.79 (d, J=3.3, 1), 3.71 (s, 2), 3.50 (dd, J=3.3, 10.2, 1), 3.43 (dd, J=2.9, 11.9, 1), 3.24–3.17 (m, 1), 2.78–2.67 (m, 1), 2.49 (t, J=7.1, 2), 2.20–2.11 (m, 1), 2.10 (s, 3), 2.06–1.93 (m, 1), 1.78–1.70 (m, 1), 1.62–1.52 (m, 3), 1.38–1.29 (m, 2), 1.20–1.06 (m, 2), 0.91 (d, J=7.2, 6); MS(ESPOS): 517.8 [M+H]$^+$.

Example 20

4-(3-Imidazol-1-yl-prop-1-yl)-piperidine-2-carboxylic acid [2-methyl-1-(3,4,5-trihydroxy-6-methylsulfanyl-tetrahydro-pyran-2-yl)-propyl]-amide

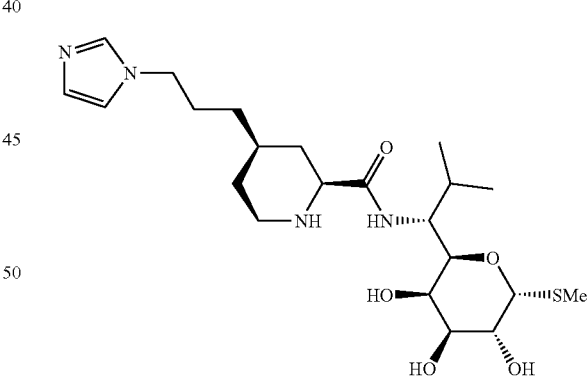

4-(3-Imidazol-1-yl-prop-1-yl)-2-[2-methyl-1-(3,4,5-trihydroxy-6-methylsulfanyl-tetrahydro-pyran-2-yl)-propylcarbamoyl]-piperidine-1-carboxylic acid tert-butyl ester.

To a mixture of NaH (60%, 11.9 mg, 0.30 mmol, 2 equiv) in dry DMF (0.2 mL) at 0° C. was added a solution of imidazole (40.4 mg, 0.60 mmol, 4 equiv) in DMF (0.25 mL) dropwise. The mixture was stirred at 0° C. for 10 min, then was cooled to −78° C. To the mixture was added a solution of Boc protected tosylate prepared in example 19 (100 mg, 0.15 mmol, 1 equiv) in dry DMF (0.4 mL) dropwise. The reaction was stirred at 0° C. for 2 hr, then at rt overnight. The reaction mixture was diluted DCM, washed with brine (3×), dried and concentrated. The residue was purified by chromatography to give the title Boc protected imidazole compound (60 mg, 71%) as a white solid. MS (ESPOS): 571.8 [M+H]$^+$.

To a solution of the above Boc protected imidazole in DCM (9 mL) with methyl sulfide (0.2 mL) were added trifluoroacetic acid (3 mL) and water (0.2 mL). The reaction mixture was stirred at rt for 1 h. The solvent was removed under vacuum and co-evaporated with toluene twice. The residue was purified by chromatography to provide the title lincosamide compound for example 2Q (10 mg, 20%) as a white solid: $^1$H NMR (300 MHz, CD$_3$OD) δ 7.63 (s, 1), 7.11 (s, 1), 6.95 (s, 1), 5.23 (d, J=5.7, 1), 4.14 (dd, J=3.2, 10.1, 1), 4.10–3.99 (m, 4), 3.79 (d, J=3.6, 1), 3.50 (dd, J=3.3, 10.2, 1), 3.27–3.21 (m, 1), 3.14–3.07 (m, 1), 2.64–2.54 (m, 1), 2.19–2.10 (m, 1), 2.10 (s, 3), 1.94–1.76 (m, 3), 1.70–1.64 (m, 1), 1.55–1.43 (m, 1), 1.30–1.18 (m, 2), 1.11–0.94 (m, 2), 0.92–0.88 (m, 6); MS (ESPOS): 471.7 [M+H]$^+$.

Example 21

4-[3-(Thiophen-2-ylsulfanyl)-prop-1-yl]-piperidine-2-carboxylic acid [2-methyl-1-(3,4,5-trihydroxy-6-methylsulfanyl-tetrahydro-pyran-2-yl)-propyl]-amide

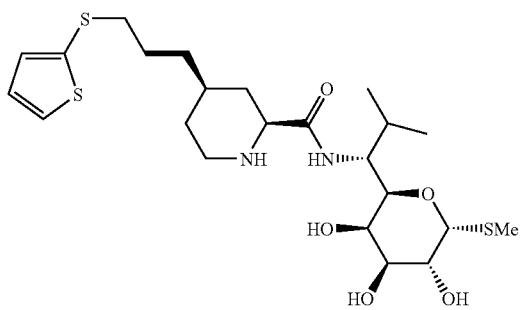

4-[3-(Thiophen-2-ylsulfanyl)-prop-1-yl]-piperidine-2-carboxylic acid [2-methyl-1-(3,4,5-trihydroxy-6-methylsulfanyl-tetrahydro-pyran-2-yl)-propyl]-amide. To a solution of protected tosylate prepared in example 19 (97 mg, 0.14 mmol, 1 equiv) in dry DMF (0.42 mL) under N$_2$ was added 2-thienyl mercaptan (Acros) (68 μL, 0.72 mmol, 5 equiv), followed by the addition of 7-methyl-1,5,7-triazabicyclo-[4.4.0]dec-5-ene (MTBU) (51.3 μL, 0.36 mmol, 2.5 equiv). The reaction mixture was stirred at rt overnight and diluted with DCM, washed with brine (3×), dried and concentrated. The residue was purified by preparative TLC (8% MeOH/DCM) to provide a clear syrup (65.5 mg, 74%): MS (ESPOS): 619.8 [M+H]$^+$.

To a solution of the above syrup in DCM (9 mL) with methyl sulfide (0.2 mL) were added trifluoroacetic acid (3 mL) and water (0.2 mL). The reaction mixture was stirred at rt for 1 h. The solvent was removed under vacuum and co-evaporated with toluene twice. The residue was purified by preparative TLC to provide the title lincosamide compound for example 21 (16 mg, 29%) as a white solid; $^1$H NMR (300 MHz, CD$_3$OD) δ 7.45–7.42 (m, 1), 7.12–7.09 (m, 1), 7.01–6.96 (m, 1), 5.23 (d, J=5.7, 1), 4.16 (dd, J=3.3, 10.2, 1), 4.10–4.01 (m, 2), 3.79 (d, J=3.3, 1), 3.50 (dd, J=3.3, 10.5, 1), 3.34–3.28 (m, 1), 3.18–3.10 (m, 1), 2.76 (t, J=7.1, 2), 2.68–2.58 (m, 1), 2.20–2.06 (m, 1), 2.10 (s, 3), 1.98–1.88 (m, 1), 1.71–1.28 (m, 6), 1.13–1.00 (m, 2), 0.90 (d, J=6.9, 6); MS (ESPOS): 519.7 [M+H]$^+$.

Example 22

4-(3-Ethylsulfanyl-prop-1-yl)-piperidine-2-carboxylic acid [2-methyl-1-(3,4,5-trihydroxy-6-methylsulfanyl-tetrahydro-pyran-2-yl)-propyl]-amide

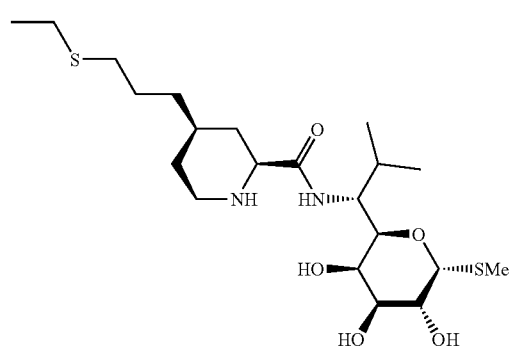

The title compound of example 22 was prepared from protected tosylate intermediate prepared in example 19, according to the procedure used in examples 19–21, using sodium ethanethiolate in the displacement step; MS (ESPOS): 465.3 [M+H]$^+$.

Example 23

4-(3-Cyano-prop-1-yl)-piperidine-2-carboxylic acid [2-methyl-1-(3,4,5-trihydroxy-6-methylsulfanyl-tetrahydro-pyran-2-yl)-propyl]-amide

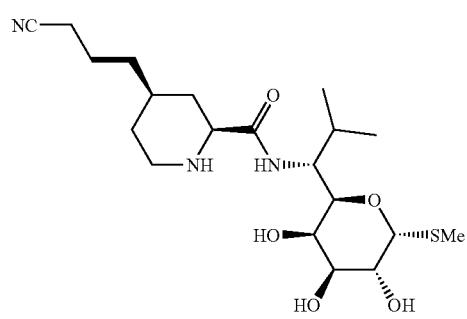

The title compound of example 23 was prepared from protected tosylate intermediate prepared in example 19, 11h according to the procedure used in examples 19–21 using sodium cyanide nucleophile in the displacement step; MS (ESPOS): 430.3 [M+H]$^+$.

Example 24

4-(3-Difluoromethylsulfanyl-prop-1-yl)-piperidine-2-carboxylic acid [2-chloro-1-(3,4,5-trihydroxy-6-methylsulfanyl-tetrahydro-pyran-2-yl)-propyl]-amide

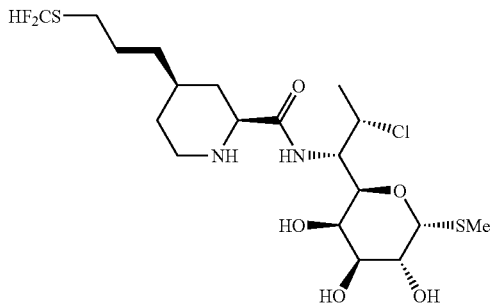

11c ($R^{9'}$=3-hydroxy-propyne).

To a mixture of 4-iodopicolinic acid methyl ester 11b (4.36 g, 16.5 mmol, 1 equiv), triphenylphosphine (346 mg, 1.32 mmol, 0.08 equiv), copper iodide (251 mg, 1.32 mmol, 0.08 equiv), palladium acetate (148 mg, 0.66 mmol, 0.04 equiv) in triethylamine (60 mL) at 23° C. was added propargyl alcohol (1.92 mL, 33.0 mmol, 2 equiv), and the reaction mixture was stirred at 23° C. overnight. The reaction mixture was concentrated under high vacuum and the black residue was purified by column chromatography (2% MeOH in methylene chloride) to yield a brown oil. The brown oil was purified again by column chromatography (100% EtOAc) to yield the desired product, 11c ($R^{9'}$=3-hydroxy-1-propyne) as a yellow oil (3.0 g, 95%): $^1$H NMR (300 MHz, CDCl$_3$) 8.70–8.74 (dd, J=0.9, 5.1, 1), 8.14 (s, 1), 7.46–7.50 (dd, J=1.8, 5.1, 1), 4.54 (d, J=6.3, 2), 4.02 (s, 3); MS (ESPOS): 192.1 [M+H]; 214.1 [M+Na]; HPLC: (Symmetry C18 3.5 µm, 4.6 30 mm Column; gradient eluent 2%–98% MeCN over 5 min; 1.5 mL/min): Rt=1.42 min.

11c ($R^{9'}$=3-hydroxy-propyl).

To a solution of 11c (R9'=3-hydroxy-1-propyne) (2.0 g, 10.5 mmol, 1.0 equiv) in MeOH (120 mL) at 23° C. was added 20 wt. % Pd(OH)2 on carbon (1.0 g) and the reaction mixture was stirred under hydrogen atmosphere overnight. The reaction mixture was filtered through celite and the filtrate was concentrated to yield the desired product, 4-(3-hydroxy-propyl)-pyridine-2-carboxylic acid methyl ester 11c ($R^{9'}$=3-hydroxy-propyl) (2.03 g, 99%) as yellow oil: $^1$H NMR (300 MHz, CDCl$_3$) 8.65 (d, J=5.1, 1), 8.03 (s, 1), 7.34–7.36 (dd, J=1.8, 5.1, 1), 4.02 (s, 3), 3.71 (t, J=6.0, 12.3, 2), 2.83 (t, J=7.8, 15.6, 2), 1.92–1.97 (m, 2); MS (ESPOS): 196.3 [M+H] MS (ESNEG): 194.2 [M–H]; HPLC: (Symmetry C18 3.5 µm, 4.6 30 mm Column; gradient eluent 2%–98% MeCN over 5 min; 1.5 mL/min): Rt=1.46 min.

11d ($R^{9'}$=3-hydroxy-propyl).

To a solution of 4-(3-Hydroxy-propyl)-pyridine-2-carboxylic acid methyl ester, 11c ($R^{9'}$=1-hydroxypropyl) (1.81 g, 9.28 mmol, 1.0 equiv) in MeOH (30 mL) and H$_2$O (20 mL) at 23° C. was added concentrated HCl (412 L, 11.1 mmol, 1.2 equiv), followed by platinum(IV) oxide (600 mg, 0.33 wt %) and the reaction mixture was stirred vigorously under hydrogen atmosphere at 1 atm for 48 h. The reaction mixture was filtered through celite washing with methanol (200 mL). The combined filtrate was concentrated under reduced pressure to yield the desired product 11d, $R^{9'}$=(3-hydroxy-propyl) as an HCl salt (2.02 g, 8.52 mmol, 91%): MS (ESPOS): 202.2 [M+H]+.

11e ($R^{9'}$=3-hydroxy-propyl, P=Cbz).

To a solution of 11d, $R^{9'}$=(3-hydroxy-propyl) (2.02 g, 8.52 mmol, 1 equiv) in dichloromethane (50 mL) at 5° C. was added triethylamine (1.54 mL, 11.07 mmol, 1.3 equiv), and the reaction mixture was stirred for 10 min. To this solution was added benzylchloroformate (1.55 mL, 11.07 mmol, 1.3 equiv) and the reaction mixture was stirred at 5° C. for 1 h, then warmed to room temperature. The reaction mixture was concentrated, and the crude product was partitioned between dichloromethane (250 mL) and water (150 mL). The organic layer was collected, dried over Na2SO4, and concentrated. The residue was purified by column chromatography (gradient from 50% to 75% EtOAc/hexane) to yield the desired product, 11e ($R^{9'}$=3-hydroxy-propyl, P=Cbz) (2.28 g, 6.80 mmol, 80%) as a yellow oil: $^1$H NMR (300 MHz, CDCl$_3$) 7.34 (s, 5), 5.19 (s, 2), 4.48 (t, J=6.3, 12.3, 1), 3.68 (bs, 3), 3.60–3.64 (m, 2), 3.38–3.42 (m, 2), 1.94–1.98 (m, 3), 1.65–1.80 (m, 2), 1.33–1.37 (m, 2), 1.20–1.24 (m, 2); MS (ESPOS): 358.0 [M+Na]; HPLC: (Symmetry C18 3.5 µm, 4.6 30 mm Column; gradient eluent 2%–98% MeCN over 5 min; 1.5 mL/min): Rt=2.50 min.

11e ($R^{9'}$=3-methanesulfonylpropyl, P=Cbz)

To a solution of alcohol intermediate 11e ($R^{9'}$=3-hydroxy-propyl, P=Cbz) prepared by general method P (2.0 g, 5.97 mmol, 1 equiv) in dichloromethane (15 mL) at 0° C. was added triethylamine (1.0 mL 7.2 mmol, 1.2 equiv), and the reaction mixture was stirred for 15 min. To this solution was added methanesulfonic anhydride (1.04 g, 5.97 mmol, 1 equiv), and the reaction mixture was stirred for a further 30 min at 0° C. The reaction mixture was partitioned between dichloromethane (250 mL) and saturated aqueous NaHCO$_3$ (100 mL). The organic layer was collected, dried over Na$_2$SO$_4$, and concentrated to yield the desired mesylate product 11e ($R^{9'}$=3-methanesulfonylpropyl, P=Cbz) (2.25 g, 5.45 mmol, 91%) as clear oil: $^1$H NMR (300 MHz, CDCl$_3$) δ 7.34 (s, 5), 5.19 (s, 2), 4.48 (t, J=6.3, 12.3, 1), 4.20 (t, J=6.3, 14.1, 2), 3.70 (bs, 3), 3.38–3.42 (m, 2), 3.02 (s, 3), 1.94–1.98 (m, 3), 1.65–1.80 (m, 2), 1.33–1.37 (m, 2), 1.20–1.24 (m, 2); MS (ESPOS): 436.3 [M+Na]; HPLC (Symmetry® C$_{18}$ 3.5 µm, 4.6×30 mm Column; gradient eluent 2%–98% MeCN over 5 min; 1.5 mL/min): R$_t$=2.86 min.

11e ($R^{9'}$=3-acetylsulfanyl-propyl, P=Cbz)

To a solution of mesylate 11e ($R^{9'}$=3-methanesulfonyl-propyl, P=Cbz) (2.25 g, 5.45 mmol, 1 equiv) in DMF (30 mL) at 5° C. was added potassium thioacetate (3.11 g, 27.3 mmol, 5 equiv) and the reaction mixture was stirred at 5° C. overnight. The reaction mixture was partitioned between EtOAc (250 mL) and saturated aq. NaHCO$_3$ (100 mL). The organic layer was collected, dried over Na$_2$SO$_4$, and concentrated. The crude product obtained was purified by column chromatography (25% EtOAc in hexane) to yield the desired thioester product 11e ($R^{9'}$=3-acetylsulfanyl-propyl, P=Cbz) (1.90 g, 4.83 mmol, 89%) as a yellow oil: $^1$H NMR (300 MHz, CDCl$_3$) δ 7.34 (s, 5), 5.12 (s, 2), 4.46 (t, J=6.3, 12.3, 1), 3.69 (bs, 3), 3.38–3.42 (m, 2), 2.81–2.85 (m, 3), 2.32 (s, 3), 1.89–2.05 (m, 3), 1.65–1.80 (m, 2), 1.33–1.37 (m, 2), 1.20–1.24 (m, 2); MS (ESPOS): 394.0 [M+H] 416.1 [M+Na]; HPLC (Symmetry® C$_{18}$ 3.5 µm, 4.6×30 mm Column; gradient eluent 2%–98% MeCN over 5 min; 1.5 mL/min): Retention time=3.28 min.

11f (R⁹'=3-Difluoromethylsulfanyl-propyl, P=Cbz).

To a solution of 11e (R⁹'=(3-acetylsulfanyl-propyl), P=Cbz) (1.90 g, 4.83 mmol, 1 equiv) in ethanol (8 mL) was added 3 N NaOH (4.5 mL). The reaction mixture was stirred at room temperature for 45 min, then concentrated to give a clear oil. The resulting oil was dissolved in ethanol (20 mL) and the reaction mixture was de-oxygenated via evacuation of the reaction flask, then the reaction mixture was saturated with chlorodifluoromethane gas (Aldrich) at 1 atm. pressure. The reaction mixture was stirred at 5° C. for 16 h, then neutralized with 1 N HCl at 0° C., and concentrated under reduced pressure. The residue was made basic with 0.5 N aqueous NaOH and washed with ether. The aqueous layer was acidified to pH 2.0 with 1N HCl, and extracted with ethyl acetate (3×100 mL). The organic layer was washed with brine (2×100 mL), dried (MgSO₄), and concentrated. The crude residue obtained was purified by column chromatography (50% EtOAc/49% Hexane/1% AcOH) to yield the desired difluoromethyl sulfide product 11f (R⁹'=(3-difluoromethylsulfanyl-propyl), P=Cbz) (0.75 g, 1.94 mmol, 40%) as a clear oil: ¹H NMR (300 MHz, CDCl₃) δ 7.36 (s, 5), 6.97 (s), 6.79 (s), 6.60 (s), 5.15 (s, 2), 4.51 (t, J=6.3, 12.3, 1), 3.38–3.42 (m, 2), 2.75 (t, J=7.2, 14.4, 1), 2.47–2.51 (m, 1), 1.89–2.05 (m, 3), 1.65–1.80 (m, 2), 1.33–1.37 (m, 2), 1.21–1.23 (m, 2); MS (ESPOS): 388.1 [M+H]+ 410.1 [M+Na]+; HPLC (Symmetry® C₁₈ 3.5 μm, 4.6×30 mm Column; gradient eluent 2%–98% MeCN over 5 min; 1.5 mL/min): Rt=2.85 min.

11f (R⁹'=3-difluoromethylsulfanyl-propyl, P=Boc).

To a solution of (750 mg, 1.94 mmol, 1 equiv) in acetonitrile (100 mL) at 23° C. was added iodotrimethylsilane (0.8 mL, 5.81 mmol, 3 equiv), and the reaction mixture was stirred for 30 min. The reaction mixture was concentrated to yield the deprotected crude product (491 mg, 1.94 mmol, 100%). To this was added dichloromethane (100 mL), triethylamine (0.54 mL, 3.88 mmol, 2 equiv), and di-tert-butyl dicarbonate (0.67 mL, 2.91 mmol, 1.5 equiv). The reaction mixture was stirred at 5° C. overnight. The reaction mixture was concentrated, and the crude product was partitioned between dichloromethane (250 mL) and water (150 mL). The organic layer was collected, dried (Na₂SO₄), and concentrated. The crude residue obtained was purified by column chromatography (50:49:1 EtOAc/hexane/AcOH) to yield the desired product 11f (R⁹'=3-difluoromethylsulfanyl-propyl, P=Boc) (671 mg, 98%) as a clear oil: ¹H NMR (300 MHz, CD₃OD) δ 7.10 (s), 6.90 (s), 6.70 (s), 4.19–4.23 (m, 1), 3.48–3.53 (m, 1), 2.68 (t, J=6.6, 13.8, 1), 2.56 (t, J=7.2, 14.4, 1), 1.80–1.95 (m, 4), 1.50–1.80 (m, 5), 1.33 (s, 9), 1.13–1.20 (m, 2); MS (ESPOS): 254.1 [M−Boc+H] MS (ESNEG): 352.2 [M−H]−.

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide To a stirred solution of 7-Cl-MTL 6b (R²=H, R³=Cl) (195 mg, 0.68 mmol, 1.2 equiv) in DMF (2.5 mL) at 23° C. was added diisopropylethylamine (0.3 mL, 1.71 mmol, 3 equiv), followed by a solution of boc protected amino acid 11f (R9'=3-difluoromethylsulfanyl-propyl, P=Boc) (200 mg, 0.57 mmol, 1 equiv) in DMF (2.5 mL), and HBTU (324 mg, 0.85 mmol, 1.5 equiv). The resulting solution was stirred at room temperature for 3 h, then concentrated to dryness. The solid residue was partitioned between ethyl acetate (300 mL) and saturated aq. NaHCO₃ (100 mL). The organic layer was collected, dried (Na₂SO₄) and concentrated. To a portion of this residue (60 mg, 0.12 mmol, 1 equiv) at 23° C. was added 1,2-dichloroethane (5 mL), water (0.2 mL) followed by neat TFA (2.0 mL), and the reaction mixture was stirred for 15 min at room temperature, then concentrated in vacuo. The crude product was purified by preparative HPLC to yield the title compound for example 24 as a white powder: ¹H NMR (300 MHz, CD₃OD) δ 7.12 (s), 6.93 (s), 6.74 (s), 5.21 (d, J=5.7, 1), 4.48 (d, J=8.4, 2) 4.40 (d, J=10.2, 1), 4.17 (d, J=9.6, 1), 3.97–4.02 (dd, J=5.4, 9.9, 1) 3.71 (d, J=3.3), 3.46–3.52 (m, 2), 2.71–2.76 (t, J=6.9, 13.8, 1), 2.05 (s, 3), 1.83 (s, 1), 1.61–1.77 (m, 5), 1.35 (d, J=6.9, 4), 1.08–1.22 (m, 3); MS (ESPOS): 507.1 [M+H]+.

Example 25

4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide

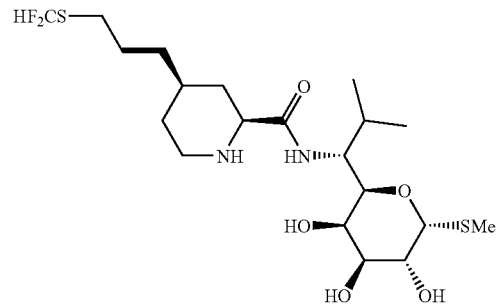

4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide. To a stirred solution of 2b (R2'=H) in DMF (2.5 mL) at 23° C. was added diisopropylethylamine (0.3 mL, 1.7 mmol, 3 equiv), followed by a solution of Boc protected amino acid 11f (R9'=3-difluoromethylsulfanyl-propyl, P=Boc) (200 mg, 0.57 mmol, 1 equiv) in DMF (2.5 mL), and HBTU. The resulting solution was stirred at room temperature for 3 h, and concentrated to dryness. The solid residue was partitioned between ethyl acetate (300 mL) and saturated aq. NaHCO₃. The organic layer was collected, dried (Na₂SO₄) and concentrated. To a portion of this residue (60 mg, 0.12 mmol, 1 equiv) at 23° C. was added 1,2-dichloroethane (5 mL), water (0.2 mL) followed by neat TFA (2.0 mL), and the reaction mixture was stirred for 15 min at room temperature, then was concentrated. The crude product was purified by preparative HPLC to yield the desired title compound for example 25 as a white powder: ¹H NMR (300 MHz, CD₃OD) δ 7.13 (s), 6.94 (s), 6.75 (s), 5.16 (d, J=5.7, 1), 4.12 (d, J=9.9, 1), 3.97–4.02 (dd, J=4.8, 10.2, 2), 3.71 (d, J=3.3, 1), 3.42–3.46 (m, 2), 2.88–2.96 (m, 2), 2.75 (t, J=7.8, 15.0, 2), 2.59–2.63 (m, 2), 2.03 (s, 3), 1.81–1.87 (m, 1), 1.61–1.70 (m, 5), 1.20–1.38 (m, 4), 0.82–0.84 (d, J=6.9, 6); MS (ESPOS): 487.1 [M+H]+.

Example 26

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide

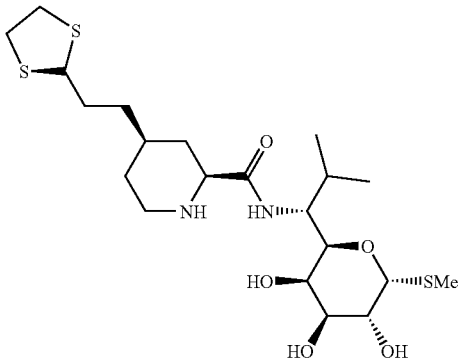

4-(3,3-Diethoxy-prop-1-ynyl)-pyridine-2-carboxylic acid methyl ester. To a dry flask were added intermediate 11b prepared in general method P (2.98 g, 11.33 mmol, 1 equiv), triphenylphosphine (238 mg, 0.91 mmol, 0.08 equiv), copper (I) iodide (172.6 mg, 0.91 mmol, 0.08 equiv), palladium acetate (101.6 mg, 0.45 mmol, 0.04 equiv) and triethylamine (42 mL). The mixture was deaerated with nitrogen, followed by addition of 3,3-Diethoxy-propyne (Aldrich) (2.90 g, 22.7 mmol, 2 equiv). The mixture was stirred at rt for 3 h. The solvent was removed under vacuum to give a dark residue. The residue was purified by chromatography to give a yellow oil 11c (R9'=3,3-Diethoxy-prop-1-ynyl) (3 g, 100%): $^1$H NMR (300 MHz, CDCl$_3$) δ 8.69 (dd, J=0.8, 5.0, 1), 8.15 (d, J=0.8, 1.4, 1), 7.49 (dd, J=1.7, 5.0, 1), 5.48 (s, 1), 3.99 (s, 3), 3.82–3.73 (m, 2), 3.71–3.62 (m, 2), 1.26 (t, J=7.2, 6). MS (ESPOS): 264.5 [M+H]$^+$.

4-(3,3-Diethoxy-1-propyl)-piperidine-1,2-dicarboxylic acid 2-methyl ester 11d (R9'=3,3-diethoxy-1-propyl). To a mixture of 11c (R9'=3,3-Diethoxy-prop-1-ynyl) (3 g) in MeOH (15 mL), acetic acid (15 mL) and water (15 mL) was added platinum oxide (1.0 g). The mixture was purged and charged with hydrogen (50 psi) and shaken at rt for 5 hr. The platinum oxide was removed by filtration and the filtrate was concentrated to give the desired product 11d (R9'=3,3-diethoxy-1-propyl) (2.45 g, 79%) as an oil: MS (ESPOS): 296.5 [M+Na]$^+$.

4-(3,3-Diethoxy-1-propyl)-piperidine-1,2-dicarboxylic acid 1-allyl ester 2-methyl ester 11e (R9'=3,3-Diethoxy-1-propyl, P=Alloc). To a solution of 11d (R9'=3,3-diethoxy-1-propyl) (2.4 g, 8.79 mmol, 1 equiv) and pyridine (1.26 mL, 11.9 mmol, 1.35 equiv) in THF (29 mL) at 0° C. was added dropwise a solution of allyl chloroformate (0.96 mL, 11.9 mmol, 1.4 equiv). The mixture was slowly warmed to rt and stirred at rt for 3 hr. The solution was filtered and solvent was removed under vacuum. The residue was purified by chromatography to furnish 11e (R9'=3,3-diethoxy-1-propyl, P=Alloc) (2.1 g, 66%) as a clear oil: MS (ESPOS): 380.6 [M+Na]$^+$.

4-(3-Oxo-propyl)-piperidine-1,2-dicarboxylic acid 1-allyl ester 2-methyl ester. A solution of 11e (R9'=3,3-diethoxy-1-propyl, P=Alloc) (2.03 g) in acetic acid (32 mL) and water (8 mL) was stirred at rt overnight. The solvent was removed under high vacuum. The residue was diluted with ethyl acetate, and washed with sat. sodium bicarbonate (1×) and brine (1×). The organic layer was dried and concentrated. The residue was purified by chromatography to give methyl ester 11e (R9'=3-oxo-propyl, P=Alloc) (1.2 g, 75%) as a clear oil: $^1$H NMR (300 MHz, CDCl$_3$) δ 9.75 (t, J=1.5, 1), 5.96–5.82 (m, 1), 5.30–5.16 (m, 2), 4.57 (d, J=5.4, 2), 4.46 (t, J=6.0, 1), 3.74–3.65 (m, 1), 3.71 (s, 3), 3.42–3.32 (m, 1), 2.48–2.41 (m, 2), 2.02–1.35 (m, 7); MS (ESPOS): 306.5 [M+Na]$^+$.

4-(2-[1,3]Dithiolan-2-yl-ethyl)-piperidine-1,2-dicarboxylic acid 1-allyl ester 2-methyl ester. To a mixture of 11e (R9'=3-oxopropyl, P=Alloc) (248 mg, 0.87 mmol, 1 equiv) and 1,2-ethanedithiol (0.147 mL, 1.75 mmol, 2 equiv) under nitrogen was added borontrifluoride-acetic acid complex (0.122 mL, 0.87 mmol, 1 equiv). The mixture was stirred vigorously for 1 hr. The mixture was diluted with hexane and washed with sat. sodium bicarbonate (3×) and brine (1×). The organic layer was dried and concentrated. The residue was purified by chromatography to furnish 11e (R9'=2-[1,3]dithiolan-2-yl-ethyl, P=Alloc) (144 mg, 46%) as an oil: MS (ESPOS): 382.5 [M+Na]$^+$.

4-(2-[1,3]Dithiolan-2-yl-ethyl)-piperidine-1,2-dicarboxylic acid 1-allyl ester 11f (R9'=(2-[1,3]dithiolan-2-yl-ethyl), P=Alloc). To a mixture of 11e (R9'=2-[1,3]dithiolan-2-yl-ethyl, P=Alloc) (144 mg, 0.40 mmol, 1 equiv) in THF (3 mL) and water (1 mL) was added lithium hydroxide monohydrate (67 mg, 1.6 mmol, 4 equiv). The mixture was stirred at rt overnight. THF was removed under vacuum. The aqueous layer was taken up in ethyl acetate, partitioned with 10% citric acid. The organic layer was washed with water (1×), brine (1×), dried and concentrated to give 11f (R9'=(2-[1,3]dithiolan-2-yl-ethyl), P=Alloc) (127 mg, 92%) as a syrup: $^1$H NMR (300 MHz, CDCl$_3$) δ 5.96–5.83 (m, 1), 5.30–5.17 (m, 2), 4.59 (d, J=5.4, 2), 4.48 (t, J=6.4, 1), 4.41 (t, J=6.9, 1), 3.75–3.64 (m, 1), 3.44–3.33 (m, 1), 3.25–3.12 (m, 4), 2.05–1.35 (m, 9). MS (ESPOS): 346.5 [M+H]$^+$.

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide. To a mixture of 2b (R2'=H) (95 mg, 0.33 mmol, 1 equiv) in dry DMF (0.8 mL) at 0° C. was added triethylamine (0.23 mL, 1.65 mmol, 5 equiv), followed by the addition of Bis(trimethylsilyl)trifluoroacetamide (0.13 mL, 0.49 mmol, 1.5 equiv). The reaction mixture was stirred at 0° C. for 10 minutes, and then was stirred at rt for 50 minutes. To the reaction mixture were added acid 11f (R9'=2-[1,3]dithiolan-2-yl-ethyl, P=Alloc) (115 mg, 0.33 mmol, 1.0 equiv) and HATU (158 mg, 0.42 mmol, 1.3 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and concentrated. The residue was purified by chromatography to give the Alloc protected lincosamide analog (133 mg, 70%) as a syrup: MS (ESPOS): 579.8 [M+H]$^+$.

To a solution of the above Alloc protected lincosamide (103 mg, 0.18 mmol, 1 equiv) in THF (2.3 mL) were added dimedone (0.25 g, 1.78 mmol, 10 equiv) and tetrakis(triphenylphosphine) palladium (41.1 mg, 0.036 mmol, 0.2 equiv). The mixture was stirred at rt overnight. The solvent was removed under vacuum and the residue was purified by chromatography to furnish the title compound of example 27 (34 mg, 49%) as a slightly yellow solid: $^1$H NMR (300 MHz, CD$_3$OD) δ 5.23 (d, J=5.7, 1), 4.45 (t, J=6.9, 1), 4.18–4.01 (m, 3), 3.81–3.77 (m, 1), 3.56–3.47 (m, 2), 3.25–3.07 (m, 5), 2.66–2.56 (m, 1), 2.18–2.13 (m, 1), 2.10 (s, 3), 1.94–1.63 (m, 4), 1.55–1.35 (m, 3), 1.12–0.98 (m, 2), 0.95–0.88 (m, 6); MS (ESPOS): 495.6 [M+H]$^+$.

Example 27

There is no Example 27.

Example 28

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide

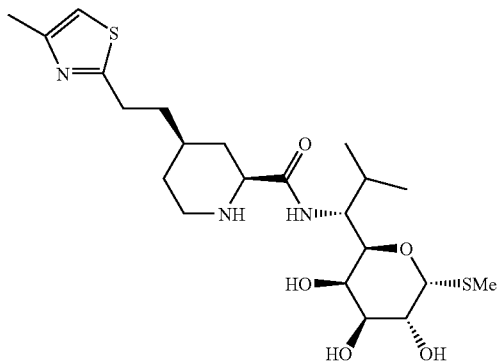

4-[2-(4-Methyl-thiazol-2-yl)-ethyl]-piperidine-1,2-dicarboxylic acid 1-allyl ester 11f (R9'=4-Methyl-thiazol-2-yl, P=Alloc). This intermediate was prepared using the reaction sequence described in general method P, Scheme 11, from intermediate 11b, using 4-tert-Butoxycarbonylethyne (Aldrich) as the alkyne. The 4-methyl thiazole moity was installed by elaboration of protected dicarboxylic acid 11e (R9'=(propionic acid tert-butyl ester, P=Alloc) by methods well known to persons skilled in the art. Ester deprotection as performed in general method P provided the desired carboxylate intermediate 11f (R9'=4-Methyl-thiazol-2-yl, P=Alloc).

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide. Coupling of 2b (R2'=H) to protected amino acid 11f (R9'=4-Methyl-thiazol-2-yl, P=Alloc) and deprotection were performed by the procedure described in example 26 to furnish the title lincosamide of example 28: (300 MHz, CD$_3$OD) δ 6.80 (s, 1) 5.07 (d, J=5.5, 1), 4.43 (dd, J=3.3, 9.9 1), 3.91–3.86 (m, 2), 3.60 (m, 1), 3.50–3.45 (m, 1), 3.30 (d, J=3.3, 10.4, 1), 2.89–2.82 (m, 2), 2.76–2.67 (m, 1), 2.19 (s, 3), 1.96 (s, 3), 1.77–1.73 (m, 1), 1.61–1.57 (m, 3), 1.22–1.09 (m, 2), 0.72 (d, J=6.9, 6); MS (ESPOS): 488.4 [M+H]$^+$.

Example 29

4-(3-Methoxyiminoprop-1-yl)-piperidine-2-carboxylic acid [2-methyl-1-(3,4,5-trihydroxy-6-methylsulfanyl-tetrahydro-pyran-2-yl)-propyl]-amide

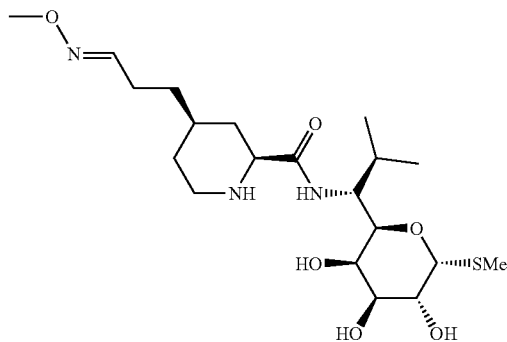

11e (R9'=3-methoxyimino-propyl, P=Alloc). To a solution of 11e (R9'=3-oxopropyl, P=Alloc) prepared in example 26 (129 mg, 0.45 mmol) in ethanol (1.3 mL) were added methoxylamine hydrochloride and pyridine. The reaction mixture was refluxed for 2 hr. The solvent was removed under vacuum. The residue was taken up into ethyl acetate, washed with 10% citric acid and brine, dried and concentrated to provide 11e (R9'=3-methoxyimino-propyl, P=Alloc) (129 mg, 91%) as a clear oil: MS (ESPOS): 334.5 [M+Na]$^+$.

4-(3-Methoxyimino-propyl)-piperidine-1,2-dicarboxylic acid 1-allyl ester 11f (R9'=(3-methoxyimino-propyl), P=Alloc). To a mixture of ester 11e (R9'=(3-methoxyimino-propyl), P=Alloc) (129 mg, 0.41 mmol, 1 equiv) in THF (1.5 mL) and water (0.5 mL) was added lithium hydroxide monohydrate (69 mg, 1.6 mmol, 4 equiv). The mixture was stirred at rt overnight. THF was removed under vacuum. The aqueous layer was taken up in ethyl acetate, partitioned with 10% citric acid. The organic layer was washed with water (1×), brine (1×), dried and concentrated to give 11f (R9'=3-methoxyimino-propyl, P=Alloc) (114 mg, 93%) as a clear oil: $^1$H NMR (300 MHz, CDCl$_3$) δ 7.31 (t, J=6.2, 0.6H), 6.60 (t, J=5.4, 0.4H), 5.96–5.82 (m, 1), 5.30–5.16 (m, 2), 4.58 (d, J=5.7, 2), 4.83 (t, J=6.5, 1), 3.83 (d, J=0.3, 1.2H), 3.78 (d, J=0.6, 1.8H), 3.77–3.62 (m, 1), 3.42–3.30 (m, 1), 2.38–2.26 (m, 1), 2.23–2.14 (m, 1), 2.08–1.85 (m, 2), 1.82–1.62 (m, 2), 1.53–1.35 (m, 3); MS (ESPOS): 321.2 [M+Na]$^+$.

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide. To a mixture of 2b (R2'=H) (109.8 mg, 0.38 mmol, 1 equiv) in dry DMF (0.9 mL) at 0° C. was added triethylamine (0.26 mL, 1.91 mmol, 5 equiv), followed by the addition of bis(trimethylsilyl)trifluoroacetamide (0.15 mL, 0.57 mmol, 1.5 equiv). The reaction mixture was stirred at 0° C. for 10 minutes, and then was stirred at rt for 50 minutes. To the reaction mixture were added the protected amino acid 11f (R9'=3-methoxyimino-propyl, P=Alloc) (113.6 mg, 0.38 mmol, 1.0 equiv) and HATU (182 mg, 0.48 mmol, 1.26 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and concentrated. The residue was purified by chromatography to furnish the Alloc protected lincosamide product (107 mg, 53%): MS (ESPOS): 532.4 [M+H]$^+$.

To a mixture of the above Alloc protected lincosamide (107 mg, 0.20 mmol, 1 equiv) in THF (2.6 mL) were added dimedone (282 mg, 2.01 mmol, 10 equiv) and tetrakis(triphenylphosphine)palladium (46.5 mg, 0.04 mmol, 0.2 equiv). The mixture was stirred at rt overnight. The solvent was removed under vacuum and the residue was purified by chromatography to give the title compound of example 29 (28 mg, 31%) as a white solid: $^1$H NMR (300 MHz, CD$_3$OD) δ 7.36 (t, J=6.2, 0.68H), 6.66 (t, J=5.4, 0.32H), 5.23 (d, J=5.7, 1), 4.16 (dd, J=3.2, 10.1, 1), 4.10–4.01 (m, 2), 3.81 (s, 1), 3.79 (d, J=3.3, 1), 3.74 (s, 2), 3.50 (dd, J=3.3, 9.9, 1), 3.30–3.22 (m, 1), 3.18–3.10 (m, 1), 2.67–2.55 (m, 1), 2.40–2.31 (m, 1), 2.25–2.12 (m, 2), 2.10 (s, 3), 1.97–1.88 (m, 1), 1.76–1.65 (m, 1), 1.59–1.38 (m, 3), 1.14–1.01 (m, 2), 0.90 (d, J=6.9, 6); MS (ESPOS): 448.4 [M+H]$^+$.

Example 30

4-(3-Ethoxyimino-prop-1-yl)-piperidine-2-carboxylic acid [2-methyl-1-(3,4,5-trihydroxy-6-methylsulfanyl-tetrahydro-pyran-2-yl)-propyl]-amide

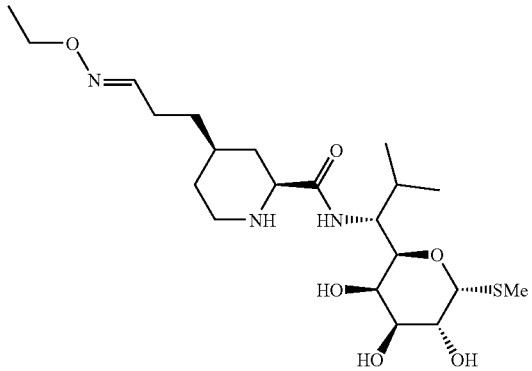

Synthesis of the title compound in example 30 was performed as described in example 29 from intermediate 11e (R9'=3-oxopropyl, P=Alloc) substituting ethoxylamine hydrochloride in the imine forming step: MS (ESPOS): 462.4 [M+H]$^+$.

Example 31

4-[2-(5-Ethyl-isoxazol-3-yl)-ethyl]-piperidine-2-carboxylic acid [2-methyl-1-(3,4,5-trihydroxy-6-methylsulfanyl-tetrahydro-pyran-2-yl)-propyl]-amide

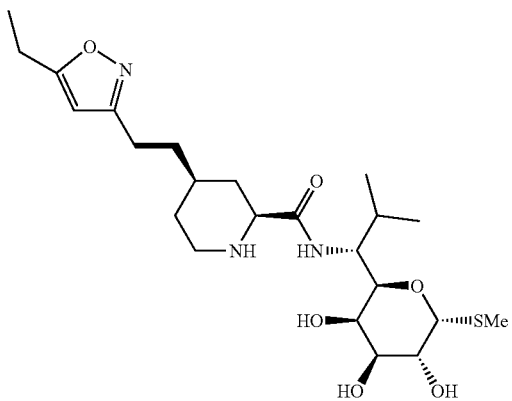

Synthesis of the title compound in example 31 was performed as in example 29 from intermediate 11e (R9'=3-oxopropyl, P=Alloc) substituting hydroxylamine hydrochloride in the imine forming step to furnish 11e (R9'=3-hydroxyimino-propyl, P=Alloc). The isoxazole heterocycle was installed by elaboration of intermediate 11e (R9'=3-hydroxyimino-propyl, P=Alloc) by cycloaddition of 1-butyne in the presence of N-chlorosuccinimide and TEA. Coupling and deprotection were performed as described in example 29: MS (ESPOS): 486.3 [M+H]$^+$.

Example 32

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide 4-Position Stereoisomer I and 4-position Stereoisomer II

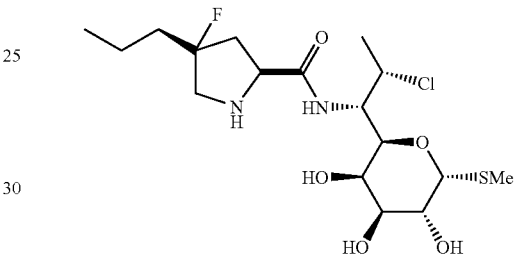

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide (position 4 stereoisomer I high Rf and position 4 stereoisomer II low Rf). To a solution of Boc protected amino acid 12d (P=Boc, R9=propyl, m=1) prepared in general method Q, synthetic sequence depicted in scheme 12 (310 mg, 1.15 mmol) in DMF (3 mL) at 0° C., 7-Cl MTL 6b (R$^2$=H, R$^3$=Cl) (306 mg, 1.15 mmol) HBTU (469 mg, 1.3 mmol) and DIEA (290 µL, 2.3 mmol) was added, left stirred at room temperature overnight. DMF was removed by rotary evaporation under high vacuum. The residue obtained was purified on silica gel column chromatography (3% MeOH in DCM) to obtain the desired Boc protected 4-F lincosamide (451 mg, 75%) a light brown oil: $^1$H NMR (300 MHz, CD$_3$OD) δ 5.29 (d, J=5.7, 1), 4.50 (m, 3), 4.10 (m, 1), 3.60 (m, 3), 2.51 (m, 1), 2.11(m, 4), 1.70 (m, 2), 1.50 (m, 9), 0.96 (t, J=7.2, 3); MS (ESPOS): 529 [M+H]+.

To a solution of the above Boc protected 4-fluoro lincosamide (451 mg, 0.85 mmol) in DCE (6 mL), triethylsilane (0.16 mL), TFA (2 mL) and water (0.16 mL) was added and stirred at room temperature for 1.5 hr. The reaction solvent was removed in vacuo. The resulting residue was purified by silica gel column chromatography using 10% MeOH in DCM as eluent to obtain the title compound for example 32 4 stereoisomer I (high TLC Rf) (165 mg, 45%): $^1$H NMR (300 MHz, CD$_3$OD) δ 5.29 (d, J=5.7, 1), 4.59 (m, 2), 4.32 (d, J=9.9, 1), 4.07 (dd, J=5.7, 10.2, 1), 3.81 (d, J=3.3, 1), 3.59 (m, 3), 3.01 (d, J=3.0, 1), 2.83 (m, 1), 2.14 (m, 4), 1.86 (m, 2), 1.50 (m, 5), 0.99 (t, J=7.2, 3); MS (ESPOS) 429 [M+H]+; and 4 stereoisomer II (low TLC Rf) (165 mg, 45%); $^1$H NMR (300 MHz, CD$_3$OD) δ 5.29 (d, J=5.7, 1), 4.59 (m, 3), 4.29 (d, J=10.2, 1), 4.08 (dd, J=5.7, 10.2, 1), 3.85 (d, J=3.3, 1), 3.59 (m, 4), 2.60 (m, 1), 2.11 (m, 3), 1.88 (m, 2), 1.50 (m, 5), 0.99 (t, J=7.2, 3); MS (ESPOS); 429 [M+H]+.

Example 33

4-Fluoro-4-propyl-piperidine-2-carboxylic acid [2-chloro-1-(3,4,5-trihydroxy-6-methylsulfanyl-tetrahydro-pyran-2-yl)-propyl]-amide

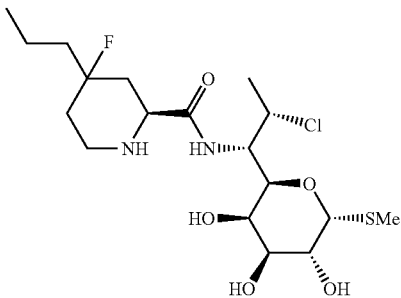

4-Fluoro-4-propyl-piperidine-1,2-dicarboxylic acid 1-tert-butyl ester, 12d (P=Boc, $R^9$=n-propyl, m=2). The synthesis of Boc protected 4-fluoro amino acid 12d from the starting material (2S)-4-oxo-piperidine-1,2-dicarboxylic acid 1-tert-butyl ester uses general method Q, depicted in scheme 12. The preparation of the starting material (2S)-4-oxo-piperidine-1,2-dicarboxylic acid 1-tert-butyl ester is described by Bousquet, Y.; Anderson, P. C.; Bogri, T.; Duceppe J.; Grenier, L.; Guse, I.; *Tetrahedron*, 1997, 53 15671–15680.

A rapidly stirred solution of 4-oxo-piperidine-1,2-dicarboxylic acid 1-tert-butyl ester 12a (m=2, P=H, $P_2$=Boc) (16.0 g, 0.066 mol) (prepared by the method described by Bousquet et al. *Tetrahedron*, 1997, 53, 15671) in DMF (200 mL) was treated with solid cesium carbonate (10.7 g, 0.033 mol) and methyl iodide (4.5 mL, 0.072 mol). The reaction mixture was stirred 5 h, diluted with EtOAc and extracted with saturated aq. sodium bicarbonate, 10% aq. citric acid and brine, the organic layer was separated and dried over sodium sulfate, filtered and evaporated to dryness. The product obtained on removal of solvent was azeotropically dried by evaporation from dry benzene to afford 14.8 g (98%) of the desired product 4-Oxo-piperidine-1,2-dicarboxylic acid 1-tert-butyl ester 2-methyl ester 12a (m=2, P=Me, $P_2$=Boc) as an oil: TLC $R_f$ 0.53 (Hexanes/EtOAc, 1:1); $^1$H NMR (300 MHz, CDCl$_3$) δ 5.33 (broad m, 0.5) rotamer, 5.06 (broad m, 0.5) rotamer, 4.31–4.19 (m, 1), 3.95 (s, 3), 3.95–3.70 (m, 1), 3.16–2.97 (m, 2), 2.71 (m, 2), 1.68 (broad s, 9).

A 0° C. stirred solution of 4-oxo-piperidine-1,2-dicarboxylic acid 1-tert-butyl ester 2-methyl ester 12a (m=2, P=Me, $P_2$=Boc) (5.17 g, 0.02 mol) in DCM (60 mL) was treated with tetraallyltin (Aldrich) (5.3 mL, 0.022 mol) followed by dropwise addition of BF$_3$.OEt$_2$ (2.5 mL, 0.02 mol). The reaction mixture was stirred 1 h, then aq. 1M potassium fluoride (38.0 mL) and celite (5 g) was added and the reaction mixture was stirred 3 h. The reaction mixture was filtered and concentrated to dryness, the residue was dissolved in DCM and washed with water and brine, dried over MgSO$_4$ and evaporated to dryness. The residue obtained was purified by silica gel column chromatography (DCM 100% to DCM:acetone 9:1) to afford 3.85 g (64%) of the desired product 4-allyl-4-hydroxy-piperidine-1,2-dicarboxylicacid 1-tert-butyl ester 2-methyl ester 12b (m=2, P=Me, $P_2$=Boc, $R^{9'}$=allyl) as an oil.

$^1$H NMR (300 MHz, CDCl$_3$) δ 6.11–5.97 (m, 1), 5.42–5.32 (m, 2), 5.06 (broad d, J=6.0, 0.5) rotamer, 4.87 (broad d, J=6.0, 0.5) rotamer, 4.18–4.03 (m, 1), 3.93 (s, 3), 2.48–2.37 (m, 2), 1.98–1.43 (m, 11); MS (ESPOS): 322.0 [M+Na]$^+$.

A stirred suspension of 12b (m=2, P=Me, $P_2$=Boc, $R^{9'}$=allyl) (3.80 mL, 1.27 mmol) and 10% Pd/C (degusa wet form 50% w/w) (1.35 g, 1.3 mmol) in MeOH (80 mL) was stirred 6 h under 1 atm hydrogen. The reaction mixture was filtered through celite and evaporated to dryness and dried azeotropically by evaporation from toluene the residue obtained (3.15 g) was used in the next step without further purification.

To a stirred –78° C. solution of DAST (1.7 mL, 1.3 mmol) in DCM (50 mL) was added 4-Hydroxy-4-propyl-piperidine-1,2-dicarboxylic acid 1-tert-butyl ester 2-methyl ester in DCM (30 mL). The reaction mixture was then stirred at for 1 h, then allowed to warm to –40° C. for 5 h. Additional DAST (0.4 mL) was added and the reaction mixture stirred an additional 2 h, saturated aq. K$_2$CO$_3$ (20 mL), and water (60 mL) was added followed by diethyl ether (500 mL) the organic layer was separated, washed with brine dried over sodium sulfate and evaporated to dryness. The resulting crude fluorinated product was purified by silica gel column chromatography (hexanes-EtOAc 9:1). The residue obtained by chromatographic purification was dissolved in dioxane (65 mL) and water (26 mL) cooled to 0° C. and treated with OsO$_4$ (0.65 mL, 4% aq. solution) and 30% H$_2$O$_2$ (10 mL). The reaction mixture was stirred overnight concentrated to dryness, the residue was dissolved in DCM and the organic layer washed with water (100 mL) 25% aq. Na$_2$SO$_3$ (2×100 mL) and brine (100 mL), dried over Na$_2$SO$_4$ and evaporated to dryness. The residue obtained was purified by silica gel column chromatography (hexanes-EtOAc 9:1) to afford (1.08 g, 34%) of the desired product 4-fluoro-4-propyl-piperidine-1,2-dicarboxylic acid 1-tert-butyl ester 2-methyl ester 12c (m=2, P=Me, $P_2$=Boc, $R^9$=n-propyl) as an oil.

$^1$H NMR (300 MHz, CDCl$_3$) δ 4.59 (dd, J=6.0, 6.0, 1), 3.82–3.69 (m, 1), 3.74 (s, 3), 3.28 (m, 1), 3.29–2.04 (m, 2), 1.91–1.71 (m, 3), 1.60–1.31 (m, 6), 1.45 (s, 9), 0.92 (t, J=7.1, 3); MS (ESPOS): 204.1 (M+H–Boc), 326.3 [M+Na]$^+$.

The synthesis of the title compound in example 33 From 12d (P=Boc, $R^9$=n-propyl, m=2) is readily accomplished using the coupling and deprotection conditions from example 32.

MS (ESPOS): 443.1 [M+M]$^+$; HPLC: C$_{18}$ 3.5 μm, 4.6×30 mm Column; gradient eluent 2%–98% MeCN over 10 min; 1.5 mL/min): R$_t$=3.738 min.

Example 34

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide

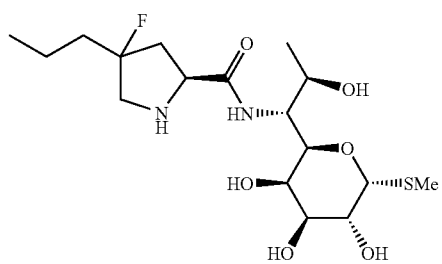

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide. A stirred suspension of 12d (P=Boc, $R^9$=$C_3H_7$, m=1) (164 mg, 0.57 mmol) prepared by general method Q, depicted in scheme 12, was suspended in dry acetonitrile (4 mL). Triethylamine (332 μL, 3.02 mmol) was added and the reaction mixture was cooled to 0° C. Isobutyl chloroformate (78 μL, 0.57 mmol) was added and after 10 min the reaction was allowed to warm to 4° C. After 1.5 h, a solution of MTL 1a (151 mg, 0.57 mmol) in 1:1 acetone:water (4 mL) was added and the reaction mixture was stirred for 10 h at rt. The reaction mixture was evaporated to dryness and chromatographed on silica (95:5 dichloromethane/MeOH to 95:8 dichloromethane/MeOH) to provide the product as a colorless oil (137 mg, 45%): TLC $R_f$=0.32 (9:1 dichloromethane/MeOH); MS (ESPOS): 411 [M+H−Boc]+, 511 [M+H]+.

To a solution of the above Boc protected lincosamide (125 mg) in DCM (2.0 mL) was added a solution of DCE (10.0 mL), trifluoroacetic acid (5 mL) methyl sulfide (0.3 mL), and water (0.3 mL). The reaction mixture was stirred at rt for 40 min then diluted with DCE (25.0 mL). The solvent was removed under vacuum and co-evaporated with DCE twice. The residue was purified by chromatography on fluorosil (20% MeOH 0.25 M $NH_3$/DCM) to provide the title compounds as a colorless solid (30.0 mg, 30%): MS (ESPOS): 411.6 [M+H]+.

Example 35

4-Fluoro-4-butyl-pyrrolidine-2-carboxylic acid [2-chloro-1-(3,4,5-trihydroxy-6-methylsulfanyl-tetrahydro-pyran-2-yl)-propyl]-amide 4-Position Stereoisomer I and 4-Position Stereoisomer II

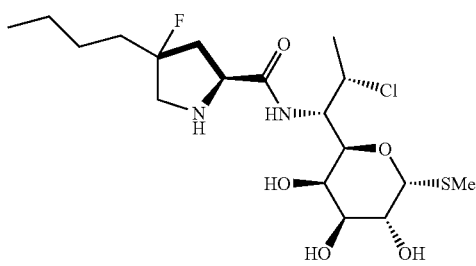

4-Hydroxy-4-butylproline methylester 12b (P=Boc, m=1, $R^9$=n-butyl). To a stirred solution n-butyllithium (165 mg, 2.6 mmol) in THF (5 mL) at −78° C. was added 12a (P=Boc, $P_2$=Me, m=1) (570 mg, 2.3 mmol) in THF (5 mL). The reaction mixture was stirred at −78° C. for 2 hr and then at −40° C. for an additional 1 hr. EtOAc (20 mL) was added, followed by $NH_4Cl$ (5 mL, 10%) and water (10 mL). Organic layer was separated, dried over sodium sulflate and evaporated to dryness. The residue obtained was purified by silica gel column chromatography using 50% EtOAc in hexanes as eluent to provide 4-hydroxy-4-butylproline methylester 12b (P=Boc, m=1, R9=n-butyl) as a colorless oil (0.52 g, 73%): $^1$H NMR (300 MHz, $CDCl_3$) δ 4.33 (m, 1), 3.76 (d, J=4.8, 3), 3.62 (m, 2), 3.28 (m, 1), 2.13 (m, 1), 2.02 (m, 1), 1.57 (m, 2), 1.29 (m, 12), 0.88 (m, 3); MS (ESPOS): 324 [M+Na]+.

4-Fluoro-4-butylproline methyl ester 12c (P=Boc, m=1, $R^9$=n-butyl). To a stirred solution of DAST (0.55 g, 3.4 mmol) in DCM (5 mL) at −78° C., 4-hydroxyproline 12b (P=Boc, m=1, R9=n-butyl) (520 mg, 1.7 mmol) in dry DCM (5 mL) was added slowly. The mixture was stirred at −78° C. for 1 h and then at −10° C. for an additional 1 h. DCM (50 mL) was added, followed by aq. $NH_4Cl$ (10%, 30 mL). The organic layer was separated, dried over sodium sulfate and evaporated to dryness. The residue obtained was purified by column chromatography using 5% EtOAc in hexanes to obtain 4-fluoro-4-butylproline methyl ester 12c (P=Boc, m=1, R9=n-butyl) (270 mg, 52%) as a colorless oil: $^1$H NMR (300 MHz, $CDCl_3$) δ 4.41 (m, 2), 3.83 (m, 1), 3.71 (s, 3), 3.45 (dd, J=12.3, 32.7, 2), 2.48 (m, 1), 1.73 (m, 2), 1.40 (m, 12), 0.89 (m, 3); MS (ESPOS): 326 [M+Na]$^+$.

4-Fluoro-4-butylproline 12d (P=Boc, m=1, R9=n-butyl). To a solution of 12c (0.27 g, 0.89 mmol) in THF (10 mL) and water (3 mL) was added lithium hydroxide monohydrate (45 mg, 1.06 mmol). The reaction mixture was stirred at room temperature overnight. THF was removed and the residue was purified by column chromatography using 10% MeOH in DCM as eluent to obtain 4-Fluoro-4-butylproline 12d (P=Boc, m=1, R9=n-butyl) (0.26 g, 100%) as a colorless oil: $^1$H NMR (300 MHz, $CD_3OD$) δ 4.30 (m, 1), 3.72 (m, 1), 3.49 (m, 1), 3.39 (m, 1), 2.58 (m, 1), 2.02 (m, 2), 1.72 (m, 13), 0.93 (t, J=6.6, 3); MS (ESNEG): 288 [M−1]$^-$.

4-Fluoro-4-butyl-pyrrolidine-2-carboxylic acid [2-chloro-1-(3,4,5-trihydroxy-6-methylsulfanyl-tetrahydro-pyran-2-yl)-propyl]-amide: 4 stereoisomer I and 4 stereoisomer II. To a solution of 12d (P=Boc, m=1, R9=n-butyl) (125 mg, 0.43 mmol) in DMF (3 mL) at 0° C., 7-Cl MTL, 6b (R2=H, R3=Cl)(117 mg, 0.43 mmol), HBTU (180 mg, 0.47 mmol) and DIEA (111 mg, 0.86 mmol) was added and left stirred at room temperature for overnight. Solvent was removed and the residue was purified on silica gel column chromatography using 2% MeOH in DCM to obtain the desired Boc protected lincosamide intermediate (170 mg, 72%) as a light brown liquid: $^1$H NMR (300 MHz, $CD_3OD$) δ 5.29 (d, J=5.4, 1), 4.57 (m, 3), 4.39 (m, 1), 4.03 (m, 2), 3.74 (m, 3), 3.25 (m, 1), 2.51 (m, 1), 2.12(m, 3), 1.85 (m, 3), 1.46 (s, 9), 1.36 (m, 6), 0.93 (t, J=6.6, 3); MS (ESPOS): 543 [M+H]$^+$.

To a solution of the above Boc protected lincosamide (170 mg, 0.31 mmol) in DCE (6 mL) was added triethylsilane (0.16 mL), TFA (2 mL) and water (0.16 mL). The reaction mixture was stirred at room temperature for 1 hr. Solvent was removed and the residue was purified on silica gel column chromatography using 10% MeOH in DCM to obtain 4-fluoro-4-butyl-pyrrolidine-2-carboxylic acid [2-chloro-1-(3,4,5-trihydroxy-6-methylsulfanyl-tetrahydro-pyran-2-yl)-propyl]-amide, 4 stereoisomer I (14 mg, 10%); $^1$H NMR (300 MHz, $CD_3OD$) δ 5.30 (d, J=6.0, 1), 4.54 (m, 3), 4.29 (d, J=10.2, 1), 4.09 (dd, J=5.6, 10.2, 1), 3.80 (d, J=3.0, 1), 3.56 (m, 3), 2.70 (m, 1), 2.14 (m, 4), 1.87 (m, 2), 1.43 (m, 7), 0.94 (t, J=7.2, 3); MS (ESPOS): 443 [M+H].
4-Fluoro-4-butyl-pyrrolidine-2-carboxylic acid [2-chloro-1-(3,4,5-trihydroxy-6-methylsulfanyl-tetrahydro-pyran-2-yl)-propyl]-amide, 4 stereoisomer II (3 mg, 2%); $^1$H NMR (300 MHz, $CD_3OD$) δ 5.30 (d, J=6.0, 1), 4.54 (m, 3), 4.29 (d, J=10.2, 1), 4.09 (dd, J=5.6, 10.2, 1), 3.80 (d, J=3.0, 1), 3.56 (m, 3), 2.70 (m, 1), 2.14 (m, 4), 1.87 (m, 2), 1.43 (m, 7), 0.94 (t, J=7.2, 3); (ESPOS): 443 [M+H]$^+$.

Example 36

4-Fluoro-4-ethyl-piperidine-2-carboxylic acid [2-chloro-1-(3,4,5-trihydroxy-6-methylsulfanyl-tetrahydro-pyran-2-yl)-propyl]-amide

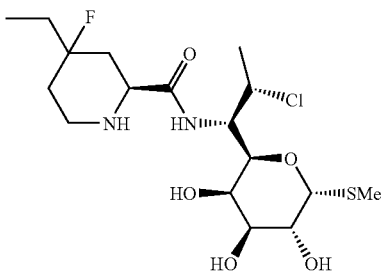

4-Fluoro-4-ethyl-piperidine-1,2-dicarboxylic acid 1-tert-butyl ester, 12d (P=Boc, m=2, $R^9$=n-ethy). The synthesis of boc-protected 4-fluoro amino acid 12d from the starting material (2S)-4-oxo-piperidine-1,2-dicarboxylic acid 1-tert-butyl ester uses general method Q, depicted in scheme 12, utilizing trimethylsilylacetylene anion as a two carbon synthon in the 4-ketone alkylation step. Preparation of the starting material, 4-oxo-piperidine-1,2-dicarboxylic acid 1-tert-butyl ester is described by Bousquet, Y.; Anderson, P. C.; Bogri, T.; Duceppe J.; Grenier, L.; Guse, I.; *Tetrahedron*, 1997, 53 15671–15680. The synthesis of the title compound in example 36 from 12d (P=Boc, m=2, $R^9$=ethyl) is readily accomplished using the coupling and deprotection conditions from example 34. MS (ESPOS): 429.1 [M+H]⁺.

Example 37

4-Propylidene-piperidine-2-carboxylic acid [2-methyl-1-(3,4,5-trihydroxy-6-methylsulfanyl-tetrahydro-pyran-2-yl)-propyl]-amide

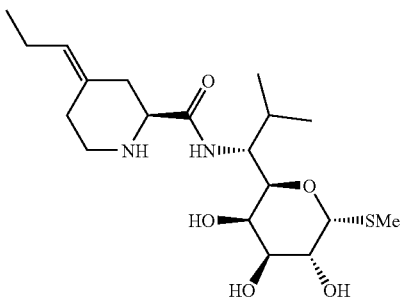

4-Oxo-piperidine-1,2-dicarboxylic acid 1-tert-butyl ester 2-methyl ester. To (2S)-4-oxo-piperidine-1,2-dicarboxylic acid 1-tert-butyl ester (0.52 g, 2.15 mmol) in methanol (10 mL), 2 M solution of TMS-diazomethane (2 mL, 4 mmol) in hexane was added and stirred at room temperature for 15 min. The reaction solvent was removed and the methyl ester product obtained (4-oxo-piperidine-1,2-dicarboxylic acid 1-tert-butyl ester 2-methyl ester) was used as such for the next reaction (0.55 g, 100%): MS (ESPOS): 258 [M+H]⁺; ¹H NMR (300 MHz, CD₃OD) δ 5.13, 4.86 (bs, 1), 4.02–4.11 (m, 1), 3.73 (s, 3), 3.67–3.72 (m, 1), 2.78 (d, J=4.2 Hz, 2), 2.51 (bs, 2), 1.46 (bs, 9).

4-Propylidene-piperidine-1,2-dicarboxylic acid 1-tert-butyl ester 2-methyl ester. Propyltriphenylphosphonium bromide (1.24 g, 3.22 mmol) in THF (10 mL) was added to hexane washed sodium hydride (123 mg, 3.22 mmol), in THF (10 mL) and stirred at room temperature for 3 h. Methyl ester 12a (P=Boc, m=2, P2=Me) (0.55 g, 2.15 mmol) in THF (5 mL) was added to the above reaction mixture slowly and then allowed to stir for additional 2 h. It was then poured into water and extracted with ethyl acetate (30 mL). The organic phase was dried with magnesium sulfate, filtered and evaporated to dryness, the resulting residue was chromatographed using 20% EtOAc in hexanes to provide the product 4-propylidene-piperidine-1,2-dicarboxylic acid 1-tert-butyl ester 2-methyl ester. (0.100 g, 16%): MS (ESPOS): 284 [M+H]+; ¹H NMR (300 MHz, CD₃OD) δ 5.18 (m, m), 4.60–4.93 (m, 1), 3.91 (m, 1), 3.67 (s, 3), 2.94–3.04 (m, 2), 2.40–2.48 (m, 2), 1.99–2.06 (m, 1), 1.85–1.97 (m, 2), 1.38 (bs, 9), 0.85 (t, J=5 Hz, 3).

4-Propylidene-piperidine-1,2-dicarboxylic acid 1-tert-butyl ester. To the 4-propylidene-piperidine-1,2-dicarboxylic acid 1-tert-butyl ester 2-methyl ester. (0.100 g, 0.353 mmol) in THF (10 mL) was added lithium hydroxide (0.50 g, 11.6 mmol) in water (2 mL) and the reaction mixture stirred at room temperature for 16 h. It was then poured into water and extracted with ether (20 mL). The water layer was then acidified with 10% HCl (5 mL) and extracted with ethyl acetate (30 mL). The product carboxylic acid 4-propylidene-piperidine-1,2-dicarboxylic acid 1-tert-butyl ester obtained after drying and removal of solvent was taken as such for the next step. MS (ESNEG): 268 [M–1]–; ¹H NMR (300 MHz, CD₃OD) δ 5.18 (m, m), 4.60–4.93 (m, 1), 3.91 (m, 1), 2.94–3.04 (m, 2), 2.40–2.48 (m, 2), 1.99–2.06 (m, 1), 1.85–1.97 (m, 2), 1.38 (bs, 9), 0.85 (t, J=5 Hz, 3).

4-Propylidene-piperidine-2-carboxylic acid [2-methyl-1-(3,4,5-trihydroxy-6-methylsulfanyl-tetrahydro-pyran-2-yl)-propyl]-amide. To a stirred solution of 2b (R2'=H) (32 mg, 0.12 mmol), DIEA (0.2 mL, 1.20 mmol), 4-propylidene-piperidine-1,2-dicarboxylic acid 1-tert-butyl ester (37 mg, 0.14 mmol) in DMF (5 mL) was added HBTU (57 mg, 0.16 mmol) and the mixture was stirred at room temperature for 2 h. Most of the DMF was removed under high vacuum, and the crude material was taken up in ethyl acetate (50 mL) and washed with saturated sodium bicarbonate (10 mL). Solvent was removed under vacuum, and the product was purified by silica gel column chromatography using ethyl acetate as eluent to obtain the desired Boc protected lincosamide (50 mg, 83%): MS (ESPOS): 503 (M–1); ¹H NMR (300 MHz, CD₃OD) δ 5.19–5.27 (m, 2), 4.10–4.26 (m, 2), 3.90–4.05 (m, 2), 3.83–3.90 (m, 2), 3.49–3.88 (m, 2), 3.06 (m, 2), 2.57 (m, 2), 1.90 (s, 3), 1.47 (bs, 9), 0.88–0.95 (m, 9).

To the above Boc protected lincosamide (50 mg, 0.10 mmol) in dichloroethane (6 mL), triethylsilane (0.15 mL) was added, followed by 93% aq. trifluoroacetic acid (2.15 mL). After stirring at rt for 1 hr, the solvent was removed at 45° C. under reduced pressure. The crude product obtained was purified by silica gel column chromatography using 10% MeOH in DCM as eluent to the title compound (5 mg, 12%): ¹H NMR (300 MHz, CD₃OD) δ 5.40 (m, 1), 5.24 (d, J=3.8 Hz, 1), 4.16–4.20 (m, 1), 4.04–4.09 (m, 2), 3.81 (t, J=2.2 Hz, 1), 3.49–3.55 (m, 2), 2.50–2.92 (m, 3), 2.00–2.25 (m, 6), 2.10 (s, 3), 0.89–0.98 (m, 9). MS (ESPOS): 403 [M+H]+.

Example 38

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide

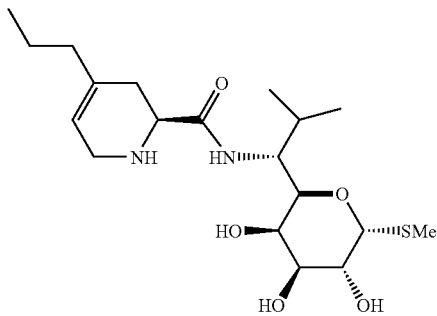

Coupling of Boc-protected Amino Acid to 2b (R$^{2'}$=H).

To a solution of Boc amino acid 21k (R$^9$=n-propyl, R$^{9b}$=H, m=1) prepared by general method S depicted in scheme 21 (69 mg, 0.26 mmol, 1 equiv), 2b (R$^{2'}$=H) (74 mg, 0.26 mmol, 1 equiv) and HBTU (107 mg, 0.28, 1.1 equiv) in DMF (2.5 mL) at 23° C. was added N,N-diisopropylethylamine (89 μL, 0.51 mmol, 2 equiv). The reaction was stirred at 23° C. for 2.5 h then concentrated in vacuo to remove DMF. The resulting residue was dissolved in EtOAc (70 mL), then washed with 1:1 brine:10% aqueous citric acid (50 mL), saturated aqueous NaHCO$_3$ (50 mL), brine (30 mL), dried (MgSO$_4$), filtered and concentrated to give 107 mg of the desired coupled product. This material was used without further purification in the final deprotection step: $^1$H NMR (300 MHz, CD$_3$OD) δ 5.39 (br d, J=14.4 Hz, 1H), 5.19 (d, J=5.7 Hz, 1H), 4.10–3.82 (m, 4H), 3.55–3.48 (m, 1H), 2.45 (br s, 2H), 2.05 (s, 3H), 2.04–1.94 (m, 2H), 1.47 (s, 9H), 1.46–1.37 (m, 2H), 0.96–0.83 (m, 9H); MS (ESPOS): 503.3 [M+H]+.

Boc-deprotection to give 4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide.

To a solution of the above Boc-carbamate lincosamide (35 mg, 0.070 mmol, 1 equiv) in DCE (5.0 mL) at 23° C. was added H$_2$O (0.20 mL) followed by TFA (2.0 mL). The reaction was stirred at 23° C. for 30 min then treated with toluene (40 mL) then concentrated to a volume of 10 mL, then treated with a second portion of toluene (40 mL) and concentrated to dryness. The crude product was purified via semi-prep HPLC (Waters Nova-Pak® HR C$_{18}$, 6 μm particle size, 60 Å pore size, 25 mm diameter×100 mm length, 5–60% acetonitrile in H$_2$O/0.1% AcOH over 30 min, 20 mL/min flow rate) to give 16 mg of pure 4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide: $^1$H NMR (300 MHz, D$_2$O) δ 5.51 (br s, 1H), 5.33 (br d, J=5.4 Hz, 1H), 4.18 (s, 2H), 4.13–3.98 (m, 2H), 3.86 (br s, 1H), 3.55–3.58 (m, 3H), 2.58–2.39 (m, 2H), 2.12 (s, 3H), 2.12–2.00 (m, 3H), 1.50–1.37 (m, 2H), 0.94–0.78 (m, 9H); $^{13}$C NMR (300 MHz, D$_2$O): δ 170.9, 136.5, 114.5, 88.4, 70.9, 69.3, 68.8, 68.2, 55.1, 53.0, 42.3, 38.3, 29.9, 27.7, 20.0, 19.9, 14.7, 13.3, 13.1; MS (ESPOS): 403.3 [M+H]+.

Example 39

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide

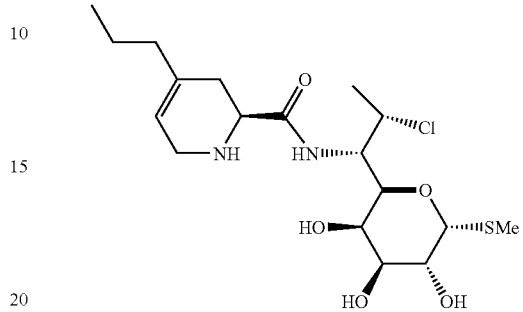

Coupling of Boc-protected amino acid to 6b (R$^2$=H, R$^3$=Cl). To a solution of Boc amino acid 21k (R9=n-propyl, m=1) prepared by general method S, depicted in scheme 21 (131 mg, 0.49 mmol, 1 equiv), 7-Cl MTL 6b (R$^2$=H, R$^3$=Cl) (132 mg, 0.49 mmol, 1 equiv) and HBTU (203 mg, 0.54, 1.1 equiv) in DMF (4.0 mL) at 23° C. was added N,N-diisopropylethylamine (170 μL, 0.97 mmol, 2 equiv). The reaction was stirred at 23° C. for 2.5 h then concentrated in vacuo to remove DMF. The resulting residue was dissolved in EtOAc (70 mL), then washed with 1:1 brine:10% aqueous citric acid (50 mL), saturated aqueous NaHCO$_3$ (25 mL), brine (30 mL), dried (MgSO$_4$), filtered and concentrated to give 276 mg of the desired coupled product. This material was used without further purification in the final deprotection step: $^1$H NMR (300 MHz, CD$_3$OD) δ 5.41 (br s, 1H), 5.28 (d, J=6.0 Hz, 1H), 4.65–4.52 (m, 1H), 4.46–4.36 (m, 1H), 4.25–4.16 (m, 1H), 4.15–3.97 (m, 2H), 3.93–3.74 (m, 2H), 3.55 (dd, J=3.3, 10.2 Hz, 1H), 2.62–2.40 (m, 2H), 2.13 (s, 3H), 2.10–1.95 (m, 2H), 1.49 (s, 9H), 1.46–1.32 (m, 5H), 0.90 (br t, J=7.2 Hz, 3H); MS (ESPOS): 523.2 [M+H]+.

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide. To a solution of the above Boc-carbamate protected lincosamide (225 mg, 0.43 mmol, 1 equiv) in DCE (25 mL) at 23° C. was added H$_2$O (1.0 mL) followed by TFA (10 mL). The reaction was stirred at 23° C. for 30 min then treated with toluene (150 mL), then concentrated to a volume of 30 μL, then treated with a second portion of toluene (150 mL) and concentrated to dryness. The crude product was purified via semi-prep HPLC (Waters Nova-Pak® HR C$_{18}$, 6 μm particle size, 60 Å pore size, 25 mm diameter×100 mm length, 5–60% acetonitrile in H$_2$O/ 0.1% AcOH over 30 min, 20 mL/min flow rate) to give 90 mg of pure 4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide: $^1$H NMR (300 MHz, D$_2$O) δ 5.53 (br s, 1H), 5.39 (br d, J=6.0 Hz, 1H), 4.66–4.55 (m, 1H), 4.46 (dd, J=1.2, 10.2 Hz, 1H), 4.33 (d, J=9.9 Hz, 1H), 4.19–4.07 (m, 2H), 3.88 (d, J=2.7 Hz, 1H), 3.74 (br s, 2H), 3.66 (dd, J=3.0, 10.2 Hz, 1H), 2.70–2.44 (m, 2H), 2.18 (s, 3H), 2.08 (br t, J=7.2 Hz, 3H), 1.52–1.37 (m, 2H), 1.42 (d, J=6.9 Hz, 3H), 0.85 (t, J=6.9 Hz, 3H); MS (ESPOS): 423.1 [M+H]+.

Example 40

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide

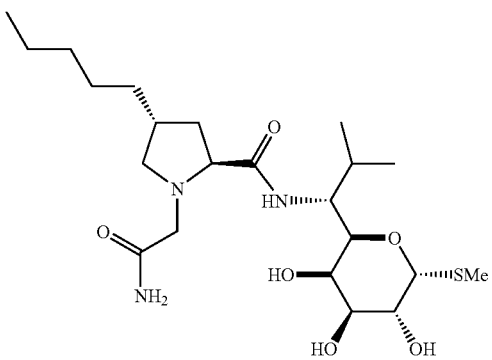

To a stirred solution of 4-pentyl-pyrrolidine-2-carboxylic acid [2-methyl-1-(3,4,5-trihydroxy-6-methylsulfanyl-tetrahydro-pyran-2-yl)-propyl]-amide (200 mg, 0.48 mmol, 1 equiv), in anhydrous acetonitrile (3 mL), at room temperature, under nitrogen atmosphere, was added triethylamine (0.2 mL, 1.44 mmol, 3 equiv) followed by bromoacetamide (80 mg, 0.58 mmol, 1.2 equiv). The resulting mixture was stirred at room temperature for 18 h, and evaporated to dryness. The residue obtained was first purified over silica gel, with an eluant of 7% methanolic-ammonia/dichloromethane. The desired fractions were collected, evaporated to dryness, and repurified by HPLC (to remove, the side-product from the reaction of the base with bromoacetamide). After lyophilization the desired title compound for example 40 was obtained (2.0 mg) as a white fluffy powder: HPLC: $R_t$=4.11 min (220.0 nm); $^1$H NMR (300 MHz, CD$_3$OD) δ (rotamers) 5.46 (d, J=5.5, 1), 4.47 (dd, J=3.02, 2.7, 1.1), 4.31–4.25 (m, 3.3), 4.11(d, J=3.02, 1.6), 2.31(s, 3), 1.65–1.52 (m, 9.5), 1.12–1.09 (m, 10.3). MS (ESPOS): 476.5 [M+H]+, (ESNEG): 474.5[M–H]–.

Example 41

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide

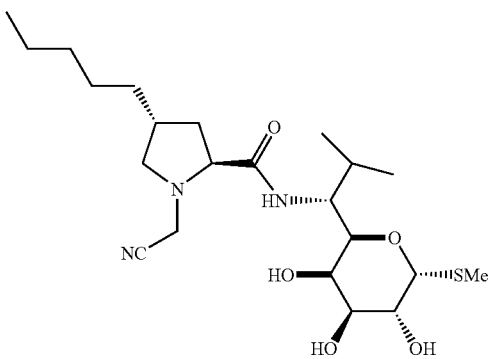

A stirred solution of crude 4-pentyl-pyrrolidine-2-carboxylic acid [2-methyl-1-(3,4,5-trihydroxy-6-methylsulfanyl-tetrahydro-pyran-2-yl)-propyl]-amide (210 mg, 0.50 mmol, 1 equiv) and triethylamine (0.21 mL, 1.51 mmol, 3 equiv), in anhydrous acetonitrile (3 mL) was treated with bromoacetonitrile (42 μl, 0.60 mmol, 1.2 equiv), at rt and under nitrogen. The resulting reaction mixture was stirred at rt for 18 h, evaporated to dryness and purified by chromatography over silica gel, with an eluant of 2.5% methanol in dichloromethane. The desired fractions were pooled, evaporated to dryness, and lyophilized to furnish the title compound (11.2 mg, 10%) as a fluffy white powder: TLC $R_f$=0.2 (5% methanol in dichloromethane); $^1$H NMR (300 MHz, CD$_3$OD) δ 5.44 (d, J=5.49, 1), 4.38–4.23 (m, 4), 2.29 (s, 3), 1.52 (m, 11), 1.16–1.09 (m, 12);. MS (ESPOS): 458.5 [M+H]+, MS (ESNEG): 456.5 [M–H]–.

Example 42

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide

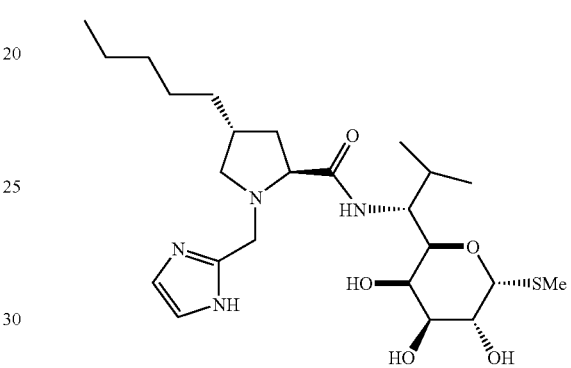

1-(1-Benzyl-1H-imidazol-2-ylmethyl)-4-pent-2-enyl-pyrrolidine-2-carboxylic acid benzyl ester. Boc protected amino acid 7d (R9'=4-pent-2-enyl) (433 mg, 1.16 mmol, 1 eq.) was stirred in 4M HCl in dioxane (5 mL) for 2 h then evaporated to dryness. The residue obtained was co-evaporated to dryness from DCM (3×20 mL). The crude HCl salt was dissolved in acetone (8 mL) and the resulting solution was treated with diisopropylethylamine (0.61 mL, 3.50 mmol, 3 equiv) followed by 1-benzyl-2-(chloromethyl-1H-imidazole (Maybridge) (338 mg, 1.39 mmol, 1.2 equiv). The reaction mixture was stirred at room temperature for 48 h, and evaporated to dryness. The residue obtained was diluted with EtOAc (200 mL), washed sequentially with 10% citric acid, brine, dried over Na$_2$SO$_4$, filtered and evaporated to dryness. The crude material obtained was purified by silica gel chromatography eluting with CH$_2$Cl$_2$/hexanes/MeOH (6:5:1), to furnish the desired N-alkylated product: 1-(1-benzyl-1H-imidazol-2-ylmethyl)-4-pent-2-enyl-pyrrolidine-2-carboxylic acid benzyl ester (257 mg, 50%): Rf=0.7 (7:2:1, CH2Cl2/hexanes/MeOH); MS (ESPOS): 444.3 [M+H]+.

1-(1-Benzyl-1H-imidazol-2-ylmethyl)-4-pent-2-enyl-pyrrolidine-2-carboxylic acid. To a stirred solution of 1-(1-benzyl-1H-imidazol-2-ylmethyl)-4-pent-2-enyl-pyrrolidine-2-carboxylic acid benzyl ester (257.2 mg, 0.6 mmol, 1 equiv) in a 4:1 THF/H$_2$O (8 mL), at room temperature, was added lithium hydroxide monohydrate (250 mg, 5.96 mmol, 10 equiv). The resulting reaction mixture was stirred at room temperature overnight, and evaporated to dryness. The residue obtained was dissolved in water (10 mL), and the pH of the resulting solution was adjusted to between 3 and 4, and extracted with EtOAc (3×100 mL). The combined organic extracts were washed with brine, dried over Na$_2$SO$_4$, filtered, and evaporated to dryness, affording the acid product 1-(1-Benzyl-1H-imidazol-2-ylmethyl)-4-pent-2-enyl-pyrrolidine-2-carboxylic acid (202 mg, 98%): Rf=0.4 (7:2:1 CH₂Cl₂/hexanes/MeOH), KMnO4 visualization stain; MS (ESPOS): 355 [M+H]+; MS (ESNEG): 352 [M–H]–.

1-(1-Benzyl-1H-imidazol-2-ylmethyl)-4-pentyl-pyrrolidine-2-carboxylic acid [2-methyl-1-(3,4,5-trihydroxy-6-methylsulfanyl-tetrahydro-pyran-2-yipropyl]-amide. To a stirred solution of 2b (R2'=H) (96.4 mg, 0.33 mmol, 1 equiv), in anhydrous DMF (1.5 mL), under N₂, at 0° C., was added, triethylamine (0.4 mL, 2.9 mmol, 8.7 equiv), followed by BSTFA (0.4 mL, 1.51 mmol, 4.6 equiv). The resulting mixture was stirred at 0° C. for 10 min, then at room temperature for 30 mins and re-cooled. To the reaction was added a solution of 1-(1-benzyl-1H-imidazol-2-ylmethyl)-4-pent-2-enyl-pyrrolidine-2-carboxylic acid (194 mg, 0.55 mmol, 1.7 equiv) followed by solid HATU (261 mg, 0.69 mmol, 2.1 equiv). The resulting mixture was stirred at room temperature for 3 h and evaporated to dryness. The resulting residue was dissolved in EtOAc, then washed with 10% aqueous citric acid, saturated aqueous NaHCO3, brine, dried (MgSO4), filtered and concentrated. The crude persilylated compound was dissolved in MeOH (60 mL) and treated with Dowex H⁺ form resin (250 mg) at room temperature for 45 min, the reaction mixture was filtered, and evaporated to dryness to provide the lincosamide product 1-(1-Benzyl-1H-imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide.

To an oven dried sealed tube, was added a solution of the above crude 1-(1-Benzyl-1H-imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide (280 mg, 0.48 mmol) in anhydrous EtOH (5 mL), 10% Pd on carbon (560 mg) and 1,4-cyclohexadiene (1.5 mL). The reaction vessel was purged with N2, sealed and stirred at room temperature for 18 h. The reaction mixture was filtered through celite, washed several times with reagent alcohol, and the combined washings and filtrate were evaporated to dryness. The resulting residue was purified by silica gel chromotography (1:9 methanolic ammonia/CH2Cl2). The desired fractions were evaporated to dryness and lyophilized, to furnish the title compound for example 42 (29.3 mg, 18%): TLC Rf=0.7 (14% methanolic ammonia/CH2Cl2), KMnO4 visualization stain; MS (ESPOS): 499.4 [M+H]+

Example 43

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide

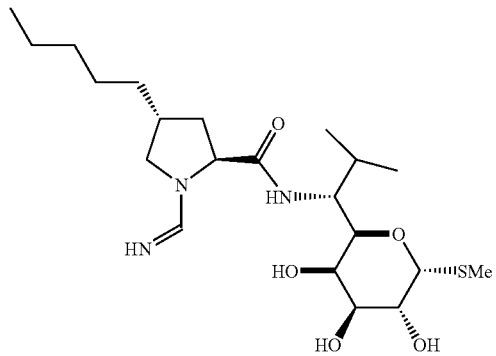

A stirred suspension of 4-pentyl-pyrrolidine-2-carboxylic acid [2-methyl-1-(3,4,5-trihydroxy-6-methylsulfanyl-tetrahydro-pyran-2-yl)-propyl]-amide (153 mg, 0.34 mmol, 1 equiv) and ethyl formimidate (Aldrich) (44 mg, 0.40 mmol, 1.2 equiv) in dioxane (1 mL) was treated with 1M aqueous NaOH (0.74 mL, 0.74 mmol, 2.2 equiv). After 1 h additional ethyl formimidate (44 mg, 0.40 mmol, 1.2 equiv) was added to the reaction mixture, and stirring was continued for 30 min. The reaction mixture was frozen and lyophilized. The lyophilized powder was purified by column chromatography to furnish the title compound (8 mg): TLC Rf=0.48 CHCl3/MeOH/32% aqueus AcOH (5:3:1); MS (ESPOS): 447.7 [M+H]+, 469.7 [M+Na]+; MS (ESNEG): 481.6 [M–H+HCl]–.

Example 44

4-Butyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide

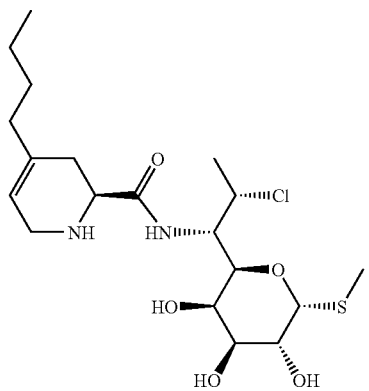

Boc amino acid 21k (R⁹=n-butyl, R⁹ᵇ=H, m=1) prepared by general method S was coupled to 7-Cl MTL 6b (R²=H, R³=Cl) this material was used without further purification in the final deprotection step. Deprotection and purification to furnish the title compound was conducted as in previous example 38.

¹H NMR (300 MHz, CD₃OD) δ 5.52 (br s, 1H), 5.29 (br d, J=5.7 Hz, 1H), 4.63–4.52 (m, 2H), 4.30 (d, J=9.6 Hz, 1H), 4.08 (dd, J=5.7 Hz, 1H), 4.00 (dd, J=4.8, 11.4 Hz, 1H), 3.81 (d, J=2.1 Hz, 1H), 3.69 (br s, 2H), 3.56 (dd, J=3.3, 10.2 Hz, 1H), 2.66–2.35 (m, 2H), 2.20–2.06 (m, 2H), 2.14 (s, 3H), 1.54–1.28 (m, 7H), 0.93 (t, J=7.2 Hz, 3H); MS (ESPOS): 437.2 [M+H]⁺.

Example 45

4-Butyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide

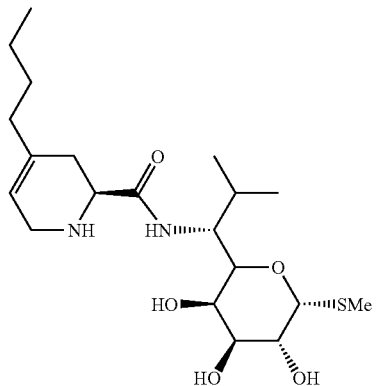

Boc amino acid 21k ($R^9$=n-butyl, $R^{9b}$=H, m=1) prepared by general method S was coupled to lincosamine 2b ($R^{2'}$=H) this material was used without further purification in the final deprotection step. Deprotection and purification to furnish the title compound was conducted as in previous example 38.

$^1$H NMR (300 MHz, D$_2$O) δ 5.52 (br s, 1H), 5.24 (d, J=5.7 Hz, 1H), 4.23 (dd, J=3.6, 10.2 Hz, 1H), 4.13–4.04 (m, 2H), 3.95 (dd, J=5.1, 11.1 Hz, 1H), 3.81 (d, J=2.7 Hz, 1H), 3.68 (br s, 2H), 3.51 (dd, J=3.3, 10.2 Hz, 1H), 2.59–2.34 (m, 2H), 2.24–2.06 (m, 3H), 2.11 (s, 3H), 1.52–1.28 (m, 4H), 0.98–0.87 (m, 9H) MS (ESPOS): 417.3 [M+H].

Example 46

5-Propyl-2,3,6,7-tetrahydro-1H-azepine-2-carboxylic acid [2-chloro-1-(3,4,5-trihydroxy-6-methylsulfanyl-tetrahydro-pyran-2-yl)-propyl]-amide

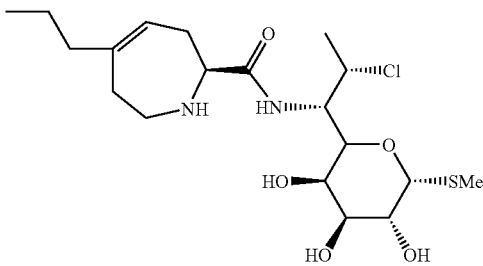

To a solution of protected cyclic amino acid 22h ($R^{9b}$=H, $R^9$=propyl) (340 mg, 0.88 mmol) in DMF (3 mL), 6b 7-Cl MTL ($R^2$=H, $R^3$=Cl) (367 mg, 0.88 mmol) TEA (332 µL, 1.76 mmol), HBTU (496 mg, 0.97 mmol) was added at 0° C., stirring at room temperature for overnight. Then solvent was removed. Purification was carried by silica gel column chromatography at 50–100% EtOAc/Hexane to provide the desired protected lincosamide 13a ($R^9$=propyl, $R^{9b}$=H, m=2, $R^2$=H, $R^3$=Cl, $P^1$=H, $P^2$=Boc) (575 mg, 90%). MS (ESPOS): 537 [M+1]$^+$.

To a solution of Boc protected lincosamide 13a ($R^9$=propyl, $R^{9b}$=H, m=2, $R^2$=H, $R^3$=Cl, $P^1$=H, $P^2$=Boc) (575 mg, 1.07 mmol) in DCE (15 mL), triethylsilane (0.5 mL), TFA (5 mL), water (0.5 mL) was added, stirring at room temperature for 1.5 hr. Reaction solvents were removed and the resulting residue was purified by chromatography on silica with 5–10% MeOH/DCM to provide the title compound (433 mg, 92%) as a colorless solid.

MS (ESPOS): 437 [M+1]$^+$.

Example 47

5-Propyl-azepane-2-carboxylic acid [2-chloro-1-(3,4,5-trihydroxy-6-methylsulfanyl-tetrahydro-pyran-2-yl)-propyl]-amide

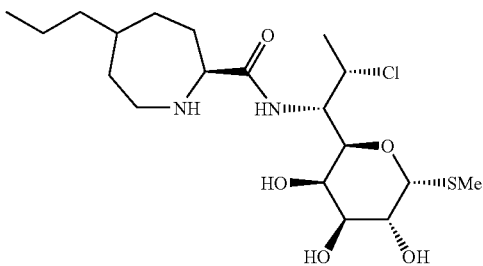

The unsaturated title compound from example 46 5-Propyl-2,3,6,7-tetrahydro-1H-azepine-2-carboxylic acid [2-chloro-1-(3,4,5-trihydroxy-6-methylsulfanyl-tetrahydro-pyran-2-yl)-propyl]-amide (433 mg, 0.99 mmol) and 10% Pd/C (80 mg), were taken MeOH (10 mL) hydrogenated at 50 psi overnight. The solvent was removed to obtain the crude material. Purification was carried by silica gel column chromatography (20% MeOH/DCM) followed by preparative HPLC (general method AC) to furnish isomer 1 $R_t$=18.3 min (10 mg, 2.3%) and isomer 2 $R_t$=18.6 min (58 mg, 13.3%).

Isomer 1: $^1$H NMR (300 MHz, CD$_3$OD) δ 5.29 (d, J=5.4, 1), 4.88 (m, 1), 4.42 (dd, J=1.8, 10.2, 1), 4.23 (d, J=9.9, 1), 4.10 (dd, J=5.7, 10.2, 1), 3.78 (d, J=3.3, 1), 3.71 (t, J=6.0, 1), 3.58 (dd, J=3.3, 10.2, 1), 3.15 (m, 1), 2.83 (m, 1), 2.13 (m, 2), 2.03 (m, 2), 1.86 (m, 2), 1.73 (m, 1), 1.50 (m, 4), 1.42 (m, 6), 0.92 (t, J=6.6, 3); MS (ESPOS): 439 [M+H]$^+$.

Isomer 2: $^1$H NMR (300 MHz, CD$_3$OD) δ 5.30 (d, J=5.7, 1), 5.30 (d, J=5.7, 1), 4.61 (m, 2), 4.29 (d, J=9.9, 1), 4.10 (dd, J=5.7, 10.2, 1), 4.00 (m, 1), 3.78 (d, J=3.0, 1), 3.58 (dd, J=3.3, 10.2, 1), 3.39 (m, 1), 3.08 (m, 1), 2.14 (m, 4), 1.96 (m, 3), 1.59 (m, 3), 1.45 (m, 3), 1.35 (m, 4), 0.93 (t, J=6.9, 3); MS (ESPOS): 439 [M+H]$^+$.

Example 48

1-Cyclopropyl-5-propyl-azepane-2-carboxylic acid [2-methyl-1-(3,4,5-trihydroxy-6-methylsulfanyl-tetrahydro-pyran-2-yl)-propyl]-amide

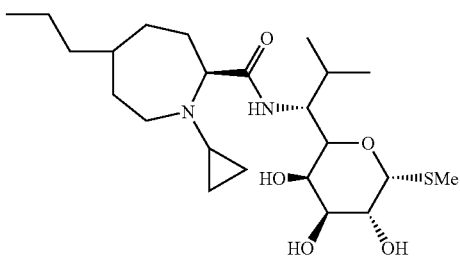

5-propyl-azepane-2-carboxylic acid [2-methyl-1-(3,4,5-trihydroxy-6-methylsulfanyl-tetrahydro-pyran-2-yl)-propyl]-amide prepared by the methods described in examples 47, 48 (68 mg, 0.16 mmol) in MeOH (2 mL), acetic acid (0.1 mL) was added, followed by 1-[(ethyoxycyclopropyl)oxy] trimethylsilane (0.2 mL, 0.96 mmol), sodium cyanoborohydride (41 mg, 0.64 mmol), and 3 Å molecular sieves, heated to reflux for 3 hrs. Molecular sieves were filtered out and the reaction solvent was removed to obtain the crude material. Purification was carried by silica gel column chromatography (10% MeOH/DCM) and HPLC to provide the title compound (44 mg, 59%). $^1$H NMR (300 MHz, CD$_3$OD) δ 5.20 (d, J=5.4, 1), 4.15 (d, J=6.6, 1), 4.08 (dd, J=5.4, 9.9, 1), 3.96 (d, J=3.0, 1), 3.88 (t, J=13.2, 1), 3.62 (m, 1), 3.56 (dd, J=3.3, 10.2, 1), 3.14 (m, 1), 2.82 (m, 1), 2.13 (m, 2), 2.05 (s, 3), 1.99–1.30 (m, 10), 0.96 (m, 9), 0.51 (m, 4); MS(ESPOS): 459 [M+H]$^+$.

Example 49

1-(5-Methyl-2-oxo-[1,3]dioxol-4-ylmethyl)-5-propyl-azepane-2-carboxylic acid [2-chloro-1-(3,4,5-trihydroxy-6-methylsulfanyl-tetrahydro-pyran-2-yl)-propyl]-amide

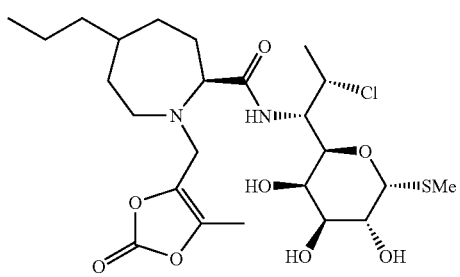

The title compound may be prepared by treatment of either isomer 1 or isomer 2 of the title compound from example 46 1 (wherein $R^2$=H, $R^3$=Cl, $R^6$=H, $R^9$=5-n-propyl, and m=3) with 4-Bromomethyl-5-methyl-[1,3]dioxol-2-one (prepared as described in in J. Alexander, et. al. *J. Med. Chem,* 1996, 39, 480–486.) in DMF in the presence of sodium carbonate.

Example 50

2-[2-Chloro-1-(3,4,5-trihydroxy-6-methylsulfanyl-tetrahydro-pyran-2-yl)propylcarbamoyl]-5-propyl-azepane-1-carboxylic acid 5-methyl-2-oxo-[1,3]dioxol-4-ylmethyl ester

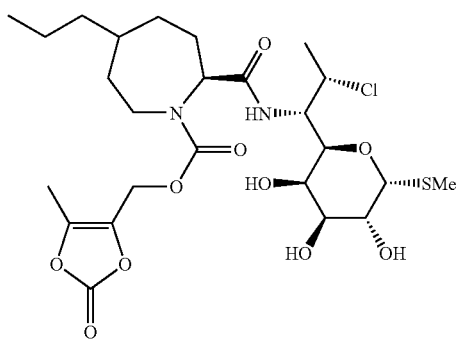

The title compound may be prepared by treatment of either isomer 1 or isomer 2 of the title compound from example 46 1 (wherein $R^2$=H, $R^3$=Cl, $R^6$=H, $R^9$=5-n-propyl, and m=3) with carbonic acid 5-methyl-2-oxo-[1,3]dioxol-4-ylmethyl ester 4-nitro-phenyl ester (prepared as described in F. Sakamoto, et. al, *Chem. Pharm. Bull.* 1984, 32 (6), 2241–2348.) in DMF in the presence of potassium bicarbonate.

Example 51

5-Methyl-azepane-2-carboxylic acid [2-chloro-1-(3,4,5-trihydroxy-6-methylsulfanyl-tetrahydro-pyran-2-yl)-propyl]-amide

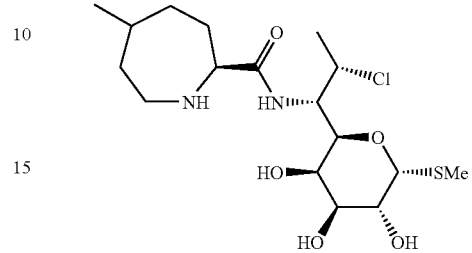

Lincosamine 6b 7-Cl MTL ($R^2$=H, $R^3$=Cl) was coupled to cyclic amino acid 22f ($R^9$=propyl, $R^{9b}$=H, m=2) prepared by general method T as depicted in general method Z to provide intermediate carbamate 13a ($R^9$=Methyl, $R^{9b}$=H, m=2, $R^2$=H, $R^3$=Cl, $P^1$=H, $P^2$=Boc) which was deprotected under acidic conditions to provide the crude unsaturated intermediate. Hydrogenation of the unsaturated compound with 10% Pd/C in MeOH at 50 psi $H_2$ provided a crude mixture of position 5 isomers. The two position 5 isomers were separated by preparative HPLC.

Isomer 1 (low $R_t$): $^1$H NMR (300 MHz, CD$_3$OD) δ 5.30 (d, J=5.7, 1), 4.58 (dd, J=6.3, 10.8, 2), 4.30 (d, J=9.9, 1), 4.10 (m, 1), 3.79 (m, 1), 3.58 (m, 1), 3.33 (m, 1), 3.13 (m, 1), 2.14 (m, 4), 1.92 (m, 3), 1.55 (m, 1), 1.44 (d, J=9.9, 6), 1.00 (d, J=9.9, 3); $R_t$: 14.2 min; MS (ESPOS): 412 [M+H]$^+$.

Isomer 2 (high $R_t$): $^1$H NMR (300 MHz, CD$_3$OD) δ 5.30 (d, J=5.7, 1), 4.59 (m, 2), 4.30 (d, J=9.9, 1), 4.10 (m, 1), 3.99 (m, 1), 3.81 (m, 1), 3.58 (m, 1), 3.14 (m, 1), 2.14 (m, 4), 1.90 (m, 3), 1.51 (m, 1), 1.44 (d, J=9.9, 6), 1.00 (d, J=9.9, 3); $R_t$=14.5 min; MS (ESPOS): 412 [M+H]$^+$.

Example 52

5-Ethyl-azepane-2-carboxylic acid [2-chloro-1-(3,4,5-trihydroxy-6-methylsulfanyl-tetrahydro-pyran-2-yl)-propyl]-amide

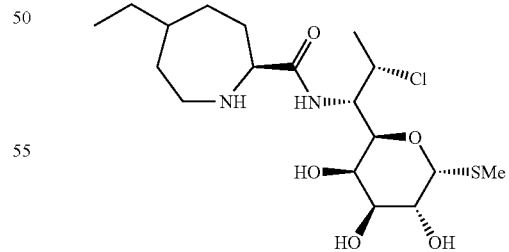

Lincosamine 6b 7-Cl MTL ($R^2$=H, $R^3$=Cl) was coupled to cyclic amino acid 22f ($R^9$=propyl, $R^{9b}$=H, m=2) prepared by general method T as depicted in general method Z to provide intermediate carbamate 13a ($R^9$=ethyl, $R^{9b}$=H, m=2, $R^2$=H, $R^3$=Cl, $P^1$=H, $P^2$=Boc) which was deprotected under acidic conditions to provide the crude unsaturated intermediate. Hydrogenation of the unsaturated compound with 10% Pd/C in MeOH at 50 psi H$_2$ provided a crude mixture of position 5 isomers. The two position 5 isomers were separated by preparative HPLC.

Isomer 1 (low R$_t$): $^1$H NMR (300 MHz, CD$_3$OD) δ 5.30 (d, J=6.0, 1), 4.59 (m, 1), 4.49 (m, 1), 4.27 (d, J=9.9, 1), 4.10 (dd, J=6.0, 10.2, 1), 3.92 (m, 1), 3.79 (m, 1), 3.55 (m, 1), 2.99 (m, 1), 2.14 (m, 4), 1.79 (m, 3), 1.45 (d, J=9.9, 6), 1.38 (m, 3), 0.99 (m, 3); R$_t$=14.6 min MS (ESPOS): 425.3 [M+H]$^+$.

Isomer 2 (high R$_t$): $^1$H NMR (300 MHz, CD$_3$OD) δ 5.30 (d, J=6.0, 1), 4.80 (m, 2), 4.29 (d, J=9.9, 1), 4.10 (dd, J=6.0, 10.2, 1), 3.98 (m, 1), 3.80 (d, J=2.7, 1), 3.59 (dd, J=3.0, 10.2, 1), 3.07 (m, 1), 2.14 (m, 4), 1.92 (m, 3), 1.52 (m, 1), 1.45 (d, J=9.9, 6), 1.32 (m, 2), 0.93 (m, 3) R$_t$: 16 min; MS (ESPOS): 425.3 [M+H]$^+$.

Example 53

5-Cyclopropylmethyl-azepane-2-carboxylic acid [2-chloro-1-(3,4,5-trihydroxy-6-methylsulfanyl-tetrahydro-pyran-2-yl)-propyl]-amide

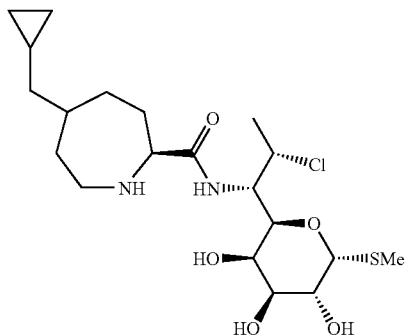

The title compound may be prepared by coupling cyclic amino acid 22f (R$^9$=cyclopropylmethyl, R$^{9b}$=H, m=2) prepared by general method T to lincosamine 6b 7-Cl MTL (R$^2$=H, R$^3$=Cl) as depicted in general method Z. Hydrogenation of the unsaturated compound with 10% Pd/C as in example 47 provides the title compound as a mixture of position 5 isomers.

Example 54

5-Cyclopropyl-azepane-2-carboxylic acid [2-chloro-1-(3,4,5-trihydroxy-6-methylsulfanyl-tetrahydro-pyran-2-yl)-propyl]-amide

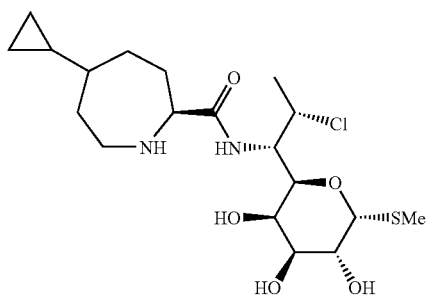

The title compound may be prepared by coupling cyclic amino acid 22f (R$^9$=cyclopropyl, R$^{9b}$=H, m=2) prepared by general method T to lincosamine 6b 7-Cl MTL (R$^2$=H, R$^3$=Cl) as depicted in general method Z. Hydrogenation of the unsaturated compound with 10% Pd/C as in example 47 provides the title compound as a mixture of position 5 isomers.

Example 55

5-Ethyl-4-methyl-azepane-2-carboxylic acid [2-chloro-1-(3,4,5-trihydroxy-6-methylsulfanyl-tetrahydro-pyran-2-yl)-propyl]-amide

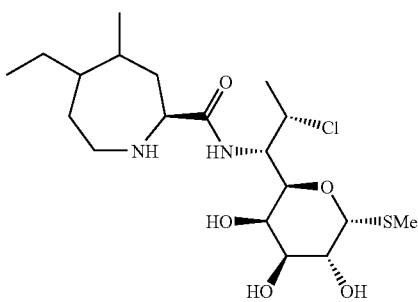

The title compound may be prepared by coupling cyclic amino acid 22f (R$^9$=ethyl, R$^{9b}$=methyl, m=2) prepared by general method T to lincosamine 6b 7-Cl MTL (R$^2$=H, R$^3$=Cl) as depicted in general method Z. Hydrogenation of the unsaturated compound with 10% Pd/C as in example 47 provides the title compound as a mixture of isomers.

Example 56

4-Ethyl-5-methyl-azepane-2-carboxylic acid [2-chloro-1-(3,4,5-trihydroxy-6-methylsulfanyl-tetrahydro-pyran-2-yl)-propyl]-amide

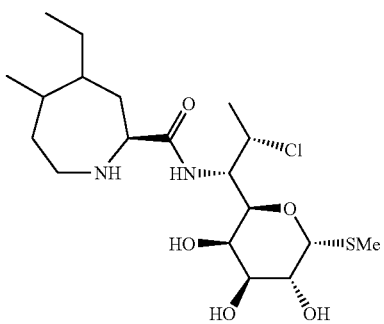

The title compound may be prepared by coupling cyclic amino acid 22f (R$^9$=methyl, R$^{9b}$=ethyl, m=2) prepared by general method T to lincosamine 6b 7-Cl MTL (R$^2$=H, R$^3$=Cl) as depicted in general method Z. Hydrogenation of the unsaturated compound with 10% Pd/C as in example 47 provides the title compound as a mixture of isomers.

Example 57

5-Ethyl-6-methyl-azepane-2-carboxylic acid [2-chloro-1-(3,4,5-trihydroxy-6-methylsulfanyl-tetrahydro-pyran-2-yl)-propyl]-amide

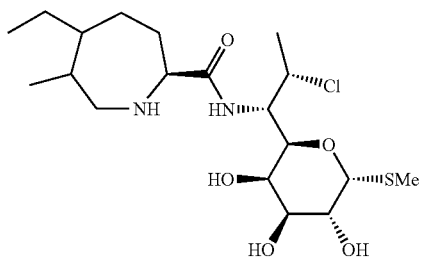

The title compound may be prepared by coupling cyclic amino acid 22f ($R^9$=methyl, $R^{9b}$=ethyl, m=1) prepared by general method T to lincosamine 6b 7-Cl MTL ($R^2$=H, $R^3$=Cl) as depicted in general method Z. Hydrogenation of the unsaturated compound with 10% Pd/C as in example 47 provides the title compound as a mixture of isomers.

Example 58

4-Propyl-azepane-2-carboxylic acid [2-chloro-1-(3,4,5-trihydroxy-6-methylsulfanyl-tetrahydro-pyran-2-yl)-propyl]-amide

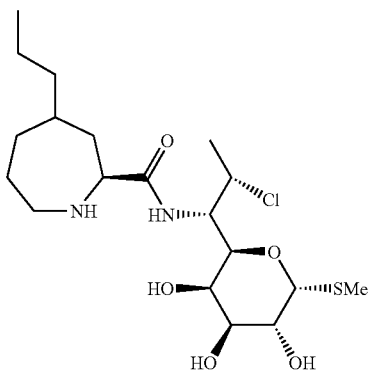

The title compound may be prepared by coupling cyclic amino acid 22f ($R^9$=H, $R^{9b}$=propyl, m=2) prepared by general method T to lincosamine 6b 7-Cl MTL ($R^2$=H, $R^3$=Cl) as depicted in general method Z. Hydrogenation of the unsaturated compound with 10% Pd/C as in example 47 provides the title compound as a mixture of position 4 isomers.

Example 59

5-Fluoro-5-propyl-azepane-2-carboxylic acid [2-chloro-1-(3,4,5-trihydroxy-6-methylsulfanyl-tetrahydro-pyran-2-yl)-propyl]-amide

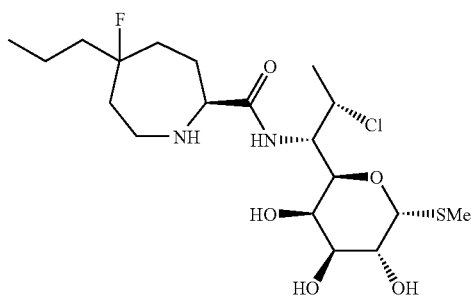

The title compound may be prepared by coupling cyclic amino acid 12d ($R^9$=propyl, m=2) to lincosamine 6b 7-Cl MTL ($R^2$=H, $R^3$=Cl) as depicted in general method Z.

Example 60

1-Methyl-4-propyl-pyrrolidine-2-carboxylic acid [cyclopropyl-(3,4,5-trihydroxy-6-methylsulfanyl-tetrahydro-pyran-2-yl)-methyl]-amide

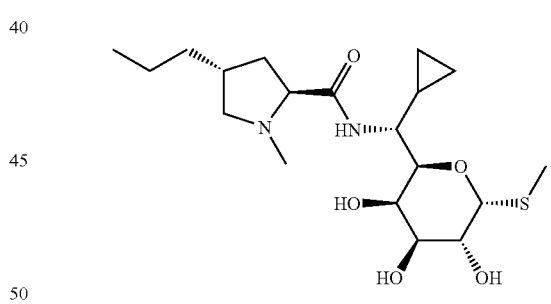

Lincosamide 23g ($R^{20}$+$R^{21}$=cyclopropyl, $R^1$=SMe) was coupled to 4-n-Propylhygric acid prepared by the method of Hoeksema, H. et. al. *Journal of the American Chemical Society*, 1967, 89 2448–2452 was coupled to as depicted in general method Z to provide the title compound.

$^1$H NMR (300 MHz, $D_2O$) δ 5.37 (d, J=5.7 Hz, 1H), 4.26–4.18 (m, 2H), 4.10 (dd, J=5.7, 9.9 Hz, 1H), 3.98 (d, J=3.0 Hz, 1H), 3.82 (dd, J=6.6, 11.1 Hz, 1H), 3.72 (d, J=8.7 Hz, 1H), 3.67 (dd, J=3.3, 7.2 Hz, 1H), 2.96–2.83 (m, 1H), 2.90 (s, 3H), 2.45–2.16 (m, 3H), 2.10 (s, 3H), 1.50–1.22 (m, 4H), 1.10–0.98 (m, 1H), 0.86 (t, J=7.2 Hz, 3H), 0.67–0.56 (m, 1H), 0.50–0.40 (m, 1H), 0.32–0.14 (m, 2H). MS (ES-POS): 403.3 [M+H]; MS (ESNEG): 437.2 [M+Cl].

Example 61

4-Propyl-piperidine-2-carboxylic acid [cyclopropyl-(3,4,5-trihydroxy-6-methylsulfanyl-tetrahydro-pyran-2-yl)-methyl]-amide

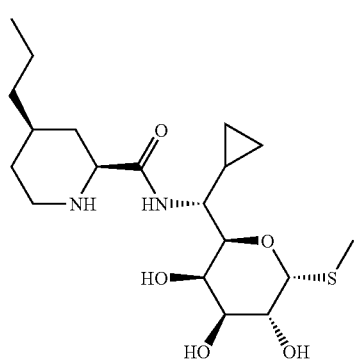

Lincosamide 23g ($R^{20}+R^{21}$=cyclopropyl, $R^1$=SMe) was coupled to 4-propyl-piperidine-1,2-dicarboxylic acid-1-tert-butyl ester 27b ($R^9$=propyl) as depicted in general method Z to provide the title compound. Intermediate 13a ($R^1$=SMe, $R^{20}+R^{21}$=cyclopropyl, $R^9$=propyl, $P^1$=H, $P^2$=carboxylic acid-t-butyl ester, m=2) which was deprotected under acidic conditions to provide the title compound.

$^1$H NMR (300 MHz, $D_2O$) δ 5.37 (d, J=5.7 Hz, 1H), 4.20 (d, J=9.0 Hz, 1H), 4.09 (dd, J=5.7, 10.2 Hz, 1H), 3.96 (d, J=3.3 Hz, 1H), 3.85 (dd, J=3.0, 12.9 Hz, 1H), 3.75–3.65 (m, 2H), 3.51–3.42 (m, 1H), 3.07–2.96 (m, 1H), 2.21–2.10 (m, 1H), 2.10 (s, 3H), 1.99–1.90 (m, 1H), 1.80–1.65 (m, 1H), 1.46–1.23 (m, 6H), 1.11–0.98 (m, 1H), 0.85 (t, J=6.6 Hz, 3H), 0.66–0.55 (m, 1H), 0.50–0.36 (m, 1H), 0.30–0.12 (m, 2H); MS (ESPOS): 403.3 [M+H]; MS (ESNEG): 437.2 [M+Cl].

Example 62

5-Propyl-azepane-2-carboxylic acid [cyclopropyl-(3,4,5-trihydroxy-6-methylsulfanyl-tetrahydro-pyran-2-yl)-methyl]-amide

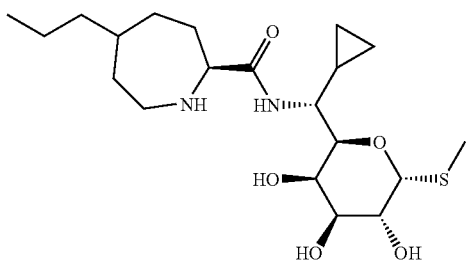

Lincosamide 23g ($R^{20}+R^{21}$=cyclopropyl, $R^1$=SMe) was coupled to 5-propyl-azepine-1,2-dicarboxylic acid-1-tert-butyl ester as depicted in general coupling method Z to provide the title compound. Intermediate 13a ($R^{20}+R^{21}$=cyclopropyl, $R^9$=propyl, $P^1$=H, $P^2$=carboxylic acid-t-butyl ester, m=3) which was deprotected under acidic conditions to provide the title compound.

MS (ESPOS): 451.2 [M+H]$^+$.

Example 63

4-Propyl-piperidine-2-carboxylic acid [phenyl-(3,4,5-trihydroxy-6-methylsulfanyl-tetrahydro-pyran-2-yl)-methyl]-amide

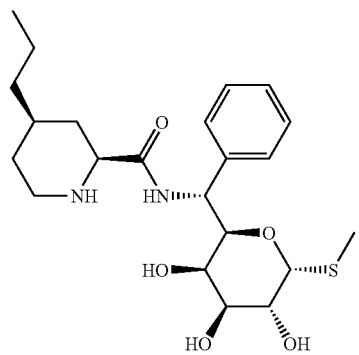

Lincosamide 23f ($R^{20}+R^{21}$=Ph, $R^1$=SMe) was prepared as depicted in scheme 23.

$^1$H NMR (300 MHz, $CDCl_3$) δ 7.41–7.26 (m, 5H), 6.90 (br d, J=9.6 Hz, 1H), 5.55 (d, J=5.4 Hz, 1H), 5.49 (dd, J=1.2, 3.3 Hz, 1H), 5.30–5.23 (m, 2H), 5.17 (dd, J=3.3, 10.8 Hz, 1H), 4.68 (dd, J=0.9, 8.4 Hz, 1H), 2.08 (s, 3H), 2.06 (s, 3H), 1.97 (s, 3H), 1.62 (s, 3H); MS (ESPOS): 530.0 [M+Na]; MS (ESNEG): 506.0 [M–H].

Lincosamide 23g ($R^{20}+R^{21}$=Ph, $R^1$=SMe) was prepared as depicted in scheme 23.

$^1$H NMR (300 MHz, $CD_3OD$) δ 7.40–7.20 (m, 5H), 5.09 (d, J=5.7 Hz, 1H), 4.16–4.05 (m, 4H), 3.58 (dd, J=3.3, 10.2 Hz, 1H), 1.38 (s, 3H); MS (ESPOS): 286.0 [M+H]; MS (ESNEG): 284.2 [M–H].

Lincosamide 23g ($R^{20}+R^{21}$=Ph, $R^1$=SMe) was coupled to 4-propyl-piperidine-1,2-dicarboxylic acid-1-tert-butyl ester 27b ($R^9$=propyl) as depicted in general method Z to provide the title compound. Intermediate 13a ($R^{20}+R^{21}$=Ph, $R^9$=propyl, $P^1$=H, $P^2$=carboxylic acid-t-butyl ester, m=2) which was deprotected under acidic conditions to provide the title compound.

$^1$H NMR (300 MHz, $D_2O$) δ 7.46–7.30 (m, 5H), 5.15 (d, J=5.7 Hz, 1H), 5.11 (d, J=9.9 Hz, 1H), 4.51 (d, J=10.2 Hz, 1H), 4.13–4.03 (m, 2H), 3.91 (dd, J=3.0, 12.9 Hz, 1H), 3.68 (dd, J=3.3, 10.2 Hz, 1H), 3.49–3.40 (m, 1H), 3.07–2.95 (m, 1H), 2.10–2.01 (m, 1H), 1.96–1.86 (m, 1H), 1.78–1.62 (m, 1H), 1.51 (s, 3H), 1.36–1.07 (m, 6H), 0.82 (t, J=6.6 Hz, 3H); MS (ESPOS): 439.3 [M+H]; MS (ESNEG): 473.2 [M+Cl]

Example 64

1-Methyl-4-propyl-pyrrolidine-2-carboxylic acid [phenyl-(3,4,5-trihydroxy-6-methylsulfanyl-tetrahydro-pyran-2-yl)-methyl]-amide

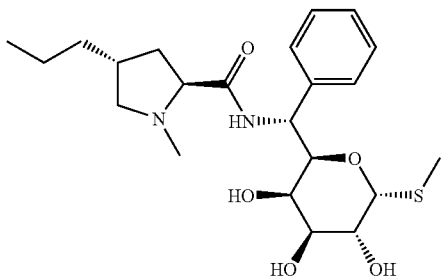

Lincosamide 23g ($R^{20}+R^{21}$=Phenyl, $R^1$=SMe) was coupled to 4-n-depicted in general method Z to provide the title compound.

$^1$H NMR (300 MHz, D$_2$O) δ 7.47–7.30 (m, 5H), 5.15 (d, J=5.7 Hz, 1H), 5.11 (d, J=10.2 Hz, 1H), 4.50 (d, J=9.9 Hz, 1H), 4.28 (dd, J=5.4, 9.3 Hz, 1H), 4.11–4.04 (m, 2H), 3.75 (dd, J=6.0, 11.1 Hz, 1H), 3.68 (dd, J=3.3, 10.5 Hz, 1H), 2.91 (s, 3H), 2.90–2.80 (m, 1H), 2.45–1.90 (m, 3H), 1.48 (s, 3H), 1.44–1.10 (m, 4H), 0.78 (t, J=7.2 Hz, 3H); MS (ESPOS): 439.3 [M+H]; MS (ESNEG): 473.2 [M+Cl].

Example 65

4-Propyl-piperidine-2-carboxylic acid [cyclopentyl-(3,4,5-trihydroxy-6-methylsulfanyl-tetrahydro-pyran-2-yl)-methyl]-amide

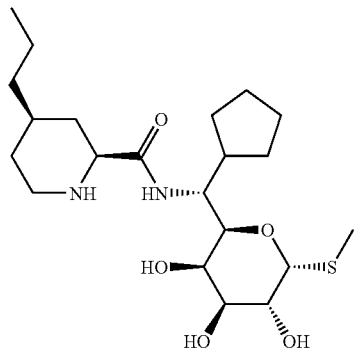

Lincosamide 23f ($R^{20}+R^{21}$=cyclopentyl, $R^1$=SMe) was prepared as depicted in scheme 23.

$^1$H NMR (300 MHz, CDCl$_3$) δ 6.29 (br d, J=9.0 Hz, 1H), 5.63 (d, J=5.7 Hz, 1H), 5.43 (d, J=3.3 Hz, 1H), 5.25 (dd, J=5.4, 11.1 Hz, 1H), 5.14 (dd, J=3.3, 11.1 Hz, 1H), 4.40–4.38 (m, 2H), 2.30–2.08 (m, 1H), 2.14 (s, 3H), 2.09 (s, 3H), 2.08 (s, 3H), 1.97 (s, 3H), 1.86–1.48 (m, 6H), 1.27–1.12 (m, 2H); MS (ESPOS): 522.2 [M+Na]; MS (ESNEG): 498.2 [M–H].

Lincosamide 23g ($R^{20}+R^{21}$=cyclopentyl, $R^1$=SMe) was prepared as depicted in scheme 23.

$^1$H NMR (300 MHz, CD$_3$OD) δ 5.28 (d, J=5.7 Hz, 1H), 4.16–4.08 (m, 2H), 3.93 (dd, J=0.9, 6.6 Hz, 1H), 3.54 (dd, J=3.0, 10.2 Hz, 1H), 2.99 (t, J=6.6 Hz, 1H), 2.17–2.04 (m, 1H), 2.07 (s, 3H), 1.88–1.51 (m, 6H), 1.42–1.26 (m, 2H)

MS (ESPOS): 278.3 [M+H]; MS (ESNEG): 276.2 [M–H].

Lincosamide 23g ($R^{20}+R^{21}$=cyclopentyl, $R^1$=SMe) was coupled to 4-propyl-piperidine-1,2-dicarboxylic acid-1-tert-butyl ester 27b ($R^9$=propyl) as depicted in general method Z to provide the title compound. Intermediate 13a ($R^{20}+R^{21}$=cyclopentyl, $R^9$=propyl, $P^1$=H, $P^2$=carboxylic acid-t-butyl ester, m=2) which was deprotected under acidic conditions to provide the title compound.

$^1$H NMR (300 MHz, D$_2$O) δ 5.37 (d, J=5.7 Hz, 1H), 4.23 (dd, J=5.4, 9.3 Hz, 1H), 4.15 (d, J=9.3 Hz, 1H), 4.09 (dd, J=5.7, 10.5 Hz, 1H), 3.90 (dd, J=3.3, 13.2 Hz, 1H), 3.63 (dd, J=3.3, 10.5 Hz, 1H), 3.49 (br d, J=12.6 Hz, 1H), 3.10–2.98 (m, 1H), 2.32–2.12 (m, 2H), 2.13 (s, 3H), 2.10–1.91 (m, 1H), 1.80–1.04 (m, 16H), 0.87 (t, J=6.6 Hz, 3H); MS (ESPOS): 431.3 [M+H]; MS (ESNEG): 465.2 [M+Cl].

Example 66

1-Methyl-4-propyl-pyrrolidine-2-carboxylic acid [cyclopentyl-(3,4,5-trihydroxy-6-methylsulfanyl-tetrahydro-pyran-2-yl)-methyl]-amide

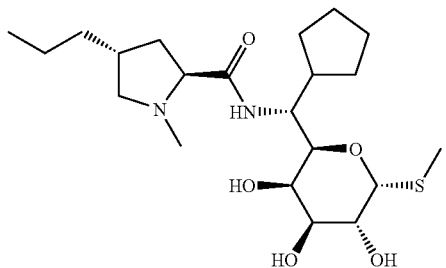

Lincosamide 23g ($R^{20}+R^{21}$=cyclopentyl, $R^1$=SMe) was coupled to 4-n-Propylhygric acid as depicted in general method Z to provide the title compound.

$^1$H NMR (300 MHz, D$_2$O) δ 5.35 (d, J=6.0 Hz, 1H), 4.31–4.22 (m, 2H), 4.16 (d, J=9.0 Hz, 1H), 4.09 (dd, J=5.7, 10.5 Hz, 1H), 3.94 (d, J=3.0 Hz, 1H), 3.85 (dd, J=6.3, 11.1 Hz, 1H), 3.63 (dd, J=3.0, 10.5 Hz, 1H), 2.95–2.85 (m, 1H), 2.93 (s, 3H), 2.45–2.13 (m, 3H), 2.13 (s, 3H), 1.84–1.03 (m, 13H), 0.87 (t, J=7.2 Hz, 3H); MS (ESPOS): 431.3 [M+H]; MS (ESNEG): 465.2 [M+Cl].

Example 67

5-Propyl-azepane-2-carboxylic acid [cyclopentyl-(3,4,5-trihydroxy-6-methylsulfanyl-tetrahydro-pyran-2-yl)-methyl]-amide

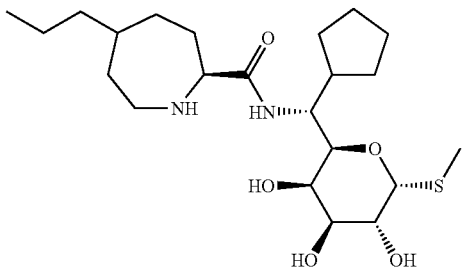

Lincosamide 23g ($R^{20}+R^{21}$=cyclopentyl, $R^1$=SMe) was coupled to 5-propyl-azepine-1,2-dicarboxylic acid-1-tert-butyl ester as depicted in general method Z to provide the title compound. Intermediate 13a ($R^1$=SMe, $R^{20}+R^{21}$=cyclopentyl, $R^9$=propyl, $P^1$=H, $P^2$=carboxylic acid-t-butyl ester, m=3) which was deprotected under acidic conditions to provide the title compound.

$^1$H NMR (300 MHz, D$_2$O) δ 5.33 (d, J=5.7 Hz, 1H), 4.24 (dd, J=4.8, 9.0 Hz, 1H), 4.19–4.11 (m, 2H), 4.07 (dd, J=5.7, 10.5 Hz, 1H), 3.90 (d, J=3.0 Hz, 1H), 3.62 (dd, J=3.3, 10.5 Hz, 1H), 3.46 (dd, J=4.2, 13.8 Hz, 1H), 3.19–3.08 (m, 1H), 2.36–2.09 (m, 3H), 2.12 (s, 3H), 2.08–1.81 (m, 2H), 1.80–1.40 (m, 8H), 1.36–1.01 (m, 7H), 0.83 (t, J=6.6 Hz, 3H); MS (ESPOS): 445.2 [M+H]; MS (ESNEG): 479.0 [M+Cl].

Example 68

1-Methyl-4-propyl-pyrrolidine-2-carboxylic acid [1-(3,4,5-trihydroxy-6-methylsulfanyl-tetrahydro-pyran-2-yl)-but-3-enyl]-amide

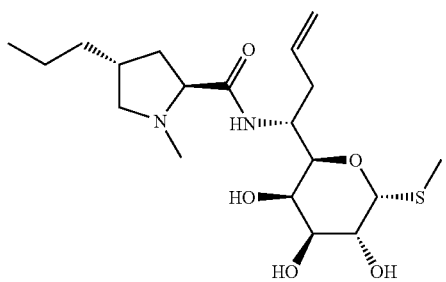

Lincosamide 23f ($R^{20}$=vinyl, $R^{21}$=H, $R^1$=SMe) was prepared as depicted in scheme 23.

$^1$H NMR (300 MHz, CDCl$_3$) δ 6.31 (br d, J=9.3 Hz, 1H), 5.80–5.62 (m, 1H), 5.64 (d, J=5.4 Hz, 1H), 5.41 (dd, J=0.9, 3.0 Hz, 1H), 5.26 (dd, J=5.4, 10.8 Hz, 1H), 5.23–5.10 (m, 3H), 4.42–4.25 (m, 2H), 3.56–2.44 (m, 1H), 2.35–2.23 (m, 1H), 2.14 (s, 3H), 2.09 (s, 3H), 2.08 (s, 3H), 1.97 (m, 3H); MS (ESNEG): 470.0 [M−H].

Lincosamide 23g ($R^{20}$=vinyl, $R^{21}$=H, $R^1$=SMe) was prepared as depicted in scheme 23.

$^1$H NMR (300 MHz, CD$_3$OD) δ 5.94–5.78 (m, 1H), 5.27 (d, J=5.7 Hz, 1H), 5.20–5.10 (m, 2H), 4.09 (dd, J=5.7, 10.2 Hz, 1H), 4.04 (dd, J=1.5, 3.3 Hz, 1H), 3.82 (dd, J=0.9, 8.1 Hz, 1H), 3.57 (dd, J=3.3, 9.9 Hz, 1H), 3.13 (dt, J=3.9, 8.4 Hz, 1H), 2.57–2.47 (m, 1H), 2.14–2.02 (m, 1H), 2.07 (s, 3H); MS (ESPOS): 272.0 [M+Na]; MS (ESNEG): 248.2 [M−H].

Lincosamide 23g ($R^{20}$=vinyl, $R^{21}$=H, $R^1$=SMe) was coupled to 4-n-Propylhygric acid as depicted in general method Z to provide the title compound. $^1$H NMR (300 MHz, D$_2$O) δ 5.84–5.68 (m, 1H), 5.37 (d, J=5.7 Hz, 1H), 5.16–5.07 (m, 2H), 4.28–4.18 (m, 2H), 4.14–4.07 (m, 2H), 3.93 (d, J=3.3 Hz, 1H), 3.82 (dd, J=6.3, 11.1 Hz, 1H), 3.66 (dd, J=3.3, 10.5 Hz, 1H), 2.91–2.83 (m, 1H), 2.91 (s, 3H), 2.67–2.58 (m, 1H), 2.40–2.10 (m, 4H), 2.11 (s, 3H), 1.52–1.22 (m, 4H), 0.87 (t, J=7.2 Hz, 3H); MS (ESPOS): 403.3 [M+H]; MS (ESNEG): 437.0 [M+Cl].

Example 69

4-Propyl-piperidine-2-carboxylic acid [1-(3,4,5-trihydroxy-6-methylsulfanyl-tetrahydro-pyran-2-yl)-but-3-enyl]-amide

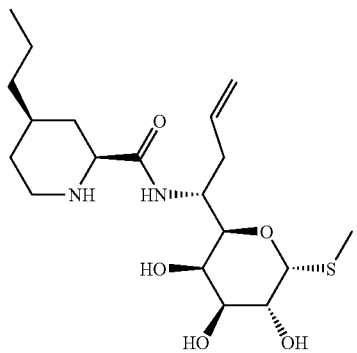

Lincosamide 23g ($R^{20}$=vinyl, $R^{21}$=H, $R^1$=SMe) was coupled to 4-propyl-piperidine-1,2-dicarboxylic acid-1-tert-butyl ester 27b ($R^9$=propyl) as depicted in general method Z to provide the title compound. Intermediate 13a ($R^{20}$=vinyl, $R^{21}$=H, $R^1$=SMe, $R^9$=propyl, $P^1$=H, $P^2$=carboxylic acid-t-butyl ester, m=2) which was deprotected under acidic conditions to provide the title compound.

$^1$H NMR (300 MHz, D$_2$O) δ 5.82–5.66 (m, 1H), 5.37 (d, J=5.7 Hz, 1H), 5.16–5.07 (m, 2H), 4.24–4.05 (m, 3H), 3.92 (d, J=3.3 Hz, 1H), 3.85 (dd, J=3.3, 12.9 Hz, 1H), 3.66 (dd, J=3.3, 10.5 Hz, 1H), 3.47 (br d, J=12.3 Hz, 1H), 3.08–2.96 (m, 1H), 2.66–2.56 (m, 1H), 2.22–2.10 (m, 2H), 2.11 (s, 3H), 1.99–1.89 (m, 1H), 1.80–1.64 (m, 1H), 1.41–1.22 (m, 6H), 0.87 (t, J=6.6 Hz, 3H); MS (ESPOS): 403.3 [M+H]; MS (ESNEG): 437.2 [M+Cl].

Example 70

5-Propyl-azepane-2-carboxylic acid [1-(3,4,5-trihydroxy-6-methylsulfanyl-tetrahydro-pyran-2-yl)-butyl]-amide

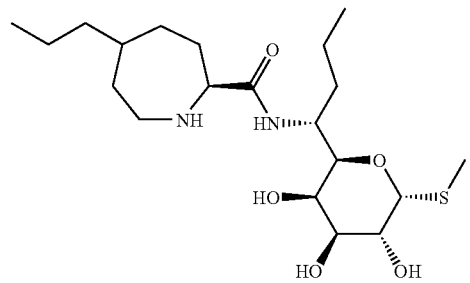

The title compound was be prepared by coupling cyclic amino acid 22f ($R^9$=propyl, $R^{9b}$=H, m=2) prepared by general method T to lincosamine 23 g ($R^{20}$=ethyl, $R^{21}$=H, $R^1$=SMe) as depicted in general method Z. Hydrogenation of the unsaturated intermediate provided the title compound.

$^1$H NMR (300 MHz, D$_2$O) δ 5.34 (d, J=5.7 Hz, 1H), 4.16–4.04 (m, 3H), 4.01 (d, J=9.3 Hz, 1H), 3.89 (d, J=3.3 Hz, 1H), 3.64 (dd, J=3.3, 10.5 Hz, 1H), 3.45 (dd, J=5.1, 13.2 Hz, 1H), 3.13 (t, J=12.0 Hz, 1H), 2.20–1.16 (m, 15H), 2.08 (s, 3H), 0.86 (t, J=7.5 Hz, 3H), 0.83 (t, J=6.9 Hz, 3H); MS (ESPOS): 419.0 [M+H]; MS (ESNEG): 453.2 [M+Cl].

Example 71

4-Propyl-piperidine-2-carboxylic acid [1-(3,4,5-trihydroxy-6-methylsulfanyl-tetrahydro-pyran-2-yl)-butyl]-amide

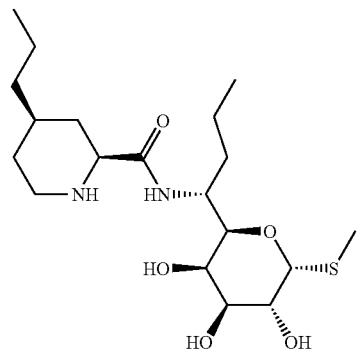

Hydrogenation of the title compound from example 69 provided the title compound.

$^1$H NMR (300 MHz, D$_2$O) δ 5.34 (d, J=6.0 Hz, 1H), 4.14–4.04 (m, 2H), 4.00 (d, J=9.3 Hz, 1H), 3.91–3.83 (m, 2H), 3.64 (dd, J=3.3, 10.5 Hz, 1H), 3.51–3.43 (m, 1H), 3.08–2.96 (m, 1H), 2.22–2.13 (m, 1H), 2.07 (s, 3H), 1.99–1.89 (m, 1H), 1.83–1.65 (m, 2H), 1.48–1.13 (m, 9H), 0.85 (t, J=7.5 Hz, 6H); MS (ESPOS): 405.4 [M+H]; MS (ESNEG): 439.2 [M+Cl].

Example 72

1-Methyl-4-propyl-pyrrolidine-2-carboxylic acid [1-(3,4,5-trihydroxy-6-methylsulfanyl-tetrahydro-pyran-2-yl)-butyl]-amide

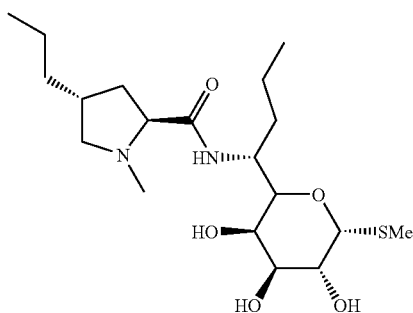

Hydrogenation of the title compound from example 68 provided the title compound.

$^1$H NMR (300 MHz, D$_2$O) δ 5.36 (d, J=6.0 Hz, 1H), 4.28–4.03 (m, 4H), 3.93 (d, J=3.0 Hz, 1H), 3.85 (dd, J=6.9, 11.1 Hz, 1H), 3.66 (dd, J=3.0, 10.2 Hz, 1H), 2.95–2.85 (m, 1H), 2.93 (s, 3H), 2.47–2.19 (m, 3H), 2.10 (s, 3H), 1.86–1.70 (m, 1H), 1.54–1.16 (m, 7H), 0.87 (t, J=6.9 Hz, 6H); MS (ESPOS): 405.4 [M+H]; MS (ESNEG): 439.2 [M+Cl].

Example 73

1-Methyl-4-propyl-pyrrolidine-2-carboxylic acid [(4-chloro-phenyl)-(3,4,5-trihydroxy-6-methylsulfanyl-tetrahydro-pyran-2-yl)-methyl]-amide

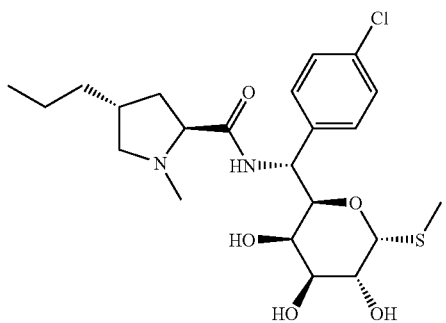

Lincosamide 23f (R$^{20}$+R$^{21}$=4-chlorophenyl, R$^1$=SMe) was prepared as depicted in scheme 23.

$^1$H NMR (300 MHz, CDCl$_3$) □ 7.34 (d, J=8.4 Hz, 2H), 7.25 (d, J=8.4 Hz, 2H), 7.16 (br d, J=9.0 Hz, 1H), 5.55 (d, J=5.4 Hz, 1H), 5.50 (d, J=2.1 Hz, 1H), 5.30–5.13 (m, 3H), 4.66 (d, J=8.7 Hz, 1H), 2.09 (s, 3H), 2.07 (s, 3H), 1.98 (s, 3H), 1.65 (s, 3H); MS (ESPOS): 563.9 [M+Na]; MS (ESNEG): 539.8 [M–H].

Lincosamide 23g (R$^{20}$+R$^{21}$=4-chlorophenyl, R$^1$=SMe) was prepared as depicted in scheme 23.

$^1$H NMR (300 MHz, CD$_3$OD) □ 7.37 (d, J=8.4 Hz, 2H), 7.31 (d, J=9.0 Hz, 2H), 5.09 (d, J=6.0 Hz, 1H), 4.13–4.03 (m, 4H), 3.58 (dd, J=3.3, 10.2 Hz, 1H), 1.41 (s, 3H); MS (ESPOS): 320.0 [M+H]; MS (ESNEG): 354.0 [M+Cl].

Lincosamide 23g (R$^{20}$+R$^{21}$=4-chlorophenyl, R$^1$=SMe) was coupled to 4-n-Propylhygric acid as depicted in general method Z to provide the title compound.

$^1$H NMR (300 MHz, D$_2$O) □ 7.43 (d, J=8.1 Hz, 2H), 7.36 (d, J=8.4 Hz, 2H), 5.18 (d, J=6.0 Hz, 1H), 5.12 (d, J=10.2 Hz, 1H), 4.48 (d, J=9.9 Hz, 1H), 4.29 (dd, J=5.4, 9.0 Hz, 1H), 4.14–4.05 (m, 2H), 3.78 (dd, J=5.7, 10.8 Hz, 1H), 3.70 (dd, J=3.3, 10.2 Hz, 1H), 2.92 (s, 3H), 2.87 (t, J=10.8 Hz, 1H), 2.26–2.11 (m, 2H), 2.07–1.94 (m, 1H), 1.52 (s, 3H), 1.46–1.12 (m, 4H), 0.81 (t, J=7.2 Hz, 3H); MS (ESPOS): 473.2 [M+H]; MS (ESNEG): 507.2 [M+Cl].

Example 74

4-Propyl-piperidine-2-carboxylic acid [(4-chloro-phenyl)-(3,4,5-trihydroxy-6-methylsulfanyl-tetrahydro-pyran-2-yl)-methyl]-amide

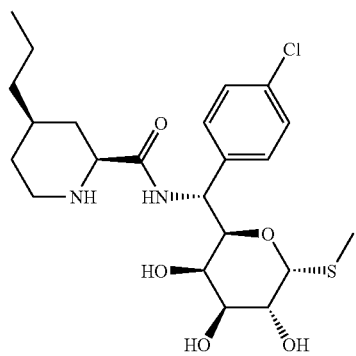

Lincosamide 23g (R$^{20}$+R$^{21}$=4-chlorophenyl, R$^1$=SMe) was coupled to 27b (R$^9$=propyl) as depicted in general method Z to provide the title compound.

$^1$H NMR (300 MHz, CD$_3$OD) δ 7.35 (s, 4H), 5.20 (d, J=9.6 Hz, 1H), 5.14 (d, J=6.0 Hz, 1H), 4.36 (d, J=9.3 Hz, 1H), 4.10 (dd, J=5.7, 10.2 Hz, 1H), 3.99 (d, J=3.0 Hz, 1H), 3.89 (dd, J=3.0, 12.6 Hz, 1H), 3.59 (dd, J=3.3, 10.2 Hz, 1H), 3.45–3.36 (m, 1H), 3.04 (dt, J=3.3, 13.2 Hz, 1H), 2.24–2.14 (m, 1H), 1.98–1.88 (m, 1H), 1.81–1.66 (m, 1H), 1.52 (s, 3H), 1.46–1.13 (m, 6H), 0.94 (t, J=7.2 Hz, 3H); MS (ESPOS): 473.2 [M+H]; MS (ESNEG): 507.2 [M+Cl].

Example 75

1-Methyl-4-propyl-pyrrolidine-2-carboxylic acid [2-methyl-1-(3,4,5-trihydroxy-6-isopropylsulfanyl-tetrahydro-pyran-2-yl)-propyl]-amide

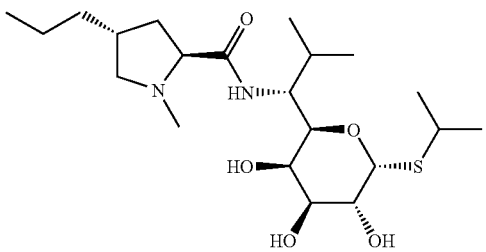

Lincosamide 23f ($R^{20}$=methyl, $R^{21}$=methyl, $R^1$=isopropyl sulfanyl) was prepared as depicted in scheme 23.

$^1$H NMR (300 MHz, CDCl$_3$) δ 6.10 (br d, J=10.5 Hz, 1H), 5.79 (d, J=5.4 Hz, 1H), 5.36 (dd, J=1.2, 3.3 Hz, 1H), 5.20 (dd, J=5.7, 11.1 Hz, 1H), 5.09 (dd, J=3.3, 10.8 Hz, 1H), 4.36 (dd, J=0.9, 9.9 Hz, 1H), 4.26 (dt, J=3.0, 10.2 Hz, 1H), 3.04–2.90 (m, 1H), 2.13 (s, 3H), 2.07 (s, 3H), 1.97 (s, 3H), 1.29 (d, J=4.8 Hz, 3H), 1.27 (d, J=5.1 Hz, 3H), 0.91 (d, J=6.9 Hz, 3H), 0.86 (d, J=6.9 Hz, 3H)

MS (ESPOS): 524.0 [M+Na]
MS (ESNEG): 500.0 [M–H]

Lincosamide 23g ($R^{20}$=methyl, $R^{21}$=methyl, $R^1$=isopropyl sulfanyl) was prepared as depicted in scheme 23.

$^1$H NMR (300 MHz, CD$_3$OD) δ 5.36 (d, J=6.0 Hz, 1H), 4.05 (dd, J=5.7, 10.2 Hz, 1H), 4.01 (dd, J=1.5, 3.3 Hz, 1H), 3.95 (dd, J=1.2, 8.7 Hz, 1H), 3.48 (dd, J=3.3, 10.5 Hz, 1H), 3.04–2.93 (m, 1H), 2.89 (dd, J=3.6, 8.4 Hz, 1H), 2.07–1.95 (m, 1H), 1.30 (d, J=6.9 Hz, 3H), 1.26 (d, J=6.9 Hz, 3H), 0.98 (d, J=6.9 Hz, 3H), 0.87 (d, J=6.6 Hz, 3H); MS (ESPOS): 280.0 [M+H]; MS (ESNEG): 278.2 [M–H]

Lincosamide 23g ($R^{20}$=methyl, $R^{21}$=methyl, $R^1$=isopropyl sulfanyl) was coupled to 4-n-Propylhygric acid as depicted in general method Z to provide the title compound.

$^1$H NMR (300 MHz, D$_2$O) δ 5.47 (d, J=6.0 Hz, 1H), 4.25 (br t, J=7.2 Hz, 1H), 4.16 (br s, 2H), 4.07 (dd, J=5.7, 10.5 Hz, 1H), 3.83 (dd, J=8.1, 11.4 Hz, 2H), 3.56 (dd, J=3.0, 10.5 Hz, 1H), 3.11–2.99 (m, 1H), 2.91 (s, 3H), 2.88 (br t, J=11.1 Hz, 1H), 2.45–2.20 (m, 3H), 2.15–2.00 (m, 1H), 1.50–1.37 (m, 2H), 1.36–1.23 (m, 8H), 0.90–0.80 (m, 9H); MS (ESPOS): 433.4 [M+H]; MS (ESNEG): 467.2 [M+Cl]

Example 76

4-Propyl-piperidine-2-carboxylic acid [2-methyl-1-(3,4,5-trihydroxy-6-isopropylsulfanyl-tetrahydro-pyran-2-yl)-propyl]-amide

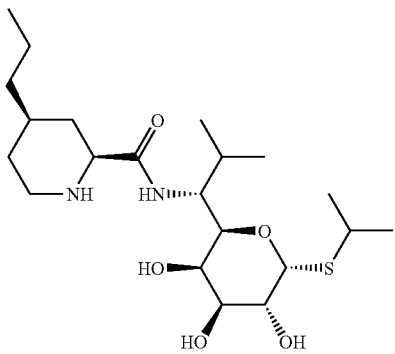

Lincosamide 23 g ($R^{20}$=methyl, $R^{21}$=methyl, $R^1$=isopropyl sulfanyl) was coupled to 4-propyl-piperidine-1,2-dicarboxylic acid-1-tert-butyl ester 27b ($R^9$=propyl) as depicted in general method Z to provide the title compound. Intermediate 13a ($R^1$=isopropyl sulfanyl, $R^{20}$=methyl, $R^{21}$=methyl, $R^9$=propyl, $P^1$=H, $P^2$=carboxylic acid-t-butyl ester, m=2) which was deprotected under acidic conditions to provide the title compound.

$^1$H NMR (300 MHz, D$_2$O) δ 5.47 (d, J=6.0 Hz, 1H), 4.14 (br s, 2H), 4.07 (dd, J=6.0, 10.5 Hz, 1H), 3.89 (dd, J=3.0, 12.6 Hz, 1H), 3.83 (d, J=3.3 Hz, 1H), 3.56 (dd, J=3.3, 10.5 Hz, 1H), 3.47 (br d, J=13.5 Hz, 1H), 3.12–2.96 (m, 2H), 2.25–1.90 (m, 3H), 1.80–1.66 (m, 1H), 1.50–1.22 (m, 12H), 0.90–0.79 (m, 9H); MS (ESPOS): 433.4 [M+H]; MS (ESNEG): 467.2 [M+Cl].

Example 77

1-Methyl-4-propyl-pyrrolidine-2-carboxylic acid [1-(6-tert-butylsulfanyl-3,4,5-trihydroxy-tetrahydro-pyran-2-yl)-2-methyl-propyl]-amide

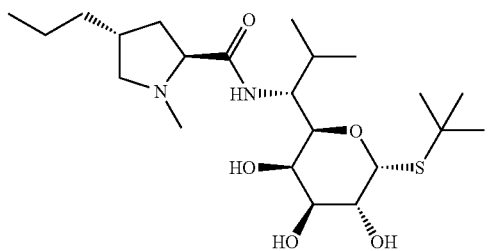

Lincosamide 23f ($R^{20}$=methyl, $R^{21}$=methyl $R^1$=tert-butyl sulfanyl) was prepared as depicted in scheme 23.

$^1$H NMR (300 MHz, CDCl$_3$) δ 6.08 (br d, J=9.3 Hz, 1H), 5.81 (d, J=5.7 Hz, 1H), 5.34 (d, J=3.0 Hz, 1H), 5.19 (dd, J=5.7, 11.1 Hz, 1H), 5.01 (dd, J=3.3, 11.1 Hz, 1H), 4.34–4.18 (m, 2H), 2.20–2.05 (m, 1H), 2.13 (s, 3H), 2.07 (s, 3H), 1.97 (s, 3H), 1.32 (m, 9H), 0.89 (t, J=6.6 Hz, 6H); MS (ESPOS): 538.0 [M+Na]; MS (ESNEG): 514.2 [M–H].

Lincosamide 23g ($R^{20}$=methyl, $R^{21}$=methyl, $R^1$=tert-butyl sulfanyl) was prepared as depicted in scheme 23.

$^1$H NMR (300 MHz, CD$_3$OD) δ 5.39 (d, J=5.7 Hz, 1H), 4.05 (dd, J=6.0, 10.8 Hz, 1H), 4.01 (dd, J=1.2, 3.3 Hz, 1H), 3.90 (dd, J=1.5, 8.7 Hz, 1H), 3.39 (dd, J=3.3, 10.5 Hz, 1H), 2.88 (dd, J=3.6, 8.1 Hz, 1H), 2.08–1.95 (m, 1H), 1.36 (s, 9H), 0.98 (d, J=6.9 Hz, 3H), 0.89 (d, J=6.9 Hz, 3H); MS (ESPOS): 294.0 [M+H]; MS (ESNEG): 292.2 [M–H]

Lincosamide 23g ($R^2$=isopropyl, $R^1$=tert-butyl sulfanyl) was coupled to 4-n-Propylhygric acid as depicted in general method Z to provide the title compound.

$^1$H NMR (300 MHz, D$_2$O) δ 5.50 (d, J=5.7 Hz, 1H), 4.26 (br t, J=7.5 Hz, 1H), 4.15 (br s, 2H), 4.08 (dd, J=5.7, 10.5 Hz, 1H), 3.90–3.82 (m, 2H), 3.50 (dd, J=3.0, 10.8 Hz, 1H), 2.93 (s, 3H), 2.91 (br t, J=11.1 Hz, 1H), 2.48–2.25 (m, 3H), 2.16–2.04 (m, 1H), 1.52–1.26 (m, 4H), 1.37 (m, 9H), 0.88 (t, J=6.9 Hz, 9H); MS (ESPOS): 447.4 [M+H]; MS (ESNEG): 481.2 [M+Cl].

Example 78

4-Propyl-piperidine-2-carboxylic acid [1-(6-tert-butylsulfanyl-3,4,5-trihydroxy-tetrahydro-pyran-2-yl)-2-methyl-propyl]-amide

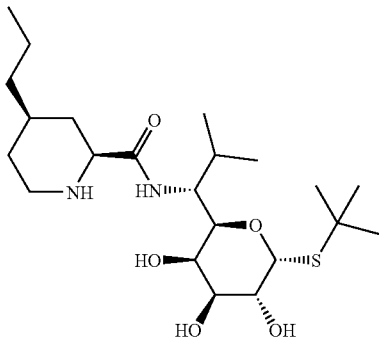

Lincosamide 23g ($R^{20}$=methyl, $R^{21}$=methyl, $R^{1}$=tert-butyl sulfanyl) was coupled to 4-propyl-piperidine-1,2-dicarboxylic acid-1-tert-butyl ester 27b ($R^{9}$=propyl) as depicted in general method Z to provide the title compound. Intermediate 13a ($R^{1}$=tert-butyl sulfanyl, $R^{20}$=methyl, $R^{21}$=methyl, $R^{9}$=propyl, $P^{1}$=H, $P^{2}$=carboxylic acid-t-butyl ester, m=2) which was deprotected under acidic conditions to provide the title compound.

$^{1}$H NMR (300 MHz, $D_{2}O$) δ 5.50 (d, J=5.7 Hz, 1H), 4.13 (br s, 2H), 4.08 (dd, J=5.7, 10.5 Hz, 1H), 3.92 (dd, J=3.0, 12.6 Hz, 1H), 3.85 (d, J=3.3 Hz, 1H), 3.51 (dd, J=3.0, 10.5 Hz, 2H), 3.06 (br t, J=10.8 Hz, 1H), 2.28–2.19 (m, 1H), 2.16–1.93 (m, 2H), 1.85–1.69 (m, 1H), 1.54–1.27 (m, 6H), 1.38 (s, 9H), 0.94–0.83 (m, 9H); MS(ESPOS): 447.4 [M+H]; MS (ESNEG): 481.0 [M+Cl].

Example 79

4-(2-Cyclopropyl-ethyl)-piperidine-2-carboxylic acid [2-chloro-1-(3,4,5-trihydroxy-6-methylsulfanyl-tetrahydro-pyran-2-yl)-propyl]-amide

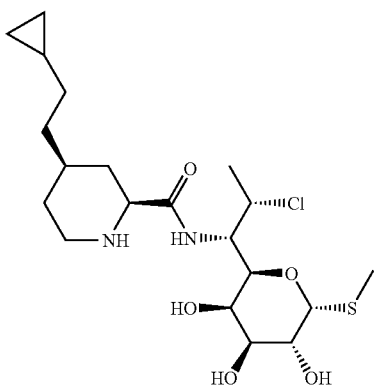

To a stirred suspension of 11b (0.5 g, 1.9 mmol, 1 equiv), triphenylphosphine (39.9 mg, 0.15 mmol, 0.08 equiv), copper (I) iodide (28.9 mg, 0.15 mmol, 0.08 equiv), palladium acetate (17 mg, 0.076 mmol, 0.04 equiv) in triethylamine (7 mL) under dry nitrogen, was added cyclopropyl acetylene (Aldrich) (0.25 g, 3.8 mmol, 2 equiv). The mixture was stirred at rt overnight. The solvent was removed under vacuum to give a dark residue. The residue was purified by column chromatography to give 11c ($R^{9'}$=2-cyclopropyl-eth-1-ynyl) (0.39 g; 100%) as a yellow oil.

$^{1}$H NMR (300 MHz, $CDCl_{3}$) δ 8.65–8.56 (m, 1), 8.06–7.99 (m, 1), 7.40–7.32 (m, 1), 3.98 (s, 3), 1.50–1.40 (m, 1), 0.96–0.81 (m, 4); MS (ESPOS): 202.0 [M+H]$^{+}$.

To a solution of 11c ($R^{9'}$=2-cyclopropyl-eth-1-ynyl) (0.39 g, 1.9 mmol) in methanol (15 mL) was added 10% palladium on carbon (0.2 g). The mixture was purged and charged with hydrogen (1 atm) and stirred at rt overnight. The palladium was removed by filtration and the filtrate was concentrated to give 4-(2-cyclopropylethyl)-pyridine-2-carboxylic acid methyl ester (0.38 g, 97%) as a yellow oil. (intermediate not shown)

$^{1}$H NMR (300 MHz, $CDCl_{3}$) δ 8.60 (d, J=4.5, 1), 8.00–7.96 (m, 1), 7.34–7.29(m, 1), 3.99 (s, 3), 2.78 (t, J=7.6, 2), 1.58–1.49 (m, 2), 0.71–0.59 (m, 1), 0.47–0.38 (m, 2), 0.06–0.02 (m, 2); MS (ESPOS): 228.2 [M+Na]$^{+}$.

To a mixture of 4-(2-cyclopropylethyl)-pyridine-2-carboxylic acid methyl ester (0.38 g) in MeOH (8 mL) and water (8 mL) were added concentrated HCl (158 µL) and platinum oxide (0.2 g). The mixture was purged and charged with hydrogen (1 atm) and stirred overnight. The platinum oxide was removed by filtration and the filtrate was evaporated to give a light yellow solid 11d ($R^{9}$=2-cyclopropylethyl) which was used without further purrification.

To the above crude residue 11d ($R^{9}$=2-cyclopropylethyl) was added 2N NaOH (3.8 mL) and t-butylalcohol (2 mL). The reaction mixture was stirred at rt for 2 h, di-t-butyl dicarbonate (0.62 g, 2.85 mmol) was then added and the mixture stirred overnight. The solvent was removed under vacuum and the resulting residue was diluted with water, then washed with ether. The aqueous layer was acidified with 2N HCl to pH=2.0, extracted twice with ethyl acetate. The combined organic layers were dried over $MgSO_{4}$ and concentrated to give 4-(2-cyclopropylethyl)-piperidine-1,2-dicarboxylic acid 1-tert-butyl ester 11f (P=Boc, $R^{9}$=2-cyclopropylethyl) (0.42 g, 77%) as a clear syrup.

MS (ESPOS): 320.3 [M+Na]$^{+}$; MS (ESNEG): 296.2 [M−H]$^{-}$.

Lincosamide 6b ($R^{2}$=H, $R^{3}$=Cl) was coupled to 4-(2-cyclopropylethyl)-piperidine-1,2-dicarboxylic acid 1-tert-butyl ester 11f (P=Boc, $R^{9}$=2-cyclopropylethyl) as depicted in general method Z to provide the title compound. Intermediate 13a ($R^{20}$=methyl, $R^{21}$=methyl, $R^{9}$=propyl, $P^{2}$=H, $P^{2}$=carboxylic acid-t-butyl ester, m=2) which was deprotected under acidic conditions to provide the title compound.

MS (ESPOS): 451.3 [M+H]$^{+}$.

Example 80

4-Cyclopropylmethyl-piperidine-2-carboxylic acid [2-chloro-1-(3,4,5-trihydroxy-6-methylsulfanyl-tetrahydro-pyran-2-yl)-propyl]-amide

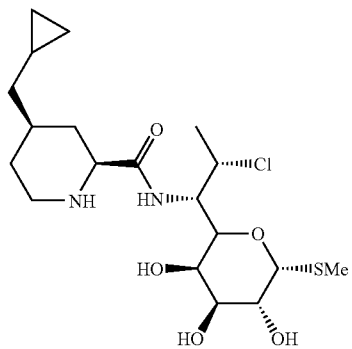

4-Cyclopropylmethylpyridine-2-carboxylic acid, compound 10b (R⁹=cyclopropylmethyl), was made by employing general method O using the starting material 4-Cyclopropylmethylpyridine prepared by alkylation of 4-picoline with cyclopropylbromide by the method described by Osuch et al, *Journal of the American Chemical Society*, 1955, 78, 1723. The modified method is shown below.

To a −78° C. solution of 4-picoline (1.1 g, 11.8 mmol) in THF (5 mL) was added a solution of LDA 2M in THF/heptane/ethylbenzene (Aldrich) (5.9 mL, 11.8 mmol) the resulting reaction mixture was stirred at −78° C. for 3 h then −40° C. for 1 h. Then cyclopropyl bromide (1.43 g, 11.8 mmol) was added at −78° C., let it warm up to room temperature and stirred at room temperature for 1 h. To the reaction mixture was added saturated aqueous NH₄Cl (10 mL) the aqueous phase was extracted with EtOAc (10×2 mL) and the combined organic extracts dried over Na₂SO₄. The solvent was removed and the product 4-Cyclopropylmethylpyridine (0.5 g, 31%) was obtained and used without further purification.

Lincosamide 6b (R²=H, R³=Cl) was coupled to 4-cyclopropylmethylpyridine-2-carboxylic acid 10b (R⁹=cyclopropylmethyl) as in general method AA to provide intermediate 13b (R¹=SMe, R²=Me, R³=H, R⁹=cyclobutylethyl, P¹=H) which was reduced by catalytic hydrogenation to the title compound.

MS (ESPOS): 437.2 [M]⁺.

Example 81

4-(2-Cyclobutyl-ethyl)-piperidine-2-carboxylic acid [2-chloro-1-(3,4,5-trihydroxy-6-methylsulfanyl-tetrahydro-pyran-2-yl)-propyl]-amide

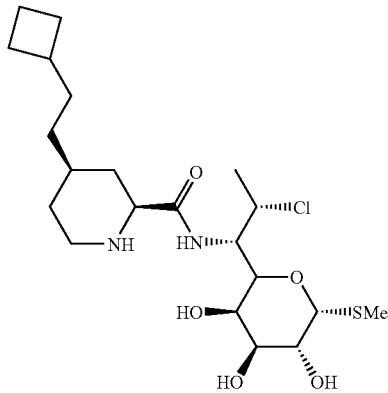

4-(Cyclobutyl-ethyl)-pyridine-2-carboxylic acid, compound 10b (R⁹=cyclobutyl-ethyl), was made by employing general Method O using the starting material 4-(Cyclobutyl-ethyl)-pyridine prepared by alkylation of 4-picoline with bromomethylcyclobutane as described in example 80.

Lincosamide 6b (R²=H, R³=Cl) was coupled to 4-(cyclobutyl-ethyl)-pyridine-2-carboxylic acid 10b (R⁹=cyclobutyl-ethyl) as in general coupling method AA to provide intermediate 13b (R¹=SMe, R²=Me, R³=H, R⁹=cyclobutyl-ethyl, P¹=H) which was reduced by catalytic hydrogenation to the title compound.

MS (ESPOS): 465.2 [M]⁺.

Example 82

4-Cyclobutylmethyl-piperidine-2-carboxylic acid [2-chloro-1-(3,4,5-trihydroxy-6-methylsulfanyl-tetrahydro-pyran-2-yl)-propyl]-amide

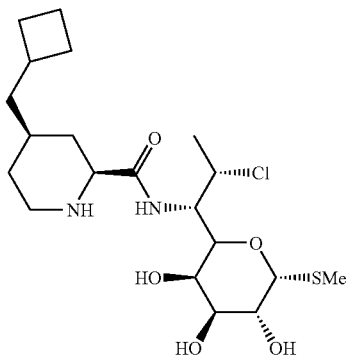

4-Cyclobutylmethylpyridine-2-carboxylic acid, compound 10b (R⁹=4-cyclobutylmethyl) was made by employing general Method O using the starting material 4-cyclobutylmethylpyridine prepared by alkylation of 4-picoline with cyclobutyl bromide as described in example 80.

Lincosamide 6b (R²=H, R³=Cl) was coupled to 4-cyclobutylmethylpyridine-2-carboxylic acid, compound 10b (R⁹=4-cyclobutylmethyl) as in general coupling method AA to provide intermediate 13b (R¹=SMe, R²=Me, R³=H, R⁹=cyclobutylethyl P¹=H) which was reduced by catalytic hydrogenation to the title compound.

MS (ESPOS): 451.2 [M+H]⁺.

Example 83

4-Cyclopropylmethyl-pyrrolidine-2-carboxylic acid [2-chloro-1-(3,4,5-trihydroxy-6-methylsulfanyl-tetrahydro-pyran-2-yl)-propyl]-amide

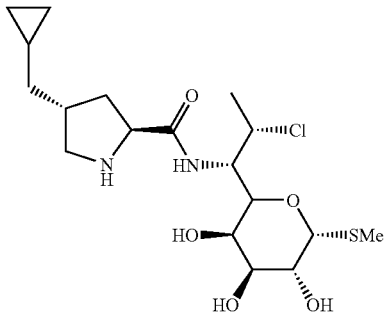

The protected amino acid intermediate (2S,4R)-4-cyclopropylmethyl-pyrrolidine-1,2-dicarboxylic acid-1-tert-butyl ester was prepared by the synthetic sequence described by Goodman et al. *Journal of Organic Chemistry*, 2003, 68, 3923 using cyclopropylmethyl triphenylphosphonium bromide (Aldrich) as the starting material in the wittig olefination step.

Lincosamine 6b (R²=H, R³=Cl) was coupled to (2S,4R)-4-cyclopropyhnethyl-pyrrolidine-1,2-dicarboxylic acid-1-tert-butyl ester as depicted in general coupling scheme 11 to provide intermediate 13a (R¹=SMe, R²=Me, R⁹=cyclopropylmethyl, P¹=H, P²=carboxylic acid-t-butyl ester, m=1) which was deprotected under acidic conditions to provide the title compound.

MS (ESPOS): 423.2 [M+H]+.

Example 84

4-(2-Cyclobutylidene-ethyl)-pyrrolidine-2-carboxylic acid [2-methyl-1-(3,4,5-trihydroxy-6-methylsulfanyl-tetrahydro-pyran-2-yl)-propyl]-amide

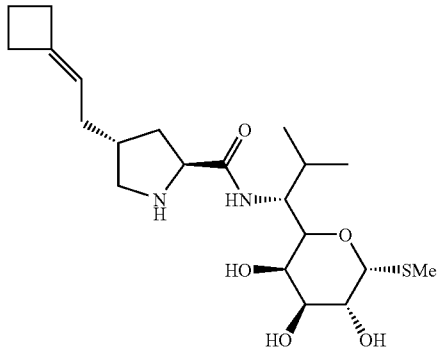

Amino acid intermediate (2S,4R)-4-(2-cyclobutylidene-ethyl)-pyrrolidine-1,2-dicarboxylic acid-1-tert-butyl ester was prepared by general method K by alkylation of pyroglutamic acid ester 7a with (2-bromo-ethylidene)-cyclobutane. The allylic halide (2-bromo-ethylidene)-cyclobutane starting material was prepared from cyclobutanone in two steps as disclosed in U.S. Pat. No. 3,711,555.

Lincosamine 2b ($R^1$=SMe, $R^2$=Me) was coupled to protected amino acid 8c ($R^{9'}$=2-cyclobutylidene-ethyl) to provide intermediate carbamate 13a ($R^1$=SMe, $R^2$=Me, $R^{9'}$=2-cyclobutylidene-ethyl, $P^1$=H, $P^2$=Boc, m=1) which was deprotected under acidic conditions to provide the title compound.

MS (ESPOS): 429.1 [M+H]+.

Example 85

4-(2-Cyclobutylidene-ethyl)-pyrrolidine-2-carboxylic acid [2-chloro-1-(3,4,5-trihydroxy-6-methylsulfanyl-tetrahydro-pyran-2-yl)-propyl]-amide

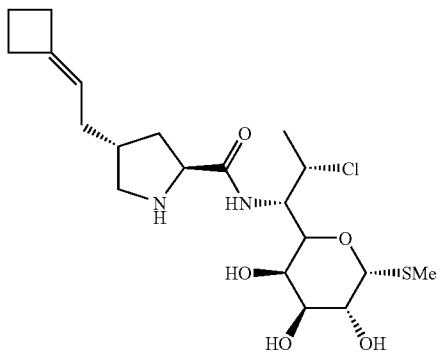

Amino acid intermediate (2S,4R)-4-(2-cyclobutylidene-ethyl)-pyrrolidine-1,2-dicarboxylic acid-1-tert-butyl ester was prepared by general method K by alkylation of pyroglutamic acid ester 7a with (2-bromo-ethylidene)-cyclobutane. The allylic halide (2-bromo-ethylidene)-cyclobutane starting material was prepared from cyclobutanone in two steps as disclosed in U.S. Pat. No. 3,711,555.

Lincosamine 6b ($R^2$=H, $R^3$=Cl) was coupled to protected amino acid 8c ($R^{9'}$=2-cyclobutylidene-ethyl) to provide intermediate carbamate 13a ($R^1$=SMe, $R^2$=Me, $R^{9'}$=2-cyclobutylidene-ethyl, $P^1$=H, $P^2$=Boc, m=1) which was deprotected under acidic conditions to provide the title compound.

MS (ESPOS): 450.1 [M+H]+.

Example 86

4-(2-Cyclobutyl-ethyl)-pyrrolidine-2-carboxylic acid [2-chloro-1-(3,4,5-trihydroxy-6-methylsulfanyl-tetrahydro-pyran-2-yl)-propyl]-amide

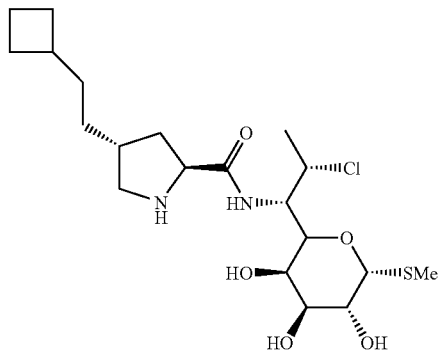

Amino acid intermediate (2S,4R)-4-(2-cyclobutyl-ethyl)-pyrrolidine-1,2-dicarboxylic acid-1-tert-butyl ester was prepared by general method K by alkylation of pyroglutamic acid ester 7a with (2-bromo-ethylidene)-cyclobutane. The allylic halide (2-bromo-ethylidene)cyclobutane starting material was prepared from cyclobutanone in two steps as disclosed in U.S. Pat. No. 3,711,555.

Lincosamine 6b ($R^2$=H, $R^3$=Cl) was coupled to protected amino acid 7d ($R^9$=2-cyclobutyl-ethyl) to provide intermediate carbamate 13a ($R^1$=SMe, $R^2$=Me, $R^9$=cyclobutyl-ethyl, $P^1$=H, $P^2$=Boc, m=1) which was deprotected under acidic conditions to provide the title compound.

MS (ESPOS): 451.2 [M]+.

Example 87

4-(2-Cyclopropyl-ethyl)-pyrrolidine-2-carboxylic acid [2-chloro-1-(3,4,5-trihydroxy-6-methylsulfanyl-tetrahydro-pyran-2-yl)-propyl]-amide

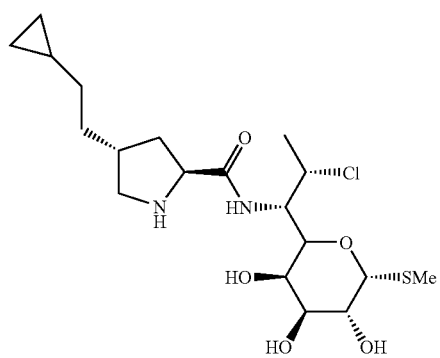

Lincosamine 2b ($R^1$=SMe, $R^2$=Me) was coupled to protected amino acid 8c ($R^9$=2-cyclopropyl-ethyl) prepared by general method M to provide intermediate carbamate 13a ($R^1$=SMe, $R^2$=Me, $R^9$=cyclopropyl-ethyl, $P^1$=H, $P^2$=carboxylic acid-t-butyl ester, m=1) which was deprotected under acidic conditions to provide the title compound.
MS (ESPOS): 437.2 [M+H]⁺.

Example 88

4-Fluoro-1-(2-hydroxy-ethyl)-4-propyl-pyrrolidine-2-carboxylic acid [2-chloro-1-(3,4,5-trihydroxy-6-=methylsulfanyl-tetrahydro-pyran-2-yl)-propyl]-amide

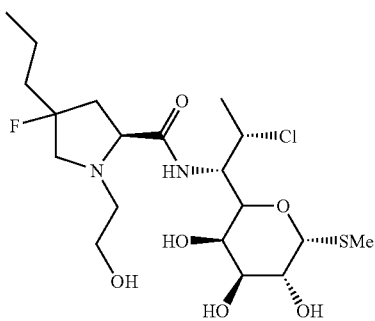

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide 18a (Example 32) was treated with ethylene oxide in methanol as detailed in scheme 19 to furnish the title compound. MS (ESPOS): 473.3 [M+H]⁺.

Example 89

4-Butyl-4-fluoro-piperidine-2-carboxylic acid [2-chloro-1-(3,4,5-trihydroxy-6-methylsulfanyl-tetrahydro-pyran-2-yl)-propyl]-amide

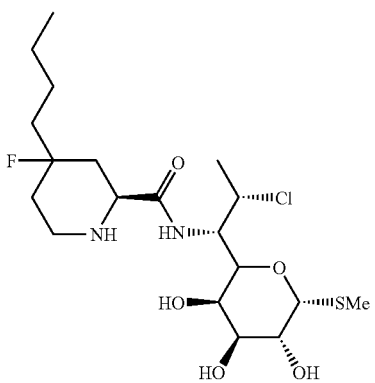

The synthesis of boc-protected 4-Fluoro-4-butyl-piperidine-1,2-dicarboxylic acid 1-tert-butyl ester, 12d (P=Boc, m=2, $R^9$=n-butyl) from the starting material (2S)-4-oxo-piperidine-1,2-dicarboxylic acid 1-tert-butyl ester uses general method Q, depicted in scheme 12 utilizing 1-butyne anion as a four carbon synthon in the 4-ketone alkylation step. Preparation of the starting material, 4-oxo-piperidine-1,2-dicarboxylic acid 1-tert-butyl ester is described by Bousquet, Y.; Anderson, P. C.; Bogri, T.; Duceppe J.; Grenier, L.; Guse, I.; *Tetrahedron*, 1997, 53 15671–15680.

Lincosamide 6b ($R^2$=H, $R^3$=Cl) was coupled to 12d (P=Boc, m=2, $R^9$=butyl) to provide intermediate 13a ($R^2$=H, $R^3$=Cl, $R^9$=butyl, $P^1$=H, $P^2$=Boc, m=2) which was deprotected under acidic conditions to provide the title compound as depicted in general method Z.
MS (ESPOS): 457.0 [M+H]⁺.

Example 90

4-Cyclopropylmethyl-4-fluoro-piperidine-2-carboxylic acid [2-chloro-1-(3,4,5-trihydroxy-6-methylsulfanyl-tetrahydro-pyran-2-yl)-propyl]-amide

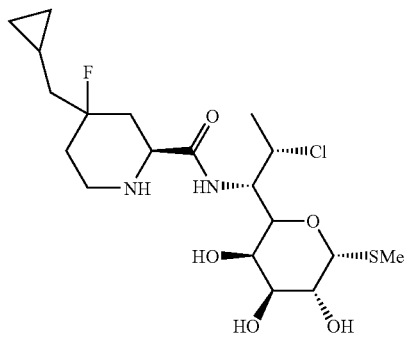

Lincosamide 6b ($R^2$=H, $R^3$=Cl) was coupled to 12d (P=Boc, m=2, $R^9$=cyclopropylmethyl) to provide intermediate 13a ($R^2$=H, $R^3$=Cl, $R^9$=cyclopropylmethyl, $P^1$=H, $P^2$=Boc, m=2) which was deprotected under acidic conditions to provide the title compound as depicted in general method Z.
MS (ESPOS): 455.0 [M+H]⁺.

Example 91

3-Butyl-azetidine-2-carboxylic acid [2-chloro-1-(3,4,5-trihydroxy-6-methylsulfanyl-tetrahydro-pyran-2-yl)-propyl]-amide

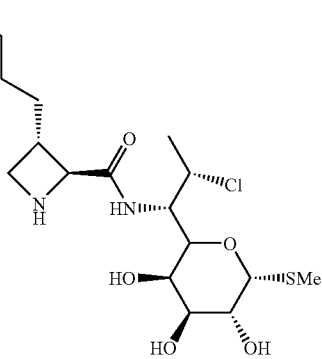

To a solution of azetedine acid 25f ($R^9$=butyl) (52 mg, 0.20 mmol, 1 equiv), 7-Cl MTL 6b ($R^2$=H, $R^3$=Cl) (58 mg, 0.20 mmol, 1 equiv) and HBTU (84 mg, 0.22 mmol, 1.1 equiv) in DMF (2.0 mL) at 23° C. was added DIPEA (88 μL, 0.51 mmol, 2.5 equiv). After stirring for 12 h at 23° C., DMF was removed in vacuo then the residue was partitioned between EtOAc (100 mL) and 1:1 brine: 10% aqueous citric acid (100 mL). The organic layer was separated and washed with 1:1 brine/saturated aqueous NaHCO$_3$ (100 mL), brine (50 mL), dried (MgSO$_4$), filtered and concentrated to furnish 82 mg (0.17 mmol, 84%) 13a ($R^2$=H, $R^3$=Cl, $R^9$=butyl, $P^1$=H, $P^2$=carboxylic acid-t-butyl ester, m=0) as a glassy solid which was used without purification in the next step.

To a solution of carbamate 13a ($R^2$=H, $R^3$=Cl, $R^9$=butyl, $P^1$=H, $P^2$=Boc, m=0) (82 mg, 0.17 mmol, 1 equiv) in 1,2-dichloroethane (10 mL) at 23° C. was added H$_2$O (0.40 mL) followed by TFA (4.0 mL). After stirring for 20 min at 23° C., toluene (50 mL) was added and the resulting solution was concentrated to dryness. The residue was purified by semi-preparative HPLC (Waters Nova-Pak® HR C$_{18}$, 6 µm particle size, 60 Å pore size, 20 mm ID×100 mm, 5–60% acetonitrile in H$_2$O w/0.1% HCl over 30 min, 20 mL/min flow rate) to give 41 mg of title compound as a white solid.

$^1$H NMR (300 MHz, CD$_3$OD) δ 5.30 (d, J=6.0 Hz, 1H), 4.64 (d, J=7.8 Hz, 1H), 4.63–4.52 (m, 2H), 4.29 (d, J=10.2 Hz, 1H), 4.07 (dd, J=5.7, 10.2 Hz, 1H), 4.00 (t, J=6.6 Hz, 1H), 3.82 (d, J=3.3 Hz, 1H), 3.75 (dd, J=8.4, 9.9 Hz, 1H), 3.56 (dd, J=3.3, 10.2 Hz, 1H), 2.92–2.76 (m, 1H), 2.14 (s, 3H), 1.90–1.67 (m, 2H), 1.45 (d, J=6.6 Hz, 3H), 1.44–1.24 (m, 4H), 0.93 (t, J=6.9 Hz, 3H); MS (ESPOS): 411.0 [M+H]$^+$.

Example 92

3-Cyclopropylmethyl-azetidine-2-carboxylic acid [2-chloro-1-(3,4,5-trihydroxy-6-methylsulfanyl-tetrahydro-pyran-2-yl)-propyl]-amide

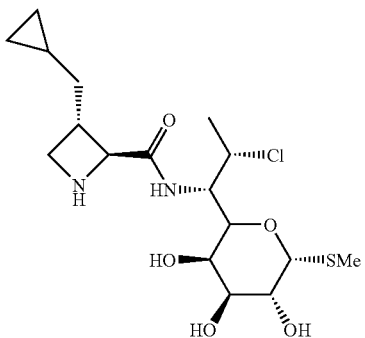

Lincosamine 6b ($R^2$=H, $R^3$=Cl) was coupled to azetedine acid 25f ($R^9$=cyclopropylmethyl) as in general method Z to provide intermediate 13a ($R^2$=H, $R^3$=Cl, $R^9$=cyclopropylmethyl, $P^1$=H, $P^2$=Boc, m=0) which was deprotected under acidic conditions to provide the title compound.

$^1$H NMR (300 MHz, CD$_3$OD) δ 5.30 (d, J=5.7 Hz, 1H), 4.70 (d, J=7.5 Hz, 1H), 4.63–4.54 (m, 2H), 4.29 (d, J=9.9 Hz, 1H), 4.08 (dd, J=5.7, 10.2 Hz, 1H), 4.02 (t, J=9.3 Hz, 1H), 3.88–3.80 (m, 2H), 3.57 (dd, J=3.3, 10.2 Hz, 1H), 3.05–2.91 (m, 1H), 2.14 (s, 3H), 1.90–1.65 (m, 1H), 1.57–1.46 (m, 1H), 1.47 (d, J=6.6 Hz, 3H), 0.80–0.64 (m, 1H), 0.58–0.47 (m, 2H), 0.16–0.10 (m, 2H); MS (ESPOS): 409.2 [M+H]$^+$.

Example 93

3-Propyl-azetidine-2-carboxylic acid [2-chloro-1-(3,4,5-trihydroxy-6-methylsulfanyl-tetrahydro-pyran-2-yl)-propyl]-amide

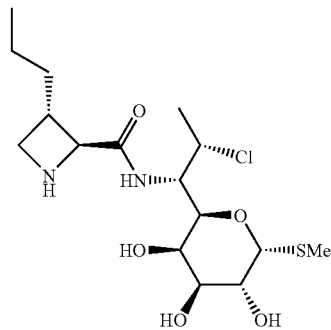

Lincosamine 6b ($R^2$=H, $R^3$=Cl) was coupled to azetedine acid 25f ($R^9$=propyl) as in general method Z to provide intermediate 13a ($R^2$=H, $R^3$=Cl, $R^9$=propyl, $P^1$=H, $P^2$=Boc, m=0) which was deprotected under acidic conditions to provide the title compound.

$^1$H NMR (300 MHz, CD$_3$OD) δ 5.31 (d, J=5.7 Hz, 1H), 4.66 (d, J=7.5 Hz, 1H), 4.63–4.54 (m, 2H), 4.31 (d, J=9.9 Hz, 1H), 4.09 (dd, J=5.4, 10.2 Hz, 1H), 4.03 (t, J=9.6 Hz, 1H), 3.83–3.74 (m, 2H), 3.57 (dd, J=3.3, 10.2 Hz, 1H), 2.95–2.80 (m, 1H), 2.15 (s, 3H), 1.88–1.66 (m, 2H), 1.47 (d, J=6.9 Hz, 3H), 1.46–1.30 (m, 2H), 0.97 (t, J=7.2 Hz, 3H); MS (ESPOS): 397.0 [M+H]$^+$.

Example 94

3-Butyl-1-(2-hydroxy-ethyl)-azetidine-2-carboxylic acid [2-chloro-1-(3,4,5-trihydroxy-6-methylsulfanyl-tetrahydro-pyran-2-yl)-propyl]-amide

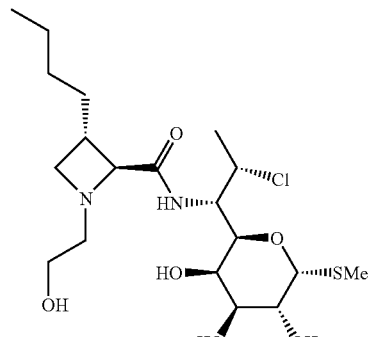

A sample of 3-Butyl-azetidine-2-carboxylic acid [2-chloro-1-(3,4,5-trihydroxy-6-methylsulfanyl-tetrahydro-pyran-2-yl)-propyl]-amide prepared in example 91 was alkylated with ethyleneoxide as depicted in scheme 19 ($R^6$=2-hydroxyethyl) to provide the title compound.

$^1$H NMR (300 MHz, CD$_3$OD) δ 5.30 (d, J=5.4 Hz, 1H), 4.67–4.57 (m, 1H), 4.46–4.37 (m, 1H), 4.29–4.24 (m, 1H), 4.13–4.06 (m, 1H), 3.83–3.78 (m, 1H), 3.67–3.55 (m, 3H), 3.44–3.32 (m, 1H), 2.75–2.57 (m, 2H), 2.44–2.34 (m, 1H), 2.14 (s, 3H), 1.80–1.40 (m, 6H), 1.39–1.20 (m, 5H), 0.95–0.86 (m, 3H); MS (ESPOS): 455.0 [M+H]$^+$.

Example 95

3-Butyl-1-methyl-azetidine-2-carboxylic acid [2-chloro-1-(3,4,5-trihydroxy-6-methylsulfanyl-tetrahydro-pyran-2-yl)-propyl]-amide

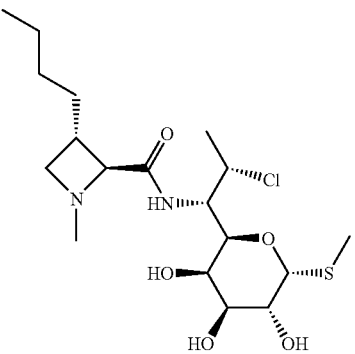

To a solution of Boc-carbamate 25f ($R^9$=butyl) (236 mg, 0.92 mmol, 1 equiv) in aqueous formaldehyde (37%, 2.0 mL) at 23° C. was added formic acid (95%, 1.0 mL). The resulting mixture was heated at reflux for 4 h, then cooled to 23° C.; treated with t-BuOH (5.0 mL) and concentrated. The crude residue was dissolved/suspended in $H_2O$ (15 mL), frozen and lyophilized. The resulting solid was dissolved in 1.0 N HCl (15 mL), filtered and concentrated. The resulting material was dissolved/suspended in $H_2O$ to yield a cloudy suspension that was filtered through a nylon membrane (0.2 μm) and concentrated to give 186 mg of white solid, of which the major component is the desired 3-butyl-1-methyl-azetidine-2-carboxylic acid hydrochloride salt. This material was used without further purification.

MS (ESPOS): 172.3 [M+H].

Lincosamine 6b ($R^2$=H, $R^3$=Cl) was coupled to 3-butyl-1-methyl-azetidine-2-carboxylic acid hydrochloride salt as in general method Z to provide the title compound.

$^1$H NMR (300 MHz, $D_2O$) δ 5.40 (d, J=5.7 Hz, 1H), 4.73 (d, J=7.8 Hz, 1H), 4.66–4.56 (m, 1H), 4.48 (dd, J=1.2, 9.9 Hz, 1H), 4.38–4.27 (m, 2H), 4.11 (dd, J=5.7, 10.5 Hz, 1H), 3.88 (d, J=3.0 Hz, 1H), 3.81 (t, J=9.6 Hz, 1H), 3.67 (dd, J=3.3, 10.5 Hz, 1H), 3.04–2.87 (m, 1H), 2.94 (s, 3H), 2.18 (s, 3H), 1.90–1.68 (m, 2H), 1.44 (d, J=6.9 Hz, 3H), 1.40–1.22. (m, 4H), 0.87 (t, J=6.9 Hz, 3H); MS (ESPOS): 425.3 [M+H]$^+$.

Example 96

3-Pentyl-azetidine-2-carboxylic acid [2-chloro-1-(3,4,5-trihydroxy-6-methylsulfanyl-tetrahydro-pyran-2-yl)-propyl]-amide

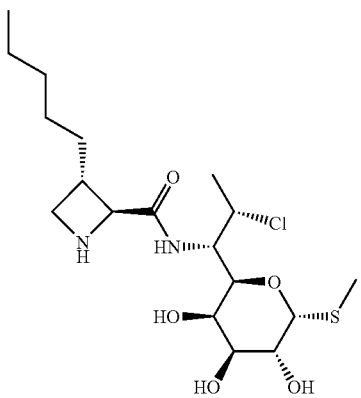

Lincosamine 6b ($R^2$=H, $R^3$=Cl) was coupled to azetedine acid 25f ($R^9$=pentyl) as in general method Z to provide intermediate 13a ($R^2$=H, $R^3$=Cl, $R^9$=pentyl, $P^1$=H, $P^2$=carboxylic acid-t-butyl ester, m=0) which was deprotected under acidic conditions to provide the title compound.

H NMR (300 MHz, $CD_3OD$) δ 5.30 (d, J=5.4 Hz, 1H), 4.63–4.53 (m, 3H), 4.30 (d, J=9.6 Hz, 1H), 4.08 (dd, J=5.7, 10.2 Hz, 1H), 4.00 (t, J=9.6 Hz, 1H), 3.81 (d, J=2.4 Hz, 1H), 3.74 (dd, J=7.8, 9.9 Hz, 1H), 3.57 (dd, J=3.3, 10.2 Hz, 1H), 2.92–2.78 (m, 1H), 2.15 (s, 3H), 1.90–1.67 (m, 2H), 1.46 (d, J=6.9 Hz, 3H), 1.44–1.26 (m, 6H), 0.92 (t, J=7.5 Hz, 3H); MS (ESPOS): 425.0 [M+H]$^+$.

Example 97

3-(3-Methyl-butyl)-azetidine-2-carboxylic acid [2-chloro-1-(3,4,5-trihydroxy-6-methylsulfanyl-tetrahydro-pyran-2-yl)-propyl]-amide

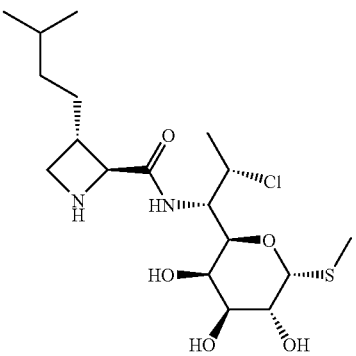

Lincosamine 6b ($R^2$=H, $R^3$=Cl) was coupled to azetedine acid 25f ($R^9$=3-methyl-butyl) as in general method Z to provide intermediate 13a ($R^2$=H, $R^3$=Cl, $R^9$=3-methyl-butyl, $P^1$=H, $P^2$=carboxylic acid-t-butyl ester, m=0) which was deprotected under acidic conditions to provide the title compound.

$^1$H NMR (300 MHz, $CD_3OD$) δ 5.31 (d, J=5.4 Hz, 1H), 4.63–4.53 (m, 2H), 4.30 (d, J=10.5 Hz, 1H), 4.08 (dd, J=5.7, 10.5 Hz, 1H), 4.00 (t, J=9.6 Hz, 1H), 3.81 (d, J=2.4 Hz, 1H), 3.74 (dd, J=8.1, 9.9 Hz, 1H), 3.57 (dd, J=3.3, 10.2 Hz, 1H), 2.88–2.75 (m, 1H), 2.15 (s, 3H), 1.90–1.67 (m, 2H), 1.63–1.50 (m, 1H), 1.46 (d, J=6.9 Hz, 3H), 1.39–1.10 (m, 3H), 0.94 (d, J=1.5 Hz, 3H), 0.92 (d, J=1.5 Hz, 3H); MS (ESPOS): 425.0 [M+H]$^+$.

Example 98

3-(3-Cyclopropyl-propyl)-azetidine-2-carboxylic acid [2-chloro-1-(3,4,5-trihydroxy-6-methylsulfanyl-tetrahydro-pyran-2-yl)-propyl]-amide

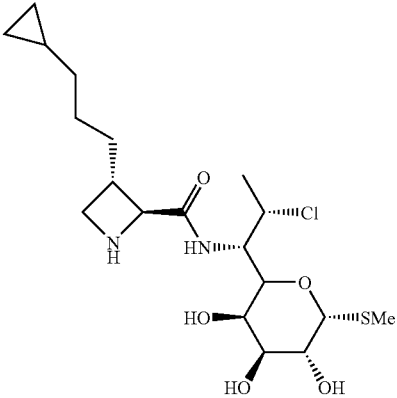

Lincosamine 6b (R²=H, R³=Cl) was coupled to azetedine acid 26f (R⁹=3-cyclopropyl-propyl) as in general method Z to provide intermediate 13a (R²=H, R³=Cl, R⁹=butyl, P¹=H, P²=carboxylic acid-t-butyl ester, m=0) which was deprotected under acidic conditions to provide the title compound.

¹H NMR (300 MHz, CD₃OD) δ 5.29 (d, J=5.7 Hz, 1H), 4.64–4.51 (m, 3H), 4.29 (d, J=10.2 Hz, 1H), 4.07 (dd, J=5.7, 10.2 Hz, 1H), 3.99 (t, J=9.9 Hz, 1H), 3.79 (d, J=3.3 Hz, 1H), 3.74 (dd, J=8.4, 9.9 Hz, 1H), 3.55 (dd, J=3.3, 10.2 Hz, 1H), 2.91–2.77 (m, 1H), 2.13 (s, 3H), 1.93–1.68 (m, 2H), 1.60–1.32 (m, 2H), 1.44 (d, J=6.9 Hz, 3H), 1.24 (q, J=10.2 Hz, 2H), 0.74–0.62 (m, 1H), 0.44–0.36 (m, 2H), 0.04–0.02 (m, 2H); MS (ESPOS): 437.2 [M+H]⁺.

Example 99

3-(3-Cyclobutyl-propyl)-azetidine-2-carboxylic acid [2-chloro-1-(3,4,5-trihydroxy-6-methylsulfanyl-tetrahydro-pyran-2-yl)-propyl]-amide

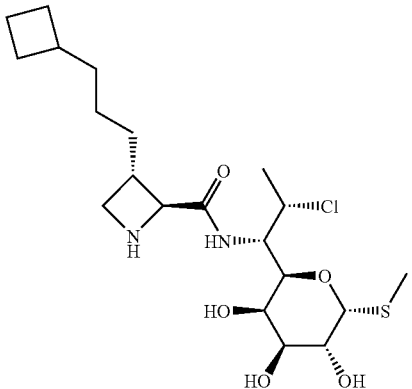

Lincosamine 6b (R²=H, R³=Cl) was coupled to azetedine acid 26f (R⁹=3-cyclobutyl-propyl) as in general method Z to provide intermediate 13a (R²=H, R³=Cl, R⁹=(3-cyclobutyl-propyl), P¹=H, P²=carboxylic acid-t-butyl ester, m=0) which was deprotected under acidic conditions to provide the title compound.

¹H NMR (300 MHz, CD₃OD) δ 5.29 (d, J=5.7 Hz, 1H), 4.63–4.46 (m, 3H), 4.28 (d, J=10.2 Hz, 1H), 4.08 (dd, J=5.4, 10.2 Hz, 1H), 3.89 (t, J=9.0 Hz, 1H), 3.79 (d, J=3.6 Hz, 1H), 3.65 (dd, J=8.1, 9.6 Hz, 1H), 3.56 (dd, J=3.0, 10.2 Hz, 1H), 2.86–2.71 (m, 1H), 2.38–2.20 (m, 1H), 2.14 (s, 3H), 2.10–1.96 (m, 2H), 1.90–1.52 (m, 6H), 1.44 (d, J=6.9 Hz, 3H), 1.44–1.14 (m, 4H). MS (ESPOS): 451.2 [M+H]

Example 100

3-(2-Cyclobutyl-ethyl)-azetidine-2-carboxylic acid [2-chloro-1-(3,4,5-trihydroxy-6-methylsulfanyl-tetrahydro-pyran-2-yl)-propyl]-amide

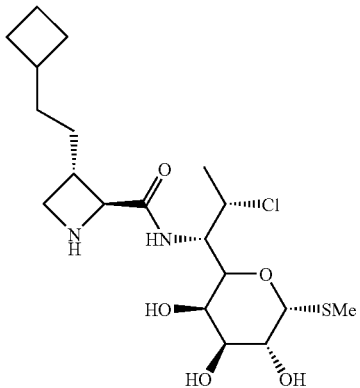

Lincosamine 6b (R²=H, R³=Cl) was coupled to azetedine acid 26f (R⁹=2-cyclobutyl-ethyl) as in general method Z to provide intermediate 13a (R²=H, R³=Cl, R⁹=2-cyclobutyl-ethyl, P¹=H, P²=carboxylic acid-t-butyl ester, m=0) which was deprotected under acidic conditions to provide the title compound.

¹H NMR (300 MHz, CD₃OD) δ 5.29 (d, J=5.7 Hz, 1H), 4.63–4.50 (m, 3H), 4.29 (d, J=10.2 Hz, 1H), 4.08 (dd, J=5.4, 10.2 Hz, 1H), 3.95 (t, J=9.3 Hz, 1H), 3.79 (d, J=3.0 Hz, 1H), 3.69 (dd, J=8.4, 9.9 Hz, 1H), 3.56 (dd, J=3.3, 10.2 Hz, 1H), 2.87–2.72 (m, 1H), 2.38–2.20 (m, 1H), 2.14 (s, 3H), 2.13–2.00 (m, 2H), 1.94–1.55 (m, 6H), 1.54–1.34 (m, 2H), 1.45 (d, J=6.6 Hz, 3H); MS (ESPOS): 437.2 [M+H]⁺.

Example 101

3-(2-Cyclopropyl-ethyl)-azetidine2-carboxylic acid [2-chloro-1-(3,4,5-trihydroxy-6-methylsulfanyl-tetrahydro-pyran-2-yl)-propyl]-amide

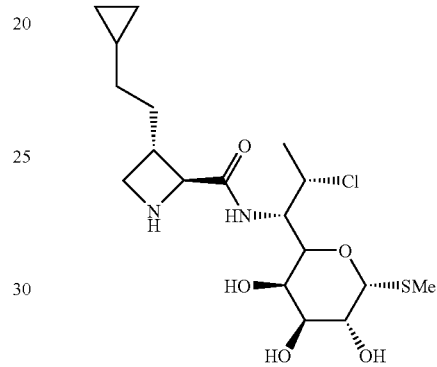

Lincosamine 6b (R²=H, R³=Cl) was coupled to azetedine acid 26f (R⁹=2-cyclopropyl-ethyl) as in general method Z to provide intermediate 13a (R²=H, R³=Cl, R⁹=2-cyclopropyl-ethyl, P¹=H, P²=carboxylic acid-t-butyl ester, m=0) which was deprotected under acidic conditions to provide the title compound.

¹H NMR (300 MHz, CD₃OD) δ 5.29 (d, J=5.7 Hz, 1H), 4.62–4.50 (m, 3H), 4.29 (d, J=10.2 Hz, 1H), 4.07 (dd, J=5.4, 10.2 Hz, 1H), 3.99 (t, J=9.6 Hz, 1H), 3.82–3.71 (m, 2H), 3.56 (dd, J=3.3, 10.2 Hz, 1H), 2.95–2.80 (m, 1H), 2.13 (s, 3H), 2.00–1.77 (m, 2H), 1.44 (d, J=6.9 Hz, 3H), 1.35–1.20 (m, 2H), 0.74–0.62 (m, 1H), 0.48–0.40 (m, 2H), 0.09–0.02 (m, 2H); MS (ESPOS): 423.2 [M+H]⁺.

Example 102

3-(3,3-Difluoropropyl)-azetidine-2-carboxylic acid [2-chloro-1-(3,4,5-trihydroxy-6-methylsulfanyl-tetrahydro-pyran-2-yl)-propyl]-amide

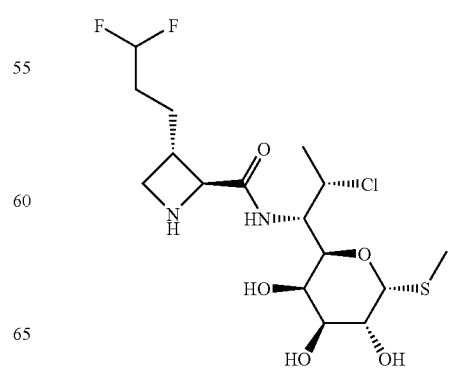

Lincosamine 6b (R²=H, R³=Cl) was coupled to azetedine acid 26f (R⁹=3,3-difluoropropyl) as in general method Z to provide intermediate 13a (R²=H, R³=Cl, R⁹=2-cyclopropyl-ethyl, P¹=H, P²=carboxylic acid-t-butyl ester, m=0) which was deprotected under acidic conditions to provide the title compound.

¹H NMR (300 MHz, CD₃OD) δ 5.93 (t, J=57 Hz, 1H), 5.29 (d, J=5.7 Hz, 1H), 4.64 (d, J=7.5 Hz, 1H), 4.60–4.51 (m, 2H), 4.29 (d, J=10.2 Hz, 1H), 4.07 (dd, J=5.7, 10.2 Hz, 1H), 4.02 (t, J=8.7 Hz, 1H), 3.82–3.74 (m, 2H), 3.55 (dd, J=3.3, 10.5 Hz, 1H), 2.96–2.82 (m, 1H), 2.13 (s, 3H), 2.06–1.76 (m, 4H), 1.44 (d, J=6.9 Hz, 3H); MS (ESPOS): 433.0 [M+H]⁺.

Example 103

4-Pentyl-pyrrolidine-2-carboxylic acid [2-methyl-1-(3,4,5-trihydroxy-6-propyl-tetrahydro-pyran-2-yl)-propyl]-amide

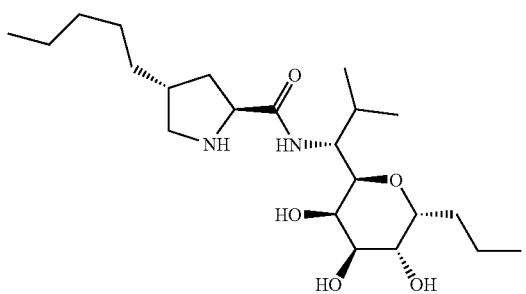

2-Methyl-1-(3,4,5-trihydroxy-tetrahydro-pyran-2-yl)-propylcarbamoyl]-4-pentyl-pyrrolidine-1-carboxylic acid tert-butyl ester. To a solution of 2-(1-Amino-2-methyl-propyl)-6-propyl-tetrahydro-pyran-3,4,5-triol prepared by general method AB (51.9 mg, 0.21 mmol, 1 equiv) in dry DMF (4.5 mL) at 0° C. was added triethylamine (117 µL, 0.84 mmol, 4 equiv), followed by the addition of BSTFA (84 µL, 0.32 mmol, 1.5 equiv). The reaction mixture was stirred at 0° C. for 10 minutes, and then was stirred at RT for 45 minutes. To the reaction mixture was added the protected amino acid 7d as prepared in general method L (R⁹=n-pentyl, P=Boc) (72 mg, 0.25 mmol, 1.2 equiv) and HATU (120 mg, 0.32 mmol, 1.5 equiv). The reaction mixture was stirred at RT for 2 h, evaporated to dryness, taken up in Et₂O (150 mL), washed with 10% citric acid (1x), saturated NaHCO₃ (1x) and brine. The organic layer was dried over MgSO₄ and concentrated to give the crude product (190 mg) as a yellow oil. The residue was taken up DCE (6 mL), trifluoroacetic acid (4 mL) containing water (0.2 mL) was added with stirring. The reaction mixture was stirred at RT for 1 h, then solvent was removed under vacuum by repeated co-evaporation from DCE. The residue was purified by column chromatography on silica 10% 0.25M NH₃ in MeOH/DCM to give the product (38.4 mg, 43%).

¹H NMR (300 MHz, D₂O) δ 4.37 (dd, J=4.7, 9.1, 1), 4.14 (dd, J=3.0, 9.6, 1), 3.97–3.90 (m, 2), 3.70 (d, J=2.8, 1), 3.62–3.51 (m, 3), 2.89 (dd, J=9.1, 11.3, 1), 2.33–2.03 (m, 1), 1.64–1.55 (m, 2), 1.52–1.45 (m, 3), 1.36–1.25 (m, 6), 1.0–0.86 (m, 12); MS (ESPOS): 416.6 [M+H].

Example 104

4-Propyl-piperidine-2-carboxylic acid [2-methyl-1-(3,4,5-trihydroxy-6-propyl-tetrahydro-pyran-2-yl)-propyl]-amide

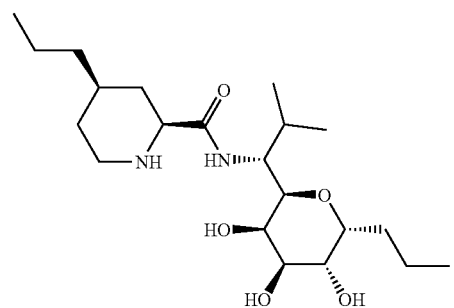

The title compound in example 2 was prepared according to the process described in example 103 using intermediate 10b, prepared in general method O (R⁹=n-propyl).

(ESPOS): 401.7 [M+H]⁺.

Example 105

4-Propyl-piperidine-2-carboxylic acid {2-methyl-1-[3,4,5-trihydroxy-6-(2,2,2-trifluoro-ethylsulfanyl)-tetrahydro-pyran-2-yl]-propyl}-amide

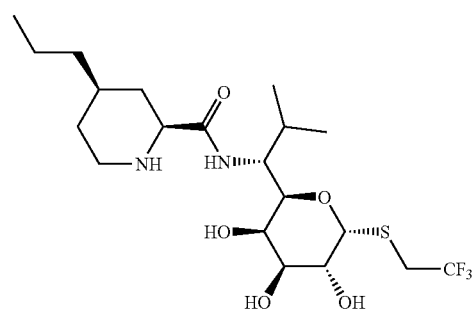

Intermediate 27a prepared in general method * 4-propyl-piperidine-1,2-dicarboxylic acid 1-tert-butyl ester.

MS (ESNEG): 270.2 [M−H]⁻.

The title compound was prepared according to the processes described in general method R and illustrated in Scheme 16, 1,1,1 trifluoroethanethiol was used as the thiol nucleophille. Coupling the protected amino acid intermediate 4-Propyl-piperidine-1,2-dicarboxylic acid 1-tert-butyl ester and deprotection were conducted as in example 103.

(ESPOS): 473.7 [M+H]⁺.

Example 106

4-Pentyl-pyrrolidine-2-carboxylic acid [1-(6-ethoxy-ethyl-3,4,5-trihydroxy-tetrahydro-pyran-2-yl)-2-methyl-propyl]-amide

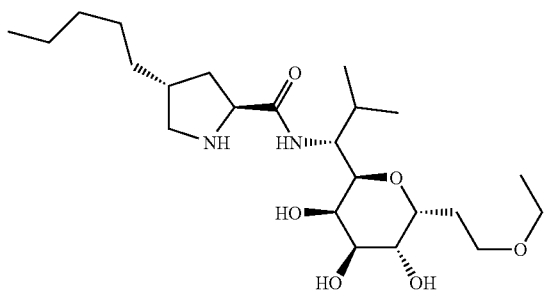

2-[1-(6-Allyl-3,4,5-tris-benzyloxy-tetrahydro-pyran-2-yl)-2-methyl-propylcarbamoyl]-4-pentyl-pyrrolidine-1-carboxylic acid tert-butyl ester. To a stirred solution of building block 15c (650 mg, 1.26 mmol, 1 equiv) and protected amino acid 7d ($R^9$=pentyl, P=Boc) (395 mg, 1.39 mmol, 1.1 equiv) in dry DMF (5.0 mL) at 0° C. was added DIEA (0.88 mL, 5.0 mmol, 4 equiv), followed by the addition of solid HATU (956 mg, 2.52 mmol, 2.0 equiv). The reaction mixture was stirred at RT for 3 h, evaporated to dryness, taken up in ethyl acetate, washed with 10% citric acid (1×), water (1×), saturated $NaHCO_3$ (1×) and brine. The organic layer was dried over $Na_2SO_4$ and concentrated. to give a yellow syrup. The filtrate was concentrated and the residue was purified by column chromatography on silica 10% EtOAc/Hexanes to 20% EtOAc/Hexanes to give the product 2-[1-(6-Allyl-3,4,5-tris-benzyloxy-tetrahydro-pyran-2-yl)-2-methyl-propylcarbainoyl]-4-pentyl-pyrrolidine-1-carboxylic acid tert-butyl ester a colorless oil (897 mg, 89%).

2-{2-Methyl-1-[3,4,5-tris-benzyloxy-6-(2-hydroxy-ethyl)-tetrahydro-pyran-2-yl]-propylcarbamoyl}-4-pentyl-pyrrolidine-1-carboxylic acid tert-butyl ester. A stirred solution of (634 mg, 0.81 mmol, 1 equiv) in DCM (60 mL) at −78° C. was treated with a stream of ozone in oxygen for 20 min a persistant pale blue color was observed. After 30 min excess ozone was removed with a stream of $N_2$ and a solution of DMS (3 mL) in DCM (10 mL) was added, the solution allowed to warm to RT overnight. The solution was evaporated to driness and the residue dissolved in EtOH (50 mL) cooled to 0° C. and treated with $NaBH_4$ (300 mg 8.1 mmol, 10 equiv) after 1 h excess $NaBH_4$ was destroyed by acidifying the reaction mixture the solvent was removed and the crude product purified by column chromatography on silica 20% EtOAc/Hexanes to give the alcohol product (304 mg, 47%).

2-{2-Methyl-1-[3,4,5-tris-benzyloxy-6-(2-ethoxy-ethyl)-tetrahydro-pyran-2-yl]-propylcarbamoyl}-4-pentyl-pyrrolidine-1-carboxylic acid tert-butyl ester. To a stirred solution of washed NaH (4.4 mg 0.183 mmol, 1 equiv) in THF (0.8 mL) at 0° C. was added alcohol intermediate 2-{2-Methyl-1-[3,4,5-tris-benzyloxy-6-(2-hydroxy-ethyl)-tetrahydro-pyran-2-yl]-propylcarbamoyl}-4-pentyl-pyrrolidine-1-carboxylic acid tert-butyl ester (144 mg, 0.183 mmol, 1 equiv) after 10 min EtI (73 µL, 0.92 mmol, 5.0 equiv) was added and the reaction mixture stirred overnight. The reaction mixture evaporated to dryness, The filtrate was concentrated and the residue was purified by preparative 30% EtOAc/Hexanes to give the product 2-{2-Methyl-1-[3,4,5-tris-benzyloxy-6-(2-ethoxy-ethyl)-tetrahydro-pyran-2-yl]-propylcarbamoyl}-4-pentyl-pyrrolidine-1-carboxylic acid tert-butyl ester (33.8 mg 22%) a colorless oil.

4-Pentyl-pyrrolidine-2-carboxylic acid [1-(6-ethoxymethyl-3,4,5-trihydroxy-tetrahydro-pyran-2-yl)-2-methyl-propyl]-amide. 2-{2-Methyl-1-[3,4,5-tris-benzyloxy-6-(2-ethoxy-ethyl)-tetrahydro-pyran-2-yl]-propylcarbamoyl}-4-pentyl-pyrrolidine-1-carboxylic acid tert-butyl ester (33.8 mg) and degussa 50% w/w wet 10% palladium/carbon (80 mg) suspended in MeOH (3 mL) was stirred 20 h under 1 atm pressure $H_2$. The reaction mixture was filtered through Celite evaporated to driness to provide the crude product which was purified by column chromatography on silica 3% to 5% MeOH/DCM to give the boc protected ether product (19 mg) which was taken up in DCE (1 mL), trifluoroacetic acid (1 mL) containing water (0.05 mL) was added with stirring. The reaction mixture was stirred at RT for 1 h, then solvent was removed under vacuum by repeated co-evaporation from DCE. Lyophylization of the TFA salt from 1:1 MeCN/water containing excess dilute HCl gave the title compound (13.0 mg 66%).

$^1$H NMR (300 MHz, $D_2O$) δ 4.47–4.38 (m, 1), 4.21–4.16 (m, 1), 4.11–4.06 (m, 1), 3.96 (dd, J=6.3, 9.6, 1), 3.81 (s, 1), 3.61–3.50 (m, 7), 2.92 (dd, J=9.9, 9.9, 1), 2.33–1.98 (m, 7), 1.96–1.82 (m, 1), 1.47–1.33 (m, 11), 1.18 (t, J=6.9, 3), 0.97–0.89 (m, 12); MS (ESPOS): 446.4 [M+H].

Example 107

1-(2-Hydroxy-ethyl)-4-pentyl-pyrrolidine-2-carboxylic acid [2-methyl-1-(3,4,5-trihydroxy-6-propyl-tetrahydro-pyran-2-yl)-propyl]-amide

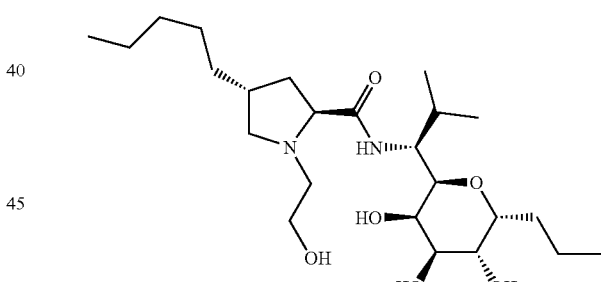

The title compound was prepared according to the process illustrated in Scheme 19. Ethylene oxide was used as the alkylating agent. To a stirred solution of 4-Pentyl-pyrrolidine-2-carboxylic acid [2-methyl-1-(3,4,5-trihydroxy-6-propyl-tetrahydro-pyran-2-yl)-propyl]-amide (example 103) (12.0 mg 0.029 mmol, 1 equiv) and TEA (100 µL) in MeOH (2 mL) at 0° C. was added condensed ethylene oxide (200 µL) was added and the reaction mixture stirred 48 h. The reaction mixture evaporated to dryness, and the resulting residue was purified by column chromatography on silica 20% 0.25M $NH_3$ in MeOH/DCM to give the crude N alkylated product. The crude product was taken up in $Et_2O$, filtered and the filtrate treated with 2M HCl in $Et_2O$, the precipetated HCl salt was collected washed with $Et_2O$ and lyophylized to give the title compound as a colorless powder (4.4 mg 34%).

MS (ESPOS): 473.6 $[M+H]^+$.

Example 108

4-Pentyl-pyrrolidine-2-carboxylic acid [2-methyl-1-(3,4,5-trihydroxy-tetrahydro-pyran-2-yl)-propyl]-amide

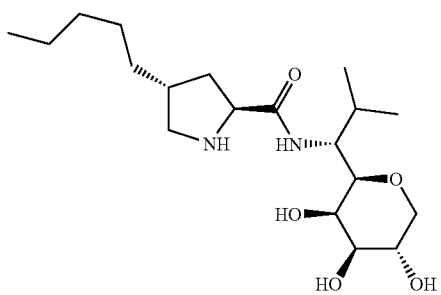

2-{2-Methyl-1-[3,4,5-tris-hydroxy-tetrahydro-pyran-2-yl]-propylcarbamoyl}-4-pentyl-pyrrolidine-1-carboxylic acid tert-butyl ester. To a stirred solution of damp Raney nickel R1 (300 mg) suspended in EtOH (5 mL) under $N_2$ was added a solution of 1-(2-(S)-4-(R)-n-pentylpyrrolidin-2-yl)-N-{1-(R)-[2-(S)-3-(S), 4-(S),5-(R)-trihydroxy-6-(R)-(methylthio)tetrahydropyran-2-yl]-2-methylprop-1-yl}acetamide. (85.0 mg 0.164 mmol, 1 equiv) in EtOH (5 mL). The reaction mixture was refluxed 2 h cooled to RT, filtered through Celite and evaporated to driness to provide the crude product (66 mg) which was purified by column chromatography on silica 3% MeOH/DCM to give the N-Boc protected des-thiomethyl product (42.7 mg 55%).

TLC $R_f$=0.27 (10% MeOH/DCM); MS (ESPOS): 473.6 $[M+H]^+$, (ESNEG): 507.5 [M+HCl].

4-Pentyl-pyrrolidine-2-carboxylic acid [2-methyl-1-(3,4,5-trihydroxy-tetrahydro-pyran-2-yl)-propyl]-amide. N-Boc protected product des-thiomethyl product was taken up DCE (5 mL), trifluoroacetic acid (5 mL) containing water (0.1 mL) was added with stirring. The reaction mixture was stirred at RT for 40 min, then solvent was removed under vacuum by repeated co-evaporation from DCE. The residue was dissolved in 1:1 MeCN/water cooled to 0° C. and 1M HCl (0.5 mL) was added, the solution was filtered and lyophylized to give the title compound (26 mg, 43%) as a colorless powder.

TLC ($CHCl_3$:MeOH:32% aq. AcOH) $R_f$=0.58; MS (ES-POS) 387.3 $[M+H]^+$.

Examples 109–127, 142, and 143 may be made according to the methods described herein.

Example 109

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide

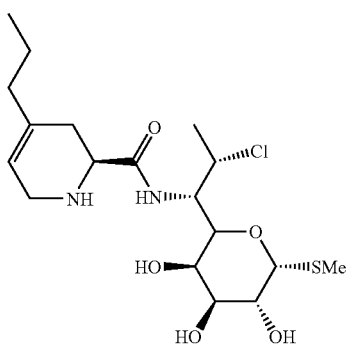

Example 110

5-Propyl-azepane-2-carboxylic acid [2-chloro-1-(3,4,5-trihydroxy-6-methylsulfanyl-tetrahydro-pyran-2-yl)-propyl]-amide

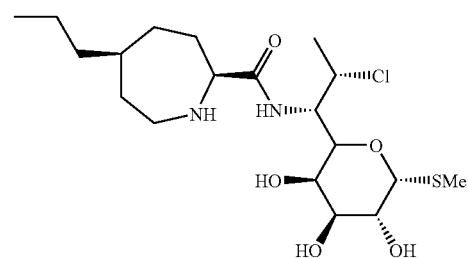

Example 111

5-Propyl-azepane-2-carboxylic acid [2-methyl-1-(3,4,5-trihydroxy-6-isopropylsulfanyl-tetrahydro-pyran-2-yl)-propyl]-amide

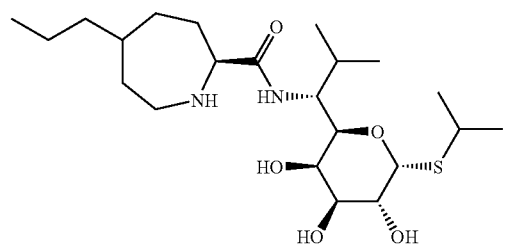

Example 112

5-Propyl-azepane-2-carboxylic acid [1-(6-tert-butyl-sulfanyl-3,4,5-trihydroxy-tetrahydro-pyran-2-yl)-2-methyl-propyl]-amide

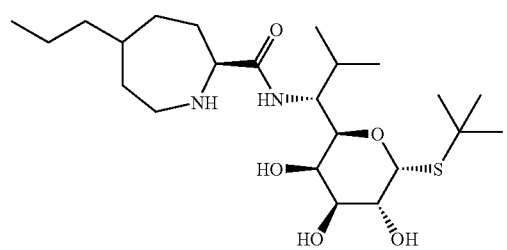

Example 113

5-Propyl-azepane-2-carboxylic acid [(4-chloro-phenyl)-(3,4,5-trihydroxy-6-methylsulfanyl-tetrahydro-pyran-2-yl)-methyl]-amide

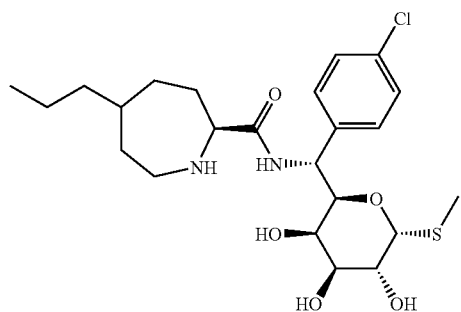

Example 114

4-Pentyl-pyrrolidine-2-carboxylic acid [2-methyl-1-(3,4,5-trihydroxy-6-propyl-tetrahydro-pyran-2-yl)-propyl]-amide

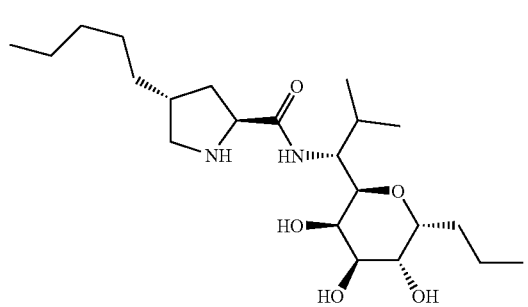

Example 115

4-Pentyl-pyrrolidine-2-carboxylic acid [1-(6-butoxy-3,4,5-trihydroxy-tetrahydro-pyran-2-yl)-2-methyl-propyl]-amide

Example 116

4-Butyl-1-methyl-pyrrolidine-2-carboxylic acid [2-methyl-1-(3,4,5-trihydroxy-6-propyl-tetrahydro-pyran-2-yl)-propyl]-amide

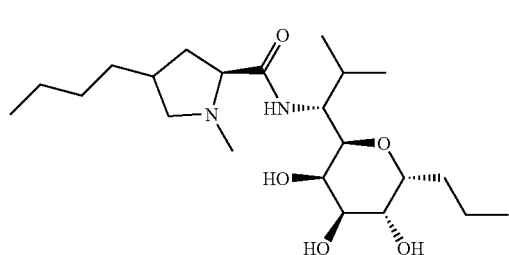

Example 117

Phosphoric acid mono-(4,5-dihydroxy-6-{2-methyl-1-[(4-pentyl-pyrrolidine-2-carbonyl)-amino]-propyl}2-propyl-tetrahydro-pyran-3-yl) ester

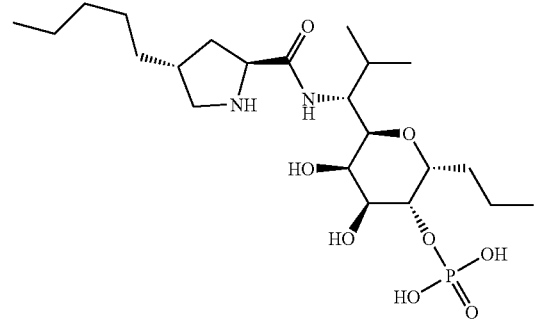

Example 118

Hexadecanoic acid 4,5-dihydroxy-6-{2-methyl-1-[(4-pentyl-pyrrolidine-2-carbonyl)-amino]-propyl}-2-propyl-tetrahydro-pyran-3-yl ester

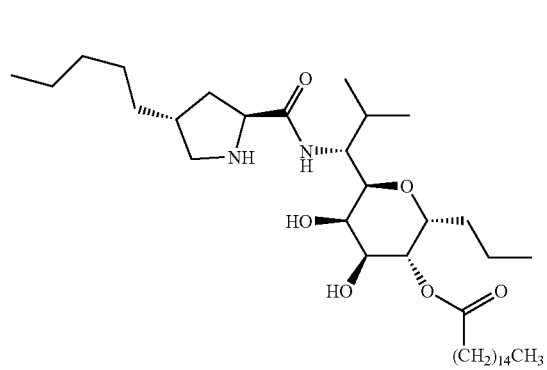

Example 119

Phosphoric acid mono-(4,5-dihydroxy-6-{2-methyl-1-[(4-propyl-pyrrolidine-2-carbonyl)-amino]-propyl}2-propyl-tetrahydro-pyran-3-yl) ester

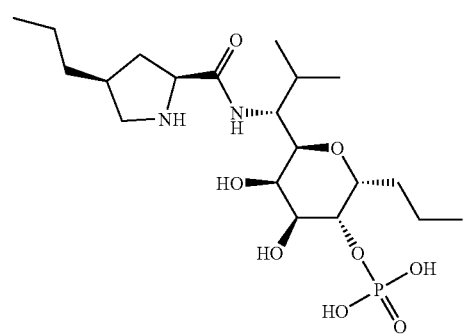

Example 120

Hexadecanoic acid 4,5-dihydroxy-6-{2-methyl-1-[(4-propyl-pyrrolidine-2-carbonyl)-amino]-propyl}-2-propyl-tetrahydro-pyran-3-yl ester

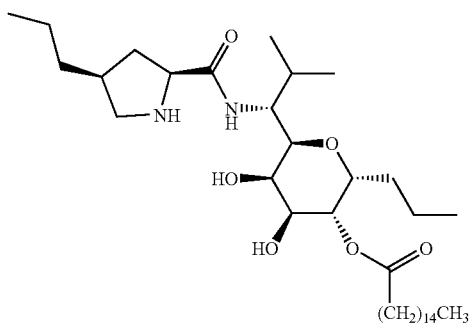

Example 121

1-(5-Methyl-2-oxo-[1,3]dioxol-4-ylmethyl)-4-pentyl-pyrrolidine-2-carboxylic acid [2-methyl-1-(3,4,5-trihydroxy-6-propyl-tetrahydro-pyran-2-yl)-propyl]-amide

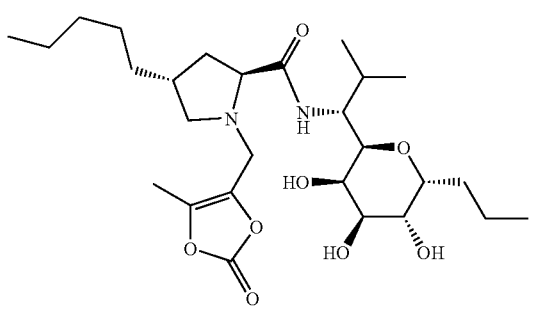

Example 122

2-[2-Methyl-1-(3,4,5-trihydroxy-6-propyl-tetrahydro-pyran-2-yl)-propylcarbamoyl]-4-pentyl-pyrrolidine-1-carboxylic acid 5-methyl-2-oxo-[1,3]dioxol-4-ylmethyl ester

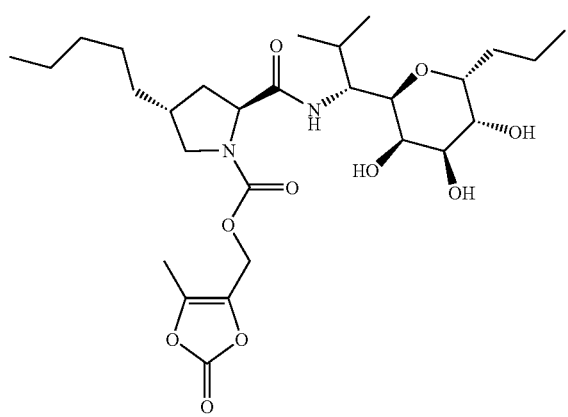

Example 123

1-(5-Methyl-2-oxo-[1,3]dioxol-4-ylmethyl)-4-propyl-pyrrolidine-2-carboxylic acid [2-methyl-1-(3,4,5-trihydroxy-6-propyl-tetrahydro-pyran-2-yl)-propyl]-amide

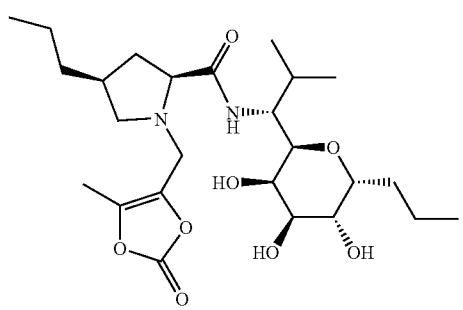

Example 124

2-[2-Methyl-1-(3,4,5-trihydroxy-6-propyl-tetrahydro-pyran-2-yl)-propylcarbamoyl]-4-propyl-pyrrolidine-1-carboxylic acid 5-methyl-2-oxo-[1,3]dioxol-4-ylmethyl ester

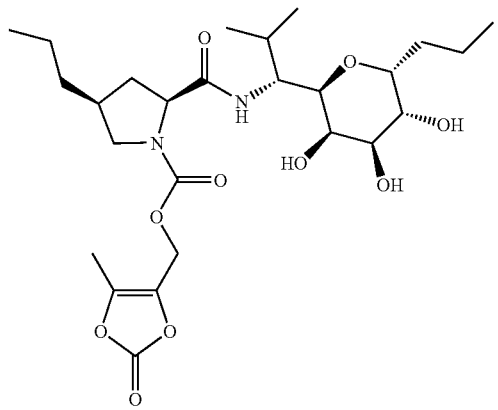

Example 125

4-Propyl-pyrrolidine-2-carboxylic acid {2-methyl-1-[3,4,5-trihydroxy-6-(2-hydroxy-ethyl)-tetrahydro-pyran-2-yl]-propyl}-amide

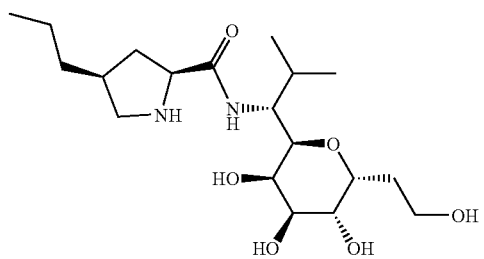

Example 126

4-Propyl-pyrrolidine-2-carboxylic acid {2-methyl-1-[3,4,5-trihydroxy-6-(3-hydroxy-propyl)-tetrahydro-pyran-2-yl]-propyl}-amide

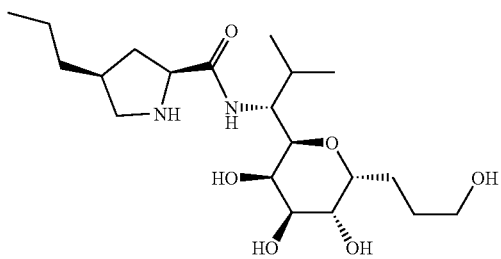

Example 127

4-Propyl-pyrrolidine-2-carboxylic acid [2-methyl-1-(3,4,5-trihydroxy-6-hydroxymethyl-tetrahydro-pyran-2-yl)-propyl]-amide

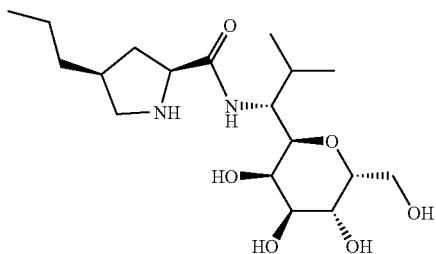

Example 142

4-Propyl-pyrrolidine-2-carboxylic acid {2-methyl-1-[3,4,5-trihydroxy-6-(2-methylsulfanyl-ethyl)-tetrahydro-pyran-2-yl]-propyl}-amide

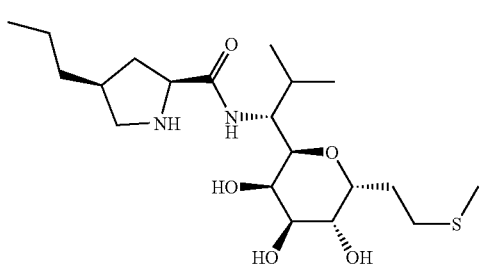

Example 143

4-Propyl-pyrrolidine-2-carboxylic acid [1-(6-cyclopropylmethyl-3,4,5-trihydroxy-tetrahydro-pyran-2-yl)-2-methyl-propyl]-amide

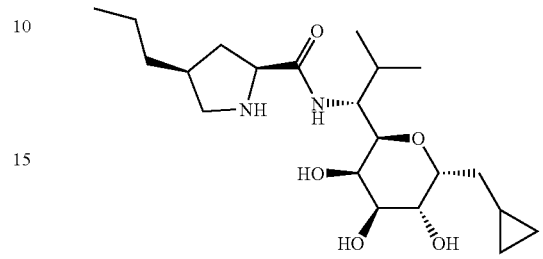

Specific prodrug examples 128–141 below are prepared from the respective parent compounds (see above) using methods as described hereinabove.

Example 128

Phosphoric acid mono-(6-{2-chloro-1-[(5-propyl-azepane-2-carbonyl)-amino]-propyl}-4,5-dihydroxy-2-methylsulfanyl-tetrahydro-pyran-3-yl) ester

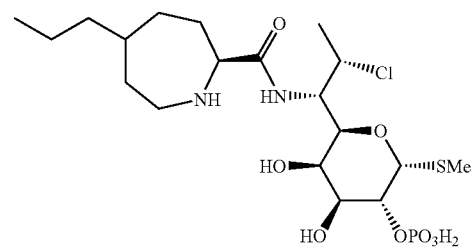

Example 129

Hexadecanoic acid 6-{2-chloro-1-[(5-propyl-azepane-2-carbonyl)-amino]-propyl}-4,5-dihydroxy-2-methylsulfanyl-tetrahydro-pyran-3-yl ester

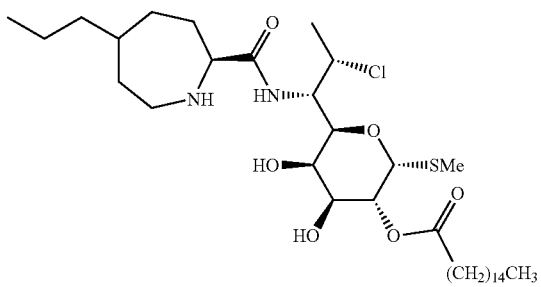

Example 130

Phosphoric acid mono-(6-{2-chloro-1-[(5-fluoro-5-propyl-azepane-2-carbonyl)-amino]-propyl}-4,5-dihydroxy-2-methylsulfanyl-tetrahydro-pyran-3-yl) ester

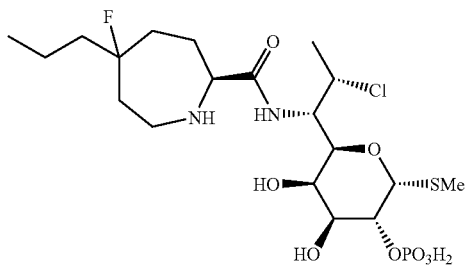

Example 131

Hexadecanoic acid 6-{2-chloro-1-[(5-fluoro-5-propyl-azepane-2-carbonyl)-amino]-propyl}-4,5-dihydroxy-2-methylsulfanyl-tetrahydro-pyran-3-yl ester

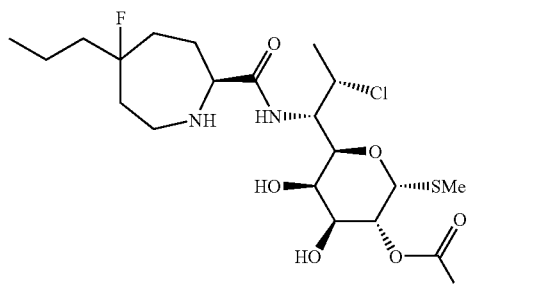

Example 132

2-[2-Chloro-1-(3,4,5-trihydroxy-6-methylsulfanyl-tetrahydro-pyran-2-yl)propylcarbamoyl]-5-fluoro-5-propyl-azepane-1-carboxylic acid 5-methyl-2-oxo-[1,3]dioxol-4-ylmethyl ester

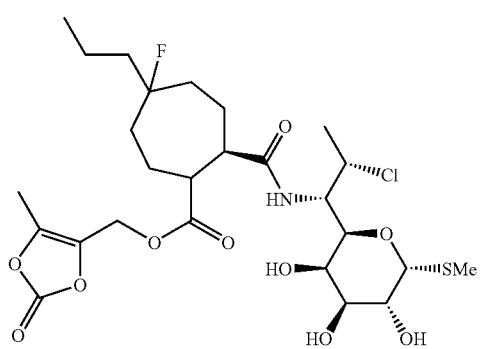

Example 133

5-Fluoro-1-(5-methyl-2-oxo-[1,3]dioxol-4-ylmethyl)-5-propyl-azepane-2-carboxylic acid [2-chloro-1-(3,4,5-trihydroxy-6-methylsulfanyl-tetrahydro-pyran-2-yl)-propyl]-amide

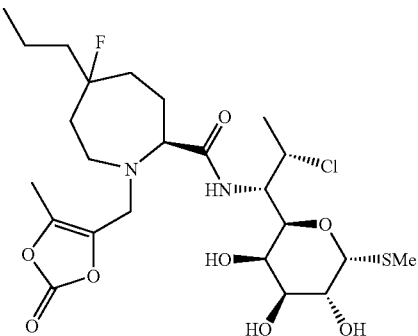

Example 134

5-Cyclopropylmethyl-1-(5-methyl-2-oxo-[1,3]dioxol-4-ylmethyl)-azepane-2-carboxylic acid [2-chloro-1-(3,4,5-trihydroxy-6-methylsulfanyl-tetrahydro-pyran-2-yl)-propyl]-amide

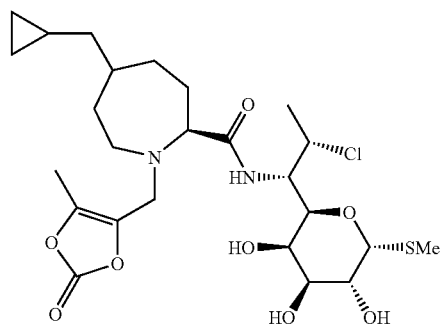

Example 135

2-[2-Chloro-1-(3,4,5-trihydroxy-6-methylsulfanyl-tetrahydro-pyran-2-yl)-propylcarbamoyl]-5-cyclopropylmethyl-azepane-1-carboxylic acid 5-methyl-2-oxo-[1,3]dioxol-4-ylmethyl ester

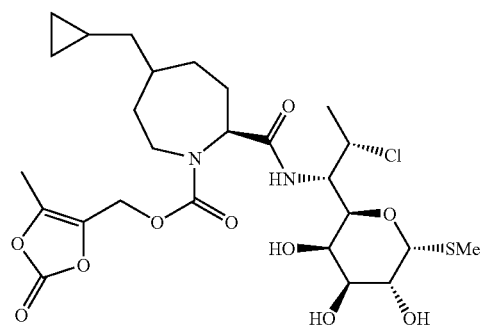

Example 136

Hexadecanoic acid 6-{2-chloro-1-[(5-cyclopropylmethyl-azepane-2-carbonyl)-amino]-propyl}-4,5-dihydroxy-2-methylsulfanyl-tetrahydro-pyran-3-yl ester

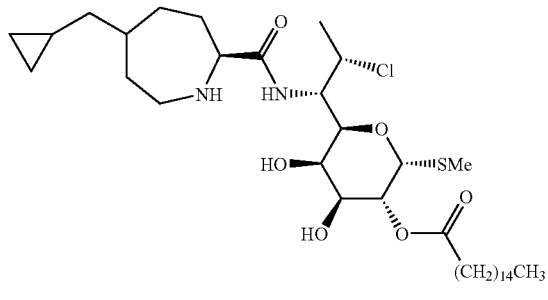

Example 137

Phosphoric acid mono-(6-{2-chloro-1-[(5-cyclopropylmethyl-azepane-2-carbonyl)-amino]-propyl}-4,5-dihydroxy-2-methylsulfanyl-tetrahydro-pyran-3-yl) ester

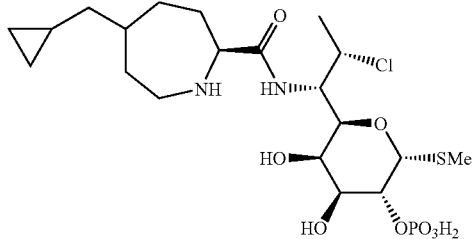

Example 138

Hexadecanoic acid 6-{2-chloro-1-[(4-fluoro-4-propyl-piperidine-2-carbonyl)-amino]-propyl}-4,5-dihydroxy-2-methylsulfanyl-tetrahydro-pyran-3-yl ester

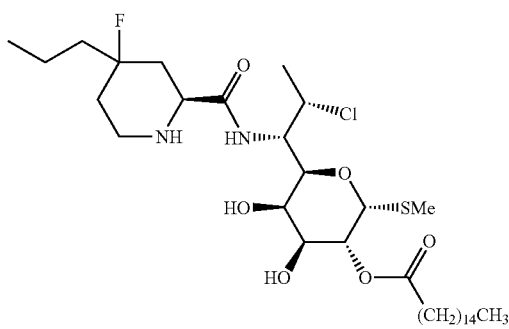

Example 139

Phosphoric acid mono-(6-{2-chloro-1-[(4-fluoro-4-propyl-piperidine-2-carbonyl)-amino]-propyl}-4,5-dihydroxy-2-methylsulfanyl-tetrahydro-pyran-3-yl) ester

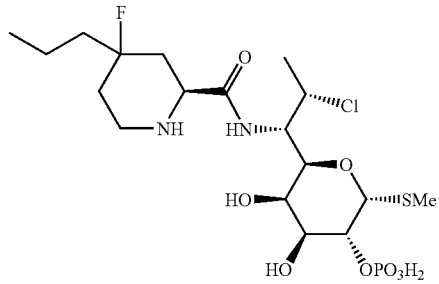

Example 140

2-[2-Chloro-1-(3,4,5-trihydroxy-6-methylsulfanyl-tetrahydro-pyran-2-yl)-propylcarbamoyl]-4-fluoro-4-propyl-piperidine-1-carboxylic acid 5-methyl-2-oxo-[1,3]dioxol-4-ylmethyl ester

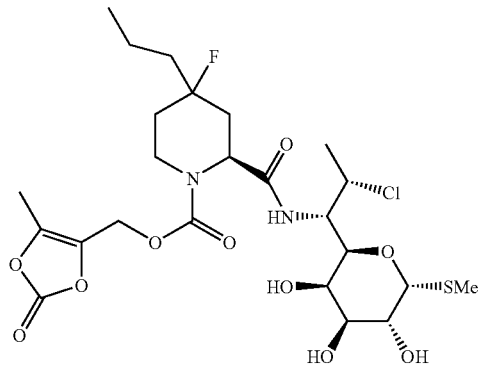

Example 141

4-Fluoro-1-(5-methyl-2-oxo-[1,3]dioxol-4-ylmethyl)-4-propyl-piperidine-2-carboxylic acid [2-chloro-1-(3,4,5-trihydroxy-6-methylsulfanyl-tetrahydro-pyran-2-yl)-propyl]-amide

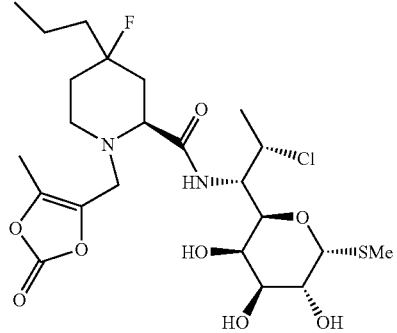

Example A

Susceptibility Testing

Compounds were tested following the microdilution method of NCCLS (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa. 2000; National Committee for Clinical Laboratory Standards. Methods for antimicrobial susceptibility testing of anaerobic bacteria; Approved standard—fifth edition. NCCLS document M11-A4, NCCLS, Wayne, Pa. 2001). Assays were performed in sterile plastic 96-well microtiter trays with round bottom wells (Greiner).

Compound Preparation

Stock solutions of test compounds and control antibiotics are prepared at 10 mg/ml in DMSO. Serial 2-fold dilutions of each drug are performed in a microtiter plate across each row using DMSO as solvent at 100-fold the desired final concentration. Wells in columns #1–11 contain drug and column #12 was kept as a growth control for the organism with no drug. Each well in the mother plate is diluted with sterile deionized water, mixed, and volumes of 10 µl distributed to each well in the resulting assay plates.

Preparation of Inoculum

Stock cultures were prepared using the Microbank™ method (Pro-Lab Diagnostics) and stored at −80° C. To propagate aerobic strains, one bead was removed from the frozen vial and aseptically streaked onto Trypticase Soy Agar (Difco), Chocolate Agar (Remel) or Blood Agar (Remel), which were incubated at 35° C. overnight. Anaerobes were cultivated in Brucella Agar (Remel) supplemented with hemin and vitamin K and incubated in anaerobiosis using an Anaerobic Jar (Mitsubishi) at 35° C. for 24 to 48 h. Standardized inocula were prepared using the direct colony suspension method according to NCCLS guidelines (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa. 2000; National Committee for Clinical Laboratory Standards. Methods for antimicrobial susceptibility testing of anaerobic bacteria; Approved standard—fifth edition. NCCLS document M11-A4, NCCLS, Wayne, Pa. 2001). Isolated colonies were selected from an 18–24 hr agar plate and resuspended in 0.9% sterile saline to match a 0.5 McFarland turbidity standard. The suspension was used within 15 minutes of preparation.

| | |
|---|---|
| Streptococcus pneumoniae VSPN1001 | Streptococcus pneumoniae ATCC 49619 |
| Streptococcus pneumoniae VSPN3026 | Streptococcus pneumoniae R6x |
| Streptococcus pneumoniae VSPN4054 | Streptococcus pneumoniae 488K |
| Streptococcus pneumoniae VSPN4021 | Streptococcus pneumoniae 9 |
| Staphylococcus aureus VSAU1017 | Staphylococcus aureus Smith |
| Staphylococcus aureus VSAU1003 | Staphylococcus aureus ATCC 25923 |
| Staphylococcus aureus VSAU4020 | Staphylococcus aureus 125 |
| Staphylococcus aureus VSAU4048 | Staphylococcus aureus 85-EPI |
| Staphylococcus aureus VSAU4065 | Staphylococcus aureus VSAU4065 |
| Staphylococcus epidermidis VSEP1001 | Staphylococcus epidermidis ATCC 12228 |
| Enterococcus faecalis VEFL1003 | Enterococcus faecalis ATCC 51299 |
| Enterococcus faecium VEFA1005 | Enterococcus faecium BM4147.1 |
| Haemophilus influenzae VHIN1003 | Haemophilus influenzae ATCC 49766 |
| Haemophilus influenzae VHIN1004 | Haemophilus influenzae ATCC 31517 |
| Haemophilus influenzae VHIN1005 acr | Haemophilus influenzae LS-2 |
| Moraxella catarrhalis VMCA1001 | Moraxella catarrhalis ATCC 25238 |
| Escherichia coli VECO2096 | Escherichia coli MG1655 |
| Escherichia coli VECO2526 tolC | Escherichia coli MG1655 tolC |
| Bacteroides fragilis VBFR1001 | Bacteroides fragilis ATCC 25285 |
| Bacteroides thetaiotaomicron VBTH 1001 | Bacteroides thetaiotaomicron ATCC #29741 |
| Clostridium difficile VCDI1001 | Clostridium difficile ATCC 9689 |

Preparation of Assay Plates for MICs Preparation of Assay Plates for MICs

Media were prepared at 1.1× concentration. Mueller-Hinton Broth MHB (Difco) supplemented with Ca++ and Mg++ as recommended by NCCLS, MHB supplemented with 5% horse lysed blood, HTM Broth (Remel), or Brucella broth (Remel) supplemented with hemin and vitamin K. For each organism, the standardized suspension was diluted into appropriate growth medium in a sterile reservoir. After mixing, wells in the drug-containing assay plates were inoculated with a volume of 90 µl. Thus, for each MIC determination, each well contains a final volume of 100 µl with an inoculum size of approximately 5*105 cfu/ml and no more than 1% DMSO.

Interpretation of MIC

The completed microtiter plates were incubated 16–20 h at 35° C. in ambient air for aerobes, and at 35° C. for 46–48 h or in an anaerobe jar (Mitsubishi) for anaerobes. Optical density of each well was determined at 600 nm using a VersaMax Microplate reader (Molecular Devices, Sunnyvale, Calif.). The MIC was defined as the lowest drug concentration causing complete suppression of visible bacterial growth.

Example 47 isomer I and Example 47 isomer II possessed in vitro potency against the Gram negative organism *Haemophilus influenzae* with an MIC≦4 µg/mL. Examples 47 isomers 1 and 2 further displayed an MIC of 0.5 µg/mL against *H. influenzae* strain ATCC 31517, compared with clindamycin, which displayed an MIC of 8 µg/mL against *H. influenzae* strain ATCC 31517.

Example B

Efficacy in Murine *S. aureus* Septicemia

Efficacy studies were performed in an *S. aureus* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995. Antimicrobial activity of MDL 63,246, a new semisynthetic glycopeptide antibiotic Antimicrob Agents Chemother. 39:1580–1588.; Misiek, M., T. A. Pursiano, F. Leitner, and K. E. Price 1973. Microbiological properties of a new cephalosporin, BL-S 339: 7-(phenylacetimidoyl-aminoacetamido)-3-(2-methyl-1,3,4-thiadiazol-5-ylthio methyl)ceph-3-em-4-carboxylic acid Antimicrob Agents Chemother. 3:40–48).

Compound Preparation

Compounds were dissolved in 2% Tween 80 for oral dosing or 0.9% NaCl solution for intravenous dosing. Compounds were administered at 1 hour after bacterial inoculation. Vancomycin or ampicillin were used as controls.

Efficacy Model

Male or female ICR mice weighing 22±2 g from MDS Pharma Services were used for the evaluation. Food and water was given ad libitum. Groups of 6 mice weighing 22±g were used for the experiment. Mice were inoculated intraperitoneally with *Staphylococcus aureus* Smith at 4 104 CFU in 0.5 ml of Brain Heart Infusion Broth (Difco) containing 5% mucin (Sigma). Mortality was recorded once daily for 7 days following bacterial inoculation.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A compound of Formula (IA):

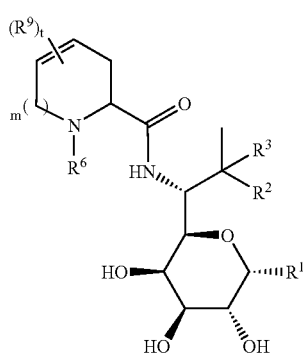

(IA)

wherein:

the

----- represents a bond that may be a double bond or a single bond;

R$^1$ is selected from the group consisting of —S-alkyl, —S-substituted alkyl, SMe, S-(2-hydroxyethyl), (heteroaryl)alkyl, hydrogen, alkyl, substituted alkyl, alkenyl, substituted alkenyl, alkoxy, substituted alkoxy, cycloalkylalkyl, halo, and substituted alkylsulfanyl;

R$^2$ and R$^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R$^2$ and R$^3$ is =NOR$^7$ and the other is absent;

R$^6$ is selected from the group consisting of hydrogen, alkyl, substituted alkyl, (carboxamido)alkyl, (carbamoyl)alkyl, alkoxycarbonyl, (alkoxycarbonyl)alkyl, (alkoxycarbonylamino)alkyl, or —N(R$^6$)— fragment is part of the amidine, N-cyanoamidine, N-hydroxyamidine, or N-alkoxyamidine structure;

R$^7$ is selected from the group consisting of hydrogen and alkyl;

R$^9$, which can be singly or multiply substituted in the ring on the same or different carbons, is independently selected from the group consisting of hydrogen, substituted alkyl, halo, substitutedalkenyl, alkenyl, (heteroaryl)alkenyl, and —S(O)$_q$R$^{13}$ where q is an integer equal to zero, one or two and R$^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m=0–2;

and wherein t=0–3;

or pharmaceutically acceptable salts and/or prodrugs thereof;

with the proviso excluding the following compounds:

the compounds when

----- is a single bond and each R$^9$ is hydrogen;

and the compounds when

----- is a single bond, R$^9$ is substituted alkyl having a single substituent said single substituent is other than halo, oxygen, hydroxy, primary amine, amine(secondary alkyl substituted by alkyl above), amine (tertiary alkyl substituted by alkyl as above), sulfur, —SH, phenyl, or —(CH$_2$)$_n$NR'R" where n is an integer of from 1 to 8 and R' and R" are hydrogen or alkyl; and the compounds when

----- is a single bond, R$^9$ is halo.

2. A compound of Formula (IA):

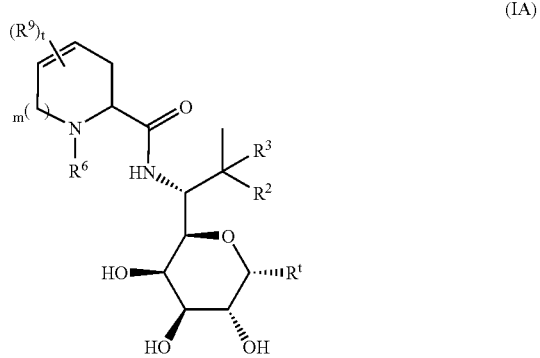

(IA)

wherein:
the

----- represents a bond that may be a double bond or a single bond;

$R^1$ is selected from the group consisting of —S-alkyl, —S-substituted alkyl, SMe, S-(2-hydroxyethyl), (heteroaryl)alkyl, hydrogen, alkyl, substituted alkyl, alkenyl, substituted alkenyl, alkoxy, substituted alkoxy, cycloalkylalkyl, halo, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =NOR$^7$ and the other is absent;

$R^6$ is selected from the group consisting of hydrogen, alkyl, substituted alkyl, (carboxamido)alkyl, (carbamoyl)alkyl, alkoxycarbonyl, (alkoxycarbonyl)alkyl, (alkoxycarbonylamino)alkyl, or —N($R^6$)— fragment is part of the amidine, N-cyanoamidine, N-hydroxyamidine, or N-alkoxyamidine structure;

$R^7$ is selected from the group consisting of hydrogen and alkyl;

$R^9$, which can be singly or multiply substituted in the ring on the same or different carbons, is independently selected from the group consisting of hydrogen, substituted alkyl, halo, substituted alkenyl, alkenyl, (heteroaryl)alkenyl, and —S(O)$_q$R$^{13}$ where q is an integer equal to zero, one or two and $R^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m=0–2;
and wherein t=0–3;

or pharmaceutically acceptable salts and/or prodrugs thereof;

with the proviso excluding the following compounds:
the compounds when

----- is a single bond and each $R^9$ is hydrogen;
and the compounds when

----- is a single bond, $R^9$ is substituted alkyl having a single substituent said single substituent is other than halo, oxygen, hydroxy, primary amine, amine(secondary alkyl substituted by alkyl above), amine (tertiary alkyl substituted by alkyl as above), sulfur, —SH, phenyl, or —(CH$_2$)$_n$NR'R" where n is an integer of from 1 to 8 and R' and R" are hydrogen or alkyl;
and the compounds when

----- is a single bond, $R^9$ is halo.

3. The compound of either claim 1 or 2 wherein wherein the nitrogen-containing ring in Formulas (I) and (II) is selected from:

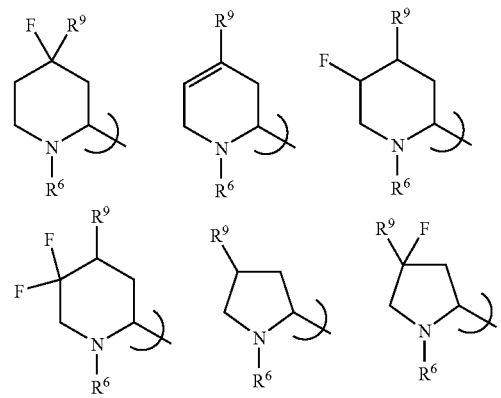

4. A compound selected from the group consisting of:
1-(2-(S)-4-(S)-(ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(R)-(ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(R)-(ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-chloro-prop-1-yl}acetamide;
1-(2-(S)-4-(S)-(ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-chloro-prop-1-yl}acetamide;
1-(2-(S)-4-(S)-(3-p-fluorophenyl)thiopyrrolidin-2-yl)-N-{1-(R)-[2-(S),3-(S),4-(S),5-(R)-(methylsulfanyl)tetrahydropyran-2-yl]-2-hydroxy-prop-1-yl}acetamide;
1-(2-(S)-4-(S)-(n-butylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(S)-(3,3,3-trifluoroprop-1-yl-thio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(S)-(2-(2-chlorophenyl)-ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(S)-(3-methylbut-1-ylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(S)-(2-ethoxythiol)-ethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;
1-(2-(S)-4-(S)-(2,2,2-trifluoroethylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

1-(2-(S)-4-(S)-(m-methylphenyl)methylsulfanylpyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

1-(2-(S)-4-(S)-(p-pyridinylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

1-(2-(S)-4-(S)-(p-trifluoromethoxyphenyl)methylsulfanyl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

1-(2-(S)-4-(S)-(o,p-dichlorophenyl)methylsulfanyl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

1-(2-(S)-4-(S)-(p-pyridinylthio)pyrrolidin-2-yl)-N-{1-(R)-[2-(S),3-(S),4-(S),5-(R)-trihydroxy-6-(R)-(methylsulfanyl)tetrahydropyran-2-yl]-2-hydroxy-prop-1-yl}acetamide;

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Fluoro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;

4-Butylsulfanyl-pyrrolidine-2-carboxylic acid [2-methyl-1-(3,4,5-trihydroxy-6-methylsulfanyl-tetrahydro-pyran-2-yl)-propyl]-amide;

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide;

1-(2-Methoxy-ethyl)-4-pentyl-pyrrolidine-2-carboxylic acid [2-methyl-1-(3,4,5-trihydroxy-6-methlylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Formylamino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Amino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Cyclohexyloxy-propyl)-piperidine-2-carboxylic acid [2-methyl-1-(3,4,5-trihydroxy-6-methylsulfanyl-tetrahydro-pyran-2-yl)-propyl]-amide;

{2-[2-Methyl-1-(3,4,5-trihydroxy-6-methylsulfanyl-tetrahydro-pyran-2-yl)-propylcarbamoyl]-4-pentyl-pyrrolidin-1-yl}-acetic acid methyl ester;

1-Methylcarbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-[3-(Furan-2-ylmethylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(Thiophen-2-ylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(2-Oxo-pyrrolidin-1-yl)-propyl]-piperidine-2-carboxylic acid [2-methyl-1-(3,4,5-trihydroxy-6-methylsulfanyl-tetrahydro-pyran-2-yl)-propyl]-amide;

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide;

4-[2-(4-Ethyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Ethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-propyl)-piperidine-2-carboxylic acid [2-methyl-1-(3,4,5-trihydroxy-6-methylsulfanyl-tetrahydro-pyran-2-yl)-propyl]-amide;

4-Pyrrol-1-ylmethyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

4-(3-Cyano-propyl)-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

4-(2-[1,2,3]Triazol-1-yl-ethyl)-piperidine-2-carboxylic acid [2-methyl-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide; and 4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide;

4-Ethylsulfanyl-pyrrolidine-2-carboxylic acid [2-chloro-1-(3,4 5-trihydroxy-6-methylsulfanyl-tetrahydro-pyran-2-yl)-propyl]-amide;

4-(4-Fluoro-phenylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Butylsulfanyl-pyrrolidine-2-carboxylic acid [2-hydroxy-1-(3,4,5-trihydroxy-6-methylsulfanyl-tetrahydro-pyran-2-yl)-propyl]-amide;

4-(3,3,3-Trifluoro-propylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(2-Chloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(3-Methyl-butylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-[2-(2-Mercapto-ethoxy)-ethylsulfanyl]-pyrrolidine-2-carboxylic acid [2-hydroxy-1-(3,4,5-trihydroxy-6-methylsulfanyl-tetrahydro-pyran-2-yl)-propyl]-amide;

4-(2,2,2-Trifluoro-ethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(3-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-4-ylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Trifluoromethoxy-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Fluoro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;

4-Butylsulfanyl-pyrrolidine-2-carboxylic acid [2-methyl-1-(3,4,5-trihydroxy-6-methylsulfanyl-tetrahydro-pyran-2-yl)-propyl]-amide;

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide;

1-(2-Methoxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Formylamino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Amino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Cyclohexyloxy-propyl)-piperidine-2-carboxylic acid [2-methyl-1-(3,4,5-trihydroxy-6-methylsulfanyl-tetrahydro-pyran-2-yl)-propyl]-amide;

{2-[2-Methyl-1-(3,4,5-trihydroxy-6-methylsulfanyl-tetrahydro-pyran-2-yl)-propylcarbamoyl]-4-pentyl-pyrrolidin-1-yl}-acetic acid methyl ester;

1-Methylcarbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-[3-(Furan-2-ylmethylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(Thiophen-2-ylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(2-Oxo-pyrrolidin-1-yl)-propyl]-piperidine-2-carboxylic acid [2-methyl-1-(3,4,5-trihydroxy-6-methylsulfanyl-tetrahydro-pyran-2-yl)-propyl]-amide;

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide;

4-[2-(4-Ethyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Ethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-propyl)-piperidine-2-carboxylic acid [2-methyl-1-(3,4,5-trihydroxy-6-methylsulfanyl-tetrahydro-pyran-2-yl)-propyl]-amide;

4-Pyrrol-1-ylmethyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

4-(3-Cyano-propyl)-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

4-(2-[1,2,3]Triazol-1-yl-ethyl)-piperidine-2-carboxylic acid [2-methyl-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide; and 4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide.

5. A compound of Formula (IB):

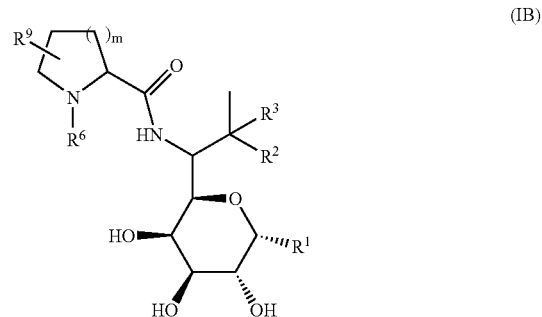

wherein:
$R^1$ is selected from the group consisting of hydrogen, alkyl, substituted alkyl, alkenyl, substituted alkenyl, alkoxy, substituted alkoxy, cycloalkylalkyl, halo, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =NOR$^7$ and the other is absent;

$R^6$ is H, alkyl, or hydroxyalkyl;

$R^7$ is H or alkyl;

R[9], which can be singly or multiply substituted in the ring on the same or different carbons, is selected from the group consisting of hydrogen, alkyl, substituted alkyl, cycloalkyl, substituted cycloalkyl, substituted oxygen, substituted nitrogen, halogen, phenyl, substituted phenyl, —$(CH_2)_n$—OH, —$(CH_2)_n$—$NR^4R^5$, and branched chain isomers thereof wherein n is an integer of from 1 to 8 inclusive and $R^4$ and $R^5$ are H or alkyl; and m is 1 or 2;

or a prodrug and/or a pharmaceutically acceptable salt thereof;

with the proviso that the compound of formula I has a minimum inhibition concentration of 32 µg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*.

6. A compound selected from the group consisting of:

4-Pentyl-pyrrolidine-2-carboxylic acid [2-methyl-1-(3,4,5-trihydroxy-tetrahydro-pyran-2-yl)-propyl]-amide;

4-Pentyl-pyrrolidine-2-carboxylic acid [2-methyl-1-(3,4,5-trihydroxy-6-propyl-tetrahydro-pyran-2-yl)-propyl]-amide;

4-Propyl-piperidine-2-carboxylic acid [2-methyl-1-(3,4,5-trihydroxy-6-propyl-tetrahydro-pyran-2-yl)-propyl]-amide;

1-(2-Hydroxy-ethyl)-4-pentyl-pyrrolidine-2-carboxylic acid [2-methyl-1-(3,4,5-trihydroxy-6-propyl-tetrahydro-pyran-2-yl)-propyl]-amide;

4-Propyl-piperidine-2-carboxylic acid {2-methyl-1-[3,4,5-trihydroxy-6-(2,2,2-trifluoro-ethylsulfanyl)-tetrahydro-pyran-2-yl]-propyl}-amide;

4-Pentyl-pyrrolidine-2-carboxylic acid [1-(6-butoxy-3,4,5-trihydroxy-tetrahydro-pyran-2-yl)-2-methyl-propyl]-amide;

4-Butyl-1-methyl-pyrrolidine-2-carboxylic acid [2-methyl-1-(3,4,5-trihydroxy-6-propyl-tetrahydro-pyran-2-yl)-propyl]-amide;

Phosphoric acid mono-(4,5-dihydroxy-6-{2-methyl-1-[(4-pentyl-pyrrolidine-2-carbonyl)-amino]-propyl}2-propyl-tetrahydro-pyran-3-yl) ester;

Hexadecanoic acid 4,5-dihydroxy-6-{2-methyl-1-[(4-pentyl-pyrrolidine-2-carbonyl)-amino]-propyl}-2-propyl-tetrahydro-pyran-3-yl ester;

Phosphoric acid mono-(4,5-dihydroxy-6-{2-methyl-1-[(4-propyl-pyrrolidine-2-carbonyl)-amino]-propyl}2-propyl-tetrahydro-pyran-3-yl) ester;

Hexadecanoic acid 4,5-dihydroxy-6-{2-methyl-1-[(4-propyl-pyrrolidine-2-carbonyl)-amino]-propyl}-2-propyl-tetrahydro-pyran-3-yl ester;

1-(5-Methyl-2-oxo-[1,3]dioxol-4-ylmethyl)-4-pentyl-pyrrolidine-2-carboxylic acid [2-methyl-1-(3,4,5-trihydroxy-6-propyl-tetrahydro-pyran-2-yl)-propyl]-amide;

2-[2-Methyl-1-(3,4,5-trihydroxy-6-propyl-tetrahydro-pyran-2-yl)-propylcarbamoyl]-4-pentyl-pyrrolidine-1-carboxylic acid 5-methyl-2-oxo-[1,3]dioxol-4-ylmethyl ester;

1-(5-Methyl-2-oxo-[1,3]dioxol-4-ylmethyl)-4-propyl-pyrrolidine-2-carboxylic acid [2-methyl-1-(3,4,5-trihydroxy-6-propyl-tetrahydro-pyran-2-yl)-propyl]-amide;

2-[2-Methyl-1-(3,4,5-trihydroxy-6-propyl-tetrahydro-pyran-2-yl)-propylcarbamoyl]-4-propyl-pyrrolidine-1-carboxylic acid 5-methyl-2-oxo-[1,3]dioxol-4-ylmethyl ester;

4-Propyl-pyrrolidine-2-carboxylic acid {2-methyl-1-[3,4,5-trihydroxy-6-(2-hydroxy-ethyl)-tetrahydro-pyran-2-yl]-propyl}-amide;

4-Propyl-pyrrolidine-2-carboxylic acid {2-methyl-1-[3,4,5-trihydroxy-6-(3-hydroxy-propyl)-tetrahydro-pyran-2-yl]-propyl}-amide;

4-Propyl-pyrrolidine-2-carboxylic acid [2-methyl-1-(3,4,5-trihydroxy-6-hydroxymethyl-tetrahydro-pyran-2-yl)-propyl]-amide;

4-Propyl-pyrrolidine-2-carboxylic acid {2-methyl-1-[3,4,5-trihydroxy-6-(2-methylsulfanyl-ethyl)-tetrahydro-pyran-2-yl]-propyl}-amide;

4-Propyl-pyrrolidine-2-carboxylic acid [1-(6-cyclopropylmethyl-3,4,5-trihydroxy-tetrahydro-pyran-2-yl)-2-methyl-propyl]-amide;

or a prodrug and/or a pharmaceutically acceptable salt thereof.

7. A pharmaceutical composition comprising a pharmaceutically acceptable carrier and a therapeutically effective amount of a compound of any one of claims 1, 2 or 5.

8. A method for the treatment of bacterial infection in a mammal comprising administering to the mammal a therapeutically effective amount of a compound of any one of claims 1, 2 or 5.

9. A method for the treatment of bacterial infection in a mammal comprising administering to the mammal a pharmaceutical composition of claim 7.

10. The method according to claim 9, wherein the compound is administered to the mammal orally, parenterally, transdermally, topically, rectally, or intranasally in a pharmaceutical composition.

11. The method according to claim 9, wherein the compound is administered in an amount of from about 0.1 to about 100 mg/kg body weight/day.

12. A compound of Formula (I):

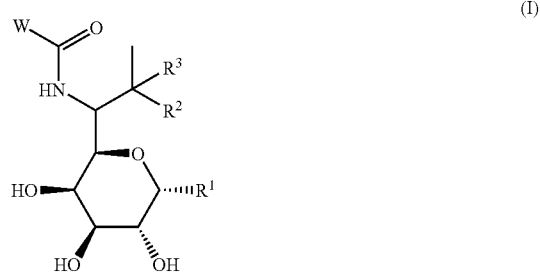

wherein:

W is a nitrogen-containing ring:

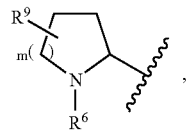

m is 0, 1, 2 or 3; wherein when m is 2, the nitrogen-containing ring may optionally contain a double bond between the 4 and 5 nitrogen-containing ring positions; wherein when m is 3, the nitrogen-containing ring may optionally contain one double bond between either the 4 and 5 nitrogen-containing ring positions or between the 5 and 6 nitrogen-containing ring positions; wherein the nitrogen-containing ring positions are consecutively numbered counterclockwise beginning with "1" at the nitrogen;

$R^1$ is selected from the group consisting of hydrogen, alkyl, substituted alkyl, hydroxyalkyl, alkenyl, substituted alkenyl, alkoxy, substituted alkoxy, cycloalkylalkyl, halo, alkylsulfanyl, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is $=NOR^7$ and the other is absent, or one of $R^2$ and $R^3$ is $=CH_2$ and the other is absent;

$R^6$ is selected from the group consisting of hydrogen, alkyl, hydroxyalkyl, cycloalkyl, substituted alkyl, iminomethyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, 5-alkyl-[1,3]dioxol-2-one-4-yl-methyl, 5-alkyl-[1,3]dioxol-2-one-4-yl-methoxy-carbonyl, or —N($R^6$)— fragment is part of the amidine, N-cyanoamidine, N-hydroxyamidine, or N-alkoxyamidine structure;

$R^7$ is H or alkyl;

$R^9$, which can be singly or multiply substituted in the ring on the same or different carbons, is independently selected from the group consisting of hydrogen, alkyl, substituted alkyl, cycloalkyl, substituted cycloalkyl, cycloalkylalkyl, substituted alkenyl, substituted oxygen, substituted nitrogen, halogen, phenyl, substituted phenyl, alkylsulfanyl, substituted alkylsulfanyl, substituted arylsulfanyl, heteroarylsulfanylalkyl, heterocyclicsulfanylalkyl, heteroarylsulfanyl, and heterocyclicsulfanyl, propylidene ($=CHCH_2CH_3$), azido, —$(CH_2)_n$—OH, —$(CH_2)_n$—$NR^4R^5$, and branched chain isomers thereof wherein n is an integer of from 1 to 8 inclusive and $R^4$ and $R^5$ are H or alkyl, alkoxyalkoxy, aryl, substituted aryl, alkenyl, substituted alkenyl, and —$S(O)_qR^{13}$ where q is an integer equal to zero, one or two and $R^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, and wherein not more than one —$S(O)_qR^{13}$ group is present on the nitrogen-containing ring;

and wherein t=0–3;

or a prodrug and/or pharmaceutically acceptable salt thereof;

with the proviso excluding the following compounds:
the compounds when

----- is a single bond and each $R^9$ is hydrogen;
and the compounds when

----- is a single bond, $R^9$ is substituted alkyl having a single substituent said single substituent is other than halo, oxygen, hydroxy, primary amine, amine(secondary alkyl substituted by alkyl above), amine (tertiary alkyl substituted by alkyl as above), sulfur, —SH, phenyl, or —$(CH_2)_n$NR'R" where n is an integer of from 1 to 8 and R' and R" are hydrogen or alkyl; and the compounds when

----- is a single bond, $R^9$ is halo.

13. A compound of Formula (IA):

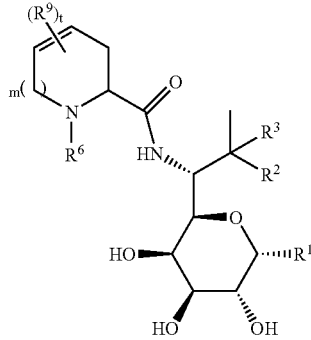

(IA)

wherein:
the

----- represents a bond that may be a double bond or a single bond;

$R^1$ is selected from the group consisting of —S-alkyl, —S-substituted alkyl, SMe, S-(2-hydroxyethyl), (heteroaryl)alkyl, hydrogen, alkyl, substituted alkyl, alkenyl, substituted alkenyl, alkoxy, substituted alkoxy, cycloalkylalkyl, halo, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is $=NOR^7$ and the other is absent;

$R^6$ is selected from the group consisting of hydrogen, alkyl substituted alkyl, (carboxamido)alkyl, (carbamoyl)alkyl, alkoxycarbonyl, (alkoxycarbonyl)alkyl, (alkoxycarbonylamino)alkyl, or —N($R^6$)— fragment is part of the amidine, N-cyanoamidine, N-hydroxyamidine, or N-alkoxyamidine structure;

$R^7$ is selected from the group consisting of hydrogen and alkyl;

$R^9$, which can be singly or multiply substituted in the ring on the same or different carbons, is independently selected from the group consisting of hydrogen, substituted alkyl, halo, substitutedalkenyl, alkenyl, (heteroaryl)alkenyl, and —$S(O)_qR^{13}$ where q is an integer equal to zero, one or two and $R^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m=0–2;
and wherein t=0–3;
or pharmaceutically acceptable salts and/or prodrugs thereof;

with the proviso excluding the following compounds:
the compounds when

----- is a single bond and each $R^9$ is hydrogen;
and the compounds when

----- is a single bond, $R^9$ is substituted alkyl having a single substituent said single substituent is other than halo, oxygen, hydroxy, primary amine, amine(secondary alkyl substituted by alkyl above), amine (tertiary alkyl substituted by alkyl as above), sulfur, —SH, phenyl, or —(CH$_2$)$_n$NR'R" where n is an integer of from 1 to 8 and R' and R" are hydrogen or alkyl; and the compounds when

----- is a single bond, $R^9$ is halo.

14. A compound of Formula (IA):

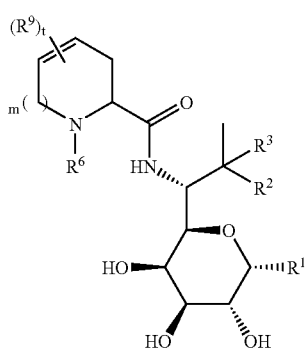

(IA)

wherein:
the

----- represents a bond that may be a double bond or a single bond;

$R^1$ is selected from the group consisting of —S-alkyl, —S-substituted alkyl, SMe, S-(2-hydroxyethyl), (heteroaryl)alkyl, hydrogen, alkyl, substituted alkyl, alkenyl, substituted alkenyl, alkoxy, substituted alkoxy, cycloalkylalkyl, halo, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =NOR$^7$ and the other is absent;

$R^6$ is selected from the group consisting of hydrogen, alkyl, substituted alkyl, (carboxamido)alkyl, (carbamoyl)alkyl, alkoxycarbonyl, (alkoxycarbonyl)alkyl, (alkoxycarbonylamino)alkyl, or —N(R$^6$)— fragment is part of the amidine, N-cyanoamidine, N-hydroxyamidine, or N-alkoxyamidine structure;

$R^7$ is selected from the group consisting of hydrogen and alkyl;

$R^9$, which can be singly or multiply substituted in the ring on the same or different carbons, is independently selected from the group consisting of hydrogen, substituted alkyl, halo, substituted alkenyl, alkenyl, (heteroaryl)alkenyl, and —S(O)$_q$R$^{13}$ where q is an integer equal to zero, one or two and R$^{13}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m=0–2;
and wherein t=0–3;
or pharmaceutically acceptable salts and/or prodrugs thereof;

with the proviso excluding the following compounds:
the compounds when

----- is a single bond and each $R^9$ is hydrogen;
and the compounds when

----- is a single bond, $R^9$ is substituted alkyl having a single substituent said single substituent is other than halo, oxygen, hydroxy, primary amine, amine(secondary alkyl substituted by alkyl above), amine (tertiary alkyl substituted by alkyl as above), sulfur, —SH, phenyl, or —(CH$_2$)$_n$NR'R" where n is an integer of from 1 to 8 and R' and R" are hydrogen or alkyl;
and the compounds when

----- is a single bond, $R^9$ is halo.

15. A compound of Formula (IA):

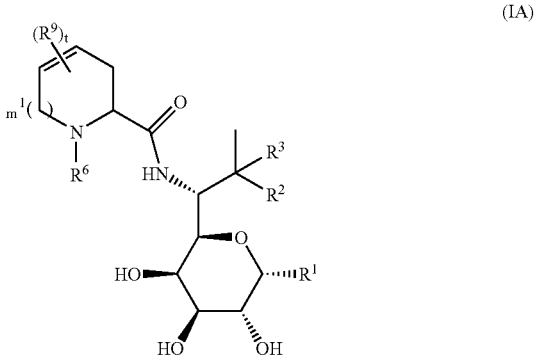

(IA)

wherein:
the

----- represents a bond that may be a double bond or a single bond;

R¹ is selected from the group consisting of —S-alkyl, —S-substituted alkyl, hydrogen, alkyl, substituted alkyl, alkenyl, substituted alkenyl, alkoxy, substituted alkoxy and halo;

R² and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent, or one of R² and R³ is =CH₂ and the other is absent;

R⁶ is selected from the group consisting of hydrogen, alkyl, substituted alkyl,
—C(O)O-alkyl, —C(O)O-substituted alkyl, —C(O)O-aryl, —C(O)O-substituted aryl,
—C(O)O-heteroaryl, —C(O)O-substituted heteroaryl, -(carboxamido)alkyl, (carbamoyl)alkyl,

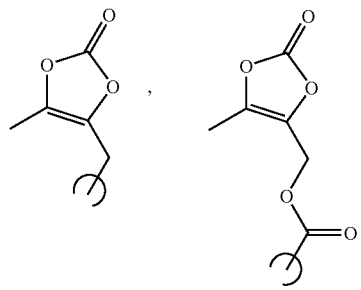

or —N(R⁶)— fragment is part of the amidine, N-cyanoamidine, N-hydroxyamidine, or N-alkoxyamidine structure;

R⁷ is selected from the group consisting of hydrogen and alkyl;

R⁹, which can be singly or multiply substituted in the ring on the same or different carbons, is independently selected from the group consisting of hydrogen, alkyl, substituted alkyl, alkoxyalkoxy, cycloalkyl, substituted cycloalkyl, substituted oxygen, substituted nitrogen, halo, aryl, substituted aryl, alkenyl, substituted alkenyl, and —S(O)$_q$R¹³ where q is an integer equal to zero, one or two and R¹³ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic;

and wherein m¹=0–2;
and wherein t=0–3;
or pharmaceutically acceptable salts and/or prodrugs thereof;

with the following provisos:
A. that in the compounds of formula (I) when

----- is a single bond,
m¹ is zero or one,
R² and R³ are independently hydrogen, alkyl, hydroxy, fluoro, cyanoalkyl or one of R² and R³ is =NOR⁷ and the other is absent, or one of R² and R³ is =CH₂ and the other is absent,
R⁶ is hydrogen, alkyl, hydroxyalkyl, —C(O)O-alkylene-cycloalkyl, —C(O)O-alkylene-substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, —C(O)O-heterocyclic, —C(O)O-substituted hetercyclic, —[C(O)O]$_p$-alkylene-heterocycle, —[C(O)O]$_p$-alkylene-substituted heterocycle, where p is zero or one, and R⁷ is selected from the group consisting of hydrogen and alkyl;

R⁹ is hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$—OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl; and then R¹ is not —S-alkyl, B. in the compounds of formula (I), when

----- is a single bond,
R² and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent, or one of R² and R³ is =CH₂ and the other is absent, with the provisos that both R² and R³ are not hydrogen; when one of R² and R³ is halo, the other is not hydrogen or hydroxy; and when one of R² and R³ is hydroxy, the other is not hydrogen or hydroxy;

R⁶ is selected from the group consisting of hydrogen, alkyl, substituted alkyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, or —N(R⁶)— fragment is part of the amidine, N-cyanoamidine, N-hydroxyamidine, or N-alkoxyamidine structure;

R⁷ is selected from the group consisting of hydrogen and alkyl; and

R¹ is selected from the group consisting of —S-alkyl, —S-substituted alkyl, hydrogen, alkyl, substituted alkyl, alkenyl, substituted alkenyl, alkoxy, substituted alkoxy and halo;

then at least one of R⁹ is other than hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$—OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl, C. in the compounds of formula (I), when

----- is a single bond,
R² and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent, or one of R² and R³ is =CH₂ and the other is absent, with the provisos that both R² and R³ are not hydrogen; when one of R² and R³ is halo, the other is not hydrogen or hydroxy; and when one of R² and R³ is hydroxy, the other is not hydrogen or hydroxy;

R⁷ is selected from the group consisting of hydrogen and alkyl; and

R¹ is selected from the group consisting of —S-alkyl, —S-substituted alkyl, (heteroaryl)alkyl, hydrogen, alkyl, substituted alkyl, alkenyl, substituted alkenyl, alkoxy, substituted alkoxy and halo;

R⁹ is independently selected from other than hydrogen, alkyl, substituted alkyl, alkoxyalkoxy, cycloalkyl, substituted cycloalkyl, substituted oxygen, substituted nitrogen, halo, phenyl, substituted phenyl, —(CH₂)$_n$— OH, —(CH₂)$_n$NR⁴R⁵, -alkylene-R$^a$ where R$^a$ is selected from monofluorophenyl or monochlorophenyl, and branched isomers thereof wherein n is an integer from 1 to 8 inclusive and R⁴ and R⁵ are hydrogen or alkyl, then R⁶ is selected from the group consisting of substituted alkyl (other than monosubstituted heterocycle or substituted heterocycle),

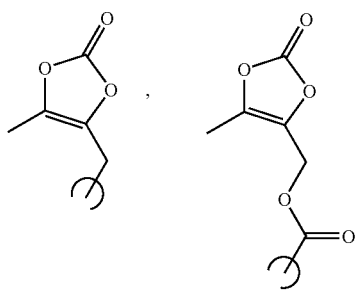

(carboxamido)alkyl, and an —N(R⁶)— fragment that is part of an amidine, N-cyanoamidine, N-hydroxyamidine, or N-alkoxyamidine structure;

wherein, as used in these provisos only, the following specific terms have the following specific meanings:

substituted alkyl refers to alkyl groups wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl), substituted cycloalkyl refers to cycloalkyl substituted with an alkyl group, wherein alkyl is as defined above or a group wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl, substituted oxygen refers to the group —OR$^d$ where R$^d$ is alkyl, haloalkyl, aryl, substituted aryl, heteroaryl, substituted heteroaryl, allkenyl, cycloalkyl, and substituted cycloalkyl, substituted nitrogen or amino refers to the group —NR$^a$R$^b$ wherein R$^a$ and R$^b$ are independently hydrogen, alkyl, haloalkyl, alkenyl, cycloalkyl, substituted cycloalkyl, aryl, substituted aryl, heteroaryl and substituted heteroaryl, substituted aryl refers to an aryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups, and substituted heteroaryl refers to a heteroaryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups.

16. The compound of any of the claims 12–15 wherein the nitrogen-containing ring in Formulas (I) and (IA) is selected from:

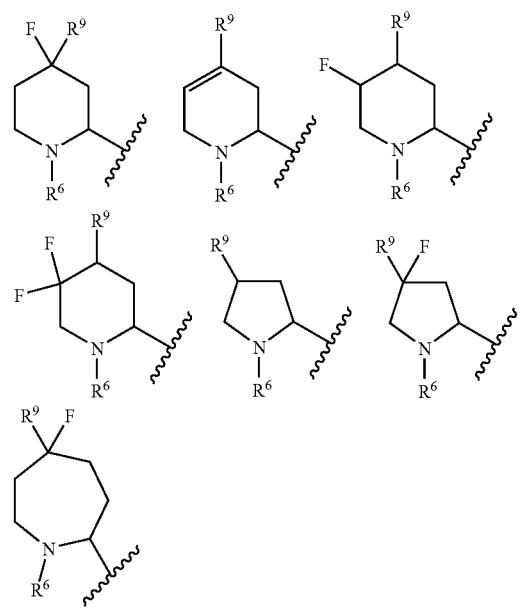

17. A compound of Formula (IB):

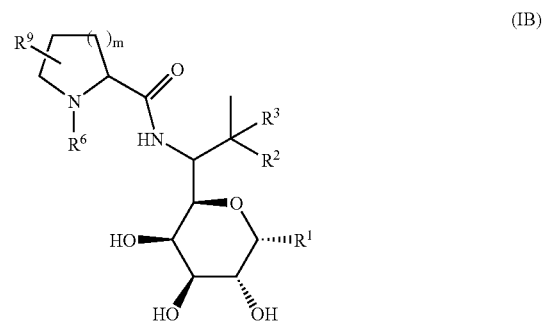

(IB)

wherein:

R¹ is selected from the group consisting of hydrogen, alkyl, substituted alkyl, alkenyl, substituted alkenyl, alkoxy, substituted alkoxy, cycloalkylalkyl, halo, and substituted alkylsulfanyl;

R² and R³ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R² and R³ is =NOR⁷ and the other is absent;

R⁶ is H, alkyl, or hydroxyalkyl;

R⁷ is H or alkyl;

R⁹, which can be singly or multiply substituted in the ring on the same or different carbons, is independently selected from the group consisting of hydrogen, alkyl, substituted alkyl, cycloalkyl, substituted cycloalkyl, substituted oxygen, substituted nitrogen, halogen, phenyl, substituted phenyl, —(CH₂)ₙ—OH, —(CH₂)ₙ—NR⁴R⁵, and branched chain isomers thereof wherein n is an integer of from 1 to 8 inclusive and R⁴ and R⁵ are H or alkyl; and m is 1 or 2;

or prodrugs and/or pharmaceutically acceptable salts thereof.

18. A compound of Formula (II):

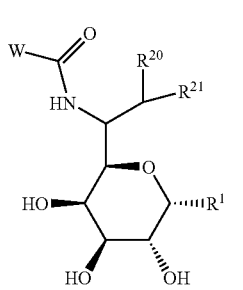

wherein:

W is a nitrogen-containing ring:

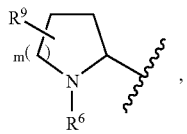

m is 0, 1, 2, or 3; wherein when m is 2, the nitrogen-containing ring may optionally contain a double bond between the 4 and 5 nitrogen-containing ring positions; wherein when m is 3, the nitrogen-containing ring may optionally contain one double bond between either the 4 and 5 nitrogen-containing ring positions or between the 5 and 6 nitrogen-containing ring positions; wherein the nitrogen-containing ring positions are consecutively numbered counterclockwise beginning with "1" at the nitrogen;

R¹ is selected from the group consisting of hydrogen, alkyl, substituted alkyl, hydroxyalkyl, alkenyl, substituted alkenyl, alkoxy, substituted alkoxy, cycloalkylalkyl, halo, alkylsulfanyl, and substituted alkylsulfanyl;

R²⁰ and R²¹ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of R²⁰ and R²¹ is =NOR⁷ and the other is absent, or one of R²⁰ and R²¹ is =CH₂ and the other is absent; or R²⁰ and R²¹ taken together are cycloalkyl, aryl, or heterocyclic group;

R⁶ is selected from the group consisting of hydrogen, alkyl, hydroxyalkyl, cycloalkyl, substituted alkyl, iminomethyl, —C(O)O-alkyl, —C(O)O-substituted alkyl, —C(O)O-aryl, —C(O)O-substituted aryl, —C(O)O-heteroaryl, —C(O)O-substituted heteroaryl, -(carboxamido)alkyl, (carbamoyl)alkyl, 5-alkyl-[1,3]dioxol-2-one-4-yl-methyl, 5-alkyl-[1,3]dioxol-2-one-4-yl-methoxy-carbonyl, or —N(R⁶)— fragment is part of the amidine, N-cyanoamidine, N-hydroxyamidine, or N-alkoxyamidine structure;

R⁷ is H or alkyl;

R⁹, which can be singly or multiply substituted in the ring on the same or different carbons, is independently selected from the group consisting of hydrogen, alkyl, substituted alkyl, cycloalkyl, substituted cycloalkyl, cycloalkylalkyl, substituted alkenyl, substituted oxygen, substituted nitrogen, halogen, phenyl, substituted phenyl, alkylsulfanyl, substituted alkylsulfanyl, substituted arylsulfanyl, heteroarylsulfanylalkyl, heterocyclicsulfanylalkyl, heteroarylsulfanyl, and heterocyclicsulfanyl, propylidene (=CHCH₂CH₃), azido, —(CH₂)ₙ—OH, —(CH₂)ₙ—NR⁴R⁵, and branched chain isomers thereof wherein n is an integer of from 1 to 8 inclusive and R⁴ and R⁵ are H or alkyl, alkoxyalkoxy, aryl, substituted aryl, alkenyl, substituted alkenyl, and —S(O)_qR¹³ where q is an integer equal to zero, one or two and R¹³ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, and wherein not more than one —S(O)_qR¹³ group is present on the nitrogen-containing ring;

or a prodrug and/or pharmaceutically acceptable salt thereof.

19. A compound selected from the group consisting of:

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Fluoro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;

4-Butylsulfanyl-pyrrolidine-2-carboxylic acid [2-methyl-1-(3,4,5-trihydroxy-6-methylsulfanyl-tetrahydro-pyran-2-yl)-propyl]-amide;

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide;

1-(2-Methoxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Formylamino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Amino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Cyclohexyloxy-propyl)-piperidine-2-carboxylic acid [2-methyl-1-(3,4,5-trihydroxy-6-methylsulfanyl-tetrahydro-pyran-2-yl)-propyl]-amide;

{2-[2-Methyl-1-(3,4,5-trihydroxy-6-methylsulfanyl-tetrahydro-pyran-2-yl)-propylcarbamoyl]-4-pentyl-pyrrolidin-1-yl}-acetic acid methyl ester;

1-Methylcarbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-[3-(Furan-2-ylmethylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(Thiophen-2-ylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(2-Oxo-pyrrolidin-1-yl)-propyl]-piperidine-2-carboxylic acid [2-methyl-1-(3,4,5-trihydroxy-6-methylsulfanyl-tetrahydro-pyran-2-yl)-propyl]-amide;

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide;

4-[2-(4-Ethyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Ethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-propyl)-piperidine-2-carboxylic acid [2-methyl-1-(3,4,5-trihydroxy-6-methylsulfanyl-tetrahydro-pyran-2-yl)-propyl]-amide;

4-Pyrrol-1-ylmethyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

4-(3-Cyano-propyl)-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

4-(2-[1,2,3]Triazol-1-yl-ethyl)-piperidine-2-carboxylic acid [2-methyl-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide; and 4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-Ethylsulfanyl-pyrrolidine-2-carboxylic acid [2-hydroxy-1-(3,4,5-trihydroxy-6-methylsulfanyl-tetrahydro-pyran-2-yl)-propyl]-amide;

4-Ethylsulfanyl-pyrrolidine-2-carboxylic acid [2-chloro-1-(3,4,5-trihydroxy-6-methylsulfanyl-tetrahydro-pyran-2-yl)-propyl]-amide;

4-(4-Fluoro-phenylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Butylsulfanyl-pyrrolidine-2-carboxylic acid [2-hydroxy-1-(3,4,5-trihydroxy-6-methylsulfanyl-tetrahydro-pyran-2-yl)-propyl]-amide;

4-(3,3,3-Trifluoro-propylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(2-Chloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(3-Methyl-butylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-[2-(2-Mercapto-ethoxy)-ethylsulfanyl]-pyrrolidine-2-carboxylic acid [2-hydroxy-1-(3,4,5-trihydroxy-6-methylsulfanyl-tetrahydro-pyran-2-yl)-propyl]-amide;

4-(2,2,2-Trifluoro-ethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(3-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-4-ylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Trifluoromethoxy-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Thiophen-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Fluoro-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(4-Methyl-benzylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyridin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-(Pyrazin-2-ylmethylsulfanyl)-pyrrolidine-2-carboxylic acid [2-hydroxy-1-(3,4,5-trihydroxy-6-methylsulfanyl-tetrahydro-pyran-2-yl)-propyl]-amide;

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide;

4-(2,4-Dichloro-benzylsulfanyl)-pyrrolidine-2-carboxylic acid [2-methyl-1-(3,4,5-trihydroxy-6-methylsulfanyl-tetrahydro-pyran-2-yl)-propyl]-amide;

4-Butylsulfanyl-pyrrolidine-2-carboxylic acid [2-methyl-1-(3,4,5-trihydroxy-6-methylsulfanyl-tetrahydro-pyran-2-yl)-propyl]-amide;

4-(3,3-Difluoro-allyl)-pyrrolidine-2-carboxylic acid [2-methyl-1-(3,4,5-trihydroxy-6-methylsulfanyl-tetrahydro-pyran-2-yl)-propyl]-amide;

1-Carbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

1-Cyanomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-allyl)-pyrrolidine-2-carboxylic acid [2-methyl-1-(3,4,5-trihydroxy-6-methylsulfanyl-tetrahydro-pyran-2-yl)-propyl]-amide;

4-(3-Pyridin-4-yl-propyl)-pyrrolidine-2-carboxylic acid [2-methyl-1-(3,4,5-trihydroxy-6-methylsulfanyl-tetrahydro-pyran-2-yl)-propyl]-amide;

1-(2-Methoxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(1H-Imidazol-2-ylmethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Formylamino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-Amino-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

4-(3-Cyclohexyloxy-propyl)-piperidine-2-carboxylic acid [2-methyl-1-(3,4,5-trihydroxy-6-methylsulfanyl-tetrahydro-pyran-2-yl)-propyl]-amide;

{2-[2-Methyl-1-(3,4,5-trihydroxy-6-methylsulfanyl-tetrahydro-pyran-2-yl)-propylcarbamoyl]-4-pentyl-pyrrolidin-1-yl}-acetic acid methyl ester;

1-Methylcarbamoylmethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-(2-[1,3]Dithiolan-2-yl-ethyl)-piperidine-2-carboxylic acid [2-methyl-1-(3,4,5-trihydroxy-6-methylsulfanyl-tetrahydro-pyran-2-yl)-propyl]-amide;

1-Iminomethyl-4-pentyl-pyrrolidine-2-carboxylic acid [2-methyl-1-(3,4,5-trihydroxy-6-methylsulfanyl-tetrahydro-pyran-2-yl)-propyl]-amide;

4-[3-(Furan-2-ylmethylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(Thiophen-2-ylsulfanyl)-propyl]-piperidine-2-carboxylic acid [2-methyl-1-(3,4,5-trihydroxy-6-methylsulfanyl-tetrahydro-pyran-2-yl)-propyl]-amide;

4-(3-Imidazol-1-yl-propyl)-piperidine-2-carboxylic acid [2-methyl-1-(3,4,5-trihydroxy-6-methylsulfanyl-tetrahydro-pyran-2-yl)-propyl]-amide;

4-[3-(2-Oxo-pyrrolidin-1-yl)-propyl]-piperidine-2-carboxylic acid [2-methyl-1-(3,4,5-trihydroxy-6-methylsulfanyl-tetrahydro-pyran-2-yl)-propyl]-amide;

4-[2-(4-Methyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Methoxyimino-propyl)-piperidine-2-carboxylic acid [2-methyl-1-(3,4,5-trihydroxy-6-methylsulfanyl-tetrahydro-pyran-2-yl)-propyl]-amide;

4-[2-(4-Ethyl-thiazol-2-yl)-ethyl]-piperidine-2-carboxylic acid [2-methyl-1-(3,4,5-trihydroxy-6-methylsulfanyl-tetrahydro-pyran-2-yl)-propyl]-amide;

4-(3-Ethylsulfanyl-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxyimino-propyl)-piperidine-2-carboxylic acid [2-methyl-1-(3,4,5-trihydroxy-6-methylsulfanyl-tetrahydro-pyran-2-yl)-propyl]-amide;

4-Pyrrol-1-ylmethyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

4-(3-Cyano-propyl)-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

4-(2-[1,2,3]Triazol-1-yl-ethyl)-piperidine-2-carboxylic acid [2-methyl-1-(3,4,5-trihydroxy-6-methylsulfanyl-tetrahydro-pyran-2-yl)-propyl]-amide;

4-Propylidene-piperidine-2-carboxylic acid [2-methyl-1-(3,4,5-trihydroxy-6-methylsulfanyl-tetrahydro-pyran-2-yl)-propyl]-amide;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-chloro-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-Fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-(3-Difluoromethylsulfanyl-propyl)-piperidine-2-carboxylic acid [2-chloro-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-methyl-1-(3,4,5-trihydroxy-6-methylsulfanyl-tetrahydro-pyran-2-yl)-propyl]-amide;

4-Propyl-1,2,3,6-tetrahydro-pyridine-2-carboxylic acid [2-chloro-1-(3,4,5-trihydroxy-6-methylsulfanyl-tetrahydro-pyran-2-yl)-propyl]-amide;

3-(3-Cyclobutyl-propyl)-azetidine-2-carboxylic acid [2-chloro-1-(3,4,5-trihydroxy-6-methylsulfanyl-tetrahydro-pyran-2-yl)-propyl]-amide 4-(3-Difluoromethylsulfanyl-propyl)-piperidine-2-carboxylic acid [2-methyl-1-(3,4,5-trihydroxy-6-methylsulfanyl-tetrahydro-pyran-2-yl)-propyl]-amide; and 4-(2-Cyclopropyl-ethyl)-piperidine-2-carboxylic acid [2-chloro-1-(3,4,5-trihydroxy-6-methylsulfanyl-tetrahydro-pyran-2-yl)-propyl]-amide.

20. A compound selected from the group consisting of:

Phosphoric acid mono-(6-{2-chloro-1-[(5-propyl-azepane-2-carbonyl)-amino]-propyl}-4,5-dihydroxy-2-methylsulfanyl-tetrahydro-pyran-3-yl) ester;

Phosphoric acid mono-(6-{2-chloro-1-[(5-fluoro-5-propyl-azepane-2-carbonyl)-amino]-propyl}-4,5-dihydroxy-2-methylsulfanyl-tetrahydro-pyran-3-yl) ester;

Phosphoric acid mono-(6-{2-chloro-1-[(5-cyclopropylmethyl-azepane-2-carbonyl)-amino]-propyl}-4,5-dihydroxy-2-methylsulfanyl-tetrahydro-pyran-3-yl) ester;

Phosphoric acid mono-(6-{2-chloro-1-[(4-fluoro-4-propyl-piperidine-2-carbonyl)-amino]-propyl}-4,5-dihydroxy-2-methylsulfanyl-tetrahydro-pyran-3-yl) ester;

Hexadecanoic acid 6-{2-chloro-1-[(5-propyl-azepane-2-carbonyl)-amino]-propyl}-4,5-dihydroxy-2-methylsulfanyl-tetrahydro-pyran-3-yl ester;

Hexadecanoic acid 6-{2-chloro-1-[(5-fluoro-5-propyl-azepane-2-carbonyl)-amino]-propyl}-4,5-dihydroxy-2-methylsulfanyl-tetrahydro-pyran-3-yl ester;

Hexadecanoic acid 6-{2-chloro-1-[(5-cyclopropylmethyl-azepane-2-carbonyl)-amino]-propyl}-4,5-dihydroxy-2-methylsulfanyl-tetrahydro-pyran-3-yl ester;

Hexadecanoic acid 6-{2-chloro-1-[(4-fluoro-4-propyl-piperidine-2-carbonyl)-amino]-propyl}-4,5-dihydroxy-2-methylsulfanyl-tetrahydro-pyran-3-yl ester.

21. A compound selected from the group consisting of:

2-[2-Chloro-1-(3,4,5-trihydroxy-6-methylsulfanyl-tetrahydro-pyran-2-yl)-propylcarbamoyl]-5-propyl-azepane-1-carboxylic acid 5-methyl-2-oxo-[1,3]dioxol-4-ylmethyl ester;

2-[2-Chloro-1-(3,4,5-trihydroxy-6-methylsulfanyl-tetrahydro-pyran-2-yl)-propylcarbamoyl]-5-fluoro-5-propyl-azepane-1-carboxylic acid 5-methyl-2-oxo-[1,3]dioxol-4-ylmethyl ester;

5-Fluoro-1-(5-methyl-2-oxo-[1,3]dioxol-4-ylmethyl)-5-propyl-azepane-2-carboxylic acid [2-chloro-1-(3,4,5-trihydroxy-6-methylsulfanyl-tetrahydro-pyran-2-yl)-propyl]-amide;

5-Cyclopropylmethyl-1-(5-methyl-2-oxo-[1,3]dioxol-4-ylmethyl)-azepane-2-carboxylic acid [2-chloro-1-(3,4,5-trihydroxy-6-methylsulfanyl-tetrahydro-pyran-2-yl)-propyl]-amide;

2-[2-Chloro-1-(3,4,5-trihydroxy-6-methylsulfanyl-tetrahydro-pyran-2-yl)-propylcarbamoyl]-5-cyclopropylmethyl-azepane-1-carboxylic acid 5-methyl-2-oxo-[1,3]dioxol-4-ylmethyl ester;

2-[2-Chloro-1-(3,4,5-trihydroxy-6-methylsulfanyl-tetrahydro-pyran-2-yl)-propylcarbamoyl]-4-fluoro-4-propyl-piperidine-1-carboxylic acid 5-methyl-2-oxo-[1,3]dioxol-4-ylmethyl ester;

4-Fluoro-1-(5-methyl-2-oxo-[1,3]dioxol-4-ylmethyl)-4-propyl-piperidine-2-carboxylic acid [2-chloro-1-(3,4,5-trihydroxy-6-methylsulfanyl-tetrahydro-pyran-2-yl)-propyl]-amide.

22. A compound of Formula (IB):

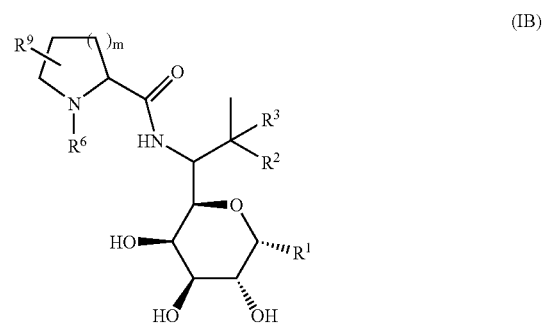

(IB)

wherein:

$R^1$ is selected from the group consisting of hydrogen, alkyl, substituted alkyl, alkenyl, substituted alkenyl, alkoxy, substituted alkoxy, cycloalkylalkyl, halo, and substituted alkylsulfanyl;

$R^2$ and $R^3$ are independently hydrogen, alkyl, substituted alkyl, alkenyl, substituted alkenyl, alkoxy, substituted alkoxy, cyano, alkylsulfanyl, substituted alkylsulfanyl, hydroxy, halo, or one of $R^2$ and $R^3$ is =$NOR^7$ and the other is absent;

$R^6$ is H, alkyl, or hydroxyalkyl;

$R^7$ is H or alkyl;

$R^9$, which can be singly or multiply substituted in the ring on the same or different carbons, is selected from the group consisting of hydrogen, alkyl, substituted alkyl, cycloalkyl, substituted cycloalkyl, substituted oxygen, substituted nitrogen, halogen, phenyl, substituted phenyl, —$(CH_2)_n$—OH, —$(CH_2)_n$—$NR^4R^5$, and branched chain isomers thereof wherein n is an integer of from 1 to 8 inclusive and $R^4$ and $R^5$ are H or alkyl; and m is 1 or 2;

or a prodrug and/or a pharmaceutically acceptable salt thereof;

with the proviso that the compound of formula I has a minimum inhibition concentration of 32 µg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*.

23. A compound selected from the group consisting of:

4-Pentyl-pyrrolidine-2-carboxylic acid [2-methyl-1-(3,4,5-trihydroxy-tetrahydro-pyran-2-yl)-propyl]-amide;

4-Pentyl-pyrrolidine-2-carboxylic acid [2-methyl-1-(3,4,5-trihydroxy-6-propyl-tetrahydro-pyran-2-yl)-propyl]-amide;

4-Propyl-piperidine-2-carboxylic acid [2-methyl-1-(3,4,5-trihydroxy-6-propyl-tetrahydro-pyran-2-yl)-propyl]-amide;

1-(2-Hydroxy-ethyl)-4-pentyl-pyrrolidine-2-carboxylic acid [2-methyl-1-(3,4,5-trihydroxy-6-propyl-tetrahydro-pyran-2-yl)-propyl]-amide;

4-Propyl-piperidine-2-carboxylic acid {2-methyl-1-[3,4,5-trihydroxy-6-(2,2,2-trifluoro-ethylsulfanyl)-tetrahydro-pyran-2-yl]-propyl}-amide;

4-Pentyl-pyrrolidine-2-carboxylic acid [1-(6-butoxy-3,4,5-trihydroxy-tetrahydro-pyran-2-yl)-2-methyl-propyl]-amide;

4-Butyl-1-methyl-pyrrolidine-2-carboxylic acid [2-methyl-1-(3,4,5-trihydroxy-6-propyl-tetrahydro-pyran-2-yl)-propyl]-amide;

Phosphoric acid mono-(4,5-dihydroxy-6-{2-methyl-1-[(4-pentyl-pyrrolidine-2-carbonyl)-amino]-propyl}-2-propyl-tetrahydro-pyran-3-yl) ester;

Hexadecanoic acid 4,5-dihydroxy-6-{2-methyl-1-[(4-pentyl-pyrrolidine-2-carbonyl)-amino]-propyl}-2-propyl-tetrahydro-pyran-3-yl ester;

Phosphoric acid mono-(4,5-dihydroxy-6-{2-methyl-1-[(4-propyl-pyrrolidine-2-carbonyl)-amino]-propyl}-2-propyl-tetrahydro-pyran-3-yl) ester;

Hexadecanoic acid 4,5-dihydroxy-6-{2-methyl-1-[(4-propyl-pyrrolidine-2-carbonyl)-amino]-propyl}-2-propyl-tetrahydro-pyran-3-yl ester;

1-(5-Methyl-2-oxo-[1,3]dioxol-4-ylmethyl)-4-pentyl-pyrrolidine-2-carboxylic acid [2-methyl-1-(3,4,5-trihydroxy-6-propyl-tetrahydro-pyran-2-yl)-propyl]-amide;

2-[2-Methyl-1-(3,4,5-trihydroxy-6-propyl-tetrahydro-pyran-2-yl)-propylcarbamoyl]-4-pentyl-pyrrolidine-1-carboxylic acid 5-methyl-2-oxo-[1,3]dioxol-4-ylmethyl ester;

1-(5-Methyl-2-oxo-[1,3]dioxol-4-ylmethyl)-4-propyl-pyrrolidine-2-carboxylic acid [2-methyl-1-(3,4,5-trihydroxy-6-propyl-tetrahydro-pyran-2-yl)-propyl]-amide;

2-[2-Methyl-1-(3,4,5-trihydroxy-6-propyl-tetrahydro-pyran-2-yl)-propylcarbamoyl]-4-propyl-pyrrolidine-1-carboxylic acid 5-methyl-2-oxo-[1,3]dioxol-4-ylmethyl ester;

4-Propyl-pyrrolidine-2-carboxylic acid {2-methyl-1-[3,4,5-trihydroxy-6-(2-hydroxy-ethyl)-tetrahydro-pyran-2-yl]-propyl}-amide;

4-Propyl-pyrrolidine-2-carboxylic acid {2-methyl-1-[3,4,5-trihydroxy-6-(3-hydroxy-propyl)-tetrahydro-pyran-2-yl]-propyl}-amide;

4-Propyl-pyrrolidine-2-carboxylic acid [2-methyl-1-(3,4,5-trihydroxy-6-hydroxymethyl-tetrahydro-pyran-2-yl)-propyl]-amide;

4-Propyl-pyrrolidine-2-carboxylic acid {2-methyl-1-[3,4,5-trihydroxy-6-(2-methylsulfanyl-ethyl)-tetrahydro-pyran-2-yl]-propyl}-amide;

4-Propyl-pyrrolidine-2-carboxylic acid [1-(6-cyclopropylmethyl-3,4,5-trihydroxy-tetrahydro-pyran-2-yl)-2-methyl-propyl]-amide;

or a prodrug and/or a pharmaceutically acceptable salt thereof.

24. A pharmaceutical composition comprising a pharmaceutically acceptable carrier and a therapeutically effective amount of a compound of any one of claims 12–15 and 17–23.

25. A method for the treatment of bacterial infection in a mammal comprising administering to the mammal a therapeutically effective amount of a compound of any one of claims 12–15 and 17–23.

26. A method for the treatment of bacterial infection in a mammal comprising administering to the mammal a pharmaceutical composition of claim 24.

27. A method according to claim 26 for the treatment of bacterial infection caused by any of the following bacterial pathogens: *H. influenzae, E. faecalis*, and *E. faecium*.

28. The method according to claim 26, wherein the compound is administered in an amount of from about 0.1 to about 100 mg/kg body weight/day.

29. The method according to claim 27, wherein the compound is administered in an amount of from 0.1 to about 100 mg/kg body weight/day.

* * * * *